United States Patent
Deng et al.

(10) Patent No.: US 12,275,729 B2
(45) Date of Patent: Apr. 15, 2025

(54) SUBSTITUTED TETRAHYDROQUINOLIN COMPOUNDS AS INDOLEAMINE 2,3-DIOXYGENASE (IDO) INHIBITORS

(71) Applicant: Merck Sharp & Dohme LLC, Rahway, NJ (US)

(72) Inventors: Yongqi Deng, Newton, MA (US); Abdelghani Achab, Melrose, MA (US); David Jonathan Bennett, Winchester, MA (US); Indu Bharathan, Somerville, MA (US); Xavier Fradera, Boston, MA (US); Craig Gibeau, Northborough, MA (US); Yongxin Han, Needham, MA (US); Derun Li, West Roxbury, MA (US); Kun Liu, Needham, MA (US); Qinglin Pu, Needham, MA (US); Sulagna Sanyal, Belmont, MA (US); David Sloman, Newton, MA (US); Wensheng Yu, Edison, NJ (US); Hongjun Zhang, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/758,717

(22) PCT Filed: Oct. 29, 2018

(86) PCT No.: PCT/US2018/057916
§ 371 (c)(1),
(2) Date: Apr. 23, 2020

(87) PCT Pub. No.: WO2019/089412
PCT Pub. Date: May 9, 2019

(65) Prior Publication Data
US 2021/0179607 A1    Jun. 17, 2021

Related U.S. Application Data

(60) Provisional application No. 62/580,273, filed on Nov. 1, 2017.

(51) Int. Cl.
*C07D 471/04* (2006.01)
*A61K 45/06* (2006.01)
*C07D 215/14* (2006.01)

(52) U.S. Cl.
CPC ............ *C07D 471/04* (2013.01); *A61K 45/06* (2013.01); *C07D 215/14* (2013.01)

(58) Field of Classification Search
None
See application file for complete search history.

(56) References Cited

U.S. PATENT DOCUMENTS

| 10,759,786 B2 * | 9/2020 | Bastian ................ A61K 31/403 |
| 2004/0236109 A1 | 11/2004 | Van Straten |
| 2008/0194615 A1 | 8/2008 | Schiemann |
| 2015/0232445 A1 | 8/2015 | Bair |

OTHER PUBLICATIONS

Chemical Abstract Registry No. 959497-04-2, indexed in the Registry File on STN CAS Online Dec. 26, 2007.*
Updated Chemical Abstract Registry No. 959497-04-2, indexed in the Registry File on STN SAS Online Dec. 26, 2007.*
Chemical Abstract Registry No. 1189671-59-7, indexed in the Registry File on STN CAS Online Oct. 23, 2009.*
Chemical Abstract Registry No. 1357728-88-1, indexed in the Registry File on STN CAS Online Feb. 28, 2012.*
Federal Register, published on 2011, vol. 76, No. 27, p. 7166.*
Chemical Abstract Registry No. 1333764-87-6, indexed in the Registry File on STN CAS Online Sep. 29, 2011.*
Jo, H et al, Development of Novel 1,2,3,4-Tetrahydroquinoline Scaffolds as Potent NF-kB Inhibitors and Cytotoxic Agents, ACS Medicinal Chemistry Letters, 2016, 385-390, 7(4).

* cited by examiner

*Primary Examiner* — Po-Chih Chen
(74) *Attorney, Agent, or Firm* — Kristi K. Harman; Catherine D. Fitch

(57) ABSTRACT

Disclosed herein is a compound of formula (I), or a pharmaceutically acceptable salt thereof (I). Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

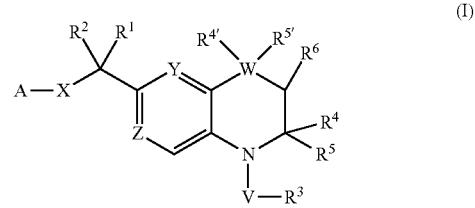

(I)

5 Claims, No Drawings

SUBSTITUTED TETRAHYDROQUINOLIN COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2018/057916, filed Oct. 29, 2018, which claims the benefit of U.S. Provisional Application No. 62/580,273, filed Nov. 1, 2017.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated inhuman immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt thereof:

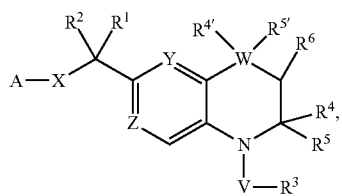

(I)

wherein:
A is selected from:
  (1) $C_{1-6}$ alkyl,
  (2) $C_{3-6}$ carbocyclyl,
  (3) aryl, and
  (4) heterocyclyl;
wherein each of the alkyl of (1), carbocyclyl of (2), aryl of (3), and heterocyclyl of (4) is optionally substituted with 1-3 substituents independently selected from:
(a) halogen,
(b) $C_{1-6}$ alkyl, optionally substituted with 1-3 halogens,
(c) —O—$C_{1-6}$ alkyl, and
(d) —CN;
X is selected from (1) —NHC(O)— and (2) —C(O) NH—;
each of Y and Z is independently selected from (1) —CH= and (2) —N=;
V is selected from:
(1) absent,
(2) —H,
(3) —$CH_2$—,
(4) —CH($CH_2$OH)—,
(5) —C(O)—,
(6) —C($CH_2$)$_n$OR,
(7) —$CO_2$, and
(8) —$SO_2$;
W is selected from:
  (1) absent,
  (2) —($CR^{4'}R^{5'}$)$_m$—, m is 1 or 2, and
  (3) —O— provided $R^{4'}$ and $R^{5'}$ are absent;
each of $R^1$ and $R^2$ is independently selected from:
  (1) H,
  (2) $C_{1-6}$ alkyl, optionally substituted with 1-3 halogens,
  (3) —OR,
  (4) $C_{2-6}$ alkenyl, and
(5) $C_{3-6}$ cycloalkyl;
or alternatively, $R^1$ and $R^2$ together with the carbon to which they are attached form a ring selected from:
(1) a 3-6 membered monocyclic carbocyclyl, optionally substituted with 1-3 substituents independently selected from (a) halogen, (b) $C_{1-6}$ alkyl, and (c) —O—$C_{1-6}$ alkylene-phenyl,
(2) a 5-8 membered bicyclic carbocyclyl, optionally substituted with 1-3 halogens, and
(3) a 3-6 membered heterocyclyl;
$R^3$ is selected from:
  (1) absent,
  (2) —H,
  (3) $C_{1-6}$ alkyl,
  (4) —OR,
  (5) —N(R)$_2$,
  (6) $C_{3-6}$ cycloalkyl,
  (7) aryl, and
  (8) heterocyclyl;
wherein each of the alkyl of (3), cycloalkyl of (6), aryl of (7), and heterocyclyl of (8) is optionally substituted with 1-3 substituents independently selected from:
(a) $C_{1-6}$ alkyl,
(b) $C_{3-6}$ cycloalkyl,
(c) ($CH_2$) OR,
(d) —OR,
(e) halogen,
(f) —($CH_2$)$_n$$CHF_2$,
(g) —($CH_2$)$_n$$CF_3$,
(h) —C(O)R,
(i) —($CH_2$)$_n$O($CH_2$)$_n$OR,
(j) —($CH_2$)$_n$—CN,
(k) —S(O)$_2$—$C_{1-6}$ alkyl, and
(l) oxo;

each occurrence of $R^{4'}$, $R^{5'}$, $R^4$, and $R^5$ is independently selected from:
  (1) —H,
  (2) —OH,
  (3) halogen, and
  (4) $C_{1-6}$ alkyl;
or alternatively, one of $R^{4'}$ and $R^{5'}$ is absent and the other is oxo;
or alternatively, one of $R^4$ and $R^5$ is absent and the other is oxo;
$R^6$ is selected from (1) H, (2) halogen, and (3) $C_{1-6}$ alkyl;
each occurrence of R is independently selected from:
  (1) —H,
  (2) $C_{1-6}$ alkyl, optionally substituted with 1-3 substituents independently selected from:
    (a) halogen,
    (b) —CN,
    (c) —O—$C_{1-6}$ alkyl,
    (d) —$NR^aR^a$, wherein each occurrence of $R^a$ is independently selected from (i) H, (ii) $C_{1-6}$ alkyl, and (iii) $C_{3-6}$ cycloalkyl,
    (e) phenyl, optionally substituted with 1-3 halogens,
    (f) —O-phenyl, and
    (g) heterocyclyl, optionally substituted with 1-3 substituents independently selected from (a) halogen and (b) $C_{1-6}$ alkyl, and
  (3) $C_{3-6}$ cycloalkyl; and
n is selected from 0, 1, 2, 3, and 4.
In one embodiment of the compound of formula (I), or a pharmaceutically acceptable salt thereof:
A is selected from:
  (1) $C_{1-4}$ alkyl,
  (2) $C_{3-6}$ cycloalkyl,
  (3) phenyl, and
  (4) heteroaryl,
  wherein each of the alkyl of (1), cycloalkyl of (2), phenyl of (3), and heteroaryl of (4) is optionally substituted with 1-3 substituents independently selected from:
    (a) halogen,
    (b) $C_{1-6}$ alkyl, optionally substituted with 1-3 halogens,
    (c) —O—$C_{1-6}$ alkyl, and
    (d) —CN.
In one embodiment of the compound of formula (I), or a pharmaceutically acceptable salt thereof:
A is selected from:
  (1) $C_{1-4}$ alkyl, optionally substituted with 1-3 halogens,
  (2) $C_{3-6}$ cycloalkyl, optionally substituted with 1-3 $C_{1-4}$ alkyl,
  (3) phenyl, and
  (4) pyridinyl,
  wherein each of the phenyl of (3) and pyridinyl of (4) is optionally substituted with 1-3 substituents independently selected from:
    (a) halogen,
    (b) —$CH_3$,
    (c) —$CHF_2$,
    (d) —$CF_3$,
    (e) —O—$CH_3$, and
    (f) —CN.
In one embodiment of the compound of formula (I), or a pharmaceutically acceptable salt thereof, Y and Z are both —CH=.
In one embodiment of the compound of formula (I), or a pharmaceutically acceptable salt thereof, Y is —CH= and Z is —N=; or Y is —N= and Z is —CH=.

In one embodiment of the compound of formula (I), or a pharmaceutically acceptable salt thereof, V is selected from:
  (1) absent,
  (2) —$CH_2$—,
  (3) —$CH(CH_2OH)$—, and
  (4) —C(O)—.
In one embodiment of the compound of formula (I), or a pharmaceutically acceptable salt thereof:
each of $R^1$ and $R^2$ is independently selected from:
  (1) —H,
  (2) $C_{1-6}$ alkyl, optionally substituted with 1-3 substituents independently selected from (a) halogen and (b) OH,
  (3) —O—$C_{1-6}$ alkyl, optionally substituted with 1-3 halogens,
  (4) $C_{2-4}$ alkenyl, and
  (5) $C_{3-6}$ cycloalkyl;
or alternatively, $R^1$ and $R^2$ together with the carbon to which they are attached form a 3-5 membered ring selected from:
  (1) cyclopropyl, optionally substituted with 1-3 substituents independently selected from (a) halogen and (b) $C_{1-4}$ alkyl,
  (2) cyclobutyl, optionally substituted with 1-3 substituents independently selected from (a) halogen and (b) $C_{1-4}$ alkyl,
  (3) spiro[2.3]hexanyl,
  (4) oxiranyl, and
  (5) oxetanyl.
In one embodiment of the compound of formula (I), or a pharmaceutically acceptable salt thereof:
each of $R^1$ and $R^2$ is independently selected from:
  (1) H,
  (2) $C_{1-4}$ alkyl, optionally substituted with 1-3 halogens,
  (3) —O—$C_{1-4}$ alkyl,
  (4) $C_{2-4}$ alkenyl, and
  (5) cyclopropyl;
or alternatively, $R^1$ and $R^2$ together with the carbon to which they are attached form a 3-5 membered ring selected from:
  (1) cyclopropyl, optionally substituted with 1-3 substituents independently selected from (a) halogen and (b) methyl,
  (2) cyclobutyl,
  (3) spiro[2.3]hexanyl,
  (4) oxiranyl, and
  (5) oxetanyl.
In one embodiment of the compound of formula (I), or a pharmaceutically acceptable salt thereof:
$R^3$ is selected from:
  (1) absent,
  (2) —H,
  (3) $C_{1-6}$ alkyl,
  (4) —OR,
  (5) —$N(R)_2$,
  (6) $C_{3-6}$ cycloalkyl,
  (7) phenyl, and
  (8) heterocyclyl;
  wherein each of the alkyl of (3), cycloalkyl of (6), phenyl of (7) and heterocyclyl of (8) is optionally substituted with 1-3 substituents independently selected from:
    (a) $C_{1-4}$ alkyl,
    (b) $C_{3-6}$ cycloalkyl,
    (c) —OR,
    (d) halogen,
    (e) —$CHF_2$,
    (f) —$CF_3$,
    (g) —C(O)R, (h) —OR,
(i) —CN,
(j) —S(O)$_2$—C$_{1-4}$ alkyl, and
(k) oxo; and
each occurrence of R is independently selected from:
(1) —H,
(2) C$_{1-4}$ alkyl, optionally substituted with 1-3 substituents independently selected from:
(a) halogen,
(b) —CN,
(c) —O—C$_{1-6}$ alkyl,
(d) —NR$^a$R$^a$, wherein each occurrence of R$^a$ is independently selected from (i) H, (ii) C$_{1-6}$ alkyl, and (iii) C$_{3-6}$ cycloalkyl,
(e) phenyl, optionally substituted with 1-3 halogens,
(f) —O-phenyl, and
(g) heterocyclyl, optionally substituted with 1-3 substituents independently selected from (a) halogen and (b) C$_{1-6}$ alkyl, and
(3) C$_{3-6}$ cycloalkyl.

In one embodiment of the compound of formula (I), or a pharmaceutically acceptable salt thereof:
R$^3$ is selected from:
(1) C$_{1-6}$ alkyl, optionally substituted with 1-3 substituents independently selected from:
(a) halogen,
(b) —OH,
(c) —O—C$_{1-4}$ alkyl,
(d) —O—C$_{1-4}$ alkylene-O—C$_{1-4}$ alkyl,
(e) cyclopropyl, and
(f) —CN,
(2) —O—C$_{1-4}$ alkyl, optionally substituted with 1-3 substituents independently selected from:
(a) halogen,
(b) —O—C$_{1-4}$ alkyl,
(c) cyclopropyl, optionally substituted with 1-3 halogens,
(d) —N(C$_{1-4}$ alkyl)(C$_{1-4}$ alkyl),
(e) phenyl, optionally substituted with 1-3 halogens,
(f) —O-phenyl, and
(g) a 4-6 membered monocyclic saturated, partially unsaturated, or aromatic heterocycyl containing 1-3 hetero atoms independently selected from O, S and N, optionally substituted with 1-3 substituents independently selected from (i) halogen and (ii) C$_{1-4}$ alkyl,
(3) —O-cyclopropyl, optionally substituted with 1-3 substituents independently selected from:
(a) halogen, and
(b) C$_{1-4}$ alkyl, optionally substituted with 1-3 halogens,
(4) O-heterocyclyl, optionally substituted with 1-3 substituents independently selected from:
(a) halogen, and
(b) C$_{1-4}$ alkyl, optionally substituted with 1-3 halogens,
(5) —NH—C$_{1-4}$ alkyl,
(6) —N(C$_{1-4}$ alkyl)(C$_{1-4}$ alkyl),
(7) C$_{3-6}$ cycloalkyl, optionally substituted with 1-3 substituents independently selected from:
(a) halogen,
(b) C$_{1-4}$ alkyl, and
(c) —O—C$_{1-4}$ alkyl,
(8) phenyl, optionally substituted with 1-3 substituents independently selected from:
(a) halogen,
(b) C$_{1-4}$ alkyl, optionally substituted with 1-3 halogens,
(c) —O—C$_{1-4}$ alkyl, optionally substituted with —CN,
(d) —CN, and
(e) —S(O)$_2$—C$_{1-4}$ alkyl,
(9) a heterocyclyl selected from:
(a) a 4-6 membered monocyclic saturated heterocycyl containing 1-3 hetero atoms independently selected from O, S and N,
(b) a 4-6 membered monocyclic aromatic heterocycyl containing 1-3 hetero atoms independently selected from O, S and N, and
(c) a 9-12 membered bicyclic heterocycyl containing 1-4 hetero atoms independently selected from O, S and N,
wherein each of the heterocyclyl of (a), (b), and (c) is optionally substituted with 1-3 substituents independently selected from:
(i) halogen,
(ii) C$_{1-4}$ alkyl, optionally substituted with 1-3 substituents independently selected from (i) halogen and (ii) —OH,
(iii) —O—C$_{1-4}$ alkyl,
(iv) —C(O)—C$_{1-4}$ alkyl,
(v) C$_{3-6}$ cycloalkyl,
(vi) —CN, and
(vii) oxo.

In one embodiment of the compound of formula (I), or a pharmaceutically acceptable salt thereof:
R$^3$ is selected from:
(1) C$_{1-4}$ alkyl, optionally substituted with 1-3 substituents independently selected from:
(a) halogen,
(b) —OH,
(c) —O—CH$_3$,
(d) —O—CH$_2$CH$_3$,
(e) —O—CH$_2$CH$_2$—O—C$_{1-4}$ alkyl,
(f) cyclopropyl, and
(g) —CN,
(2) —O—C$_{1-4}$ alkyl, optionally substituted with 1-3 substituents independently selected from:
(a) halogen,
(b) —O—CH$_3$,
(c) —O—CH$_2$CH$_3$,
(d) cyclopropyl, optionally substituted with 1-3 halogens,
(e) —N(CH$_3$)(CH$_3$),
(f) phenyl, optionally substituted with 1-3 halogens,
(g) —O-phenyl, and
(h) a 4-6 membered monocyclic saturated, partially unsaturated, or aromatic heterocycyl containing 1-3 hetero atoms independently selected from O, S and N, optionally substituted with 1-3 substituents independently selected from (i) halogen and (ii) C$_{1-4}$ alkyl,
(3) —O-cyclopropyl, optionally substituted with 1-3 substituents independently selected from:
(a) halogen,
(b) —CH$_3$, optionally substituted with 1-3 halogens, and
(c) —CH$_2$H$_3$, optionally substituted with 1-3 halogens,
(4) —O-heterocyclyl, optionally substituted with 1-3 substituents independently selected from:
(a) halogen,
(b) —CH$_3$, optionally substituted with 1-3 halogens, and
(c) —CH$_2$H$_3$, optionally substituted with 1-3 halogens,
(5) —NH—CH$_3$,
(6) —N(CH$_3$)(CH$_3$),-

(7) $C_{3-6}$ cycloalkyl, optionally substituted with 1-3 substituents independently selected from:
 (a) halogen,
 (b) $C_{1-4}$ alkyl, and
 (c) —O—$C_{1-4}$ alkyl,
(8) phenyl, optionally substituted with 1-3 substituents independently selected from:
 (a) halogen,
 (b) $C_{1-4}$ alkyl, optionally substituted with 1-3 halogens,
 (c) —O—$C_{1-4}$ alkyl, optionally substituted with —CN,
 (d) —CN, and
 (e) —S(O)$_2$—CH$_3$,
(9) a heterocyclyl selected from:
 (a) a 4-6 membered monocyclic saturated heterocycyl selected from azetidinyl, morpholinyl, oxanyl, oxetanyl, oxolanyl, pyrrolodinyl, and tetrahydrofuranyl,
 (b) a 4-6 membered monocyclic aromatic heterocycyl selected from oxadiazolyl, oxazolyl, pyrazolyl, pyrazinyl, pyridinyl, pyrimidinyl, thiazolyl, and triazolyl, and
 (c) a 9-12 membered bicyclic heterocycyl selected from 5,6-dihydro-4H-pyrrolo[1,2-b]pyrazolyl, quinazolinyl, quinolinyl, pyrazolo[1,5-a]pyrimidinyl, tetrahydroquinolinyl, and [1,2,4]triazolo[1,5-a]pyrimidinyl,
 wherein each of the heterocyclyl of (a), (b), and (c) is optionally substituted with 1-3 substituents independently selected from:
  (i) halogen,
  (ii) $C_{1-4}$ alkyl, optionally substituted with 1-3 substituents independently selected from (i) halogen and (ii) —OH,
  (iii) —O—CH$_3$,
  (iv) —O—CH$_2$CH$_3$,
  (v) —C(O)—CH$_3$,
  (vi) —C(O)—CH$_2$CH$_3$,
  (vii) cyclopropyl, and
  (viii) —CN.

In one embodiment of the compound of formula (I), or a pharmaceutically acceptable salt thereof:
 each occurrence of $R^{4'}$, $R^{5'}$, $R^4$, and $R^5$ is independently selected from:
  (1) —H,
  (2) —OH,
  (3) halogen,
  (4) —CH$_3$, and
  (5) —CH$_2$CH$_3$.
 or alternatively, one of $R^{4'}$ and $R^{5'}$ is absent and the other is oxo;
 or alternatively, one of $R^4$ and $R^5$ is absent and the other is oxo;

In one embodiment of the compound of formula (I), or a pharmaceutically acceptable salt thereof, $R^6$ is selected from (1) H, (2) halogen, (3) —CH$_3$, and (4) —CH$_2$CH$_3$.

In one embodiment of the compound of formula (I), or a pharmaceutically acceptable salt thereof, the compound is of formula Ia, formula If, or Ig:

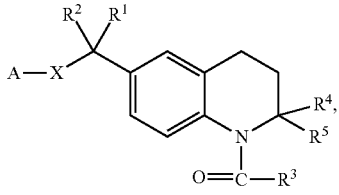
(Ia)

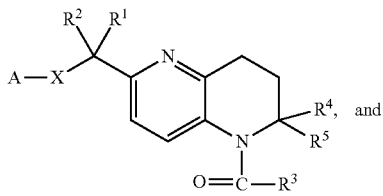
(If)

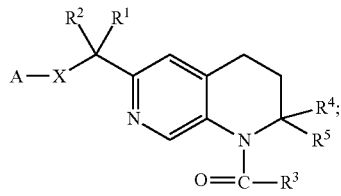
(Ig)

wherein:
A is selected from:
 (1) $C_{1-4}$ alkyl, optionally substituted with 1-3 halogens,
 (2) $C_{3-6}$ cycloalkyl, optionally substituted with $C_{1-4}$ alkyl,
 (3) phenyl, and
 (4) pyridinyl,
wherein each of the phenyl of (3) and pyridinyl of (4) is optionally substituted with 1-3 substituents independently selected from:
 (a) halogen,
 (b) —CH$_3$,
 (c) —CHF$_2$,
 (d) —CF$_3$,
 (e) —O—CH$_3$, and
 (f) —CN;
X is selected from (1) —NHC(O)— and (2) —C(O)NH—;
each of $R^1$ and $R^2$ is independently selected from:
 (1) —H,
 (2) $C_{1-6}$ alkyl, optionally substituted with 1-3 substituents independently selected from (a) halogen and (b) OH,
 (3) —O—$C_{1-6}$ alkyl, optionally substituted with 1-3 halogens,
 (4) $C_{2-4}$ alkenyl, and
 (5) $C_{3-6}$ cycloalkyl;
or alternatively, $R^1$ and $R^2$ together with the carbon to which they are attached form a 3-5 membered ring selected from:
 (1) cyclopropyl, optionally substituted with 1-3 substituents independently selected from (a) halogen and (b) $C_{1-4}$ alkyl,
 (2) cyclobutyl, optionally substituted with 1-3 substituents independently selected from (a) halogen and (b) $C_{1-4}$ alkyl,
 (3) spiro[2.3]hexanyl,
 (4) oxiranyl, and
 (5) oxetanyl;
$R^3$ is selected from:
 (1) $C_{1-6}$ alkyl, optionally substituted with 1-3 substituents independently selected from:
  (a) halogen,
  (b) —OH,
  (c) —O—$C_{1-4}$ alkyl,
  (d) —O—$C_{1-4}$ alkylene-O—$C_{1-4}$ alkyl,
  (e) cyclopropyl, and
  (f) —CN, (2) —O—$C_{1-4}$ alkyl, optionally substituted with 1-3 substituents independently selected from:
(a) halogen,
(b) —O—$C_{1-4}$ alkyl,
(c) cyclopropyl, optionally substituted with 1-3 halogens,
(d) —N($C_{1-4}$ alkyl)($C_{1-4}$ alkyl),
(e) phenyl, optionally substituted with 1-3 halogens,
(f) —O-phenyl, and
(g) a 4-6 membered monocyclic saturated, partially unsaturated, or aromatic heterocycyl containing 1-3 hetero atoms independently selected from O, S and N, optionally substituted with 1-3 substituents independently selected from (i) halogen and (ii) $C_{1-4}$ alkyl,
(3) —O-cyclopropyl, optionally substituted with 1-3 substituents independently selected from:
(a) halogen, and
(b) $C_{1-4}$ alkyl, optionally substituted with 1-3 halogens,
(4) O-heterocyclyl, optionally substituted with 1-3 substituents independently selected from:
(a) halogen, and
(b) $C_{1-4}$ alkyl, optionally substituted with 1-3 halogens,
(5) —NH—$C_{1-4}$ alkyl,
(6) —N($C_{1-4}$ alkyl)($C_{1-4}$ alkyl),
(7) $C_{3-6}$ cycloalkyl, optionally substituted with 1-3 substituents independently selected from:
(a) halogen,
(b) $C_{1-4}$ alkyl, and
(c) —O—$C_{1-4}$ alkyl,
(8) phenyl, optionally substituted with 1-3 substituents independently selected from:
(a) halogen,
(b) $C_{1-4}$ alkyl, optionally substituted with 1-3 halogens,
(c) —O—$C_{1-4}$ alkyl, optionally substituted with —CN,
(d) —CN, and
(e) —S(O)$_2$—$C_{1-4}$ alkyl, and
(9) a heterocyclyl selected from:
(a) a 4-6 membered monocyclic saturated heterocycyl containing 1-3 hetero atoms independently selected from O, S and N,
(b) a 4-6 membered monocyclic aromatic heterocycyl containing 1-3 hetero atoms independently selected from O, S and N, and
(c) a 9-12 membered bicyclic heterocyclyl containing 1-4 hetero atoms independently selected from O, S and N,
wherein each of the heterocyclyl of (a), (b), and (c) is optionally substituted with 1-3 substituents independently selected from:
(i) halogen,
(ii) $C_{1-4}$ alkyl, optionally substituted with 1-3 substituents independently selected from (i) halogen and (ii) —OH,
(iii) —O—$C_{1-4}$ alkyl,
(iv) —C(O)—$C_{1-4}$ alkyl,
(v) $C_{3-6}$ cycloalkyl,
(vi) —CN, and
(vii) oxo; and
each of $R^4$ and $R^5$ is independently selected from:
(1) H,
(2) —OH,
(3) halogen,
(4) —CH$_3$, and
(5) —CH$_2$CH$_3$;
or alternatively, one of $R^4$ and $R^5$ is absent and the other is oxo.

In one embodiment of the compound of formula (Ia), (If) or (Ig), or a pharmaceutically acceptable salt thereof:
A is selected from:
(1) phenyl, and
(2) pyridinyl,
wherein each of the phenyl of (1) and pyridinyl of (2) is optionally substituted with 1-3 substituents independently selected from:
(a) halogen,
(b) —CH$_3$,
(c) —CHF$_2$,
(d) —CF$_3$,
(e) —O—CH$_3$, and
(f) —CN;
each of $R^1$ and $R^2$ is independently selected from:
(1) H,
(2) $C_{1-6}$ alkyl, optionally substituted with 1-3 substituents independently selected from (a) halogen and (b) —OH,
(3) —O—$C_{1-6}$ alkyl, optionally substituted with 1-3 halogens,
(4) $C_{2-4}$ alkenyl, and
(5) $C_{3-6}$ cycloalkyl;
or alternatively, $R^1$ and $R^2$ together with the carbon to which they are attached form a 3-5 membered ring selected from:
(1) cyclopropyl, optionally substituted with 1-3 substituents independently selected from (a) halogen and (b) $C_{1-4}$ alkyl,
(2) cyclobutyl, optionally substituted with 1-3 substituents independently selected from (a) halogen and (b) $C_{1-4}$ alkyl,
(3) oxiranyl, and
(4) oxetanyl;
$R^3$ is selected from:
(1) $C_{1-4}$ alkyl, optionally substituted with 1-3 substituents independently selected from:
(a) halogen,
(b) —OH,
(c) —O—$C_{1-4}$ alkyl,
(d) —O—$C_{1-4}$ alkylene-O—$C_{1-4}$ alkyl,
(e) cyclopropyl, and
(f) —CN,
(2) —O—$C_{1-4}$ alkyl, optionally substituted with 1-3 substituents independently selected from:
(a) halogen,
(b) —O—$C_{1-4}$ alkyl,
(c) cyclopropyl, optionally substituted with 1-3 halogens,
(d) —N($C_{1-4}$ alkyl)($C_{1-4}$ alkyl),
(e) phenyl, optionally substituted with 1-3 halogens,
(f) —O-phenyl, and
(g) a 4-6 membered monocyclic saturated, partially unsaturated, or aromatic heterocycyl containing 1-3 hetero atoms independently selected from O, S and N, optionally substituted with 1-3 substituents independently selected from (i) halogen and (ii) $C_{1-4}$ alkyl,
(3) —O-cyclopropyl, optionally substituted with 1-3 substituents independently selected from:
(a) halogen, and
(b) $C_{1-4}$ alkyl, optionally substituted with 1-3 halogens,
(4) $C_{3-6}$ cycloalkyl, optionally substituted with 1-3 substituents independently selected from:
(a) halogen,
(b) $C_{1-4}$ alkyl, and
(c) —O—$C_{1-4}$ alkyl, (5) phenyl, optionally substituted with 1-3 substituents independently selected from:
   (a) halogen,
   (b) $C_{1-4}$ alkyl, optionally substituted with 1-3 halogens,
   (c) —O—$C_{1-4}$ alkyl, optionally substituted with —CN,
   (d) —CN, and
   (e) —S(O)$_2$—$C_{1-4}$ alkyl, and
(6) a heterocyclyl selected from:
   (a) a 4-6 membered monocyclic saturated heterocycyl selected from azetidinyl, morpholinyl, oxanyl, oxetanyl, oxolanyl, pyrrolodinyl, and tetrahydrofuranyl,
   (b) a 4-6 membered monocyclic aromatic heterocycyl selected from oxadiazolyl, oxazolyl, pyrazolyl, pyrazinyl, pyridinyl, pyrimidinyl, thiazolyl, and triazolyl, and
   (c) a 9-12 membered bicyclic heterocycyl selected from 5,6-dihydro-4H-pyrrolo[1,2-b]pyrazolyl, quinazolinyl, quinolinyl, pyrazolo[1,5-a]pyrimidinyl, tetrahydroquinolinyl, and [1,2,4]triazolo[1,5-a]pyrimidinyl,
wherein each of the heterocyclyl of (a), (b), and (c) is optionally substituted with 1-3 substituents independently selected from:
   (i) halogen,
   (ii) $C_{1-4}$ alkyl, optionally substituted with 1-3 substituents independently selected from (i) halogen and (ii) —OH,
   (iii) —O—CH$_3$,
   (iv) —O—CH$_2$CH$_3$,
   (v) —C(O)—CH$_3$,
   (vi) —C(O)—CH$_2$CH$_3$,
   (vii) cyclopropyl, and
   (viii) —CN; and
each of $R^4$ and $R^5$ is independently selected from:
   (1) H,
   (2) —OH,
   (3) —CH$_3$, and
   (4) —CH$_2$CH$_3$.

In one embodiment of the compound of formula (Ia), (If), or (Ig), or a pharmaceutically acceptable salt thereof:
A is phenyl, optionally substituted with 1-3 halogens;
each of $R^1$ and $R^2$ is independently selected from:
   (1) H, and
   (2) $C_{1-4}$ alkyl, optionally substituted with 1-3 halogens;
or alternatively, $R^1$ and $R^2$ together with the carbon to which they are attached form a 3-5 membered ring selected from:
   (1) cyclopropyl, optionally substituted with 1-3 halogens,
   (2) cyclobutyl, optionally substituted with 1-3 halogens,
   (3) oxiranyl, and
   (4) oxetanyl;
$R^3$ is selected from:
   (1) phenyl, optionally substituted with 1-3 halogens,
   (2) —O-cyclopropyl, optionally substituted with 1-3 substituents independently selected from:
      (a) halogen, and
      (b) —CH$_3$, optionally substituted with 1-3 halogens,
   (3) $C_{3-6}$ cycloalkyl, optionally substituted with 1-3 substituents independently selected from:
      (a) halogen,
      (b) —CH$_3$, and
      (c) —O—CH$_3$, and
   (4) a 4-6 membered monocyclic aromatic heterocycyl selected from oxadiazolyl, oxazolyl, pyrazolyl, pyrazinyl, pyridinyl, pyrimidinyl, thiazolyl, and triazolyl, each of which is optionally substituted with 1-3 substituents independently selected from:
      (a) halogen,
      (b) —CH$_3$, optionally substituted with 1-3 halogens,
      (c) —O—CH$_3$, and
      (d) cyclopropyl; and
each of $R^4$ and $R^5$ is H.

In one embodiment of the compound of formula (Ia), (If), or (Ig), or a pharmaceutically acceptable salt thereof:
A is phenyl, optionally substituted with 1-3 halogens;
each of $R^1$ and $R^2$ is independently selected from:
   (1) H, and
   (2) $C_{1-4}$ alkyl, optionally substituted with 1-3 halogens;
or alternatively, $R^1$ and $R^2$ together with the carbon to which they are attached form a 3-5 membered ring selected from:
   (1) cyclopropyl, optionally substituted with 1-3 halogens, and
   (2) cyclobutyl, optionally substituted with 1-3 halogens; and
$R^3$ is selected from:
   (1) phenyl, optionally substituted with 1-3 halogens,
   (2) —O-cyclopropyl, optionally substituted with 1-3 halogens,
   (3) $C_{3-6}$ cycloalkyl, optionally substituted with 1-3 substituents independently selected from:
      (a) halogen, and
      (b) —CH$_3$, and
   (4) a 4-6 membered monocyclic aromatic heterocycyl selected from pyridinyl and pyrimidinyl, each of which is optionally substituted with 1-3 substituents independently selected from:
      (a) halogen,
      (b) —CH$_3$, optionally substituted with 1-3 halogens, and
      (c) cyclopropyl.

In one embodiment of the compound of formula (I), or a pharmaceutically acceptable salt thereof, the compound is of formula (Ih), (Ii), or (Ij):

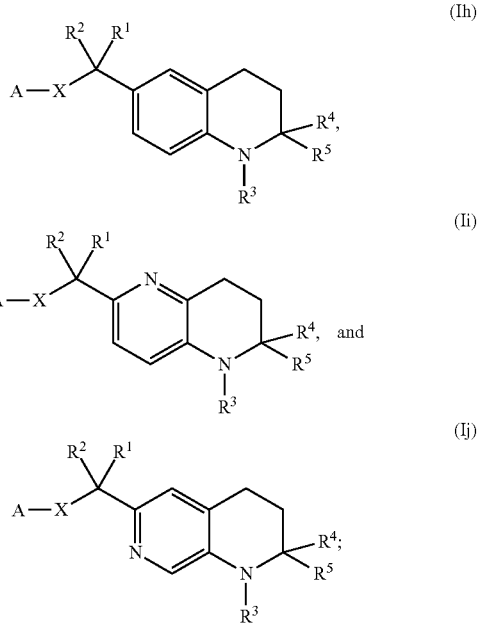

wherein:
A is selected from:
   (1) $C_{1-4}$ alkyl, optionally substituted with 1-3 halogens,
   (2) $C_{3-6}$ cycloalkyl, optionally substituted with $C_{1-4}$ alkyl, (3) phenyl, and
(4) pyridinyl,
wherein each of the phenyl of (3) and pyridinyl of (4) is optionally substituted with 1-3 substituents independently selected from:
(a) halogen,
(b) —$CH_3$,
(c) —$CHF_2$,
(d) —$CF_3$,
(e) —O—$CH_3$, and
(f) —CN;
X is selected from (1) —NHC(O)— and (2) —C(O)NH—;
each of $R^1$ and $R^2$ is independently selected from:
(1) —H,
(2) $C_{1-6}$ alkyl, optionally substituted with 1-3 substituents independently selected from (a) halogen and (b) OH,
(3) —O—$C_{1-6}$ alkyl, optionally substituted with 1-3 halogens,
(4) $C_{2-4}$ alkenyl, and
(5) $C_{3-6}$ cycloalkyl;
or alternatively, $R^1$ and $R^2$ together with the carbon to which they are attached form a 3-5 membered ring selected from:
(1) cyclopropyl, optionally substituted with 1-3 substituents independently selected from (a) halogen and (b) $C_{1-4}$ alkyl,
(2) cyclobutyl, optionally substituted with 1-3 substituents independently selected from (a) halogen and (b) $C_{1-4}$ alkyl,
(3) spiro[2.3]hexanyl,
(4) oxiranyl, and
(5) oxetanyl;
$R^3$ is selected from:
(1) $C_{1-6}$ alkyl, optionally substituted with 1-3 substituents independently selected from:
 (a) halogen,
 (b) —OH,
 (c) —O—$C_{1-4}$ alkyl,
 (d) —O—$C_{1-4}$ alkylene-O—$C_{1-4}$ alkyl,
 (e) cyclopropyl, and
 (f) —CN,
(2) —O—$C_{1-4}$ alkyl, optionally substituted with 1-3 substituents independently selected from:
 (a) halogen,
 (b) —O—$C_{1-4}$ alkyl,
 (c) cyclopropyl, optionally substituted with 1-3 halogens,
 (d) —N($C_{1-4}$ alkyl)($C_{1-4}$ alkyl),
 (e) phenyl, optionally substituted with 1-3 halogens,
 (f) —O-phenyl, and
 (g) a 4-6 membered monocyclic saturated, partially unsaturated, or aromatic heterocycyl containing 1-3 hetero atoms independently selected from O, S and N, optionally substituted with 1-3 substituents independently selected from (i) halogen and (ii) $C_{1-4}$ alkyl,
(3) —O-cyclopropyl, optionally substituted with 1-3 substituents independently selected from:
 (a) halogen, and
 (b) $C_{1-4}$ alkyl, optionally substituted with 1-3 halogens,
(4) O-heterocyclyl, optionally substituted with 1-3 substituents independently selected from:
 (a) halogen, and
 (b) $C_{1-4}$ alkyl, optionally substituted with 1-3 halogens,
(5) —NH—$C_{1-4}$ alkyl,
(6) —N($C_{1-4}$ alkyl)($C_{1-4}$ alkyl),
(7) $C_{3-6}$ cycloalkyl, optionally substituted with 1-3 substituents independently selected from:
 (a) halogen,
 (b) $C_{1-4}$ alkyl, and
 (c) —O—$C_{1-4}$ alkyl,
(8) phenyl, optionally substituted with 1-3 substituents independently selected from:
 (a) halogen,
 (b) $C_{1-4}$ alkyl, optionally substituted with 1-3 halogens,
 (c) —O—$C_{1-4}$ alkyl, optionally substituted with —CN,
 (d) —CN, and
 (e) —$S(O)_2$—$C_{1-4}$ alkyl, and
(9) a heterocyclyl selected from:
 (a) a 4-6 membered monocyclic saturated heterocycyl containing 1-3 hetero atoms independently selected from O, S and N,
 (b) a 4-6 membered monocyclic aromatic heterocycyl containing 1-3 hetero atoms independently selected from O, S and N, and
 (c) a 9-12 membered bicyclic heterocycyl containing 1-4 hetero atoms independently selected from O, S and N,
 wherein each of the heterocyclyl of (a), (b), and (c) is optionally substituted with 1-3 substituents independently selected from:
 (i) halogen,
 (ii) $C_{1-4}$ alkyl, optionally substituted with 1-3 substituents independently selected from (i) halogen and (ii) —OH,
 (iii) —O—$C_{1-4}$ alkyl,
 (iv) —C(O)—$C_{1-4}$ alkyl,
 (v) $C_{3-6}$ cycloalkyl,
 (vi) —CN, and
 (vii) oxo; and
each of $R^4$ and $R^5$ is independently selected from:
(1) H,
(2) —OH,
(3) —$CH_3$, and
(4) —$CH_2CH_3$;
or alternatively, one of $R^4$ and $R^5$ is absent and the other is oxo.
In one embodiment of the compound of formula (Ih), (Ii), or (Ij), or a pharmaceutically acceptable salt thereof:
A is selected from:
(1) phenyl, and
(2) pyridinyl,
wherein each of the phenyl of (1) and pyridinyl of (2) is optionally substituted with 1-3 substituents independently selected from:
(a) halogen,
(b) —$CH_3$,
(c) —$CHF_2$,
(d) —$CF_3$,
(e) —O—$CH_3$, and
(f) —CN;
each of $R^1$ and $R^2$ is independently selected from:
(1) H,
(2) $C_{1-6}$ alkyl, optionally substituted with 1-3 substituents independently selected from (a) halogen and (b) —OH,
(3) O—$C_{1-6}$ alkyl, optionally substituted with 1-3 halogens,
(4) $C_{2-4}$ alkenyl, and
(5) $C_{3-6}$ cycloalkyl;
or alternatively, $R^1$ and $R^2$ together with the carbon to which they are attached form a 3-5 membered ring selected from:

(1) cyclopropyl, optionally substituted with 1-3 substituents independently selected from (a) halogen and (b) $C_{1-4}$ alkyl,
(2) cyclobutyl, optionally substituted with 1-3 substituents independently selected from (a) halogen and (b) $C_{1-4}$ alkyl,
(3) oxiranyl, and
(4) oxetanyl;
$R^3$ is selected from:
(1) $C_{1-4}$ alkyl, optionally substituted with 1-3 substituents independently selected from:
  (a) halogen,
  (b) —OH,
  (c) —O—$C_{1-4}$ alkyl,
  (d) —O—$C_{1-4}$ alkylene-O—$C_{1-4}$ alkyl,
  (e) cyclopropyl, and
  (f) —CN,
(2) $C_{3-6}$ cycloalkyl, optionally substituted with 1-3 substituents independently selected from:
  (a) halogen,
  (b) $C_{1-4}$ alkyl, and
  (c) —O—$C_{1-4}$ alkyl,
(3) phenyl, optionally substituted with 1-3 substituents independently selected from:
  (a) halogen,
  (b) $C_{1-4}$ alkyl, optionally substituted with 1-3 halogens,
  (c) —O—$C_{1-4}$ alkyl, optionally substituted with —CN,
  (d) —CN, and
  (e) —S(O)$_2$—$C_{1-4}$ alkyl, and
(4) a heterocyclyl selected from:
  (a) a 4-6 membered monocyclic saturated heterocycyl selected from azetidinyl, morpholinyl, oxanyl, oxetanyl, oxolanyl, pyrrolodinyl, and tetrahydrofuranyl,
  (b) a 4-6 membered monocyclic aromatic heterocycyl selected from oxadiazolyl, oxazolyl, pyrazolyl, pyrazinyl, pyridinyl, pyrimidinyl, thiazolyl, and triazolyl, and
  (c) a 9-12 membered bicyclic heterocycyl selected from 5,6-dihydro-4H-pyrrolo[1,2-b]pyrazolyl, quinazolinyl, quinolinyl, pyrazolo[1,5-a]pyrimidinyl, tetrahydroquinolinyl, and [1,2,4]triazolo[1,5-a]pyrimidinyl,
wherein each of the heterocyclyl of (a), (b), and (c) is optionally substituted with 1-3 substituents independently selected from:
  (i) halogen,
  (ii) $C_{1-4}$ alkyl, optionally substituted with 1-3 substituents independently selected from (i) halogen and (ii) —OH,
  (iii) —O—CH$_3$,
  (iv) —O—CH$_2$CH$_3$,
  (v) —C(O)—CH$_3$,
  (vi) —C(O)—CH$_2$CH$_3$,
  (vii) cyclopropyl, and
  (viii) —CN; and
each of $R^4$ and $R^5$ is independently selected from:
(1) H,
(2) OH,
(3) —CH$_3$, and
(4) —CH$_2$CH$_3$.

In one embodiment of the compound of formula (Ih), (Ii), or (Ij), or a pharmaceutically acceptable salt thereof:
A is phenyl, optionally substituted with 1-3 halogens;
each of $R^1$ and $R^2$ is independently selected from:
(1) H, and
(2) $C_{1-4}$ alkyl, optionally substituted with 1-3 halogens;
or alternatively, $R^1$ and $R^2$ together with the carbon to which they are attached form a 3-5 membered ring selected from:
(1) cyclopropyl, optionally substituted with 1-3 halogens,
(2) cyclobutyl, optionally substituted with 1-3 halogens,
(3) oxiranyl, and
(4) oxetanyl;
$R^3$ is selected from:
(1) $C_{3-6}$ cycloalkyl, optionally substituted with 1-3 substituents independently selected from:
  (a) halogen,
  (b) —CH$_3$, and
  (c) —O—CH$_3$, and
(2) a 4-6 membered monocyclic aromatic heterocycyl selected from oxadiazolyl, oxazolyl, pyrazolyl, pyrazinyl, pyridinyl, pyrimidinyl, thiazolyl, and triazolyl, each of which is optionally substituted with 1-3 substituents independently selected from:
  (a) halogen,
  (b) —CH$_3$, optionally substituted with 1-3 halogens,
  (c) —O—CH$_3$, and
  (d) cyclopropyl; and
each of $R^4$ and $R^5$ is H.

In one embodiment of the compound of formula (Ih), (Ii), or (Ij), or a pharmaceutically acceptable salt thereof:
A is phenyl, optionally substituted with 1-3 halogens;
each of $R^1$ and $R^2$ is independently selected from:
(1) H, and
(2) $C_{1-4}$ alkyl, optionally substituted with 1-3 halogens;
or alternatively, $R^1$ and $R^2$ together with the carbon to which they are attached form a 3-5 membered ring selected from:
(1) cyclopropyl, optionally substituted with 1-3 halogens, and
(2) cyclobutyl, optionally substituted with 1-3 halogens; and $R^3$ is a 4-6 membered monocyclic heterocycyl selected from pyridinyl and pyrimidinyl, each of which is optionally substituted with 1-3 substituents independently selected from:
  (a) halogen,
  (b) —CH$_3$, optionally substituted with 1-3 halogens, and
  (c) cyclopropyl.

In one embodiment of the compound of formula (I), or a pharmaceutically acceptable salt thereof:
A is selected from $C_{1-6}$ alkyl, $C_{3-6}$ cycloalkyl, $C_{6-10}$ aryl and $C_{3-10}$ heterocyclyl; wherein the alkyl, cycloalkyl, aryl and heterocyclyl are optionally substituted with 1 to 3 substituents independently selected from halogen, —CN, —CF$_3$, —NH$_2$, $C_{1-6}$ alkyl, OR, C(O)OR, and $C_{3-6}$ cycloalkyl;
R is selected from H, $C_{1-6}$ alkyl, and $C_{3-6}$ cycloalkyl;
X is selected from —NHC(O)—, and —C(O)NH—;
Y and Z are independently selected from —CH and N;
V is absent or selected from hydrogen, —C(CH$_2$)OR, —CH(CH$_2$OH)—, C(O), CO$_2$, and SO$_2$;
W is absent, or is C provided $R^4$ and $R^5$ are present, or is O provided $R^4$ and $R^5$ are absent;
$R^1$ and $R^2$ are independently selected from H, $C_{1-6}$ alkyl, OR, $C_{2-6}$ alkenyl, $C_{3-6}$ cycloalkyl, or $R^1$ and $R^2$ can combine to form $C_{3-6}$ cycloalkyl, or $C_{3-6}$ heterocyclyl;
$R^3$ is absent or selected from hydrogen, $C_{1-6}$ alkyl, OR, N(R)$_2$, (CH$_2$)C$_{3-6}$ cycloalkyl, O—C$_{3-6}$ cycloalkyl, NHC$_{3-6}$ cycloalkyl, (CH$_2$)C$_{6-10}$ aryl and C$_{3-10}$ heterocyclyl; said alkyl, cycloalkyl, aryl and heterocyclyl optionally substituted with 1 to 3 groups of $C_{1-6}$ alkyl, $C_{3-6}$ cycloalkyl, $(C_{1-6}$ alkyl)$_n$OR, OR, halogen, (CH$_2$)$_n$CF$_2$, (CH$_2$)$_n$CF$_3$, C(O)R, (CH$_2$)$_n$O(CH$_2$)$_n$OR, (CH$_2$)$_n$CN;

$R^{4'}$, $R^{5'}$, $R^4$ and $R^5$ are independently selected from H, OH, halogen, and $C_{1-6}$ alkyl, or one of $R^{4'}$ and $R^5$ is absent and the other is =O, OH, or halogen, or one of $R^4$ and $R^5$ is absent and the other is =O, OH, or halogen;

$R^6$ is hydrogen, halogen, or $R^6$ may combine with one of $R^{4'}$ or $R^5$ to form a fused cyclopropyl group;

And n is 0, 1, 2, 3, or 4.

In one embodiment of the compound of formula (I), A is unsubstituted or substituted $C_{1-6}$ alkyl. A subembodiment of this aspect of the invention is realized when the unsubstituted or substituted alkyl is selected from the group consisting of $CH_3$, $(CH_2)_nCH(CH_3)_2$.

In one embodiment of the compound of formula (I), A is unsubstituted or substituted $C_{3-6}$ cycloalkyl. A subembodiment of this aspect of the invention is realized when the unsubstituted or substituted cycloalkyl is selected from the group consisting of cyclopropyl, cyclobutyl, cyclopentyl and cyclohexyl.

In one embodiment of the compound of formula (I), A is unsubstituted or substituted $C_{6-10}$ aryl. A subembodiment of this aspect of the invention is realized when the unsubstituted or substituted aryl is phenyl. A further subembodiment of this aspect of the invention is realized when A is phenyl substituted with 1 to 3 groups selected from halogen, $C_{1-6}$ alkyl and OR. A further embodiment of this aspect of the invention is realized when A is phenyl substituted with 1 to 3 groups of halogen selected from the group consisting of chlorine and fluorine. Still a further embodiment of this aspect of the invention is realized when A is phenyl substituted with 1 to 3 groups of chlorine. Still a further embodiment of this aspect of the invention is realized when A is phenyl substituted with 1 to 3 groups of fluorine. Yet a further embodiment of this aspect of the invention is realized when A is phenyl substituted with $C_{1-6}$ alkyl. Yet a further embodiment of this aspect of the invention is realized when A is phenyl substituted with 1 to 3 groups selected from $CH_3$, $CH(CH_3)_2$, and $OCH_3$.

In one embodiment of the compound of formula (I), A is unsubstituted or substituted $C_{3-10}$ heterocyclyl. A subembodiment of this aspect of the invention is realized when the unsubstituted or substituted heterocyclyl is selected from the group consisting of pyridinyl, isoxazolyl, oxadiazolyl, pyrazolyl, and benzimidazolyl. A further subembodiment of this aspect of the invention is realized when A is unsubstituted or substituted pyridinyl. A further subembodiment of this aspect of the invention is realized when A is unsubstituted or substituted isoxazolyl. A further subembodiment of this aspect of the invention is realized when A is unsubstituted or substituted oxadiazolyl. A further subembodiment of this aspect of the invention is realized when A is unsubstituted or substituted pyrazolyl. A further subembodiment of this aspect of the invention is realized when A is unsubstituted or substituted benzimidazolyl. A further subembodiment of this aspect of the invention is realized when A is substituted pyridinyl, isoxazolyl, oxadiazolyl, or pyrazolyl, substituted with 1 to 3 groups of halogen.

In one embodiment of the compound of formula (I), X is —NHC(O)—.

In one embodiment of the compound of formula (I), X is —C(O)NH—.

In one embodiment of the compound of formula (I), Y is —CH=.

In one embodiment of the compound of formula (I), Y is —N=.

In one embodiment of the compound of formula (I), Z is —CH=.

In one embodiment of the compound of formula (I), Z is —N=.

In one embodiment of the compound of formula (I), Y and Z are —CH=.

In one embodiment of the compound of formula (I), both Y and Z are —N=.

In one embodiment of the compound of formula (I), Y is —CH= and Z is —N=.

In one embodiment of the compound of formula (I), Y is —N= and Z is —CH=.

An aspect of the invention is realized wherein if V is absent $R^3$ is present, and if $R^3$ is absent V is present.

In one embodiment of the compound of formula (I), V is absent and $R^3$ is present. In one embodiment of the compound of formula (I), $R^3$ is absent and $V^3$ is present.

In one embodiment of the compound of formula (I), V is hydrogen.

In one embodiment of the compound of formula (I), V is —C(O)—.

In one embodiment of the compound of formula (I), V is —SO₂—.

In one embodiment of the compound of formula (I), W is —CH₂— and $R^{4'}$ and $R^{5'}$ are absent.

In one embodiment of the compound of formula (I), W, $R^{4'}$ and $R^{5'}$ are all absent. A subembodiment of this aspect is realized when W, $R^{4'}$ and $R^{5'}$ are all absent thereby forming indolyl.

In one embodiment of the compound of formula (I), W is —C—, provided $R^{4'}$ and $R^{5'}$ are present.

A subembodiment of this aspect is realized when both $R^{4'}$ and $R^{5'}$ are $C_{1-6}$ alkyl. Another subembodiment of this aspect is realized when one of $R^{4'}$ and $R^{5'}$ is hydrogen and the other is $C_{1-6}$ alkyl. Still another subembodiment of this aspect is realized when one of $R^{4'}$ and $R^{5'}$ is absent and the other is =O, OH, or halogen.

In one embodiment of the compound of formula (I), W is —O— provided $R^{4'}$ and $R^{5'}$ are absent.

In one embodiment of the compound of formula (I), both $R^1$ and $R^2$ are hydrogen.

In one embodiment of the compound of formula (I), $R^1$ and $R^2$ combine to form $C_{3-6}$ cycloalkyl. A subembodiment of this aspect is realized when $R^1$ and $R^2$ combine to form a compound selected from the group consisting of cyclopropyl, cyclobutyl, cyclopentyl and cyclohexyl.

Another subembodiment of this aspect is realized when $R^1$ and $R^2$ combine to form cyclopropyl.

Another subembodiment of this aspect is realized when $R^1$ and $R^2$ combine to form cyclobutyl.

Another subembodiment of this aspect is realized when $R^1$ and $R^2$ combine to form cyclopentyl.

Another subembodiment of this aspect is realized when $R^1$ and $R^2$ combine to form cyclohexyl.

In one embodiment of the compound of formula (I), $R^1$ and $R^2$ combine to form $C_{3-6}$ heterocyclyl. A subembodiment of this aspect is realized when $R^1$ and $R^2$ combine to form a compound selected from the group consisting of oxetanyl and orixanyl. A subembodiment of this aspect is realized when $R^1$ and $R^2$ combine to form a compound selected from the group consisting of oxetanyl. A subembodiment of this aspect is realized when $R^1$ and $R^2$ combine to form a compound selected from the group consisting of orixanyl.

In one embodiment of the compound of formula (I), one of $R^1$ and $R^2$ is hydrogen and the other is $C_{1-6}$ alkyl. In a subembodiment of this aspect the $C_{1-6}$ alkyl is $CH(CH_3)_2$ or $CH_3$.

In one embodiment of the compound of formula (I), one of $R^1$ and R is hydrogen and the other is $C_{2-6}$ alkenyl. In a subembodiment of this aspect the $C_{2-6}$ alkenyl is $CH_2CH=CH_2$.

In one embodiment of the compound of formula (I), one of $R^1$ and $R^2$ is hydrogen and the other is $C_{3-6}$ cycloalkyl. In a subembodiment of this aspect the $C_{3-6}$ cycloalkyl is cyclopropyl.

In one embodiment of the compound of formula (I), $R^3$ is unsubstituted or substituted $C_{1-6}$ alkyl. A subembodiment of this aspect is realized when the alkyl is $CH_3$, $CH_2CF_3$, $CH_2CN$, $CH_2O(CH_2)_2OCH_3$, $CH(CH_3)OCH_3$, $CH(OH)CH(CH_3)_2$, $CH_2C(CH_3)_2OH$, $(CH_2)_2OC(CH_3)_3$, $CH_2CH(CH_3)OH$, $CH(CH_3)_2$, $CH_2OCH_3$, and $CH_2CH(CH_3)_2$. A further subembodiment of this aspect is realized when $R^3$ is unsubstituted or substituted $C_{1-6}$ alkyl which is $CH_2CH(CH_3)_2$. A further subembodiment of this aspect is realized when $R^3$ is unsubstituted or substituted $C_{1-6}$ alkyl which is $CH(CH_3)OCH_3$.

In one embodiment of the compound of formula (I), $R^3$ is —OR. A subembodiment of this aspect is realized when —OR is $OC_{1-6}$ alkyl, or $OC_{3-6}$ cycloalkyl wherein said alkyl is optionally substituted. A further subembodiment of this aspect is realized when —OR is $OCH_3$, $O(CH_2)_2OCH_3$, —$OC(CH_3)_3$, O-cyclopropyl, or O-cyclobutyl. A further subembodiment of this aspect is realized when OR is $OCH_3$. A further subembodiment of this aspect is realized when —OR is O-cyclopropyl. A further subembodiment of this aspect is realized when —OR is O-cyclobutyl.

In one embodiment of the compound of formula (I), $R^3$ is $N(R)_2$. A subembodiment of this aspect is realized when R is H. Another subembodiment of this aspect is realized when one of the R groups is H and the other R is $C_{1-6}$ alkyl. Still another aspect is realized when both R groups are $C_{1-6}$ alkyl. Still another aspect is realized when $R^3$ is $NHCH(CH_3)_2$, NHcyclopropyl, or $N(CH_3)_2$.

In one embodiment of the compound of formula (I), $R^3$ is unsubstituted or substituted $(CH_2)_n$ $C_{3-6}$ cycloalkyl. A subembodiment of this aspect is realized when the n in $(CH_2)_nC_{3-6}$ cycloalkyl is 0.

A subembodiment of this aspect is realized when the n in $(CH_2)_nC_{3-6}$ cycloalkyl is 1. A subembodiment of this aspect is realized when the unsubstituted or substituted cycloalkyl is selected from the group consisting of cyclopropyl, cyclobutyl, cyclopentyl and cyclohexyl. Another subembodiment of this aspect is realized when the cycloalkyl is unsubstituted or substituted cyclopropyl. Another subembodiment of this aspect is realized when the cycloalkyl is unsubstituted or substituted cyclobutyl. Another subembodiment of this aspect is realized when the cycloalkyl is unsubstituted or substituted cyclopentyl. Another subembodiment of this aspect is realized when the cycloalkyl is unsubstituted or substituted cyclohexyl.

In one embodiment of the compound of formula (I), $R^3$ is unsubstituted or substituted $(CH_2)_nC_{6-10}$ aryl. Another subembodiment of this aspect is realized when the unsubstituted or substituted aryl is $(CH_2)$phenyl. Another subembodiment of this aspect is realized when the unsubstituted or substituted aryl is $(CH_2)$phenyl and n is 0. Another subembodiment of this aspect is realized when the unsubstituted or substituted aryl is $(CH_2)$phenyl and n is 1.

In one embodiment of the compound of formula (I), $R^3$ is unsubstituted or substituted $C_{3-10}$ heterocyclyl. A subembodiment of this aspect is realized when the unsubstituted or substituted heterocyclyl is selected from the group consisting of pyridinyl, pyrimidinyl, pyranyl, tetrahydropyranyl, furanyl, tetrahydrofuranyl, oxazolyl, triazolyl, oxadiazolyl, azetidinyl, oxiranyl, pyrrolyl, isoxazolyl, pyrazolyl, quinolinyl, isoquinolinyl, thiazolyl, and morpholinyl. Yet another aspect is realized when the unsubstituted or substituted heterocyclyl is selected from the group consisting of tetrahydropyranyl, tetrahydrofuranyl, oxadiazolyl, pyrazolyl, and pyrimidinyl. Another subembodiment of this aspect of the invention is realized when the unsubstituted or substituted heterocyclyl is pyridinyl. Another subembodiment of this aspect is realized when the unsubstituted or substituted heterocyclyl is pyranyl. Another subembodiment of this aspect is realized when the unsubstituted or substituted heterocyclyl is tetrahydropyranyl.

Another subembodiment of this aspect is realized when the unsubstituted or substituted heterocyclyl is furanyl. Another subembodiment of this aspect is realized when the unsubstituted or substituted heterocyclyl is tetrahydrofuranyl. Another subembodiment of this aspect is realized when the unsubstituted or substituted heterocyclyl is oxazolyl. Another subembodiment of this aspect is realized when the unsubstituted or substituted heterocyclyl is triazolyl. Another subembodiment of this aspect is realized when the unsubstituted or substituted heterocyclyl is oxadiazolyl. Another subembodiment of this aspect is realized when the unsubstituted or substituted heterocyclyl is azetidinyl. Another subembodiment of this aspect is realized when the unsubstituted or substituted heterocyclyl is oxiranyl. Another subembodiment of this aspect is realized when the unsubstituted or substituted heterocyclyl is pyrrolyl. Another subembodiment of this aspect is realized when the unsubstituted or substituted heterocyclyl is isoxazolyl. Another subembodiment of this aspect is realized when the unsubstituted or substituted heterocyclyl is morpholinyl. Another subembodiment of this aspect is realized when the unsubstituted or substituted heterocyclyl is pyrazolyl. Another subembodiment of this aspect is realized when the unsubstituted or substituted heterocyclyl is quinolinyl or isoquinolinyl. Another subembodiment of this aspect is realized when the unsubstituted or substituted heterocyclyl is pyrimidinyl.

In one embodiment of the compound of formula (I), V is absent and $R^3$ is selected from the group consisting of unsubstituted or substituted $(CH_2)_nC_{3-6}$ cycloalkyl, $(CH_2)_nC_{6-10}$ aryl, $C_{3-10}$ heterocyclyl. A subembodiment of this aspect is realized when the unsubstituted or substituted heterocyclyl is selected from the group consisting of pyridinyl, pyrimidinyl, pyranyl, tetrahydropyranyl, furanyl, tetrohydrofuranyl, oxazolyl, triazolyl, oxadiazolyl, azetidinyl, oxiranyl, pyrrolyl, isoxazolyl, pyrazolyl, quinolinyl, isoquinolinyl, and morpholinyl. A further subembodiment of this aspect is realized when the unsubstituted or substituted heterocyclyl is pyridinyl, pyrimidinyl, azetidinyl, oxiranyl, pyrazolyl, tetrahydropyranyl, and tetrahydrofuranyl. Another subembodiment of this aspect is realized when the unsubstituted or substituted aryl is phenyl. Another subembodiment of this aspect is realized when the unsubstituted or substituted cycloalkyl is selected from cyclopropyl, cyclobutyl, cyclopentyl and cyclohexyl. Another subembodiment of this aspect is realized when the unsubstituted or substituted cycloalkyl is cyclopropyl.

In one embodiment of the compound of formula (I), $R^4$ and $R^5$ are both hydrogen.

In one embodiment of the compound of formula (I), $R^4$ and $R^5$ are both $C_{1-6}$ alkyl. A subembodiment of this aspect is realize when $R^4$ and $R^5$ are both $CH_3$.

In one embodiment of the compound of formula (I), one of $R^4$ and $R^5$ is hydrogen and the other is $C_{1-6}$ alkyl. A subembodiment of this aspect is realized when one of $R^4$ and $R^5$ is hydrogen and the other is $CH_3$.

In one embodiment of the compound of formula (I), one $R^4$ and $R^5$ is absent and the other is =O, OH, or halogen.

In one embodiment of the compound of formula (I), $R^6$ is hydrogen.

In one embodiment of the compound of formula (I), $R^6$ is combined with one of $R^{4'}$ or $R^{5'}$ to form a cyclopropyl group that is a fused part of the tetrahydroquinoline structure.

In one embodiment of the compound of formula (Ia), or a pharmaceutically acceptable salt thereof, A is unsubstituted or substituted phenyl or pyridinyl. A subembodiment of formula Ia is realized when X is —NHC(O)—. Another subembodiment of formula Ia is realized when X is —C(O)NH—.

Another subembodiment of formula Ia is realized when $R^1$ and $R^2$ are independently selected from the group consisting of hydrogen, $C_{1-6}$ alkyl and $C_{2-6}$ alkenyl. A further subembodiment of formula Ia is realized when $R^1$ and $R^2$ are both hydrogen, or $CH_3$. A further subembodiment of formula Ia is realized when one of $R^1$ and $R^2$ is hydrogen and the other is selected from $CH_3$ and $CH(CH_3)_2$. Another subembodiment of formula Ia is realized when one of $R^1$ and $R^2$ is hydrogen and the other is selected from $CH_3$. Another subembodiment of formula Ia is realized when one of $R^1$ and $R^2$ is hydrogen and the other is selected from $CH(CH_3)_2$.

A further subembodiment of formula Ia is realized when one of $R^1$ and $R^2$ is hydrogen and the other is selected from $C_{3-6}$ cycloalkyl. A subembodiment of this aspect is realized when the cycloalkyl is cyclopropyl, cyclobutyl, cyclopentyl or cyclohexyl. A subembodiment of this aspect is realized when the cycloalkyl is cyclopropyl. A subembodiment of this aspect is realized when the cycloalkyl is cyclobutyl.

A further subembodiment of formula Ia is realized when $R^1$ and $R^2$ combine to form $C_{3-6}$ heterocyclyl. A subembodiment of this aspect is realized when the heterocyclyl is oxetanyl. A subembodiment of this aspect is realized when the heterocyclyl is oxiranyl.

Another embodiment of formula Ia is realized when $R^1$ and $R^2$ combine to form a compound selected from the group consisting of cyclopropyl, cyclobutyl, cyclopentyl and cyclohexyl.

Another subembodiment of this aspect of formula Ia is realized when $R^1$ and $R^2$ combine to form cyclopropyl. Another subembodiment of this aspect of formula Ia is realized when $R^1$ and $R^2$ combine to form cyclobutyl.

In another embodiment of formula Ia, $R^3$ is selected from a group consisting of unsubstituted or substituted $C_{1-6}$ alkyl, $OC_{1-6}$ alkyl, $N(R)_2$, cyclopropyl, O-cyclopropyl, cyclobutyl, O-cyclobutyl, cyclopentyl and cyclohexyl, phenyl, pyridinyl, pyrimidinyl, pyranyl, tetrahydropyranyl, furanyl, tetrohydrofuranyl, oxazolyl, triazolyl, oxadiazolyl, azetidinyl, oxiranyl, pyrrolyl, isoxazolyl, pyrazolyl, quinolinyl, isoquinolinyl, and morpholinyl. In another embodiment of formula Ia, $R^3$ is selected from a group consisting of unsubstituted or substituted $C_{1-6}$ alkyl, $OC_{1-6}$ alkyl, $N(R)_2$, cyclopropyl, O-cyclopropyl, cyclobutyl, phenyl, pyridinyl, pyrimidinyl, azetidinyl, oxiranyl, oxadiazolyl, pyrazolyl, tetrahydropyranyl, and tetrahydrofuranyl. Another subembodiment of formula Ia is realized when $R^3$ is unsubstituted or substituted pyridinyl or pyrimidinyl.

A subembodiment of this aspect of formula Ia is realized when $R^3$ is unsubstituted or substituted $C_{1-6}$ alkyl or $OC_{1-6}$ alkyl. A subembodiment of this aspect of formula Ia is realized when $R^3$ is selected from the group consisting of $CH_3$, $CH_2CF_3$, $CH_2CN$, $CH_2O(CH_2)_2OCH_3$, $CH(CH_3)OCH_3$, $CH(OH)CH(CH_3)_2$, $CH_2(C(CH_3)_2OH$, $(CH_2)_2OC(CH_3)_3$, $CH_2CH(CH_3)OH$, $CH(CH_3)_2$, $CH_2OCH_3$, $CH_2CH(CH_3)_2$, $OCH_3$, $O(CH_2)_2OCH_3$, and —$OC(CH_3)_3$. A further subembodiment of this aspect is realized when $R^3$ is unsubstituted or substituted $C_{1-6}$ alkyl which is $CH_2CH(CH_3)_2$, or $CH(CH_3)OCH_3$.

Another subembodiment of this aspect of formula Ia is realized when $R^3$ is selected from the group consisting of unsubstituted or substituted cyclopropyl, O-cyclopropyl, cyclobutyl, O-cyclobutyl, cyclopentyl and cyclohexyl. Another subembodiment of this aspect of formula Ia is realized when $R^3$ is unsubstituted or substituted cyclopropyl. Another subembodiment of this aspect of formula Ia is realized when $R^3$ is unsubstituted or substituted cyclobutyl. Another subembodiment of this aspect of formula Ia is realized when $R^3$ is unsubstituted or substituted O-cyclobutyl. Another subembodiment of this aspect of formula Ia is realized when $R^3$ is unsubstituted or substituted O-cyclopropyl.

Another subembodiment of this aspect of formula Ia is realized when $R^3$ is unsubstituted or substituted phenyl.

Another subembodiment of this aspect of formula Ia is realized when $R^3$ is selected from the group consisting of unsubstituted or substituted pyridinyl, pyrimidinyl, azetidinyl, oxiranyl, oxadiazolyl, pyrazolyl, tetrahydropyranyl, and tetrahydrofuranyl. Another subembodiment of formula Ia is realized when $R^3$ is unsubstituted or substituted pyridinyl or pyrimidinyl.

An embodiment of formula Ia is realized when $R^4$ and $R^5$ are both hydrogen.

Still another embodiment of formula Ia is realized when A is unsubstituted or substituted phenyl or pyridinyl, X is —NHC(O)— or —C(O)NH—, $R^1$ and $R^2$ are independently selected from the group consisting of hydrogen, $C_{1-6}$ alkyl, $C_{3-6}$ cycloalkyl, and $C_{2-6}$ alkenyl, one of $R^1$ and $R^2$ is hydrogen and the other is $C_{1-6}$ alkyl, $C_{3-6}$ cycloalkyl, or both of $R^1$ and $R^2$ are hydrogen or $CH_3$, or $R^1$ and $R^2$ combine to form a compound selected from the group consisting of cyclopropyl, cyclobutyl, oxetanyl, or oxiranyl, $R^3$ is selected from a group consisting of unsubstituted or substituted $C_{1-6}$ alkyl, $OC_{1-6}$ alkyl, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl and $R^4$ and $R^5$ are both hydrogen. A subembodiment of this aspect of formula Ia is realized when A is unsubstituted or substituted phenyl, $R^1$ and $R^2$ are both hydrogen, or $CH_3$, or one of $R^1$ and $R^2$ is hydrogen and the other is selected from $CH_3$, $CH_2CH_3$, $CH_2CH=CH_2$, and unsubstituted or substituted cyclopropyl, and $R^3$ is $CH_2CH(CH_3)_2$, or unsubstituted or substituted phenyl. A subembodiment of this aspect of formula Ia is realized when A is unsubstituted or substituted phenyl, $R^1$ and $R^2$ combine to form cyclopropyl, cyclobutyl, oxetanyl, or oxiranyl, and $R^3$ is $CH_2CH(CH_3)_2$, or unsubstituted or substituted phenyl.

A subembodiment of this aspect of formula Ia is realized when A is unsubstituted or substituted phenyl, $R^1$ and $R^2$ combine to form cyclopropyl, cyclobutyl, oxetanyl, or oxiranyl, and $R^3$ is cyclopropyl, O-cyclopropyl, cyclobutyl, O-cyclobutyl.

In one embodiment of the compound of formula (I), or a pharmaceutically acceptable salt thereof the compound is of formula (Ib):

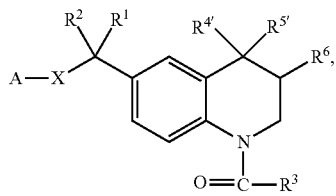

(Ib)

wherein,

A, X, $R^1$, $R^2$, $R^3$, $R^{4'}$, $R^{5'}$, and $R^6$ are as described herein.

A subembodiment of formula Ib is realized when A is unsubstituted or substituted phenyl or pyridinyl.

A subembodiment of formula Ib is realized when X is —NHC(O)—.

Another subembodiment of formula Ib is realized when X is —C(O)NH—.

Another subembodiment of formula Ib is realized when $R^1$ and $R^2$ are independently selected from the group consisting of hydrogen, $C_{1-6}$ alkyl and $C_{2-6}$ alkenyl. A further subembodiment of formula Ib is realized when $R^1$ and $R^2$ are both hydrogen, or $CH_3$. A further subembodiment of formula Ib is realized when one of $R^1$ and $R^2$ is hydrogen and the other is selected from $CH_3$ and $CH(CH_3)_2$. Another subembodiment of formula Ib is realized when one of $R^1$ and $R^2$ is hydrogen and the other is selected from $CH_3$. Another subembodiment of formula Ib is realized when one of $R^1$ and $R^2$ is hydrogen and the other is selected from $CH(CH_3)_2$.

A further subembodiment of formula Ib is realized when one of $R^1$ and $R^2$ is hydrogen and the other is selected from $C_{3-6}$ cycloalkyl. A subembodiment of this aspect is realized when the cycloalkyl is cyclopropyl, cyclobutyl, cyclopentyl or cyclohexyl. A subembodiment of this aspect is realized when the cycloalkyl is cyclopropyl. A subembodiment of this aspect is realized when the cycloalkyl is cyclobutyl.

Another embodiment of formula Ib is realized when $R^1$ and $R^2$ combine to form a compound selected from the group consisting of cyclopropyl, cyclobutyl, cyclopentyl, oxetanyl, oxiranyl, and cyclohexyl. Another subembodiment of this aspect of formula Ib is realized when $R^1$ and $R^2$ combine to form cyclopropyl. Another subembodiment of this aspect of formula Ib is realized when $R^1$ and $R^2$ combine to form cyclobutyl. Another subembodiment of this aspect of formula Ib is realized when $R^1$ and $R^2$ combine to form oxetanyl. Another subembodiment of this aspect of formula Ib is realized when $R^1$ and $R^2$ combine to form oxiranyl.

In another embodiment of formula Ib, $R^3$ is selected from a group consisting of unsubstituted or substituted $C_{1-6}$ alkyl, $OC_{1-6}$ alkyl, $N(R)_2$, cyclopropyl, O-cyclopropyl, cyclobutyl, O-cyclobutyl, cyclopentyl and cyclohexyl, phenyl, pyridinyl, pyrimidinyl, pyranyl, tetrahydropyranyl, furanyl, tetrahydrofuranyl, oxazolyl, triazolyl, oxadiazolyl, azetidinyl, oxiranyl, pyrrolyl, isoxazolyl, pyrazolyl, quinolinyl, isoquinolinyl, and morpholinyl. In another embodiment of formula Ib, $R^3$ is selected from a group consisting of unsubstituted or substituted $C_{1-6}$ alkyl, $OC_{1-6}$ alkyl, $N(R)_2$, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl. Another subembodiment of formula Ia is realized when $R^3$ is optionally substituted with 1 to 3 groups of $C_{1-6}$ alkyl, $C_{3-6}$ cycloalkyl, $(C_{1-6}$ alkyl$)_n$OR, OR, halogen, $(CH_2)_n CF_2$, $(CH_2)_n CF_3$, C(O)R, and $(CH_2)_n CN$.

A subembodiment of this aspect of formula Ib is realized when $R^3$ is unsubstituted or substituted $C_{1-6}$ alkyl or $OC_{1-6}$ alkyl. A subembodiment of this aspect of formula Ib is realized when $R^3$ is selected from the group consisting of $CH_3$, $CH_2CF_3$, $CH_2CN$, $CH_2O(CH_2)_2OCH_3$, $CH(CH_3)OCH_3$, $CH(OH)CH(CH_3)_2$, $CH_2(C(CH_3)_2OH$, $(CH_2)_2OC(CH_3)_3$, $CH_2CH(CH_3)OH$, $CH(CH_3)_2$, $CH_2OCH_3$, $CH_2CH(CH_3)_2$, $OCH_3$, $O(CH_2)_2OCH_3$, and —$OC(CH_3)_3$. A further subembodiment of this aspect is realized when $R^3$ is unsubstituted or substituted $C_{1-6}$ alkyl which is $CH_2CH(CH_3)_2$, or $CH(CH_3)OCH_3$.

Another subembodiment of this aspect of formula Ib is realized when $R^3$ is selected from the group consisting of unsubstituted or substituted cyclopropyl, O-cyclopropyl, cyclobutyl, O-cyclobutyl, cyclopentyl and cyclohexyl. Another subembodiment of this aspect of formula Ib is realized when $R^3$ is unsubstituted or substituted cyclopropyl. Another subembodiment of this aspect of formula Ib is realized when $R^3$ is unsubstituted or substituted cyclobutyl. Another subembodiment of this aspect of formula Ib is realized when $R^3$ is unsubstituted or substituted phenyl.

Another subembodiment of this aspect of formula Ib is realized when $R^3$ is selected from the group consisting of unsubstituted or substituted pyridinyl, pyrimidinyl, azetidinyl, oxiranyl, oxadiazolyl, pyrazolyl, tetrahydropyranyl, and tetrahydrofuranyl. Another subembodiment of formula Ib is realized when $R^3$ is unsubstituted or substituted pyridinyl or pyrimidinyl.

An embodiment of formula Ib is realized when one of $R^{4'}$ and $R^{5'}$ is hydrogen and the other is halogen, or $R^4$ and $R^5$ are both halogen or hydrogen.

An embodiment of formula Ib is realized when $R^6$ is hydrogen, halogen, or OH, or $R^6$ my combine with one of $R^{4'}$ or $R^{5'}$ to form a fused cyclopropyl group.

An embodiment of formula Ib is realized when one of $R^4$ and $R^5$ is hydrogen and the other is combined with $R^6$ to form a fused cyclopropyl group.

Still another embodiment of formula Ib is realized when A is unsubstituted or substituted phenyl or pyridinyl, X is —NHC(O)— or —C(O)NH—, $R^1$ and $R^2$ are independently selected from the group consisting of hydrogen, $C_{1-6}$ alkyl, $C_{3-6}$ cycloalkyl, and $C_{2-6}$ alkenyl, one of $R^1$ and $R^2$ is hydrogen and the other is $C_{1-6}$ alkyl, $C_{3-6}$ cycloalkyl, or both of $R^1$ and $R^2$ are hydrogen or $CH_3$, or $R^1$ and $R^2$ combine to form a compound selected from the group consisting of cyclopropyl, cyclobutyl, oxetanyl, and oxiranyl, $R^3$ is selected from a group consisting of unsubstituted or substituted $C_{1-6}$ alkyl, $OC_{1-6}$ alkyl, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl, $R^{4'}$ and $R^5$ are both halogen and $R^6$ is hydrogen.

A subembodiment of this aspect of formula Ib is realized when A is unsubstituted or substituted phenyl, $R^1$ and $R^2$ are both hydrogen, or $CH_3$, or one of $R^1$ and $R^2$ is hydrogen and the other is selected from $CH_3$, $CH_2CH_3$, $CH_2CH=CH_2$, and unsubstituted or unsubstituted cyclopropyl, and $R^3$ is $CH_2CH(CH_3)_2$, or unsubstituted or substituted phenyl.

A subembodiment of this aspect of formula Ib is realized when A is unsubstituted or substituted phenyl, $R^1$ and $R^2$ are both hydrogen, or $CH_3$, or one of $R^1$ and $R^2$ is hydrogen and the other is selected from $CH_3$, $CH_2CH_3$, $CH_2CH=CH_2$, and unsubstituted or unsubstituted cyclopropyl, and $R^3$ is cyclopropyl, O-cyclopropyl, cyclobutyl, O-cyclobutyl.

In one embodiment of the compound of formula (I), or a pharmaceutically acceptable salt thereof, the compound is of formula (Ic):

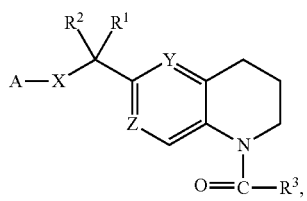

(Ic)

wherein,

A, X, R¹, R², R³, Y and Z are as described herein.

A subembodiment of formula Ic is realized when Y is N and Z is CH. Another subembodiment of formula Ic is realized when Y is C and Z is N.

Still another embodiment of formula Ic is realized when A is unsubstituted or substituted phenyl or pyridinyl, X is —NHC(O)— or —C(O)NH—, R¹ and R² are independently selected from the group consisting of hydrogen, $C_{1-6}$ alkyl, $C_{3-6}$ cycloalkyl, and $C_{2-6}$ alkenyl, one of R¹ and R² is hydrogen and the other is $C_{1-6}$ alkyl, $C_{3-6}$ cycloalkyl, or both of R¹ and R² are hydrogen or CH₃, or R¹ and R² combine to form a compound selected from the group consisting of cyclopropyl, cyclobutyl, oxetanyl, and oxiranyl, and R³ is selected from a group consisting of unsubstituted or substituted $C_{1-6}$ alkyl, $OC_{1-6}$ alkyl, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl. Another subembodiment of formula Ic is realized when R³ is unsubstituted or substituted pyridinyl or pyrimidinyl. Another subembodiment of formula Ic is realized when R³ is unsubstituted or substituted phenyl.

A subembodiment of this aspect of formula Ic is realized when Y is N and Z is CH or Y is CH and Z is N, A is unsubstituted or substituted phenyl, R¹ and R² are both hydrogen, or CH₃, or one of R¹ and R² is hydrogen and the other is selected from CH₃, CH₂CH₃, CH₂CH═CH₂, and unsubstituted or substituted cyclopropyl, and R³ is unsubstituted or substituted phenyl, cyclopropyl, O-cyclopropyl, cyclobutyl, O-cyclobutyl, tetrahydrofuranyl or tetrahydropyranyl.

A subembodiment of this aspect of formula Ic is realized when Y is N and Z is CH or Y is CH and Z is N, A is unsubstituted or substituted phenyl, R¹ and R² combine to form a compound selected from the group consisting of cyclopropyl, cyclobutyl, oxetanyl, and oxiranyl, and R³ is unsubstituted or substituted phenyl, cyclopropyl, O-cyclopropyl, cyclobutyl, O-cyclobutyl, tetrahydrofuranyl or tetrahydropyranyl.

Another embodiment of the compound of formula (I), or a pharmaceutically acceptable salt thereof, is the compound of formula (Id):

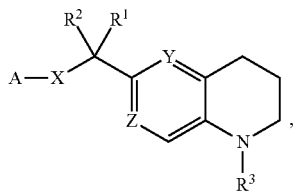

(Id)

wherein,

A, X, R¹, R², R³, Y and Z are as described herein.

A subembodiment of formula Id is realized when Y is N and Z is CH. Another subembodiment of formula Id is realized when Y is CH and Z is N.

Another subembodiment of formula Id is realized when both Y and Z are CH.

Still another embodiment of formula Id is realized when Y and Z, respectively, are selected from the group consisting of Y═N and Z═CH; Y═CH and Z═N; and Y═Z═CH; A is unsubstituted or substituted phenyl or pyridinyl, X is —NHC(O)— or —C(O)NH—, R¹ and R² are independently selected from the group consisting of hydrogen, $C_{1-6}$ alkyl, $C_{3-6}$ cycloalkyl, and $C_{2-6}$ alkenyl, one of R¹ and R² is hydrogen and the other is $C_{1-6}$ alkyl, $C_{3-6}$ cycloalkyl, or both of R¹ and R² are hydrogen or CH₃, or R¹ and R² combine to form a compound selected from the group consisting of cyclopropyl, cyclobutyl, oxetanyl, and oxiranyl, and R³ is selected from a group consisting of unsubstituted or substituted $C_{1-6}$ alkyl, $OC_{1-6}$ alkyl, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl. A subembodiment of formula Id is realized when R³ is selected from a group consisting of unsubstituted or substituted pyridinyl, pyrimidinyl, azetidinyl, oxiranyl, oxadiazolyl, pyrazolyl, tetrahydropyranyl, and tetrahydrofuranyl. Another subembodiment of the invention of formula Id is realized when R³ is unsubstituted or substituted pyridinyl or pyrimidinyl. Another subembodiment of formula Id is realized when R³ is unsubstituted or substituted phenyl.

A subembodiment of this aspect of formula Id is realized when Y═N and Z═CH; Y═CH and Z═N, or Y═Z═CH, A is unsubstituted or substituted phenyl, R¹ and R² are both hydrogen, or CH₃, or one of R¹ and R² is hydrogen and the other is selected from CH₃, CH₂CH₃, CH₂CH═CH₂, and unsubstituted to substituted cyclopropyl, and R³ is unsubstituted or substituted phenyl, cyclopropyl, O-cyclopropyl, cyclobutyl, O-cyclobutyl, tetrahydropyranyl, tetrahydrofuranyl, pyrazolyl, azetidinyl, pyrimidinyl, or oxiranyl. Another subembodiment of formula Id is realized when R³ is unsubstituted or substituted pyridinyl or pyrimidinyl. Another subembodiment of formula Id is realized when R³ is unsubstituted or substituted phenyl.

A subembodiment of this aspect of formula Id is realized when Y is N and Z is CH; Y is CH and Z is N, or Y═Z═CH, A is unsubstituted or substituted phenyl, R¹ and R² combine to form a compound selected from the group consisting of cyclopropyl, cyclobutyl, oxetanyl, and oxiranyl, and R³ is unsubstituted or substituted phenyl, cyclopropyl, O-cyclopropyl, cyclobutyl, O-cyclobutyl, tetrahydropyranyl, tetrahydrofuranyl, pyrazolyl, azetidinyl, pyrimidinyl, or oxiranyl.

Another subembodiment of formula Id is realized when R³ is unsubstituted or substituted pyridinyl or pyrimidinyl. Another subembodiment of formula Id is realized when R³ is unsubstituted or substituted phenyl.

Another embodiment of the invention of the compound of formula (I), or a pharmaceutically acceptable salt thereof, is the compound of formula (e):

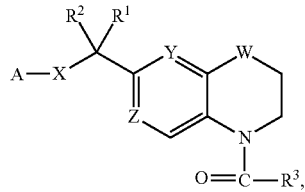

(Ie)

wherein,

A, X, $R^1$, $R^2$, $R^3$, Y and Z are as described herein and W is O or is absent.

A subembodiment of formula Ie is realized when Y=N and Z=CH; or Y=CH and Z=N and W is O or is absent. Another subembodiment of formula Ie is realized when both Y and Z are CH and W is O or is absent. Still another subembodiment of formula Ie is realized when A is unsubstituted or substituted phenyl or pyridinyl, X is —NHC(O)— or —C(O)NH—, $R^1$ and $R^2$ are independently selected from the group consisting of hydrogen, $C_{1-6}$ alkyl, $C_{3-6}$ cycloalkyl, and $C_{2-6}$alkenyl, or one of $R^1$ and $R^2$ is hydrogen and the other is $C_{1-6}$ alkyl, $C_{3-6}$ cycloalkyl, or both of $R^1$ and $R^2$ are hydrogen or $CH_3$, or $R^1$ and $R^2$ combine to form a compound selected from the group consisting of cyclopropyl, cyclobutyl, oxetanyl and oxiranyl, and $R^3$ is selected from a group consisting of $N(R)_2$, unsubstituted or substituted $C_{1-6}$ alkyl, $OC_{1-6}$ alkyl, cyclopropyl, O-cyclopropyl, cyclobutyl, O-cyclobutyl, phenyl, pyridinyl, pyrimidinyl, azetidinyl, oxiranyl, oxadiazolyl, pyrazolyl, tetrahydropyranyl, and tetrahydrofuranyl.

A subembodiment of this aspect of formula Ie is realized when both Y and Z are CH, or Y=N and Z=CH; or Y=CH and Z=N, W is O or is absent, A is unsubstituted or substituted phenyl, $R^1$ and $R^2$ are both hydrogen, or $CH_3$, or one of $R^1$ and $R^2$ is hydrogen and the other is selected from $CH_3$, $CH_2CH_3$, $CH_2CH=CH_2$, and unsubstituted to substituted cyclopropyl, and $R^3$ is $N(R)_2$, unsubstituted or substituted phenyl, cyclopropyl, O-cyclopropyl, cyclobutyl, O-cyclobutyl, tetrahydropyranyl, tetrahydrofuranyl, pyrazolyl, azetidinyl, or oxiranyl.

A subembodiment of this aspect of formula Ie is realized when both Y and Z are CH, or Y=N and Z=CH; or Y=CH and Z=N, W is O or is absent, A is unsubstituted or substituted phenyl, $R^1$ and $R^2$ combine to form a compound selected from the group consisting of cyclopropyl, cyclobutyl, oxetanyl and oxiranyl, and $R^3$ is $N(R)_2$, unsubstituted or substituted phenyl, cyclopropyl, O-cyclopropyl, cyclobutyl, O-cyclobutyl, tetrahydropyranyl, tetrahydrofuranyl, pyrazolyl, azetidinyl, or oxiranyl.

In another embodiment of the invention, a compound disclosed herein is selected from the group consisting of the compound exemplified in Examples 1 to 430, or a pharmaceutically acceptable salt thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Carbocyclyl" refers to a nonaromatic (i.e., saturated or partially unsaturated) monocyclic carbocyclic radical or a fused bicyclic, bridged bicyclic, or spirocyclic carbocyclic radical having the specified ring carbon atoms. For example, "$C_{3-8}$ carbocyclyl" refers to a nonaromatic 3 to 8-membered monocyclic carbocyclic radical or a nonaromatic 6 to 8-membered fused bicyclic, bridged bicyclic, or spirocyclic carbocyclic radical. The carbocycle may be attached by any atom of the cycle which results in the creation of a stable structure. Non-limiting examples of 3 to 8-membered monocyclic carbocycles include cyclopropyl, cyclobutyl, cyclopentyl, cyclopentenyl, cyclohexyl, cyclohexenyl, cycloheptanyl and cycloheptenyl. Non-limiting examples of 6 to 8-membered fused bicyclic carbocyclic radicals include, but are not limited to, bicyclo[3.3.0]octane. Non-limiting examples of 5 to 8-membered bridged bicyclic carbocyclic radicals include, but are not limited to, bicyclo[1.1.1]pentanyl, bicyclo[2.2.2]heptanyl, bicyclo[2.2.2]octanyl, and bicyclo[3.2.1]octanyl. Non-limiting examples of 6 to 8-membered spirocyclic carbocyclic radicals include, but are not limited to, spiro[3,3]heptanyl and spiro[3,4]octanyl.

"Cycloalkyl" refers to a monocyclic saturated carbocyclic ring having the specified number of ring carbon atoms. For example, $C_{3-8}$ cycloalkyl refers to a cycloalkyl group as defined herein having 3 to 8 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, the heterocyclyl is a 4-6 membered monocyclic saturated heterocycyl containing 1-3 hetero atoms independently selected from O, S and N.

In one embodiment, the heterocyclyl is a 4-6 membered monocyclic aromatic heterocycyl containing 1-3 hetero atoms independently selected from O, S and N.

In one embodiment, the heterocyclyl is a 9-12 membered bicyclic heterocycyl containing 1-4 hetero atoms independently selected from O, S and N.

In one embodiment, the heterocyclyl is a 4-6 membered monocyclic saturated heterocycyl selected from azetidinyl, morpholinyl, oxanyl, oxetanyl, oxolanyl, pyrrolodinyl, and tetrahydrofuranyl.

In one embodiment, the heterocyclyl is a 4-6 membered monocyclic aromatic heterocycyl selected from oxadiazolyl, oxazolyl, pyrazolyl, pyrazinyl, pyridinyl, pyrimidinyl, thiazolyl, and triazolyl.

In one embodiment, the heterocyclyl is a 9-12 membered bicyclic heterocycyl selected from 5,6-dihydro-4H-pyrrolo[1,2-b]pyrazolyl, quinazolinyl, quinolinyl, pyrazolo[1,5-a]pyrimidinyl, tetrahydroquinolinyl, and [1,2,4]triazolo[1,5-a]pyrimidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s).

Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)—, (S)—or (R,S)— configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)— configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{13}$C, $^{18}$F, $^{15}$O and $^{13}$N, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or overtime as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chloro-deoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following synthetic schemes and examples are intended to be illustrative only and not limiting in any way. Abbreviations used are those conventional in the art unless defined as the following.

ACN acetonitrile
aq. aqueous
Boc tert-butyloxycarbonyl
Boc$_2$O di-tert-butyl dicarbonate
Calc'd calculated
Celite diatomaceous earth used as a filtration medium
Cu(I)I copper(I) iodide
CV column volume
° C. degree celcius
DAST (dimethylamino)sulfur trifluoride
DCM dichloromethane
DIEA N,N-diisopropylethylamine
DIPEA N,N-diisopropylethylamine
DMA dimethylamine
DMF N,N-dimethylformamide
DMSO dimethylsulfoxide
dppf or DPPF 1,1'-bis(diphenylphosphino)ferrocene
dtbpf 1,1'-bis(di-t-butylphosphino)ferrocene
EDC N-(3-dimethylaminopropyl)-N'-ethylcarbodiimide hydrochloride
EDCI 1-ethyl-3-(3-dimethylaminopropyl)carbodiimide
EI electron ionization
EMEM Eagle's minimal essential medium
eq. equivalent
Et ethyl
Et$_2$O diethyl ether
Et$_3$N triethylamine
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HCl hydrochloric acid
HPLC high pressure liquid chromatography
K$_3$PO$_4$ potassium phosphate tribasic
kg kilogram
KHMDS potassium bis(trimethylsilyl)amide
KO$^t$Bu potassium tert-butoxide L liter
LC liquid chromatography
LCMS liquid chromatography and mass spectrometry
LDA lithium diisopropylamide
LiHMDS lithium bis(trimethylsilyl)amide
LiOH lithium hydroxide
M molar
Me methyl
MeOH methanol
MeMgBr methyl magnesium bromide
mg miligram
$MgSO_4$ magnesium sulfate
mmol milimole
MS mass spectrometry
MTBE methyl tert-butyl ether
min minutes
mL milliliter(s)
m/z mass to charge ratio
nm nanometer
nM nanomolar
N normal
$N_2$ nitrogen
$Na_2SO_4$ sodium sulfate
NaH sodium hydride
$NaHCO_3$ sodium bicarbonate
NaHMDS sodium bis(trimethylsilyl)amide
$NaN_3$ sodium azide
NaOH sodium Hydroxide
$NH_4Cl$ ammonium chloride
OTBDPS tert-butyldiphenylsilyl
OTf trifluoromethanesulfonate
$Pd_2(dba)_3$ tris(dibenzylideneacetone)dipalladium(0)
$PdCl_2(dppf)$ 1,1'-bis(diphenylphosphino)ferrocene]palladium(II) dichloride
$Pd(dppf)_2Cl_2$ 1,1'-bis(diphenylphosphino)ferrocene]dichloropalladium(II)
$PdCl_2(dtbpf)$ 1,1'-bis(di-tert-butylphosphino)ferrocene] dichloropalladium(II)
PE petroleum ether
PG protecting group
PMP P-methoxyphenyl
$POCl_3$ phosphorus oxychloride
PS polystyrene
RPMI Roswell Park Memorial Institute
RT, rt or r.t. room temperature
sat. saturated
$T_3P$ propylphosphonic anhydride solution
TBAF tetrabutylammonium fluoride
TBAT tetrabutylammonium difluorotriphenylsilicate
TBS tert-butyldimethylsilyl ether
TBSCl tert-butyldimethylsilyl chloride
t-BuOH tert-butanol
t-BuONO tert-butyl nitrite
TEA triethyl amine
TEMPO (2,2,6,6-tetramethylpiperidin-1-yl)oxyl
TFA trifluoroacetic acid
THF tetrahydrofuran
TLC thin layer chromatography
TMPMgCl 2,2,6,6-tetramethylpiperidinylmagnesium chloride
$TMSCF_3$ trifluoromethyltrimethylsilane
TBSCl tert-butyldimethylsilyl chloride
$TMSCHN_2$ or $TMSCH_2N_2$ trimethylsilyldiazomethane
TMSCN trimethylsilyl cyanide
TosCl toluenesulfonyl chloride
uL microliter(s)

XPhos Pd G2 chloro(2-dicyclohexylphosphino-2',4',6'-triisopropyl-1,1'-biphenyl)[2-(2'-amino-1,1'-biphenyl)]palladium(II)
XPhos Pd G3 2-Dicyclohexylphosphino-2',4',6'-triisopropyl-1,1'-biphenyl)[2-(2'-amino-1,1'-biphenyl)]palladium(II) methanesulfonate The following examples are intended to be illustrative only and not limiting in any way. Abbreviations used are those conventional in the art or the following.

EXAMPLES

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

Example 1: 4-chloro-N-((1-(3-methylbutanoyl)-1,2,3,4-tetrahydroquinolin-6-yl)methyl)benzamide

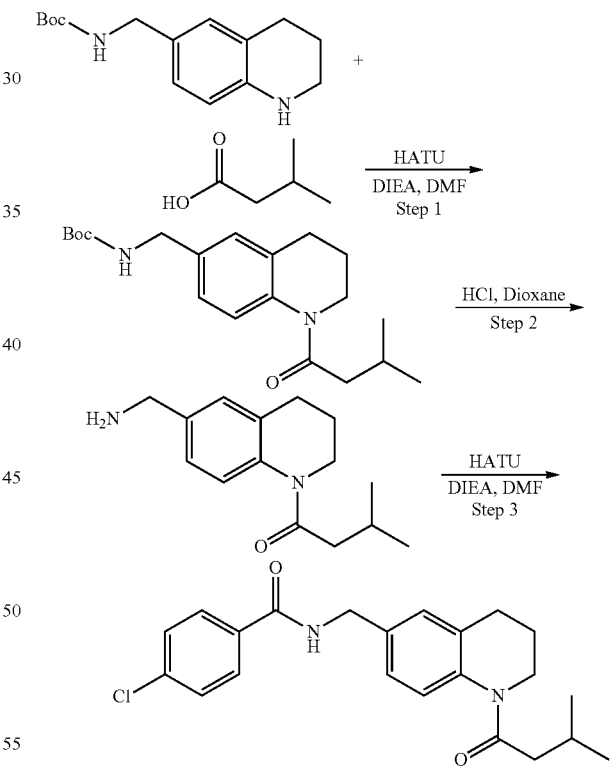

Step 1. tert-butyl ((1-(3-methylbutanoyl)-1,2,3,4-tetrahydroquinolin-6-yl)methyl)carbamate To a mixture of tert-butyl ((1,2,3,4-tetrahydroquinolin-6-yl)methyl)carbamate (0.5 g, 1.906 mmol), 3-methylbutanoic acid (0.292 g, 2.86 mmol) and DIEA (0.333 ml, 1.906 mmol) in DMF (5 ml) at 0° C. was added HATU (1.087 g, 2.86 mmol). The mixture was stirred for 0.5 h and LCMS showed the completion of reaction. Water (10 ml) was added, followed by EtOAc (20 ml). The organic was collected, washed with water (3×10 ml) and concentrated. The residue was purified by flash chromatography (5-50% EtOAc/Hex) which afforded the title compound as a solid. LCMS m/z (M+H) calc'd: 347.2; found: 347.2

Step 2. 1-(6-(aminomethyl)-3,4-dihydroquinolin-1 (2H)-yl)-3-methylbutan-1-one To tert-butyl ((1-(3-methylbutanoyl)-1,2,3,4-tetrahydroquinolin-6-yl)methyl)carbamate, was added hydrogen chloride in dioxane (2338 μl, 4N, 9.35 mmol). The mixture was stirred at RT for 1 h and a precipitate was formed during the reaction. LCMS showed the reaction went to completion. Ethyl ether (30 ml) was added, a solid was collected by filtration, and the solid was washed with ethyl ether (2×30 ml). The product (solid) was used directly in the next step. LCMS m/z (M+H) calc'd: 247.2; found: 247.1

Step 3. 4-chloro-N-((1-(3-methylbutanoyl)-1,2,3,4-tetrahydroquinolin-6-yl)methyl)benzamide To the mixture of 1-(6-(aminomethyl)-3,4-dihydroquinolin-1(2H)-yl)-3-methylbutan-1-one hydrochloride (50 mg, 0.177 mmol), 3-chlorobenzoic acid (33.2 mg, 0.212 mmol) and DIEA (0.093 ml, 0.530 mmol) in DMF (1 mL) was added HATU (101 mg, 0.265 mmol) at 0° C. The reaction mixture was stirred for 2 h and LCMS showed the completion of reaction. Ethyl acetate (10 ml) and water (5 ml) were added and the organic was collected, washed with water (3×5 ml) and dried over sodium sulfate. The mixture was concentrated and the residue purified using flash column to give the desired product as a solid. LCMS m/z (M+H) calc'd: 385.2; found (M+H): 385.3. $^1$H NMR (500 MHz, DMSO-$d_6$): δ 9.31 (s, 1H); 8.14 (s, 1H), 8.02 (m, 1H), 7.92 (m, 1H), 7.45 (m, 2H), 7.15 (m, 2H), 4.45 (m, 2H), 3.66 (m, 2H), 2.65 (m, 2H), 2.35 (m, 2H), 2.10 (m, 3H), 0.94 (d, 6H)

The compounds in the following table were prepared in a similar manner as Example 1:

| Ex. # | Structure | Chemical Names | Mass [M + H$^+$] | Hela IC$_{50}$, nM |
|---|---|---|---|---|
| 1 | 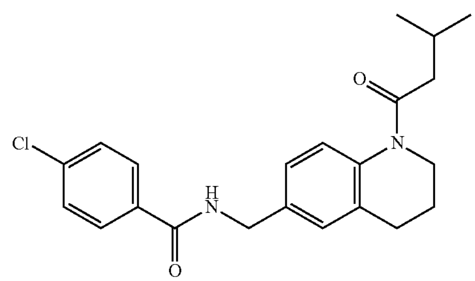 [SMILES: CC(C)CC(=O)N1CCCc2cc(CNC(=O)c3ccc(Cl)cc3)ccc21] | 4-chloro-N-{[1-(3-methylbutanoyl)-1,2,3,4-tetrahydroquinolin-6-yl]methyl}benzamide | Calc'd 385 found 385 | 15.8 |
| 2 | 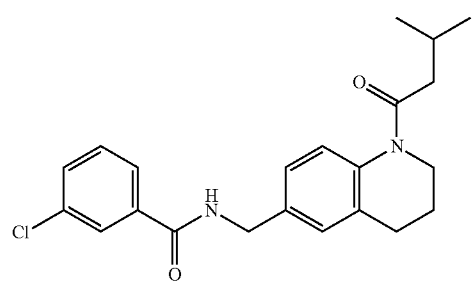 [SMILES: CC(C)CC(=O)N1CCCc2cc(CNC(=O)c3cccc(Cl)c3)ccc21] | 3-chloro-N-{[1-(3-methylbutanoyl)-1,2,3,4-tetrahydroquinolin-6-yl]methyl}benzamide | Calc'd 385 found 385 | 103.1 |
| 3 | 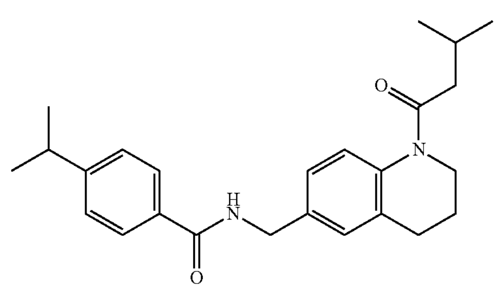 [SMILES: CC(C)CC(=O)N1CCCc2cc(CNC(=O)c3ccc(C(C)C)cc3)ccc21] | N-{[1-(3-methylbutanoyl)-1,2,3,4-tetrahydroquinolin-6-yl]methyl}-4-(propan-2-yl)benzamide | Calc'd 393 found 393 | 209.4 |

| Ex. # | Structure | Chemical Names | Mass [M + H⁺] | Hela IC$_{50}$, nM |
|---|---|---|---|---|
| 4 | 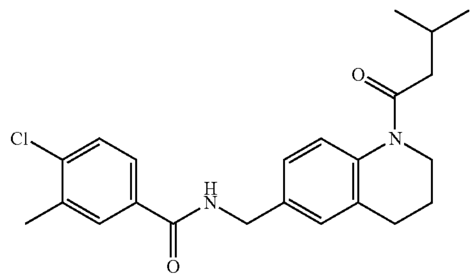 [SMILES: Cc1cc(C(=O)NCc2ccc3c(c2)CCCN3C(=O)CC(C)C)ccc1Cl] | 4-chloro-3-methyl-N-{[1-(3-methylbutanoyl)-1,2,3,4-tetrahydroquinolin-6-yl]methyl}benzamide | Calc'd 399 found 399 | 298.0 |
| 5 | 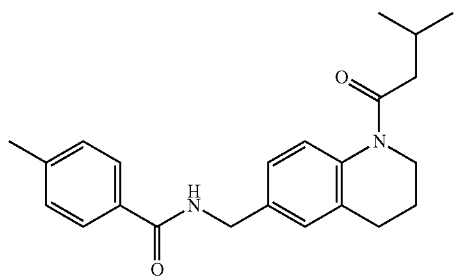 [SMILES: Cc1ccc(C(=O)NCc2ccc3c(c2)CCCN3C(=O)CC(C)C)cc1] | 4-methyl-N-{[1-(3-methylbutanoyl)-1,2,3,4-tetrahydroquinolin-6-yl]methyl}benzamide | Calc'd 365 found 365 | 77.9 |
| 6 | 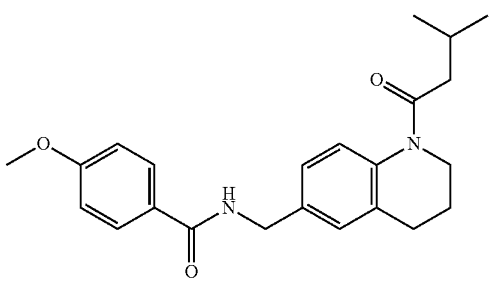 [SMILES: COc1ccc(C(=O)NCc2ccc3c(c2)CCCN3C(=O)CC(C)C)cc1] | 4-methoxy-N-{[1-(3-methylbutanoyl)-1,2,3,4-tetrahydroquinolin-6-yl]methyl}benzamide | Calc'd 381 found 381 | 56.4 |
| 7 | 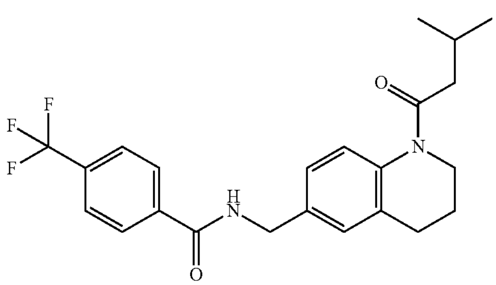 [SMILES: CC(C)CC(=O)N1CCCc2cc(CNC(=O)c3ccc(C(F)(F)F)cc3)ccc21] | N-{[1-(3-methylbutanoyl)-1,2,3,4-tetrahydroquinolin-6-yl]methyl}-4-(trifluoromethyl)benzamide | Calc'd 419 found 419 | 42.5 |
| 8 | 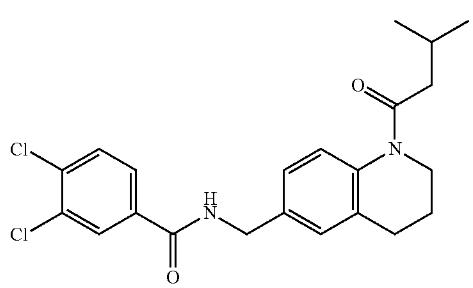 [SMILES: CC(C)CC(=O)N1CCCc2cc(CNC(=O)c3ccc(Cl)c(Cl)c3)ccc21] | 3,4-dichloro-N-{[1-(3-methylbutanoyl)-1,2,3,4-tetrahydroquinolin-6-yl]methyl}benzamide | Calc'd 419 found 419 | 275.8 |

-continued

| Ex. # | Structure | Chemical Names | Mass [M + H⁺] | Hela IC$_{50}$, nM |
|---|---|---|---|---|
| 9 | 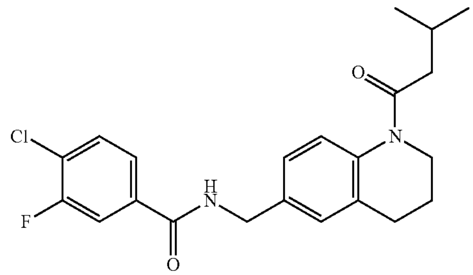 [SMILES: CC(C)CC(=O)N1CCCc2cc(CNC(=O)c3ccc(Cl)c(F)c3)ccc21] | 4-chloro-3-fluoro-N-{[1-(3-methylbutanoyl)-1,2,3,4-tetrahydroquinolin-6-yl]methyl}benzamide | Calc'd 403 found 403 | 49.3 |
| 10 | 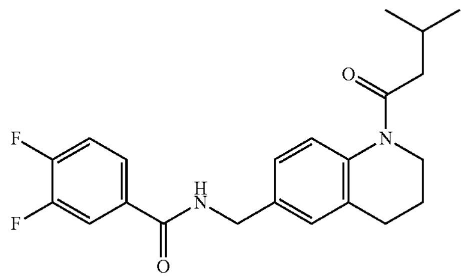 [SMILES: CC(C)CC(=O)N1CCCc2cc(CNC(=O)c3ccc(F)c(F)c3)ccc21] | 3,4-difluoro-N-{[1-(3-methylbutanoyl)-1,2,3,4-tetrahydroquinolin-6-yl]methyl}benzamide | Calc'd 387 found 387 | 161.2 |
| 11 | 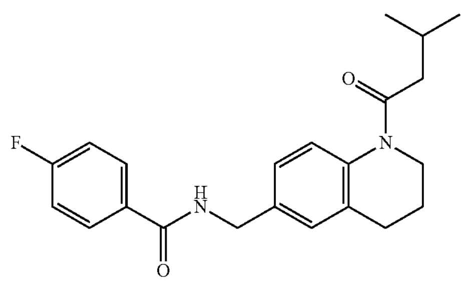 [SMILES: CC(C)CC(=O)N1CCCc2cc(CNC(=O)c3ccc(F)cc3)ccc21] | 4-fluoro-N-{[1-(3-methylbutanoyl)-1,2,3,4-tetrahydroquinolin-6-yl]methyl}benzamide | Calc'd 369, found 369.1 | 41.4 |
| 12 | 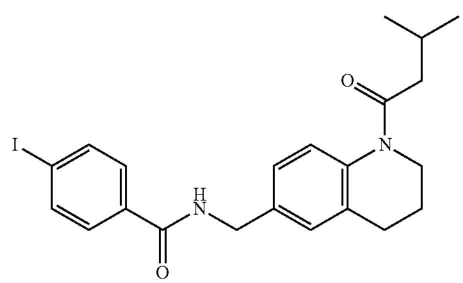 [SMILES: CC(C)CC(=O)N1CCCc2cc(CNC(=O)c3ccc(I)cc3)ccc21] | 4-iodo-N-{[1-(3-methylbutanoyl)-1,2,3,4-tetrahydroquinolin-6-yl]methyl}benzamide | Calc'd 477 found 477.1 | 21.1 |
| 13 | 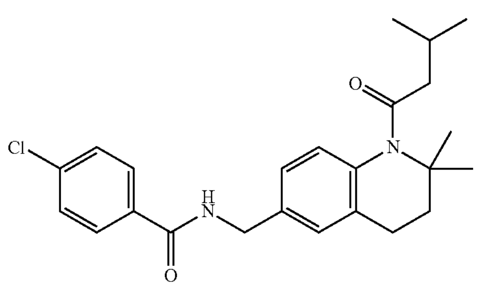 [SMILES: CC(C)CC(=O)N1c2ccc(CNC(=O)c3ccc(Cl)cc3)cc2CCC1(C)C] | 4-chloro-N-{[2,2-dimethyl-1-(3-methylbutanoyl)-1,2,3,4-tetrahydroquinolin-6-yl]methyl}benzamide | Calc'd 413 found 413 | 98.6 |

Example 14. 4-chloro-N-{[1-(3-chlorobenzene-1-carbonyl)-1,2,3,4-tetrahydroquinolin-6-yl]methyl}benzamide

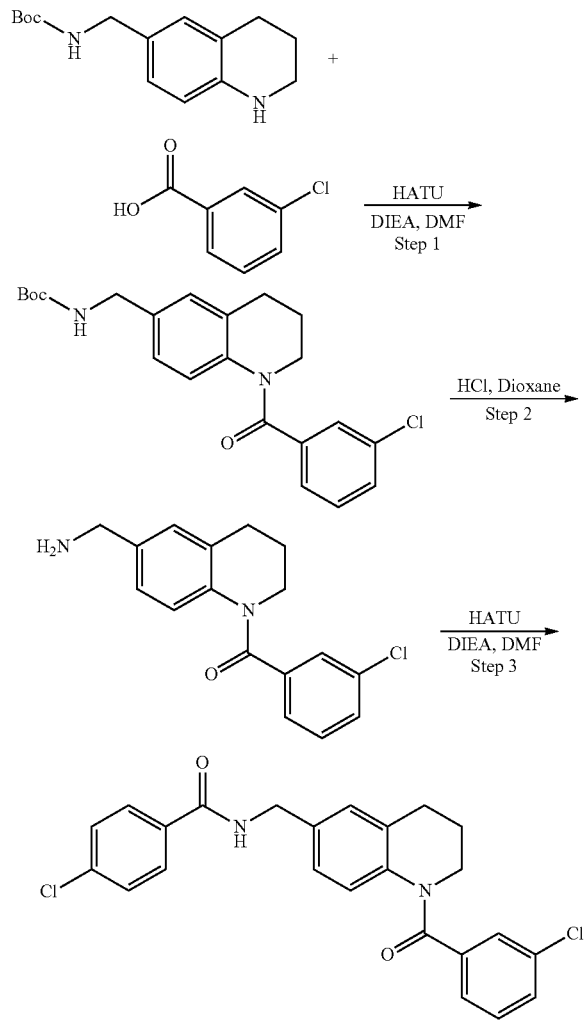

Step 1. tert-butyl ((1-(3-chlorobenzoyl)-1,2,3,4-tetrahydroquinolin-6-yl)methyl)carbamate To a mixture of tert-butyl ((1,2,3,4-tetrahydroquinolin-6-yl)methyl)carbamate (0.5 g, 1.906 mmol), 3-chlorobenzoic acid (0.446 g, 2.86 mmol) and DIEA (0.333 ml, 1.906 mmol) in DMF (5 ml) at 0° C. was added HATU (1.087 g, 2.86 mmol). The mixture was stirred for 0.5 h and LCMS showed the completion of the reaction. Water (10 ml) was added, followed by EtOAc (20 ml). The organic was collected, washed with water (3×10 ml) and concentrated. Purification by flash chromatography (5-50% EtOAc/Hex) afforded the title compound as a solid. LCMS m/z (M+H$^+$) calc'd: 40.1; found: 401

Step 2. (6-(aminomethyl)-3,4-dihydroquinolin-1(2H)-yl)(3-chlorophenyl)methanone To a 50 ml round bottom flask containing tert-butyl ((1-(3-chlorobenzoyl)-1,2,3,4-tetrahydroquinolin-6-yl)methyl)carbamate, was added hydrogen chloride in dioxane (2338 μl, 4 N, 9.35 mmol). The reaction mixture was stirred at RT for 1 h and a precipitate was formed. LCMS showed the completion of the reaction. Ethyl ether (30 ml) was added, a solid was collected by filtration, and the solid was washed with ethyl ether (2×30 ml). The product (solid) was used in the next step without further purification. LCMS m/z (M+H$^+$) calc'd: 301.1; found: 301

Step 3. 4-chloro-N-((1-(3-chlorobenzoyl)-1,2,3,4-tetrahydroquinolin-6-yl)methyl)benzamide To a reaction mixture of (6-(aminomethyl)-3,4-dihydroquinolin-1(2H)-yl)(3-chlorophenyl)methanone (88 mg, 0.177 mmol), 3-chlorobenzoic acid (33.2 mg, 0.212 mmol), and DIEA (0.093 ml, 0.530 mmol) in DMF (1 mL) was added HATU (101 mg, 0.265 mmol) at 0° C. The reaction mixture was stirred for 2 h and LCMS showed the completion of the reaction. Ethyl acetate (10 ml) and water (5 ml) were added, the organic was collected, washed with water (3×5 ml), and dried over sodium sulfate. The mixture was concentrated and the residue was purified using flash column (5-50% EtOAc/Hex) to give the desired product as a solid. LCMS m/z (M+H$^+$) calc'd: 385.2; found: 385.3. $^1$H NMR (500 MHz, DMSO-d$_6$): δ 9.31 (s, 1H); 8.14 (s, 1H), 8.02 (m, 1H), 7.92 (m, 1H), 7.87 (s, 1H), 7.83 (m, 1H), 7.69 (m, 1H), 7.58 (m, 1H), 7.45 (m, 2H), 7.15 (m, 2H), 4.45 (m, 2H), 3.66 (2H, m), 2.65 (2H, m), 2.35 (2H, m).

| Ex. # | Structure | Chemical Names | Mass [M + H$^+$] | Hela IC$_{50}$, nM |
|---|---|---|---|---|
| 14 | 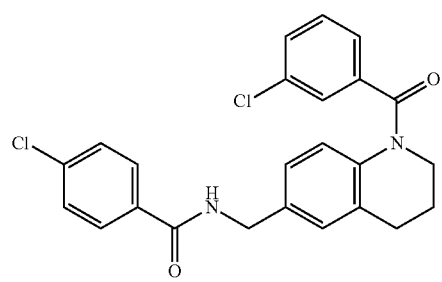 [SMILES: O=C(NCc1ccc2c(c1)CCCN2C(=O)c1cccc(Cl)c1)c1ccc(Cl)cc1] | 4-chloro-N-((1-(3-chlorobenzoyl)-1,2,3,4-tetrahydroquinolin-6-yl)methyl)benzamide | Calc'd 439, found 439 | 4.8 |

-continued

| Ex. # | Structure | Chemical Names | Mass [M + H⁺] | Hela IC$_{50}$, nM |
|---|---|---|---|---|
| 15 | 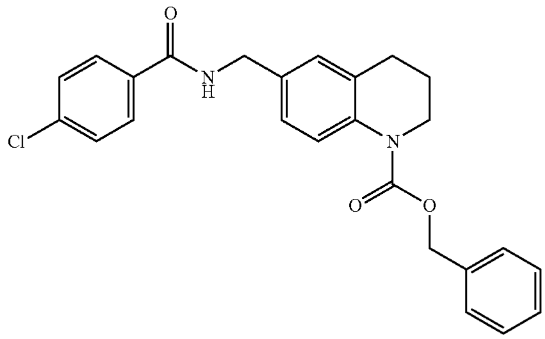 [SMILES: O=C(NCc1ccc2c(c1)CCCN2C(=O)OCc1ccccc1)c1ccc(Cl)cc1] | benzyl 6-((4-chlorobenzamido)methyl)-3,4-dihydroquinoline-1(2H)-carboxylate | Calc'd 435, found 435 | 36.9 |
| 16 | 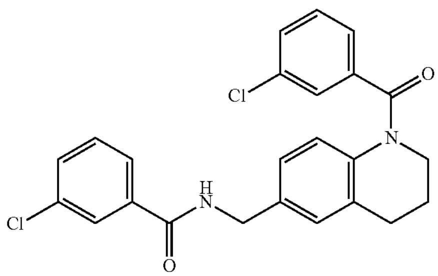 [SMILES: O=C(NCc1ccc2c(c1)CCCN2C(=O)c1cccc(Cl)c1)c1cccc(Cl)c1] | 3-chloro-N-((1-(3-chlorobenzoyl)-1,2,3,4-tetrahydroquinolin-6-yl)methyl)benzamide | Calc'd 439, found 439 | 118.4 |
| 17 | 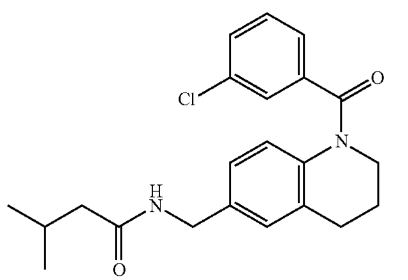 [SMILES: CC(C)CC(=O)NCc1ccc2c(c1)CCCN2C(=O)c1cccc(Cl)c1] | N-{[1-(3-chlorobenzene-1-carbonyl)-1,2,3,4-tetrahydroquinolin-6-yl]methyl}-3-methylbutanamide | Calc'd 385, found 385 | 701.6 |
| 18 | 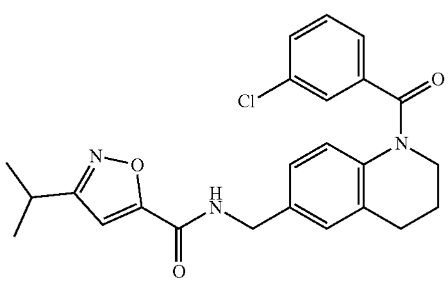 [SMILES: CC(C)c1cc(C(=O)NCc2ccc3c(c2)CCCN3C(=O)c2cccc(Cl)c2)on1] | N-{[1-(3-chlorobenzene-1-carbonyl)-1,2,3,4-tetrahydroquinolin-6-yl]methyl}-3-(propan-2-yl)-1,2-oxazole-5-carboxamide | Calc'd 438, found 438 | 185.6 |
| 19 | 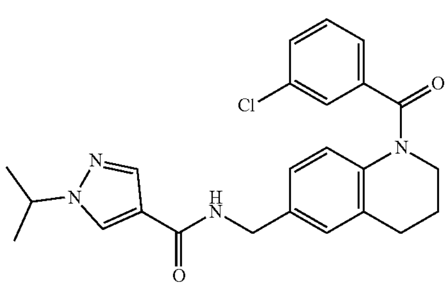 [SMILES: CC(C)n1cc(C(=O)NCc2ccc3c(c2)CCCN3C(=O)c2cccc(Cl)c2)cn1] | N-{[1-(3-chlorobenzene-1-carbonyl)-1,2,3,4-tetrahydroquinolin-6-yl]methyl}-1-(propan-2-yl)-1H-pyrazole-4-carboxamide | Calc'd 437, found 437 | 434.8 |

-continued

| Ex. # | Structure | Chemical Names | Mass [M + H⁺] | Hela IC$_{50}$, nM |
|---|---|---|---|---|
| 20 | 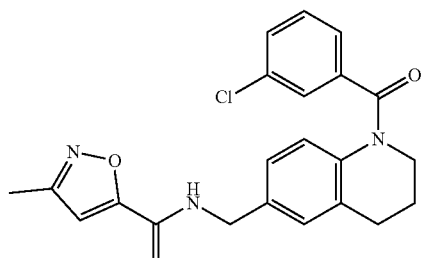 | N-{[1-(3-chlorobenzene-1-carbonyl)-1,2,3,4-tetrahydroquinolin-6-yl]methyl}-3-methyl-1,2-oxazole-5-carboxamide | Calc'd 410, found 410 | 59.6 |
| 21 | 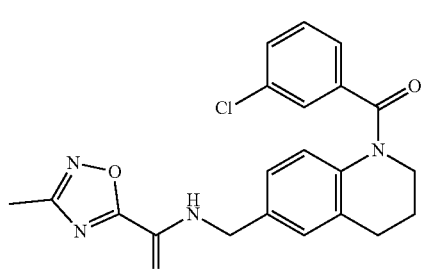 | N-{[1-(3-chlorobenzene-1-carbonyl)-1,2,3,4-tetrahydroquinolin-6-yl]methyl}-3-methyl-1,2,4-oxadiazole-5-carboxamide | Calc'd 411, found 411 | 40.5 |
| 22 | 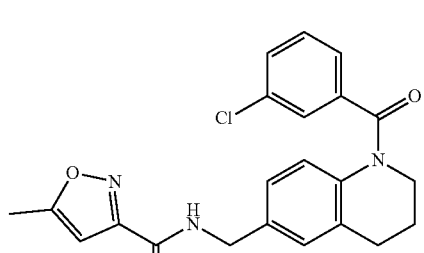 | N-{[1-(3-chlorobenzene-1-carbonyl)-1,2,3,4-tetrahydroquinolin-6-yl]methyl}-5-methyl-1,2-oxazole-3-carboxamide | Calc'd 410, found 410 | 45.0 |
| 23 | 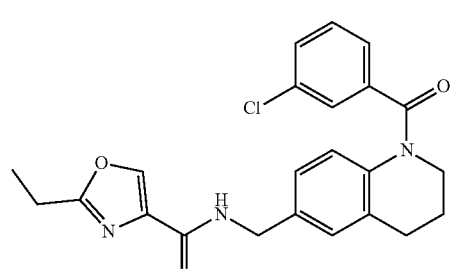 | N-{[1-(3-chlorobenzene-1-carbonyl)-1,2,3,4-tetrahydroquinolin-6-yl]methyl}-2-ethyl-1,3-oxazole-4-carboxamide | Calc'd 424, found 424 | 77.6 |
| 24 | 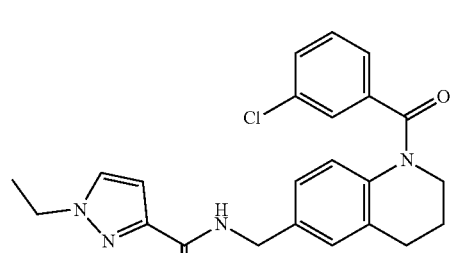 | N-{[1-(3-chlorobenzene-1-carbonyl)-1,2,3,4-tetrahydroquinolin-6-yl]methyl}-1-methyl-1H-pyrazole-3-carboxamide | Calc'd 423, found 423 | 99.8 |

| Ex. # | Structure | Chemical Names | Mass [M + H⁺] | Hela IC₅₀, nM |
|---|---|---|---|---|
| 25 | 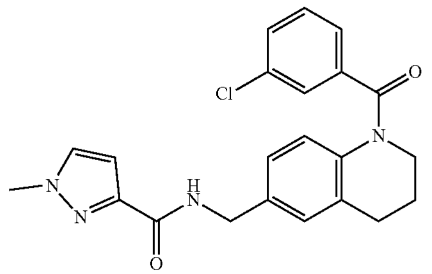 [SMILES: Cn1ccc(C(=O)NCc2ccc3c(c2)CCCN3C(=O)c2cccc(Cl)c2)n1] | N-{[1-(3-chlorobenzene-1-carbonyl)-1,2,3,4-tetrahydroquinolin-6-yl]methyl}-1-methyl-1H-pyrazole-3-carboxamide | Calc'd 409, found 409 | 136.4 |

Example 26. 4-chloro-N-(1-(1-(3-methylbutanoyl)-1,2,3,4-tetrahydroquinolin-6-yl)ethyl)benzamide

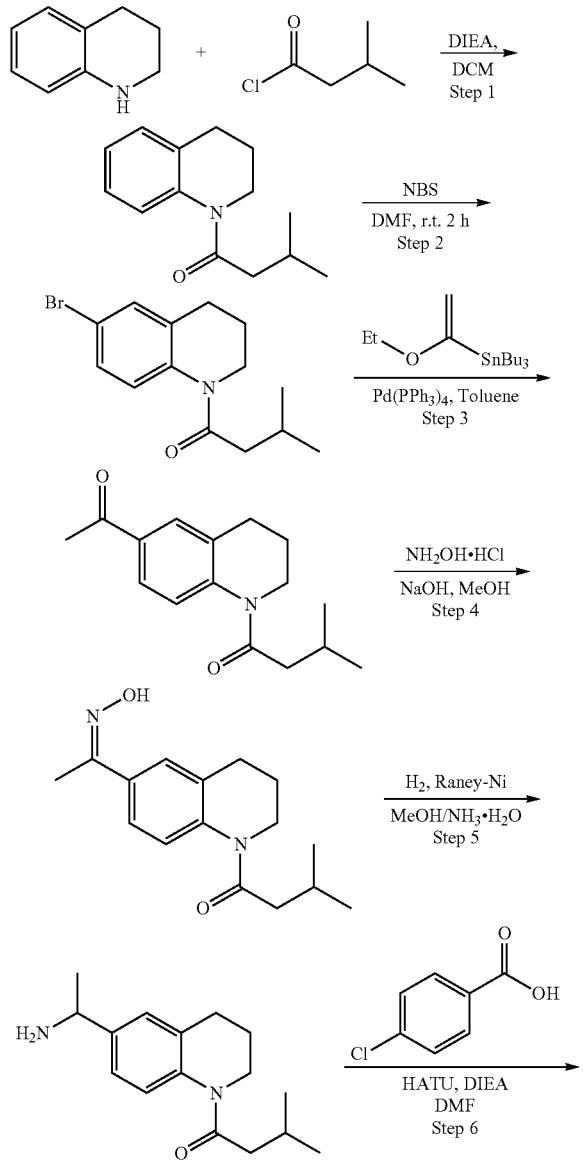

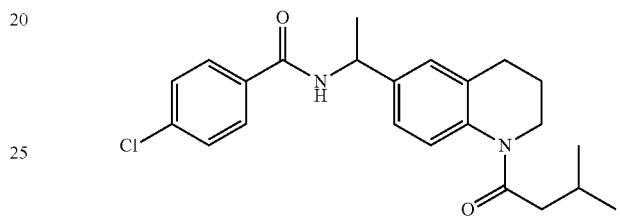

Step 1. 1-(3,4-dihydroquinolin-1(2H)-yl)-3-methylbutan-1-one

To a stirred solution of 1,2,3,4-tetrahydroquinoline (250 mg, 1.877 mmol) and Et₃N (1.1 mL, 7.94 mmol) in DCM (4 mL) was added 3-methylbutanoyl chloride (339 mg, 2.82 mmol) dropwise at 0° C. under nitrogen atmosphere. After the addition was finished, the reaction was stirred at 20° C. The reaction was monitored by LCMS, after stirring for 1 h, the reaction was quenched with MeOH (2 mL). The solvent was removed by vacuum and the residue was re-dissolved in DCM (20 mL) and washed with brine. The organic layer was collected and concentrated in vacuo to give the crude title compound as an oil which was used in the next step without further purification. LCMS m/z (M+H⁺) calc'd 218.1, found 218.1

Step 2. 1-(6-bromo-3,4-dihydroquinolin-1(2H)-yl)-3-methylbutan-1-one

To a solution of 1-(3,4-dihydroquinolin-1(2H)-yl)-3-methylbutan-1-one (341 mg, 1.412 mmol) in DMF (5 mL) was added NBS (302 mg, 1.695 mmol) portion wise, the resulting mixture was stirred at 20° C. The reaction was monitored by LCMS and after stirring for 3 h, the reaction was finished. Then the reaction mixture was poured into water (150 mL) and extracted with EtOAc (2×50 ml). The organic phase was washed with aq. NH₄Cl (50 mL), and dried over Na₂SO₄. After filtration, the solution was concentrated in vacuo to give the crude title compound as an oil, which was used in next step without further purification. (M+H⁺) calc'd 298.1, found 298.1

Step 3. 1-(6-acetyl-3,4-dihydroquinolin-1(2H)-yl)-3-methylbutan-1-one

To a solution of 1-(6-bromo-3,4-dihydroquinolin-1(2H)-yl)-3-methylbutan-1-one (378 mg, 1.149 mmol) in toluene (10 mL) was added tributyl(1-ethoxyvinyl)stannane (0.617 mL, 1.827 mmol) and Pd(PPh$_3$)$_4$ (133 mg, 0.115 mmol). After the addition was finished, the reaction was stirred at 120° C. The reaction was monitored by LCMS, and after stirring for 16 h, the reaction was found to be complete. The reaction mixture was cooled to RT and the solvent was removed in vacuo. The residue was re-dissolved in THF (6 mL), and 1M HCl (5 mL) was added. After stirring at RT for 12 h, the mixture was diluted with EtOAc (30 mL), and washed with sat. NaHCO$_3$ (50 mL). The organic layers were dried over Na$_2$SO$_4$, filtered and concentrated in vacuo. The residue was purified by silica gel chromatography (SiO2, pet. ether/EtOAc=1/20 to 1/5) to give the title compound as an oil. LCMS m/z (M+H$^+$) calc'd 260.2, found 260.2

Step 4. (Z)-1-(6-(1-(hydroxyimino)ethyl)-3,4-dihydroquinolin-1(2H)-yl)-3-methylbutan-1-one To a suspension of hydroxylamine hydrochloride (60 mg, 0.863 mmol) in ethanol (3 mL) was added a suspension of sodium hydroxide (34 mg, 0.850 mmol) in EtOH (0.5 mL). The reaction mixture was stirred at RT for 15 min. The precipitated sodium hydrochloride was filtered off A solution of 1-(6-acetyl-3,4-dihydroquinolin-1(2H)-yl)-3-methylbutan-1-one (244 mg, 0.706 mmol) in ethanol (3 mL) was added. The reaction solution was stirred at RT and the reaction was monitored by LCMS. After stirring for 16 h, the reaction was complete. The mixture was concentrated in vacuo and the residue was purified by silica gel chromatography (SiO2, pet. ether/EtOAc=1/20 to 1/10) to give the title compound as an oil. LCMS m/z (M+H$^+$) calc'd 275.2, found 275.2

Step 5. 1-(6-(1-aminoethyl)-3,4-dihydroquinolin-1(2H)-yl)-3-methylbutan-1-one To a solution of (Z)-1-(6-(1-(hydroxyimino)ethyl)-3,4-dihydroquinolin-1(2H)-yl)-3-methylbutan-1-one (125 mg, 0.342 mmol) and ammonia hydrate (1.5 mL, 9.74 mmol) ((25-28)%) in MeOH (10 mL) was added Raney nickel (150 mg, 2.56 mmol) and the mixture was stirred at RT under hydrogen (15 Psi). The reaction was monitored by LCMS and after stirring for 16 h, the reaction was finished. The catalyst was filtered off and the filtrate was concentrated in vacuo to give the crude title compound as a solid, which was used in next step without further purification. LCMS m/z (M+H$^+$) calc'd 262.2, found 262.2

Step 6. 4-chloro-N-(1-(1-(3-methylbutanoyl)-1,2,3,4-tetrahydroquinolin-6-yl)ethyl)benzamide To a stirring solution of 1-(6-(1-aminoethyl)-3,4-dihydroquinolin-1(2H)-yl)-3-methylbutan-1-one (94 mg, 0.361 mmol) and Et$_3$N (0.5 mL, 3.61 mmol) in DCM (5 mL) was added a solution of 4-chlorobenzoyl chloride (330 mg, 1.886 mmol) in DCM (4 mL) dropwise at 0° C. under nitrogen atmosphere. After the addition was finished, the reaction was stirred at 20° C. and was monitored by LCMS. After stirring for 2 h, the reaction was finished. The mixture was quenched with MeOH (3 mL), concentrated in vacuo and the residue was re-dissolved in EtOAc (50 mL), diluted with water (100 mL), and extracted with EtOAc (2×50 mL). The combined organic layers were washed with sat. NaHCO$_3$ (40 mL) and brine (50 mL), dried over Na$_2$SO$_4$, filtered and concentrated in vacuo. The residue was purified by prep-HPLC(Column: Waters Xbridge Prep OBD C18 100×19 mm×5 um; Condition: water (0.1% TFA)-CH$_3$CN; Begin B: 30; End B: 60; Gradient Time (min): 10; FlowRate (mL/min): 25) to give the title compound as a solid. $^1$H NMR (400 MHz, CDCl$_3$) δ 7.73 (d, J=8.4 Hz, 2H), 7.42 (d, J=8.4 Hz, 2H), 7.16-7.23 (m, 2H), 6.33 (br d, J=7.5 Hz, 1H), 5.30 (quin, J=7.0 Hz, 1H), 3.78 (br t, J=6.5 Hz, 2H), 2.72 (br t, J=6.2 Hz, 2H), 2.42 (d, J=7.0 Hz, 2H), 2.19 (quind, J=6.8, 13.45 Hz, 1H), 1.97 (quin, J=6. 6 Hz, 2H), 1.61 (d, J=6.8 Hz, 3H), 0.92 (br s, 3H), 0.91 (br s, 3H), LCMS m/z (M+H$^+$) calc'd 399.2, found 399.2

Chiral Separation Conditions:

Column & dimensions (mm): OJ-H, 21×250 mm; Outlet Pressure (bar): 100; UV wavelength (nm): 220; Flow rate (ml/min): 70; Modifier: MeOH w/0.25% DMEA; % modifier in CO2:15; Diluent: MeOH; Diluent volume (mL): 2; Injection volume (mL): 0.75; Retention time (min): 3.2, 4.8

The compounds in the following table were prepared in a similar manner as Example 26:

| Ex. # | Structure | Chemical Names | Mass [M + H$^+$] | Hela IC$_{50}$, nM |
|---|---|---|---|---|
| 26 | 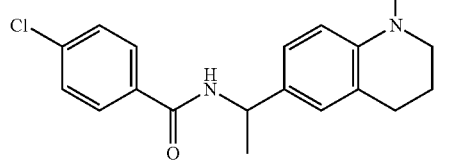<br>Isomer 1 | 4-chloro-N-{1-[1-(3-methylbutanoyl)-1,2,3,4-tetrahydroquinolin-6-yl]ethyl}benzamide | Calc'd 399 found 399 | 4.3 |

| Ex. # | Structure | Chemical Names | Mass [M + H+] | Hela IC$_{50}$, nM |
|---|---|---|---|---|
| 27 | Isomer 2 | 4-chloro-N-{(1S)-1-[1-(3-methyl-butanoyl)-1,2,3,4-tetrahydroquinolin-6-yl]ethyl}benzamide | Calc'd 399, found 399 | 42.2 |
| 28 | Racemic | 4-chloro-N-{(1R)-1-[1-(3-methyl-butanoyl)-1,2,3,4-tetrahydroquinolin-6-yl]ethyl}benzamide | Calc'd 399, found 399 | 3.8 |

Example 29. 4-chloro-N-(1-(1-(3-chlorobenzoyl)-1,2,3,4-tetrahydroquinolin-6-yl)ethyl)benzamide

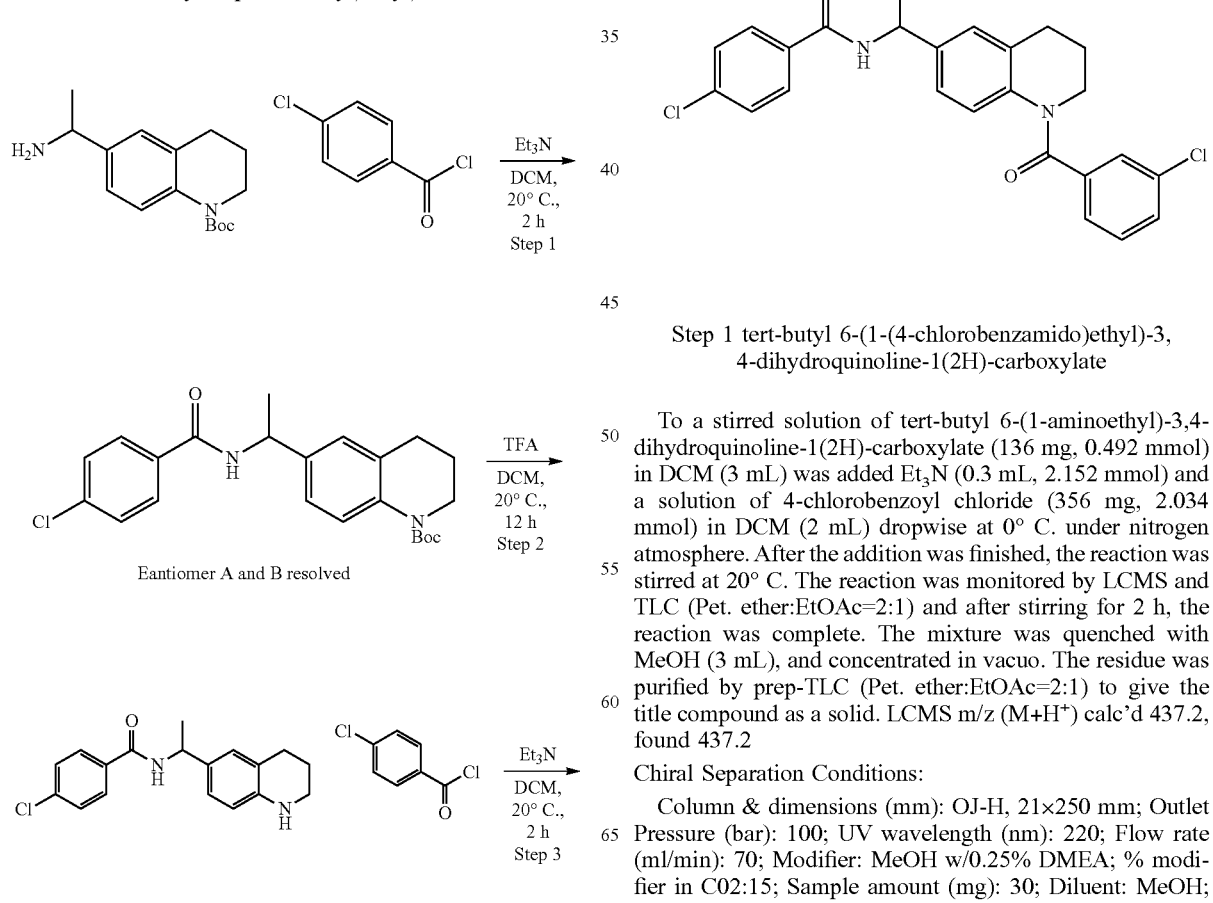

Step 1 tert-butyl 6-(1-(4-chlorobenzamido)ethyl)-3,4-dihydroquinoline-1(2H)-carboxylate To a stirred solution of tert-butyl 6-(1-aminoethyl)-3,4-dihydroquinoline-1(2H)-carboxylate (136 mg, 0.492 mmol) in DCM (3 mL) was added Et$_3$N (0.3 mL, 2.152 mmol) and a solution of 4-chlorobenzoyl chloride (356 mg, 2.034 mmol) in DCM (2 mL) dropwise at 0° C. under nitrogen atmosphere. After the addition was finished, the reaction was stirred at 20° C. The reaction was monitored by LCMS and TLC (Pet. ether:EtOAc=2:1) and after stirring for 2 h, the reaction was complete. The mixture was quenched with MeOH (3 mL), and concentrated in vacuo. The residue was purified by prep-TLC (Pet. ether:EtOAc=2:1) to give the title compound as a solid. LCMS m/z (M+H$^+$) calc'd 437.2, found 437.2

Chiral Separation Conditions:

Column & dimensions (mm): OJ-H, 21×250 mm; Outlet Pressure (bar): 100; UV wavelength (nm): 220; Flow rate (ml/min): 70; Modifier: MeOH w/0.25% DMEA; % modifier in C02:15; Sample amount (mg): 30; Diluent: MeOH;

Diluent volume (mL): 2; Injection volume (mL): 0.3; Peak 1: RT=2.01 min; Peak 2: RT=3.22 min Step 2. 4-chloro-N-(1-(1,2,3,4-tetrahydroquinolin-6-yl)ethyl)benzamide To a stirred solution of tert-butyl 6-(1-(4-chlorobenzamido)ethyl)-3,4-dihydro-quinoline-1(2H)-carboxylate (104 mg, 0.251 mmol) in DCM (2 mL) was added TFA (0.5 mL, 6.48 mmol), and the resulting mixture was stirred at 20° C. The reaction was monitored by LCMS and TLC (DCM:MeOH=10:1). After stirring for 12 h the reaction was complete. The mixture was concentrated in vacuo to give the crude title compound as an oil which was used in next step without further purification. LCMS m/z (M+H$^+$) calc'd 315.1, found 315.1

Step 3. 4-chloro-N-(1-(1-(3-chlorobenzoyl)-1,2,3,4-tetrahydroquinolin-6-yl)ethyl)benzamide To a stirred solution of 4-chloro-N-(1-(1,2,3,4-tetrahydroquinolin-6-yl)ethyl)benzamide (125 mg, 0.292 mmol) in DCM (3 mL) were added Et$_3$N (0.6 mL, 4.30 mmol) and a solution of 3-chlorobenzoyl chloride (260 mg, 1.486 mmol) in DCM (2 mL) dropwise at 0° C. under nitrogen atmosphere. After the addition was finished, the reaction was stirred at 20° C. The reaction was monitored by LCMS, and after stirring for 2 h the reaction was complete. The mixture was quenched with MeOH (3 mL), and concentrated in vacuo. The residue was purified by prep-TLC (Pet. ether: EtOAc=2:1) to give the title compound as an oil. 1H NMR (400 MHz, CDCl3) δ 7.70 (d, J=8.6 Hz, 2H), 7.40 (d, J=8.6 Hz, 2H), 7.38 (br s, 1H), 7.32-7.37 (m, 1H), 7.23 (d, J=4.6 Hz, 2H), 7.18 (s, 1H), 6.95 (br d, J=8.2 Hz, 1H), 6.83 (br s, 1H), 6.24 (br d, J=7.2 Hz, 1H), 5.24 (quin, J=7.0 Hz, 1H), 3.86 (t, J=6.2 Hz, 2H), 2.86 (t, J=6.6 Hz, 2H), 2.04 (quin, J=6.4 Hz, 2H), 1.56 (d, J=7.0 Hz, 3H). LCMS m/z (M+H$^+$) calc'd 453.2, found 453.2

Chiral Separation Conditions:

After SFC separation, two chiral isomers were obtained; Column: OD (250 mm×30 mm×5 um); Condition: 0.1% NH$_3$H$_2$O EtOH; Begin B: 40%; End B: 40%; FlowRate (ml/min): 50; Injections: 120

The compounds in the following table were prepared in a similar manner as Example 29.

| Ex. # | Structure | Chemical Names | Mass [M + H$^+$] | Hela IC$_{50}$, nM |
|---|---|---|---|---|
| 29 | Isomer 1 | 4-chloro-N-{1-[1-(3-chlorobenzene-1-carbonyl)-1,2,3,4-tetrahydroquinolin-6-yl]ethyl}benzamide | Calc'd 453, found 453 | 21.1 |
| 30 | Isomer 2 | 4-chloro-N-{1-[1-(3-chlorobenzene-1-carbonyl)-1,2,3,4-tetrahydroquinolin-6-yl]ethyl}benzamide | Calc'd 453, found 453 | 3.9 |
| 31 | Isomer 1 | 4-fluoro-N-{(1R)-1-[1-(1-fluorocyclopropane-1-carbonyl)-1,2,3,4-tetrahydroquinolin-6-yl]ethyl}benzamide | Calc'd 385, found 385 | 1226.0 |

-continued

| Ex. # | Structure | Chemical Names | Mass [M + H⁺] | Hela IC$_{50}$, nM |
|---|---|---|---|---|
| 32 | Isomer 2 | 4-fluoro-N-{(1S)-1-[1-(1-fluorocyclopropane-1-carbonyl)-1,2,3,4-tetrahydroquinolin-6-yl]ethyl}benzamide | Calc'd 385, found 385 | 27.5 |
| 33 | Isomer 1 | 5-fluoro-N-{(1R)-1-[1-(1-fluorocyclopropane-1-carbonyl)-1,2,3,4-tetrahydroquinolin-6-yl]ethyl}pyridine-2-carboxamide | Calc'd 386, found 386 | 728.8 |
| 34 | Isomer 2 | 5-fluoro-N-{(1S)-1-[1-(1-fluorocyclopropane-1-carbonyl)-1,2,3,4-tetrahydroquinolin-6-yl]ethyl}pyridine-2-carboxamide | Calc'd 386, found 386 | 800.1 |

Example 35. N-(4-chlorophenyl)-2-(1-(3-methylbutanoyl)-1,2,3,4-tetrahydroquinolin-6-yl)acetamide

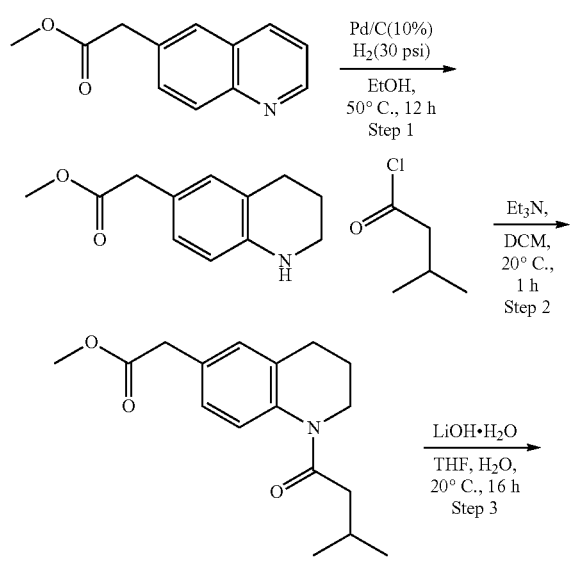

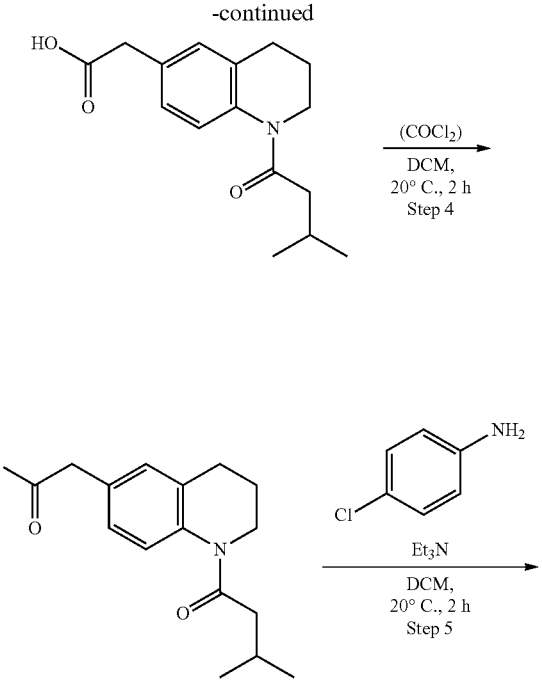

-continued

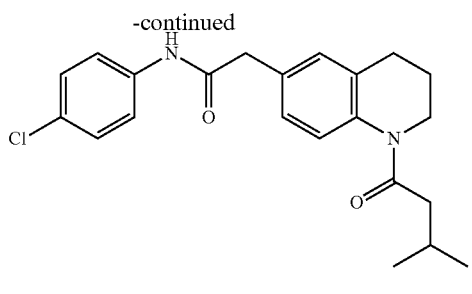

Step 1. methyl 2-(1,2,3,4-tetrahydroquinolin-6-yl)acetate

To a solution of methyl 2-(quinolin-6-yl)acetate (700 mg, 3.30 mmol) in ethanol (20 mL) was added Pd/C (400 mg, 0.376 mmol)(10%), and the reaction was stirred at 50° C. under 30 psi of hydrogen. The reaction was monitored by LCMS. After stirring for 12 h the reaction was finished. The catalyst was removed off by filtration, and the filtrate was concentrated in vacuo to give the title compound as an oil. LCMS m/z (M+H$^+$) calc'd 206.1, found 206.0

Step 2. methyl 2-(1-(3-methylbutanoyl)-1,2,3,4-tetrahydroquinolin-6-yl)acetate To a stirred solution of methyl 2-(1,2,3,4-tetrahydroquinolin-6-yl)acetate (673 mg, 2.95 mmol) in DCM (10 mL) were added Et$_3$N (1.4 mL, 10.10 mmol) and 3-methylbutanoyl chloride (534 mg, 4.43 mmol) dropwise at 0° C. under nitrogen atmosphere. After the addition was finished the reaction was stirred at 20° C. for 2 h and LCMS showed the reaction was complete. The mixture was quenched with MeOH (2 mL), then the solvent was removed in vacuo. The residue was re-dissolved in DCM (50 mL) and diluted with water (100 mL), extracted with DCM (30 mL×2), the combined organic layers were washed with brine (30 mL), dried over Na$_2$SO$_4$, filtered and concentrated in vacuo. The residue was purified by column chromatography on silica gel (SiO$_2$) (eluting with Petroleum ether/ethyl acetate=15:1 to 5:1) to give methyl 2-(1-(3-methylbutanoyl)-1,2,3,4-tetrahydroquinolin-6-yl)acetate as an oil. LCMS m/z (M+H$^+$) calc'd 290.1, found 290.0

Step 3. 2-(1-(3-methylbutanoyl)-1,2,3,4-tetrahydroquinolin-6-yl)acetic acid

To a solution of methyl 2-(1-(3-methylbutanoyl)-1,2,3,4-tetrahydroquinolin-6-yl)acetate (150 mg, 0.518 mmol) in THF (3 mL) was added lithium hydroxide hydrate (44 mg, 1.049 mmol) and the reaction was stirred at RT. The reaction was monitored by LCMS. After stirring for 16 h, the reaction was finished. Then the reaction was quenched by the addition of 1M HCl (1 mL) and the solvent was removed in vacuo to afford the crude title compound as a solid which was used directly in the next step. LCMS m/z (M+H$^+$) calc'd 276.2, found 276

Step 4. 2-(1-(3-methylbutanol)-1,2,3,4-tetrahydroquinolin-6-yl)acetyl chloride To a solution of 2-(1-(3-methylbutanoyl)-1,2,3,4-tetrahydroquinolin-6-yl)acetic acid (169 mg, 0.491 mmol) in DCM (5 mL) was added oxalyl dichloride (0.1 mL, 1.172 mmol) under nitrogen at 0° C. Then DMF (20 μL, 0.258 mmol) was added to the mixture and the resulting solution was stirred at 20° C. The reaction was monitored by TLC (DCM:MeOH=10:1) and after stirring for 1 h, the reaction was finished. The solvent was removed off by concentration in vacuo to give the crude title compound as a solid, which was used in the next step without further purification.

Step 5. N-(4-chlorophenyl)-2-(1-(3-methylbutanol)-1,2,3,4-tetrahydroquinolin-6-yl)acetamide To a stirred solution of 4-chloroaniline (131 mg, 1.026 mmol) in DCM (3 mL) were added TEA (0.3 mL, 2.152 mmol) and a solution of 2-(1-(3-methylbutanoyl)-1,2,3,4-tetrahydroquinolin-6-yl)acetyl chloride (201 mg, 0.684 mmol) in DCM (3 mL) dropwise at 0° C. under nitrogen atmosphere. After the addition, the reaction was stirred at 20° C. The reaction was monitored by LCMS and after stirring for 2 h, the reaction was finished. The mixture was quenched with MeOH (3 mL), concentrated in vacuo, the residue was re-dissolved in EtOAc (50 mL), diluted with water (100 mL), and extracted with EtOAc (2×30 mL). The combined organic layers were washed with brine (50 mL), dried over Na$_2$SO$_4$, filtered and concentrated in vacuo. The residue was purified by prep-HPLC (Column: Agela ASB 150×25 mm×5 um; Condition: water (0.1% TFA)-CH$_3$CN; Begin B: 49; End B: 69; Gradient Time (min): 10; FlowRate (mL/min): 25 to give the title compound. $^1$H NMR (400 MHz, CDCl$_3$) δ 7.41 (br d, J=8.6 Hz, 2H), 7.28 (br s, 1H), 7.26 (br s, 2H), 7.14 (br s, 2H), 4.49 (br s, 1H), 3.81 (br t, J=6.2 Hz, 2H), 3.71 (s, 2H), 2.71-2.78 (m, 2H), 2.45 (d, J=7.0 Hz, 2H), 2.19 (td, J=6.5, 13.2 Hz, 1H), 2.00 (quin, J=6.6 Hz, 2H), 0.92 (br s, 6H); LCMS m/z (M+H$^+$) calc'd 385.2, found 385.1

| Ex. # | Structure | Chemical Names | Mass [M + H]+ | Hela IC$_{50}$, nM |
|---|---|---|---|---|
| 35 | 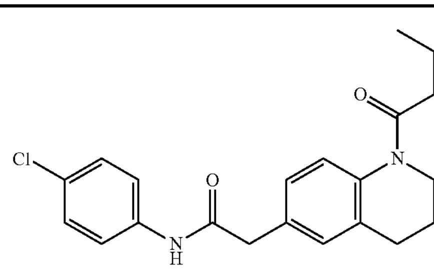 | N-(4-chlorophenyl)-2-(1-(3-methylbutanoyl)-1,2,3,4-tetrahydroquinolin-6-yl)acetamide | Calc'd 385, found 385 | 6.9 |

Example 36. 2-(1-(cyclopropanecarbonyl)-1,2,3,4-tetrahydroquinolin-6-yl)-N-(4-fluorophenyl)propanamide

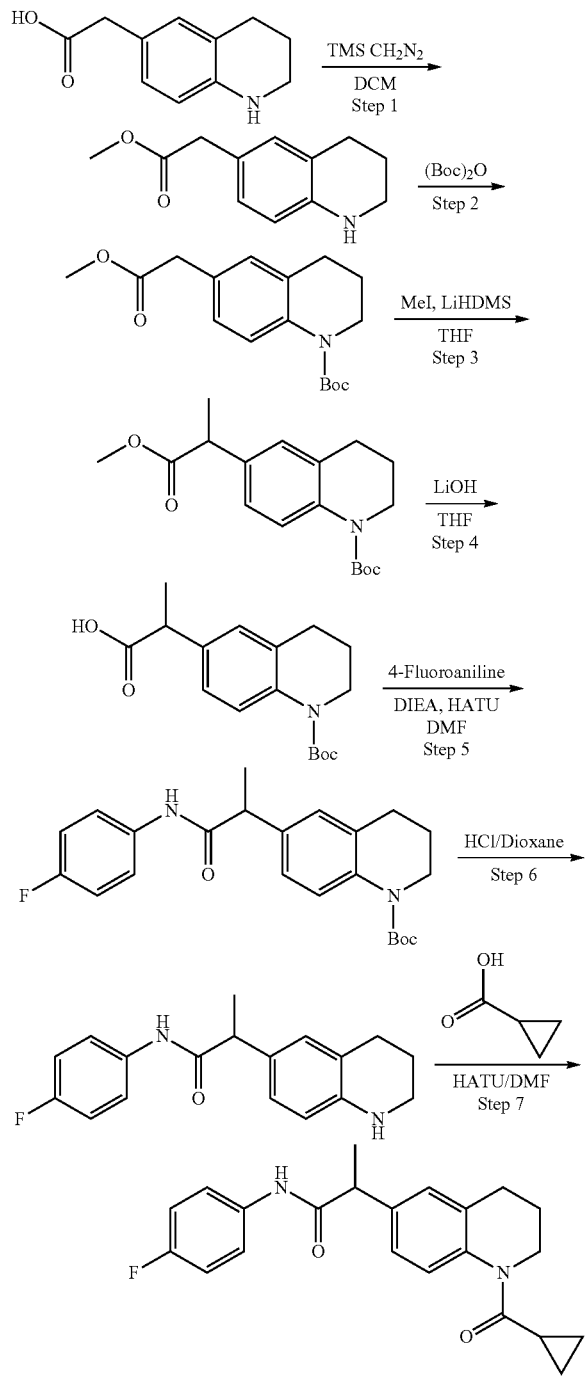

Step 1. methyl 2-(1,2,3,4-tetrahydroquinolin-6-yl)acetate

To a suspension of 2-(1,2,3,4-tetrahydroquinolin-6-yl) acetic acid (1 g, 5.23 mmol) in DCM (5 ml) at 0° C. was added trimethylsilyldiazomethane in hexane (7.84 ml, 15.69 mmol) dropwise. Gas was evolved from the reaction mixture during the addition. After the completion of addition, the mixture was concentrated and purified using flash column chromatography (eluting with hexane/ethyl acetate:ethanol=3:1, starting with 100% hexane, end with 20% hexane) to give the desired product as an oil. LCMS m/z (M+H) calc'd: 206.1; found: 206.1.

Step 2. tert-butyl 6-(2-methoxy-2-oxoethyl)-3,4-dihydroquinoline-1(2H)-carboxylate To a solution of methyl 2-(1,2,3,4-tetrahydroquinolin-6-yl)acetate (2000 mg, 9.74 mmol) in ACN (10 ml) was added BOC-anhydride (2.71 ml, 11.69 mmol) at RT. The reaction was monitored by TLC and the starting material was found converted after 24 h as shown by LCMS. The solvent was removed under vacuum and the residue was purified using Combi-Flash, eluting with Hexane/ethyl acetate:ethanol (3:1) with starting hexane=100% and end Hexane=20%. The desired product was obtained as an oil. LCMS m/z (M+H) calc'd: 306.1; found: 306.1.

Step 3. tert-butyl 6-(1-methoxy-1-oxopropan-2-yl)-3,4-dihydroquinoline-1(2H)-carboxylate To a solution of tert-butyl 6-(2-methoxy-2-oxoethyl)-3,4-dihydroquinoline-1(2H)-carboxylate (1000 mg, 3.27 mmol) in THF (20 ml) at −78° C. was added potassium hexamethyldisilazide (3930 µl, 3.93 mmol)) under nitrogen. The reaction mixture was left for 2 h at this temperature and iodomethane (410 µl, 6.55 mmol) was added and the reaction mixture was brought to RT. After stirring for 60 min, the reaction was quenched with sat. $NH_4C_1$, diluted with EA and sat. aq. NaCl. The organic layer was separated, dried and solvent removed. The residue was purified using combi-flash, eluted with Hx-EA9 0→30% and gave a mixture of bis- and mono-methylated intermediate. The two intermediates were separated using prep-HPLC and tert-butyl 6-(1-methoxy-1-oxopropan-2-yl)-3,4-dihydroquinoline-1(2H)-carboxylate (580 mg, 1.816 mmol) was obtained as an oil. LCMS m/z (M+H) calc'd: 320.2; found: 320.1

Step 4. 2-(1-(tert-butoxcarbonyl)-1,2,3,4-tetrahydroquinolin-6-yl)propanoic acid To a solution of tert-butyl 6-(1-methoxy-1-oxopropan-2-yl)-3,4-dihydroquinoline-1(2H)-carboxylate (580 mg, 1.816 mmol) in tetrahydrofuran (10 ml) was added lithium hydroxide (9.08 ml, 9.08 mmol). The resulting solution was stirred at RT overnight, the reaction went to completion. The THF was removed under vacuum and to the resulting residue was added HCl (1N) to acidify it to pH~5. The formed precipitate was collected by filtration and dried under vacuum to give the desired product as a solid which was used without further purification. LCMS m/z (M+H) calc'd: 306.2; found: 306.1

Step 5. Tert-butyl 6-(1-((4-fluorophenyl)amino)-1-oxopropan-2-yl)-3,4-dihydroquinoline-1(2H)-carboxylate To a solution of 2-(1-(tert-butoxycarbonyl)-1,2,3,4-tetrahydroquinolin-6-yl)propanoic acid (450 mg, 1.474 mmol) and DIEA (0.772 ml, 4.42 mmol) in DMF (5 ml) was added HATU (840 mg, 2.210 mmol) at 0° C. The formed reaction mixture was stirred for 0.5 h and 4-fluoroaniline (0.212 ml, 2.210 mmol) was added. The resulting mixture was warmed up to RT and stirred for 1 h. LCMS showed the complete conversion of reaction. The reaction mixture was added to a mixture of ice-water and the formed precipitate, which was collected by filtration. After drying in air, the crude product was purified using Combi-Flash, eluting with Hexane/ethyl acetate:ethanol (3:1) starting hexane=100% and end Hexane=20%. The desired product was obtained as a solid. LCMS m/z (M+H) calc'd: 399.2; found: 399.1

Intermediate can be resolved using the following chiral separation conditions. All final compounds were made using material collected under peak 2 unless specified otherwise.

Column & dimensions (mm): AD-H, 21×250; Outlet Pressure (bar): 100; UV wavelength (nm): 220; Flow rate (ml/min): 70; Modifier: MeOH w/0.25% DMEA; % modifier in CO2: 25 Sample amount (mg): 600; Diluent: MeOH; Diluent volume (mL): 13

Injection volume (mL): 0.3; Instrument: Multigram II; Retention time (min): peak 1, RT=3.1, peak 2, RT=3.9

Step 6. N-(4-fluorophenyl)-2-(1,2,3,4-tetrahydroquinolin-6-yl)propanamide

To tert-butyl 6-(1-((4-fluorophenyl)amino)-1-oxopropan-2-yl)-3,4-dihydroquinoline-1(2H)-carboxylate (580 mg, 1.456 mmol) was added HCl in dioxane (4 N, 1.8 ml) and the reaction mixture was stirred at RT. After 1 h, LCMS showed the reaction was complete. Ethyl ether (20 ml) was added and the formed solid was filtered, which was washed with ethyl ether and was dried in air to give the desired product as a solid. LCMS m/z (M+H) calc'd: 299.1; found: 299.1

Step 7. 2-(1-(cyclopropanecarbonyl)-1,2,3,4-tetrahydroquinolin-6-yl)-N-(4-fluorophenyl)propanamide To a solution of N-(4-fluorophenyl)-2-(1,2,3,4-tetrahydroquinolin-6-yl)propanamide hydrochloride (20 mg, 0.060 mmol) in DMF (0.5 ml) were added DIEA (0.031 ml, 0.179 mmol) and HATU (34.1 mg, 0.090 mmol) at 0° C. After stirring for 20 min, N-(4-fluorophenyl)-2-(1,2,3,4-tetrahydroquinolin-6-yl)propanamide hydrochloride (20 mg, 0.060 mmol) was added and the reaction mixture was warmed up to RT with stirring for 1 h. The reaction was completed and the crude mixture was purified by mass-directed reverse HPLC purification (on reverse HPLC on a 19×100 mm, Waters CSH C18 column, 5p particle size, flow rate 25 ml/min, linear gradient, 5% ACN/H2O to 50% ACN/H2O, total run time 15 min, buffering with 0.16% TFA) to give the title compound as a solid. $^1$H NMR (400 MHz, DMSO-$d_6$) δ 10.07 (s, 1H), 7.58 (m, 2H), 7.35 (m, 1H), 7.16 (m, 2H), 7.06 (m, 2H), 3.75 (m, 2H), 3.60 (m, 1H), 2.68 (m, 2H), 1.88 (m, 1H), 1.81 (m, 2H), 1.79 (s, 3H), 0.73 (m, 2H), 0.72 (m, 2H). m/z=262.2 [M+H]$^+$ 521.4 [2M+H]$^+$. LCMS m/z (M+H) calc'd: 367.2; found (M+H): 367.1

If a compound is not made from chiral resolved intermediate, it can be separated using following chiral separation condition: Column & dimensions (mm): IG, 21×250; Outlet Pressure (bar): 100; UV wavelength (nm): 220; Flow rate (ml/min): 70; Modifier: MeOH w/0.25% DMEA; % modifier in C02:25; Sample amount (mg): 40; Diluent: MeOH; Diluent volume (mL): 1; Injection volume (mL): 2.0

The compounds in the following table were prepared in a similar manner as Example 36:

| Ex. # | Structure | Chemical Names | Mass [M + H]+ | Hela IC$_{50}$, nM |
|---|---|---|---|---|
| 36 | 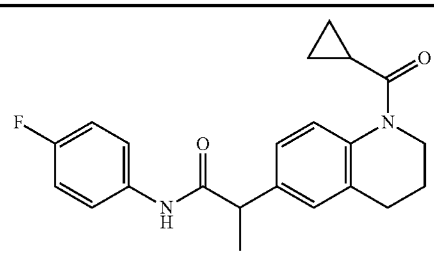 | 2-[1-(cyclopropanecarbonyl)-1,2,3,4-tetrahydroquinolin-6-yl]-N-(4-fluorophenyl)propanamide | Calc'd 367, found 367 | 5.8 |
| 37 | 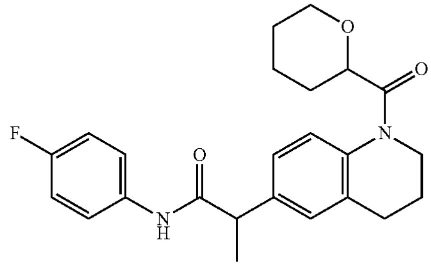 [SMILES: CC(C(=O)Nc1ccc(F)cc1)c1ccc2c(c1)CCCN2C(=O)C1CCCCO1] | N-(4-fluorophenyl)-2-[1-(oxane-2-carbonyl)-1,2,3,4-tetrahydroquinolin-6-yl]propanamide | Calc'd 411, found 411 | 4.8 |
| 38 | 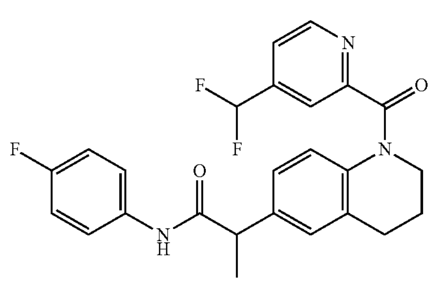 [SMILES: CC(C(=O)Nc1ccc(F)cc1)c1ccc2c(c1)CCCN2C(=O)c1cc(C(F)F)ccn1] | 2-{1-[4-(difluoromethyl)pyridine-2-carbonyl]-1,2,3,4-tetrahydroquinolin-6-yl}-N-(4-fluorophenyl)propanamide | Calc'd 454, found 454 | 5.7 |

| Ex. # | Structure | Chemical Names | Mass [M + H]+ | Hela IC$_{50}$, nM |
|---|---|---|---|---|
| 39 | 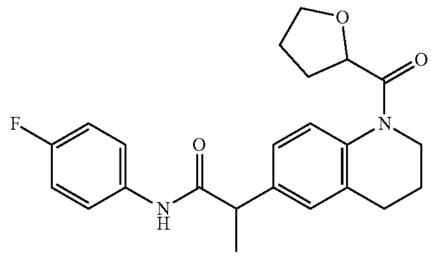 [SMILES: CC(C(=O)Nc1ccc(F)cc1)c1ccc2c(c1)CCCN2C(=O)C1CCCO1] | N-(4-fluorophenyl)-2-[1-(oxolane-2-carbonyl)-1,2,3,4-tetrahydroquinolin-6-yl]propanamide | Calc'd 397, found 397 | 5.4 |
| 40 | 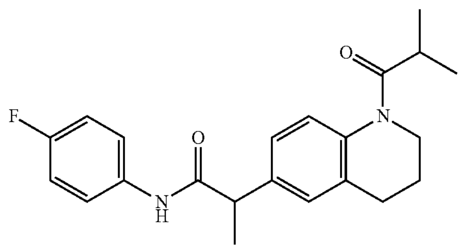 [SMILES: CC(C)C(=O)N1CCCc2cc(C(C)C(=O)Nc3ccc(F)cc3)ccc21] | N-(4-fluorophenyl)-2-[1-(2-methylpropanoyl)-1,2,3,4-tetrahydroquinolin-6-yl]propanamide | Calc'd 369, found 369 | 5.0 |
| 41 | 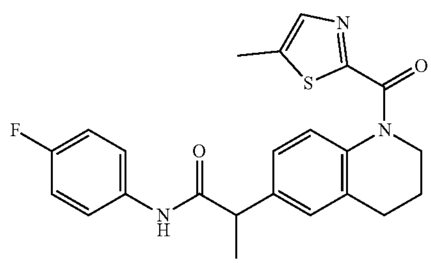 [SMILES: Cc1cnc(C(=O)N2CCCc3cc(C(C)C(=O)Nc4ccc(F)cc4)ccc32)s1] | N-(4-fluorophenyl)-2-[1-(5-methyl-1,3-thiazole-2-carbonyl)-1,2,3,4-tetrahydroquinolin-6-yl]propanamide | Calc'd 424, found 424 | 4.6 |
| 42 | 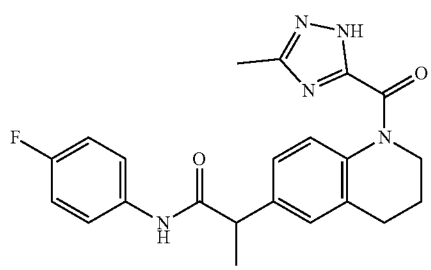 [SMILES: Cc1n[nH]c(C(=O)N2CCCc3cc(C(C)C(=O)Nc4ccc(F)cc4)ccc32)n1] | N-(4-fluorophenyl)-2-[1-(3-methyl-1H-1,2,4-triazole-5-carbonyl)-1,2,3,4-tetrahydroquinolin-6-yl]propanamide | Calc'd 408, found 408 | 38.4 |
| 43 | 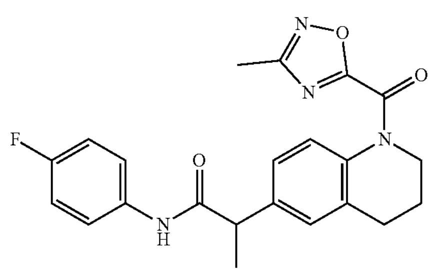 [SMILES: Cc1noc(C(=O)N2CCCc3cc(C(C)C(=O)Nc4ccc(F)cc4)ccc32)n1] | N-(4-fluorophenyl)-2-[1-(3-methyl-1H-1,2,4-oxadiazole-5-carbonyl)-1,2,3,4-tetrahydroquinolin-6-yl]propanamide | Calc'd 409, found 409 | 4.2 |
| 44 | 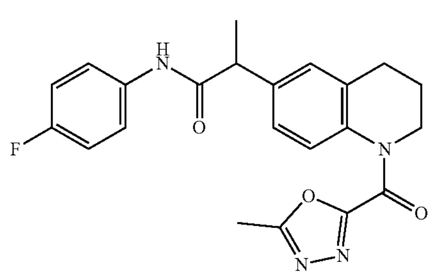 [SMILES: Cc1nnc(C(=O)N2CCCc3cc(C(C)C(=O)Nc4ccc(F)cc4)ccc32)o1] | N-(4-fluorophenyl)-2-[1-(5-methyl-1,3,4-oxadiazole-2-carbonyl)-1,2,3,4-tetrahydroquinolin-6-yl]propanamide | Calc'd 409, found 409 | 16.8 |

| Ex. # | Structure | Chemical Names | Mass [M + H]+ | Hela IC$_{50}$, nM |
|---|---|---|---|---|
| 45 | 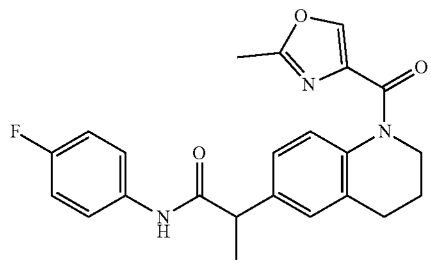 [SMILES: Cc1nc(C(=O)N2CCCc3cc(C(C)C(=O)Nc4ccc(F)cc4)ccc32)co1] | N-(4-fluorophenyl)-2-[1-(2-methyl-1,3-oxazole-4-carbonyl)-1,2,3,4-tetrahydroquinolin-6-yl]propanamide | Calc'd 408, found 408 | 5.9 |
| 46 | 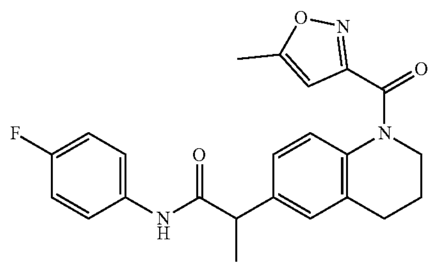 [SMILES: Cc1cc(C(=O)N2CCCc3cc(C(C)C(=O)Nc4ccc(F)cc4)ccc32)no1] | N-(4-fluorophenyl)-2-[1-(5-methyl-1,2-oxazole-3-carbonyl)-1,2,3,4-tetrahydroquinolin-6-yl]propanamide | Calc'd 408, found 408 | 3.9 |
| 47 | 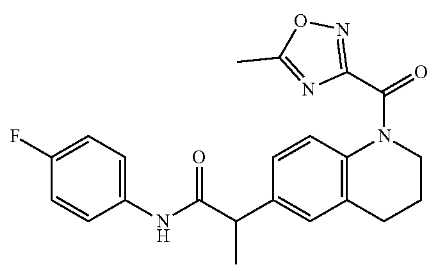 [SMILES: Cc1nc(C(=O)N2CCCc3cc(C(C)C(=O)Nc4ccc(F)cc4)ccc32)no1] | N-(4-fluorophenyl)-2-[1-(5-methyl-1,2,4-oxadiazole-3-carbonyl)-1,2,3,4-tetrahydroquinolin-6-yl]propanamide | Calc'd 409, found 409 | 3.4 |
| 48 | 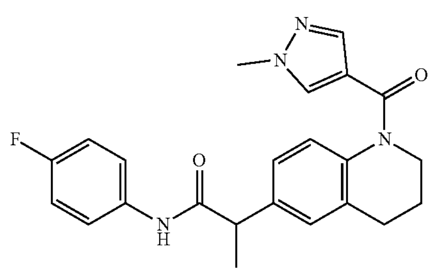 [SMILES: CC(C(=O)Nc1ccc(F)cc1)c1ccc2c(c1)CCCN2C(=O)c1cnn(C)c1] | N-(4-fluorophenyl)-2-[1-(1-methyl-1H-pyrazole-4-carbonyl)-1,2,3,4-tetrahydroquinolin-6-yl]propanamide | Calc'd 407, found 407 | 15.8 |
| 49 | 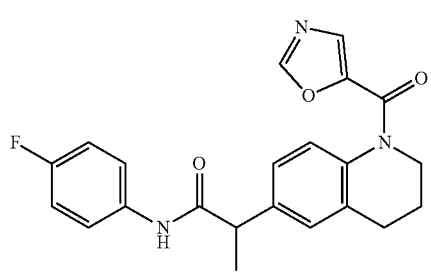 [SMILES: CC(C(=O)Nc1ccc(F)cc1)c1ccc2c(c1)CCCN2C(=O)c1cnco1] | N-(4-fluorophenyl)-2-[1-(1,3-oxazole-5-carbonyl)-1,2,3,4-tetrahydroquinolin-6-yl]propanamide | Calc'd 394, found 394 | 30.0 |

-continued

| Ex. # | Structure | Chemical Names | Mass [M + H]+ | Hela IC$_{50}$, nM |
|---|---|---|---|---|
| 50 | Racemic | 2-[1-(3-chlorobenzene-1-carbonyl)-1,2,3,4-tetrahydroquinolin-6-yl]-N-(4-fluorophenyl)propanamide | Calc'd 437, found 437 | 2.5 |
| 51 | 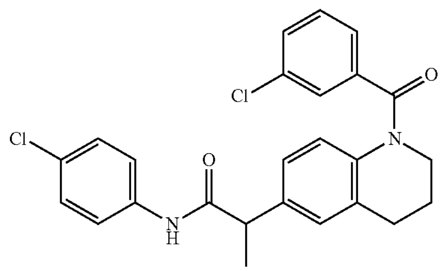 [SMILES: CC(C(=O)Nc1ccc(Cl)cc1)c1ccc2c(c1)CCCN2C(=O)c1cccc(Cl)c1] | 2-[1-(3-chlorobenzene-1-carbonyl)-1,2,3,4-tetrahydroquinolin-6-yl]-N-(4-chlorophenyl)propanamide | Calc'd 453, found 453 | 2.0 |
| 52 | Isomer 1 | (2S)-2-[1-(3-chlorobenzene-1-carbonyl)-1,2,3,4-tetrahydroquinolin-6-yl]-N-(4-fluorophenyl)propanamide | Calc'd 437, found 437 | 4.9 |
| 53 | Isomer 2 | (2R)-2-[1-(3-chlorobenzene-1-carbonyl)-1,2,3,4-tetrahydroquinolin-6-yl]-N-(4-fluorophenyl)propanamide | Calc'd 437, found 437 | 2.2 |
| 54 | Isomer 1 | (2S)-2-[1-(3-chlorobenzene-1-carbonyl)-1,2,3,4-tetrahydroquinolin-6-yl]-N-(5-fluoropyridin-2-yl)propanamide | Calc'd 438, found 438 | 18.0 |

| Ex. # | Structure | Chemical Names | Mass [M + H]+ | Hela IC$_{50}$, nM |
|---|---|---|---|---|
| 55 | Isomer 2 | (2R)-2-[1-(3-chlorobenzene-1-carbonyl)-1,2,3,4-tetrahydroquinolin-6-yl]-N-(5-fluoropyridin-2-yl)propanamide | Calc'd 438, found 438 | 2.4 |
| 56 | Isomer 1 | (2S)-2-[1-(3-chlorobenzene-1-carbonyl)-1,2,3,4-tetrahydroquinolin-6-yl]-N-(4-chlorophenyl)propanamide | Calc'd 453, found 453 | 3.1 |
| 57 | Isomer 2 | (2R)-2-[1-(3-chlorobenzene-1-carbonyl)-1,2,3,4-tetrahydroquinolin-6-yl]-N-(4-chlorophenyl)propanamide | Calc'd 453, found 453 | 2.3 |
| 58 | 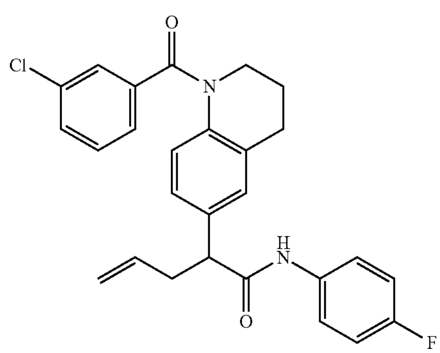 [SMILES: C=CCC(C(=O)Nc1ccc(F)cc1)c1ccc2c(c1)CCCN2C(=O)c1cccc(Cl)c1] | 2-[1-(3-chlorobenzene-1-carbonyl)-1,2,3,4-tetrahydroquinolin-6-yl]-N-(4-fluorophenyl)pent-4-enamide | Calc'd 463, found 463.1 | 4.3 |
| 59 | 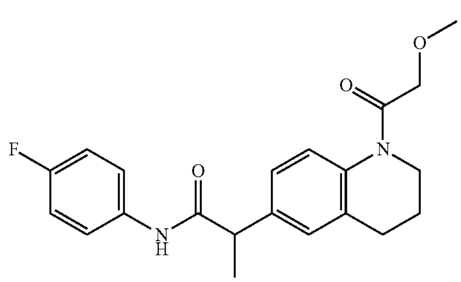 [SMILES: COCC(=O)N1CCCc2cc(C(C)C(=O)Nc3ccc(F)cc3)ccc21] | N-(4-fluorophenyl)-2-[1-(methoxyacetyl)-1,2,3,4-tetrahydroquinolin-6-yl]propanamide | Calc'd 371, found 371 | 20.0 |

| Ex. # | Structure | Chemical Names | Mass [M + H]+ | Hela IC$_{50}$, nM |
|---|---|---|---|---|
| 60 | Isomer 1 | (2R)-2-[1-(cyclopropanecarbonyl)-1,2,3,4-tetrahydroquinolin-6-yl]-N-(5-fluoropyridin-2-yl)propanamide | Calc'd 368, found 368 | 123.5 |
| 61 | Isomer 2 | (2S)-2-[1-(cyclopropanecarbonyl)-1,2,3,4-tetrahydroquinolin-6-yl]-N-(5-fluoropyridin-2-yl)propanamide | Calc'd 368, found 368 | 9.4 |
| 62 | Isomer 1 | (2R)-2-[1-(1-fluorocyclopropane-1-carbonyl)-1,2,3,4-tetrahydroquinolin-6-yl]-N-(5-fluoropyridin-2-yl)propanamide | Calc'd 386, found 386 | 523.8 |
| 63 | Isomer 2 | (2S)-2-[1-(1-fluorocyclopropane-1-carbonyl)-1,2,3,4-tetrahydroquinolin-6-yl]-N-(5-fluoropyridin-2-yl)propanamide | Calc'd 386, found 386 | 16.5 |
| 64 | 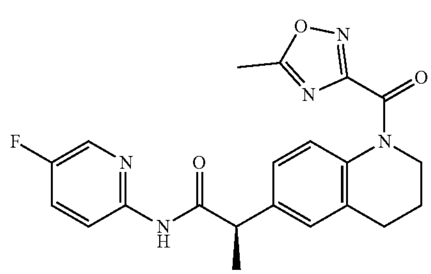 [SMILES: Cc1nc(C(=O)N2CCCc3cc([C@@H](C)C(=O)Nc4ccc(F)cn4)ccc32)no1] | (2R)-N-(5-fluoropyridin-2-yl)-2-[1-(5-methyl-1,2,4-oxadiazole-3-carbonyl)-1,2,3,4-tetrahydroquinolin-6-yl]propanamide | Calc'd 410, found 410 | 44.4 |

| Ex. # | Structure | Chemical Names | Mass [M + H]+ | Hela IC$_{50}$, nM |
|---|---|---|---|---|
| 65 | 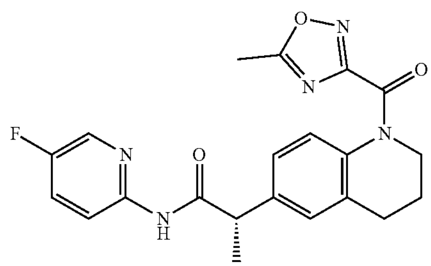 [SMILES: Cc1nc(C(=O)N2CCCc3cc([C@H](C)C(=O)Nc4ccc(F)cn4)ccc32)no1] | (2S)-N-(5-fluoropyridin-2-yl)-2-[1-(5-methyl-1,2,4-oxadiazole-3-carbonyl)-1,2,3,4-tetrahydroquinolin-6-yl]propanamide | Calc'd 410, found 410 | 1.9 |
| 66 | 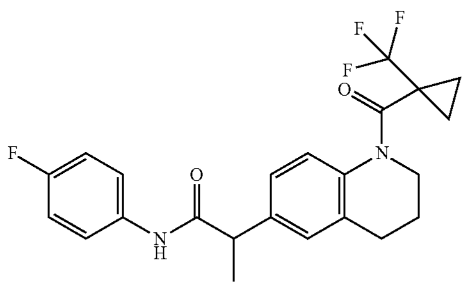 [SMILES: CC(C(=O)Nc1ccc(F)cc1)c1ccc2c(c1)CCCN2C(=O)C1(C(F)(F)F)CC1] | N-(4-fluorophenyl)-2-{1-[1-(trifluoromethyl)cyclopropane-1-carbonyl]-1,2,3,4-tetrahydroquinolin-6-yl}propanamide | Calc'd 435, found 435 | 7.2 |
| 67 | 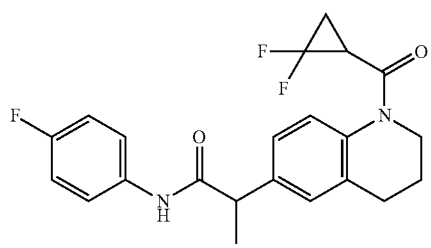 [SMILES: CC(C(=O)Nc1ccc(F)cc1)c1ccc2c(c1)CCCN2C(=O)C1CC1(F)F] | 2-[1-(2,2-difluorocyclopropane-1-carbonyl)-1,2,3,4-tetrahydroquinolin-6-yl]-N-(4-fluorophenyl)propanamide | Calc'd 403, found 367 | 4.1 |
| 68 | 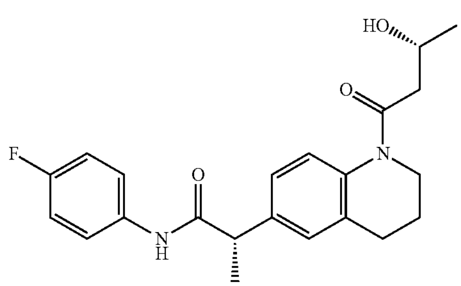 [SMILES: C[C@H](C(=O)Nc1ccc(F)cc1)c1ccc2c(c1)CCCN2C(=O)C[C@@H](C)O] | (2S)-N-(4-fluorophenyl)-2-{1-[(3R)-3-hydroxybulanoyl]-1,2,3,4-tetrahydroquinolin-6-yl}propanamide | Calc'd 385, found 385 | 296.0 |
| 69 | 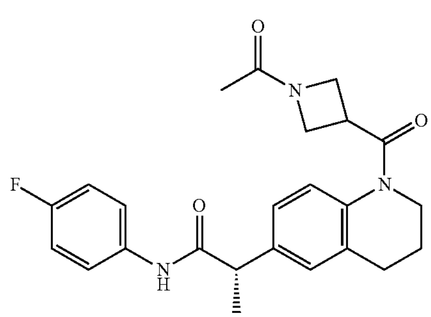 [SMILES: CC(=O)N1CC(C(=O)N2CCCc3cc([C@H](C)C(=O)Nc4ccc(F)cc4)ccc32)C1] | (2S)-2-[1-(1-acetylazetidine-3-carbonyl)-1,2,3,4-tetrahydroquinolin-6-yl]-N-(4-fluorophenyl)propanamide | Calc'd 424, found 424 | 9017.0 |

-continued

| Ex. # | Structure | Chemical Names | Mass [M + H]+ | Hela IC$_{50}$, nM |
|---|---|---|---|---|
| 70 | 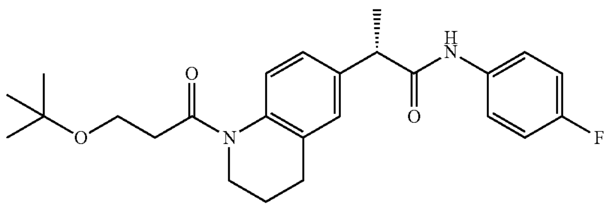 [SMILES: C[C@H](C(=O)Nc1ccc(F)cc1)c1ccc2c(c1)CCCN2C(=O)CCOC(C)(C)C] | (2S)-2-[1-(3-tert-butoxypropanoyl)-1,2,3,4-tetrahydroquinolin-6-yl]-N-(4-fluorophenyl)propanamide | Calc'd 427, found 427 | 3380.0 |
| 71 | 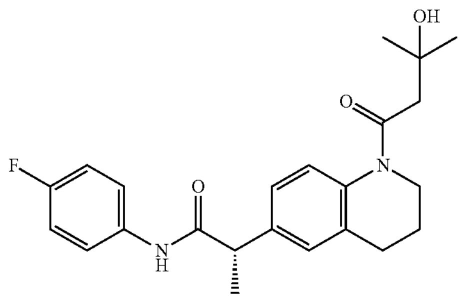 [SMILES: C[C@H](C(=O)Nc1ccc(F)cc1)c1ccc2c(c1)CCCN2C(=O)CC(C)(C)O] | (2S)-N-(4-fluorophenyl)-2-[1-(3-hydroxy-3-methylbutanoyl)-1,2,3,4-tetrahydroquinolin-6-yl]propanamide | Calc'd 399, found 399 | 30.3 |
| 72 | Isomer 1 | (2S)-N-(4-fluorophenyl)-2-{1-[(2R)-2-hydroxy-3-methylbutanoyl]-1,2,3,4-tetrahydroquinolin-6-yl}propanamide | Calc'd 399, found 399 | 43.8 |
| 73 | Isomer 2 | (2S)-N-(4-fluorophenyl)-2-{1-[(2S)-2-hydroxy-3-methylbutanoyl]-1,2,3,4-tetrahydroquinolin-6-yl}propanamide | Calc'd 399, found 399 | 380.6 |
| 74 | 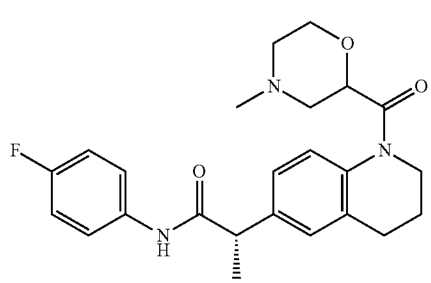 [SMILES: C[C@H](C(=O)Nc1ccc(F)cc1)c1ccc2c(c1)CCCN2C(=O)C1CN(C)CCO1] | (2S)-N-(4-fluorophenyl)-2-[1-(4-methylmorpholine-2-carbonyl)-1,2,3,4-tetrahydroquinolin-6-yl]propanamide | Calc'd 426, found 399 | 460.0 |

| Ex. # | Structure | Chemical Names | Mass [M + H]+ | Hela IC$_{50}$, nM |
|---|---|---|---|---|
| 75 | Isomer 1 | (2S)-N-(4-fluorophenyl)-2-{1-[(2S)-2-methoxypropanoyl]-1,2,3,4-tetrahydroquinolin-6-yl}propanamide | Calc'd 385, found 385 | 61.8 |
| 76 | Isomer 2 | (2S)-N-(4-fluorophenyl)-2-[1-(2-methoxypropanoyl)-1,2,3,4-tetrahydroquinolin-6-yl]propanamide | Calc'd 385, found 385 | 25.9 |
| 77 | 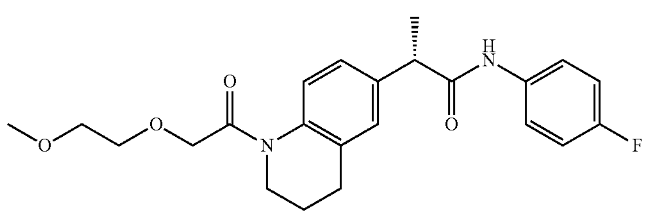 [SMILES: COCCOCC(=O)N1CCCc2cc([C@H](C)C(=O)Nc3ccc(F)cc3)ccc21] | (2S)-N-(4-fluorophenyl)-2-{1-[(2-methoxyethoxy)acetyl]-1,2,3,4-tetrahydroquinolin-6-yl}propanamide | Calc'd 415, found 415 | 1236.0 |
| 78 | 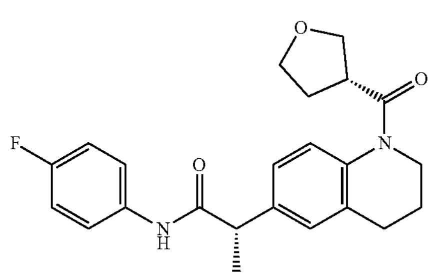 [SMILES: C[C@H](C(=O)Nc1ccc(F)cc1)c1ccc2c(c1)CCCN2C(=O)[C@@H]1CCOC1] | (2S)-N-(4-fluorophenyl)-2-{1-[(3R)-oxolane-3-carbonyl]-1,2,3,4-tetrahydroquinolin-6-yl}propanamide | Calc'd 397, found 397 | 51.6 |
| 79 | 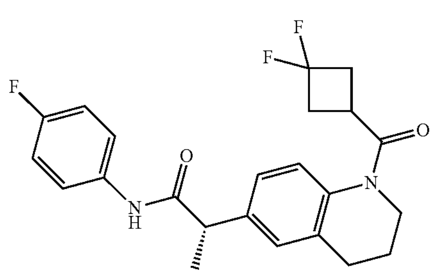 [SMILES: C[C@H](C(=O)Nc1ccc(F)cc1)c1ccc2c(c1)CCCN2C(=O)C1CC(F)(F)C1] | (2S)-2-[1-(3,3-difluorocyclobutane-1-carbonyl)-1,2,3,4-tetrahydroquinolin-6-yl]-N-(4-fluorophenyl)propanamide | Calc'd 417, found 417 | 34.7 |

-continued

| Ex. # | Structure | Chemical Names | Mass [M + H]+ | Hela IC$_{50}$, nM |
|---|---|---|---|---|
| 80 | 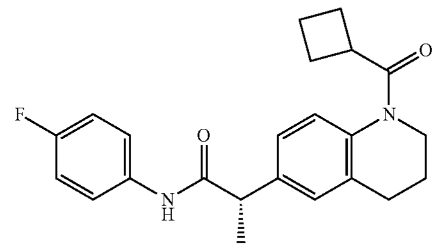 [SMILES: C[C@H](C(=O)Nc1ccc(F)cc1)c1ccc2c(c1)CCCN2C(=O)C1CCC1] | (2S)-2-[1-(cyclobutanecarbonyl)-1,2,3,4-tetrahydroquinolin-6-yl]-N-(4-fluorophenyl)propanamide | Calc'd 381, found 381 | 4.5 |
| 81 | 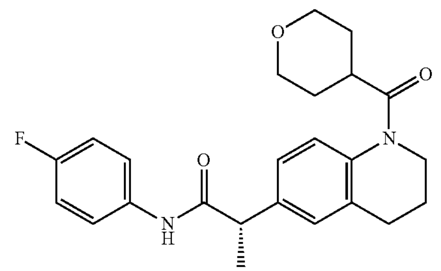 [SMILES: C[C@H](C(=O)Nc1ccc(F)cc1)c1ccc2c(c1)CCCN2C(=O)C1CCOCC1] | (2S)-N-(4-fluorophenyl)-2-[1-(oxane-4-carbonyl)-1,2,3,4-tetrahydroquinolin-6-yl]propanamide | Calc'd 411, found 411 | 4.8 |
| 82 | 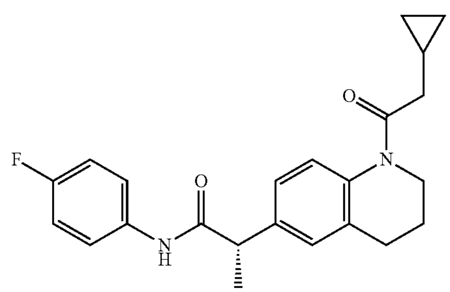 [SMILES: C[C@H](C(=O)Nc1ccc(F)cc1)c1ccc2c(c1)CCCN2C(=O)CC1CC1] | (2S)-2-[1-(cyclopropylacetyl)-1,2,3,4-tetrahydroquinolin-6-yl]-N-(4-fluorophenyl)propanamide | Calc'd 381, found 381 | 10.9 |
| 83 | 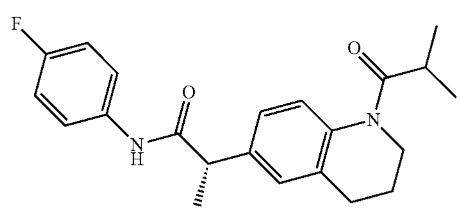 [SMILES: CC(C)C(=O)N1CCCc2cc([C@H](C)C(=O)Nc3ccc(F)cc3)ccc21] | (2S)-N-(4-fluorophenyl)-2-[1-(2-methylpropanoyl)-1,2,3,4-tetrahydroquinolin-6-yl]propanamide | Calc'd 369, found 369 | 9.4 |
| 84 | 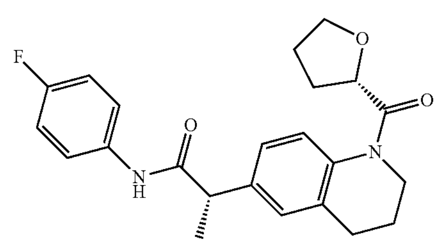 [SMILES: C[C@H](C(=O)Nc1ccc(F)cc1)c1ccc2c(c1)CCCN2C(=O)[C@@H]1CCCO1] | (2S)-N-(4-fluorophenyl)-2-{1-[(2S)-oxolane-2-carbonyl]-1,2,3,4-tetrahydroquinolin-6-yl}propanamide | Calc'd 397, found 397 | 32.3 |
| 85 | 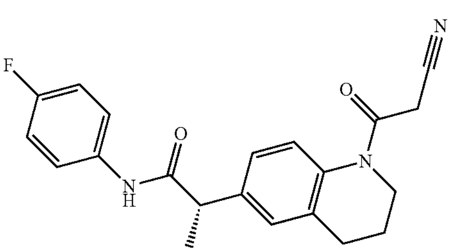 [SMILES: C[C@H](C(=O)Nc1ccc(F)cc1)c1ccc2c(c1)CCCN2C(=O)CC#N] | (2S)-2-[1-(cyanoacetyl)-1,2,3,4-tetrahydroquinolin-6-yl]-N-(4-fluorophenyl)propanamide | Calc'd 366, found 366 | 2535.0 |

-continued

| Ex. # | Structure | Chemical Names | Mass [M + H]+ | Hela IC$_{50}$, nM |
|---|---|---|---|---|
| 86 | 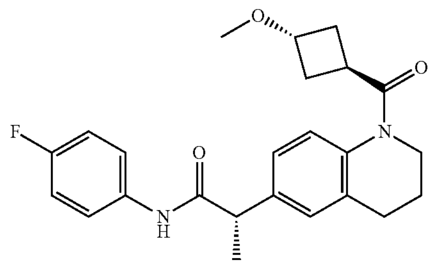 [SMILES: CO[C@H]1C[C@H](C(=O)N2CCCc3cc([C@H](C)C(=O)Nc4ccc(F)cc4)ccc32)C1] | (2S)-N-(4-fluorophenyl)-2-[1-(trans-3-methoxycyclobutane-1-carbonyl)-1,2,3,4-tetrahydroquinolin-6-yl]propanamide | Calc'd 411, found 411 | 17.6 |
| 87 | Isomer 1 | (2S)-N-(4-fluorophenyl)-2-{1-[(2R)-oxane-2-carbonyl]-1,2,3,4-tetrahydroquinolin-6-yl}propanamide | Calc'd 411, found 411 | 2.1 |
| 88 | Isomer 2 | (2S)-N-(4-fluorophenyl)-2-{1-[(2S)-oxane-2-carbonyl]-1,2,3,4-tetrahydroquinolin-6-yl}propanamide | Calc'd 411, found 411 | 3.1 |
| 89 | 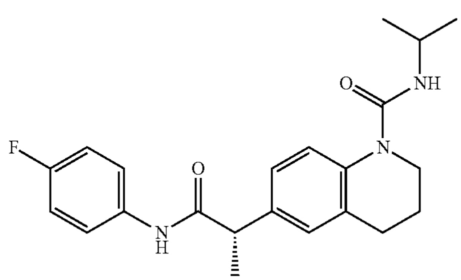 [SMILES: CC(C)NC(=O)N1CCCc2cc([C@H](C)C(=O)Nc3ccc(F)cc3)ccc21] | 6-{(2S)-1-[(4-fluorophenyl)amino]-1-oxopropan-2-yl}-N-(propan-2-yl)-3,4-dihydroquinoline-1(2H)-carboxamide | Calc'd 384, found 384 | 3.2 |
| 90 | 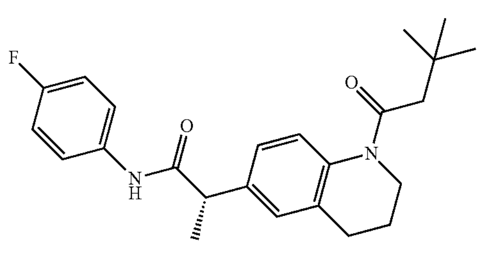 [SMILES: C[C@H](C(=O)Nc1ccc(F)cc1)c1ccc2c(c1)CCCN2C(=O)CC(C)(C)C] | (2S)-2-[1-(3,3-dimethylbutanoyl)-1,2,3,4-tetrahydroquinolin-6-yl]-N-(4-fluorophenyl)propanamide | Calc'd 397, found 397 | 7.0 |

| Ex. # | Structure | Chemical Names | Mass [M + H]+ | Hela IC$_{50}$, nM |
|---|---|---|---|---|
| 91 | 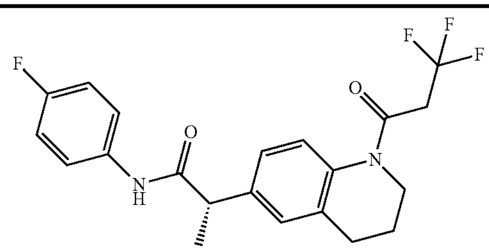 | (2S)-N-(4-fluorophenyl)-2-[1-(3,3,3-trifluoropropanoyl)-1,2,3,4-tetrahydroquinolin-6-yl]propanamide | Calc'd 409, found 409 | 105.1 |

Example 92. N-(1-(1-(1-(3-chlorophenyl)-2-hydroxyethyl)-1,2,3,4-tetrahydroquinolin-6-yl)ethyl)-4-fluorobenzamide

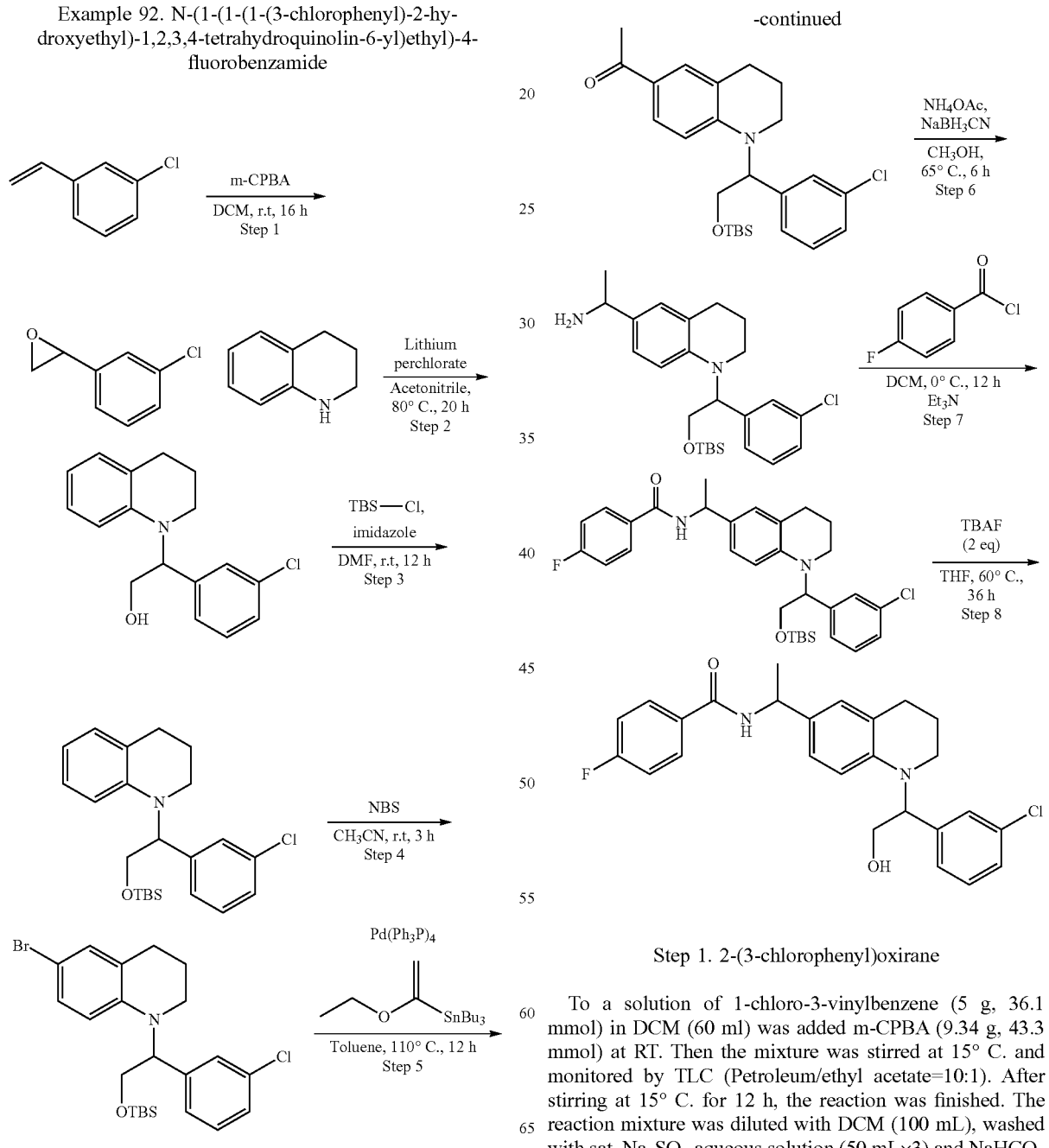

Step 1. 2-(3-chlorophenyl)oxirane

To a solution of 1-chloro-3-vinylbenzene (5 g, 36.1 mmol) in DCM (60 ml) was added m-CPBA (9.34 g, 43.3 mmol) at RT. Then the mixture was stirred at 15° C. and monitored by TLC (Petroleum/ethyl acetate=10:1). After stirring at 15° C. for 12 h, the reaction was finished. The reaction mixture was diluted with DCM (100 mL), washed with sat. Na$_2$SO$_3$ aqueous solution (50 mL×3) and NaHCO$_3$ aqueous solution (50 mL×2), followed by brine (50 mL).

The organic phase was dried over anhydrous sodium sulfate, filtered and concentrated under reduced pressure. The residue was purified by column chromatography (SiO2, Petroleum/ethyl acetate=10:1) to give the title compound as an oil.

Step 2.
2-(3,4-dihydroquinolin-1(2H)-yl)-2-phenylethanol

To a solution of 1, 2, 3, 4-tetrahydroquinoline (2000 mg, 15.02 mmol) in ACN (50 mL) were added 2-(3-chlorophenyl)oxirane (2321 mg, 15.02 mmol), lithium perchlorate (3195 mg, 30.0 mmol) at 15° C. After the addition was finished, the reaction was stirred at 80° C. The reaction was monitored by TLC (Petroleum ether/ethyl acetate=3:1). After stirring at 80° C. for 20 h, the reaction was finished. Then the reaction was diluted with DCM (100 mL), and washed with brine (50 mL). The organic phase was dried over anhydrous sodium sulfate, filtered and concentrated under reduced pressure. The residue was purified by column chromatography (SiO$_2$, Petroleum ether/ethyl acetate=3:1) to give the title compound as an oil. MS (ESI) m/z: 288.0 [M+H+].

Step 3. 6-(1-aminoethyl)-2-benzyl-3,4-dihydroisoquinolin-1(2H)-one

To a solution of 2-(3-chlorophenyl)-2-(3,4-dihydroquinolin-1(2H)-yl)ethanol (1480 mg, 5.14 mmol) in DMF (15 mL) were added 1H-imidazole (700 mg, 10.29 mmol), tert-butylchlorodimethylsilane (853 mg, 5.66 mmol) at 20° C. The mixture was then stirred at the same temperature and the reaction was monitored by TLC (Petroleum.ether/ethyl acetate=5:1). After the reaction was stirred at 20° C. for 12 h, the reaction was finished and then diluted with ethyl acetate (100 mL), and washed with water (100 mL), brine (20 mL). The organic phase was dried over anhydrous sodium sulfate, filtered and concentrated under reduced pressure. The residue was purified by column chromatography (SiO$_2$, Petroleum ether/ethyl acetate=10:1) to give the title compound as an oil. MS (ESI) m/z: 402.3 [M+H$^+$].

Step 4. 6-bromo-1-(2-((tert-butyldimethylsilyl)oxy)-1-(3-chlorophenyl)ethyl)-1,2,3,4-tetrahydroquinoline To a solution of 1-(2-((tert-butyldimethylsilyl)oxy)-1-(3-chlorophenyl)ethyl)-1,2,3,4-tetrahydroquinoline (600 mg, 1.492 mmol) in CH$_3$CN (10 ml) was added NBS (266 mg, 1.492 mmol) at 0° C. After the addition, the mixture was stirred at 20° C. and the reaction was monitored by TLC (Petroleum.ether/ethyl acetate=10:1). After stirring at 20° C. for 3 h, the reaction was found to be complete. The reaction was diluted with DCM (50 mL), and washed with Na$_2$SO$_3$ aqueous solution (20 mL). The organic phase was dried over anhydrous sodium sulfate, filtered and concentrated under reduced pressure to give the title compound as an oil which was used directly in the next step. MS (ESI) m/z: 481.8 [M+H$^+$].

Step 5. 1-(1-(2-((tert-butyldimethylsilyl)oxy)-1-(3-chlorophenyl)ethyl)-1,2,3,4-tetrahydroquinolin-6-yl)ethanone To a solution of 6-bromo-1-(2-((tert-butyldimethylsilyl)oxy)-1-(3-chlorophenyl)ethyl)-1,2,3,4-tetrahydroquinoline (900 mg, 1.871 mmol) in toluene (10 mL) were added tributyl(1-ethoxyvinyl)stannane (1950 mg, 5.40 mmol), Pd(PPh$_3$)$_4$ (216 mg, 0.187 mmol) at 20° C. Then the mixture was stirred at 110° C. and was monitored by LC-MS. After stirring at 110° C. for 12 h, the reaction was cooled to RT and the solvent was removed, the residue was re-dissolved in THF (6 mL), and 3.0 M HCl (2.0 ml, 6.00 mmol) was added at 20° C. After stirring at 20° C. for 2 h, the reaction was found to be complete. The pH of the reaction mixture was adjusted to 8 with aqueous NaHCO$_3$ solution (30 mL) and extracted with DCM (40 mL). The organic layer was washed with brine (10 mL), dried over anhydrous sodium sulfate, filtered and concentrated under reduced pressure. The residue was purified by column chromatography (SiO$_2$, Petroleum ether/ethyl acetate=3:1) to give the title compound as an oil. MS (ESI) m/z: 445.0 [M+H$^+$].

Step 6. (1-(2-((tert-butyldimethylsilyl)oxy)-1-(3-chlorophenyl)ethyl)-1,2,3,4-tetrahydroquinolin-6-yl)methanamine To a solution of 1-(1-(2-((tert-butyldimethylsilyl)oxy)-1-(3-chlorophenyl)ethyl)-1,2,3,4-tetrahydroquinolin-6-yl)ethanone (350 mg, 0.788 mmol) in MeOH (4 mL) were added NH$_4$OAc (122 mg, 1.588 mmol) and NaBH$_3$CN (198 mg, 3.15 mmol) at 20° C. Then the mixture was stirred at 65° C. and was monitored by TLC (Petroleum.ether/ethyl acetate=1:1). After stirring at 65° C. for 6 h, the reaction was complete. The reaction was diluted with DCM (50 mL), washed with sat. NaHCO$_3$ (50 mL) and brine (20 mL). The organic phase was dried over anhydrous sodium sulfate, filtered and concentrated under reduced pressure to give the title compound as an oil which was used directly in the next step. MS (ESI) m/z: 446.0 [M+H$^+$].

Step 7. N-(1-(1-(2-((tert-butyldimethylsilyl)oxy)-1-(3-chlorophenyl)ethyl)-1,2,3,4-tetrahydroquinolin-6-yl)ethyl)-4-fluorobenzamide To a solution of 1-(1-(2-((tert-butyldimethylsilyl)oxy)-1-(4-chlorophenyl)ethyl)-1,2,3,4-tetrahydroquinolin-6-yl)ethanamine (200 mg, 0.449 mmol) and Et3N (0.20 mL, 1.435 mmol) in DCM (8 mL) was added a solution of 4-fluorobenzoyl chloride (107 mg, 0.674 mmol) in DCM (2 mL) at 0° C. After the addition, the mixture was stirred at RT and was monitored by LC-MS and TLC (Petroleum.ether/ethyl acetate=10:1). After stirring at 15° C. for 12 h, the reaction was finished. Then the reaction was diluted with DCM (40 mL), washed with brine (20 mL), dried over anhydrous sodium sulfate, filtered and concentrated under reduced pressure to give the title compound as an oil which was used directly in the next step. MS (ESI) m/z: 568.0 [M+H$^+$].

Step 8. N-(1-(1-(1-(3-chlorophenyl)-2-hydroxyethyl)-1,2,3,4-tetrahydroquinolin-6-yl)ethyl)-4-fluorobenzamide To a solution of N-(1-(1-(2-((tert-butyldimethylsilyl)oxy)-1-(4-chlorophenyl)ethyl)-1,2,3,4-tetrahydroquinolin-6-yl)ethyl)-4-fluorobenzamide (230 mg, 0.405 mmol) in THF (3 mL) was added TBAF (1.0 ml, 1.000 mmol) at 20° C. Then the mixture was stirred at 20° C. and was monitored by TLC (Pet. ether/EtOAc=3:1). After stirring at 20° C. for 36 h, the reaction was finished. The solvent was removed and the residue was purified by pre-HPLC (Column:Phenomenex Synergi C18 150×30 mm×4 um, Condition water (0.1% TFA)-CH$_3$CN Begin B 46 End B 66) to give the title compound as a solid. MS (ESI) m/z: 452.9 [M+H+].

After SFC separation, four chiral isomers were obtained; Column: AS (250 mm×30 mm, 5 um) Condition: 0.1% NH3.H2O IPA, Begin B: 40%, End B: 40%; FlowRate (mL/min): 60; Injections: 120

The compounds in the following table were prepared in a similar manner as Example 92:

| Ex. # | Structure | Chemical Names | Mass [M + H]+ | Hela IC$_{50}$, nM |
|---|---|---|---|---|
| 92 | Isomer 2 | N-(1-(1-1-(3-chlorophenyl)-2-hydroxyethyl)-1,2,3,4-tetrahydroquinolin-6-yl)ethyl)-4-fluorobenzamide | Calc'd 453, found 453 | 6.0 |
| 93 | Isomer 1 | N-(1-(1-1-(3-chlorophenyl)-2-hydroxyethyl)-1,2,3,4-tetrahydroquinolin-6-yl)ethyl)-4-fluorobenzamide | Calc'd 453, found 453 | 5.7 |
| 94 | Isomer 3 | N-(1-(1-1-(3-chlorophenyl)-2-hydroxyethyl)-1,2,3,4-tetrahydroquinolin-6-yl)ethyl)-4-fluorobenzamide | Calc'd 453, found 453 | 236.3 |
| 95 | Isomer 4 | N-(1-(1-1-(3-chlorophenyl)-2-hydroxyethyl)-1,2,3,4-tetrahydroquinolin-6-yl)ethyl)-4-fluorobenzamide | Calc'd 453, found 453 | 544.9 |

Example 96. 1-(1-(cyclopropanecarbonyl)-1,2,3,4-tetrahydroquinolin-6-yl)-N-(5-fluoropyridin-2-yl)cyclobutane-1-carboxamide

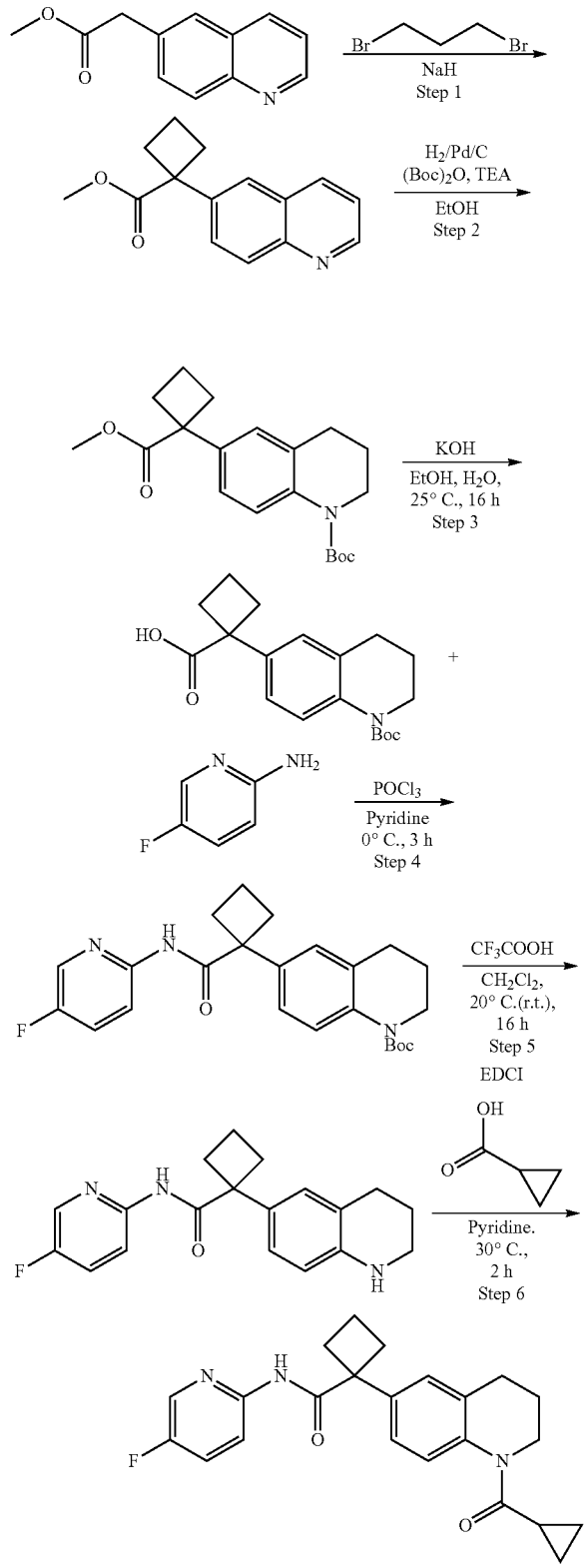

Step 1. methyl-1-(quinolin-6-cyclobutane-1-carboxylate

To a 2-L round bottom flask was added methyl 2-(quinolin-6-yl)acetate (56 g, 278 mmol, 1.0 eq) and 1,3-dibromopropane (56.2 g, 278 mmol, 28.4 mL, 1.0 eq) in DMF (1.1 L) at 5° C. Then NaH (24.5 g, 612 mmol, 60% purity, 2.2 eq) was added in portions at 5° C. and bubble was observed when one-third NaH was added. The reaction suspension was stirred at 18° C. for 2 h. LCMS showed the starting material was consumed completely. The reaction suspension was poured into sat. $NH_4Cl$ (1 L). The mixture was extracted with EtOAc (3×1 L). The combined organic layer was washed with brine (1 L) and was dried with anhydrous $Na_2SO_4$. After filtration, the solvent was removed under vacuum and the crude product was purified using silica gel chromatography (eluted with DCM) to obtain the title compound as an oil. MS (ESI) m/z: 242 [M+H$^+$]

Step 2. tert-butyl 6-(1-(methoxycarbonyl)cyclobutyl)-3,4-dihydroquinoline-1(2H)-carboxylate To a dry hydrogenation flask (1 L) purged with nitrogen was added Pd/C (11 g, 10% purity) and EtOH (45 mL) in the bottle. Then methyl 1-(quinolin-6-yl)cyclobutane-1-carboxylate (36 g, 149 mmol, 1 eq) and $Boc_2O$ (39.1 g, 179 mmol, 41.1 mL, 1.2 eq) were added in the reaction suspension. The suspension was degassed under vacuum and purged with $H_2$ three times. The reaction suspension was stirred at 50° C. under $H_2$ (30 Psi) for 12 h. Additional $Boc_2O$ (9.77 g, 44.8 mmol, 10.3 mL, 0.3 eq) and TEA (7.55 g, 74.6 mmol, 10.4 mL, 0.5 eq) was added in the reaction suspension at 50° C. and the reaction mixture was stirred for additional 2.5 h. The reaction progress was checked using TLC (Petroleum ether: Ethyl acetate=8:1, product Rf=0.63) which showed the starting material was consumed completely. The reaction mixture was filtered through a pad of Celite. The filtrate was concentrated and was purified by silica gel chromatography (Petroleum ether/Ethyl acetate=1:0-20:1) to give the title compound as a solid. MS (ESI) m/z: 346 [M+H$^+$]

Step 3. 1-(1-(tert-butoxcarbonyl)-1,2,3,4-tetrahydroquinolin-6-yl)cyclobutane-1-carboxylic acid To a stirred solution of tert-butyl 6-(1-(methoxycarbonyl)cyclobutyl)-3,4-dihydroquinoline-1(2H)-carboxylate (655 mg, 1.915 mmol) in EtOH (10 mL) and water (5 mL) was added KOH (376 mg, 6.70 mmol) at 15° C. After the addition was finished, the reaction was stirred at 25° C. for 16 h. LCMS showed the reaction was complete. The reaction mixture was neutralized by the addition of aq. HCl (1 N) until pH~6, and extracted by EtOAc (30 mL×3). The organic layers were collected, washed with brine, and dried over $Na_2SO_4$. After filtration, the filtrate was concentrated in vacuo. The residue was purified by silica gel chromatography ($SiO_2$, $CH_2Cl_2$/MeOH=20:1 to 10:1) to give the title compound as a solid. MS (ESI) m/z: 354.2 [M+Na$^+$]

Step 4. tert-butyl 6-(1-((5-fluoropyridin-2-yl)carbamoyl)cyclobutyl)-3,4-dihydroquinoline-1(2H)-carboxylate To a stirred solution of 1-(1-(tert-butoxycarbonyl)-1,2,3,4-tetrahydroquinolin-6-yl)cyclobutane-1-carboxylic acid (200 mg, 0.602 mmol) and 5-fluoropyridin-2-amine (88 mg, 0.782 mmol) in pyridine (5 mL) was added $POCl_3$ (1.131 mL, 12.13 mmol) at 0° C. After the addition was finished, the reaction was stirred at 0° C. The reaction was monitored by LC-MS. After stirring at 0° C. for 3 h, the reaction was finished. The reaction was cooled to RT, quenched by the addition of water (30 mL), and extracted by EtOAc (3×20 mL). The organic layers were collected, washed with brine, and dried over $Na_2SO_4$. After filtration, the filtrate was concentrated in vacuo to give the title compound as an oil which was used in the next step without further purification. MS (ESI) m/z: 426.3 [M+H$^+$]

Step 5. N-(5-fluoropyridin-2-yl)-1-(1,2,3,4-tetrahydroquinolin-6-yl)cyclobutane-1-carboxamide To a stirred solution of tert-butyl 6-(1-((5-fluoropyridin-2-yl)carbamoyl)cyclobutyl)-3,4-dihydroquinoline-1(2H)-carboxylate (140 mg, 0.328 mmol) in DCM (5 mL) was added TFA (0.2 mL, 2.60 mmol) at 20° C. After the addition was finished, the reaction was stirred at 20° C. The reaction was monitored by LC-MS, after stirring at 20° C. for 16 h, the reaction was finished. Then the reaction was quenched by the addition of water (60 mL), and extracted by DCM (3×20 mL). The organic layers were collected, washed with brine, and dried over $Na_2SO_4$. After filtration, the filtrate was concentrated in vacuo to give the title compound as an oil which was used in the next step without further purification. MS (ESI) m/z: 326.1 [M+H+]

Step 6 1-(1-(cyclopropanecarbonyl)-1,2,3,4-tetrahydroquinolin-6-yl)-N-(5-fluoropyridin-2-yl)cyclobutane-1-carboxamide To a stirred solution of N-(5-fluoropyridin-2-yl)-1-(1,2,3,4-tetrahydroquinolin-6-yl)cyclobutane-1-carboxamide (70 mg, 0.214 mmol) in pyridine (3 mL) were added cyclopropanecarboxylic acid (32 mg, 0.372 mmol) and EDCI (123 mg, 0.643 mmol) at 30° C. After the addition was finished, the reaction was stirred at 30° C. and was monitored by LC-MS. The reaction was finished after stirring at 30° C. for 2 h. Then the pH of the reaction mixture was adjusted by adding aq. HCl (6M) until pH~6. The solvent was removed under vacuum, the residue was purified by prep-HPLC (Column Phenomenex Synergi C18 150×30 mm×4 um Condition water (0.225% FA)-$CH_3CN$ Begin B 40 End B 60 Gradient Time (min) 11 100% B Hold Time (min) 2 Flow-Rate (ml/min) 25 Injections 6 followed by lyophilization to give the title compound as a solid. $^1$H NMR (400 MHz, $CD_3OD$) δ 8.12-8.16 (m, 2H), 7.97 (br d, J=7.8 Hz, 1H), 7.55-7.61 (m, 1H), 7.35 (d, J=8.3 Hz, 2H), 3.89-3.93 (m, 2H), 3.06 (t, J=6.8 Hz, 2H), 2.90 (br s, 2H), 2.70 (br d, J=7.0 Hz, 2H), 2.01-2.13 (m, 4H), 1.94 (s, 1H), 1.01-1.05 (m, 2H), 0.90 (dd, J=7.89, 3.07 Hz, 2H); ESI m/z: 395 [M+H$^+$]

The compounds in the following table were prepared in a similar manner as Example 96.

| Ex. # | Structure | Chemical Name | Mass [M + H]+ | Hela IC$_{50}$, nM |
|---|---|---|---|---|
| 96 | 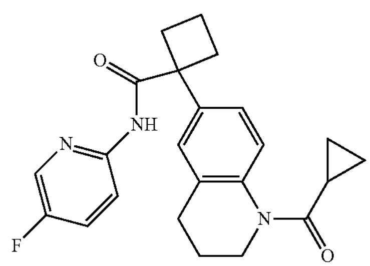 [SMILES: O=C(C1CC1)N1CCCc2cc(C3(C(=O)Nc4ccc(F)cn4)CCC3)ccc21] | 1-[1-(cyclopropanecarbonyl)-1,2,3,4-tetrahydroquinolin-6-yl]-N-(5-fluoropyridin-2-yl)cyclobutane-1-carboxamide | Calc'd 394, found 394 | 6.2 |
| 97 | 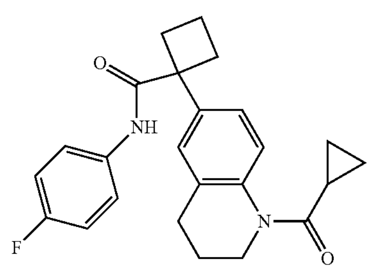 [SMILES: O=C(C1CC1)N1CCCc2cc(C3(C(=O)Nc4ccc(F)cc4)CCC3)ccc21] | 1-[1-(cyclopropanecarbonyl)-1,2,3,4-tetrahydroquinolin-6-yl]-N-(4-fluorophenyl)cyclobutane-1-carboxamide | Calc'd 393, found 393 | 1.7 |
| 98 | 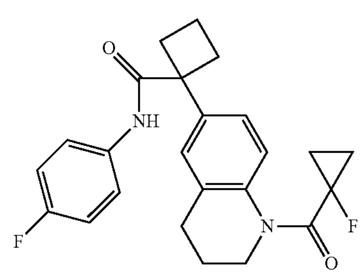 [SMILES: O=C(N1CCCc2cc(C3(C(=O)Nc4ccc(F)cc4)CCC3)ccc21)C1(F)CC1] | 1-[1-(1-fluorocyclopropane-1-carbonyl)-1,2,3,4-tetrahydroquinolin-6-yl]-N-(4-fluorophenyl)cyclobutane-1-carboxamide | Calc'd 411, found 411 | 3.3 |

-continued

| Ex. # | Structure | Chemical Name | Mass [M + H]+ | Hela IC$_{50}$, nM |
|---|---|---|---|---|
| 99 | 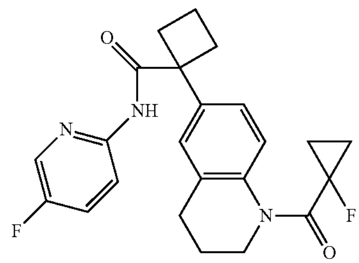 [SMILES: O=C(N1CCCc2cc(C3(C(=O)Nc4ccc(F)cn4)CCC3)ccc21)C1(F)CC1] | 1-[1-(1-fluorocyclopropane-1-carbonyl)-1,2,3,4-tetrahydroquinolin-6-yl]-N-(5-fluoropyridin-2-yl)cyclobutane-1-carboxamide | Calc'd 412, found 412 | 16.8 |
| 100 | 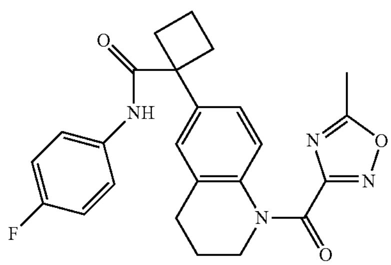 [SMILES: Cc1nc(C(=O)N2CCCc3cc(C4(C(=O)Nc5ccc(F)cc5)CCC4)ccc32)no1] | N-(4-fluorophenyl)-1-[1-(5-methyl-1,2,4-oxadiazole-3-carbonyl)-1,2,3,4-tetrahydroquinolin-6-yl]cyclobutane-1-carboxamide | Calc'd 435, found 435 | 1.2 |
| 101 | 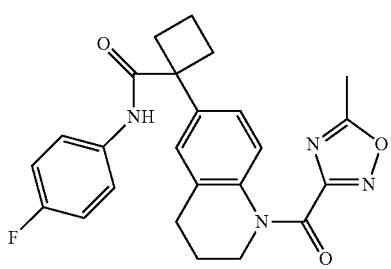 [SMILES: Cc1nc(C(=O)N2CCCc3cc(C4(C(=O)Nc5ccc(F)cc5)CCC4)ccc32)no1] | N-(5-fluoropyridin-2-yl)-1-[1-(5-methyl-1,2,4-oxadiazole-3-carbonyl)-1,2,3,4-tetrahydroquinolin-6-yl]cyclobutane-1-carboxamide | Calc'd 436, found 436 | 1.9 |
| 102 | 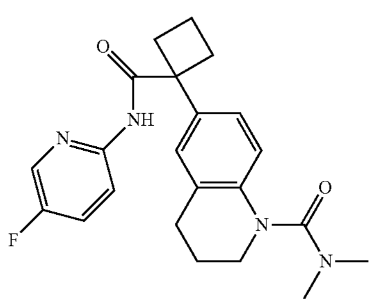 [SMILES: CN(C)C(=O)N1CCCc2cc(C3(C(=O)Nc4ccc(F)cn4)CCC3)ccc21] | 6-{1-[(5-fluoropyridin-2-yl)carbamoyl]cyclobutyl}-N,N-dimethyl-3,4-dihydroquinoline-1(2H)-carboxamide | Calc'd 397, found 397 | 149.3 |
| 103 | 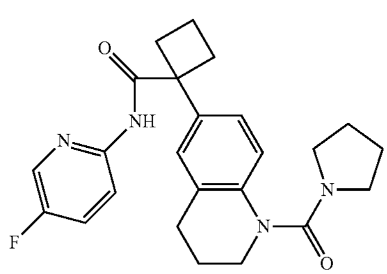 [SMILES: O=C(N1CCCC1)N1CCCc2cc(C3(C(=O)Nc4ccc(F)cn4)CCC3)ccc21] | N-(5-fluoropyridin-2-yl)-1-[1-(pyrrolidine-1-carbonyl)-1,2,3,4-tetrahydroquinolin-6-yl]cyclobutane-1-carboxamide | Calc'd 423, found 423 | 76.7 |

-continued

| Ex. # | Structure | Chemical Name | Mass [M + H]+ | Hela IC$_{50}$, nM |
|---|---|---|---|---|
| 104 | 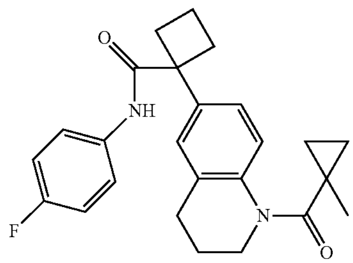 [SMILES: CC1(C(=O)N2CCCc3cc(C4(C(=O)Nc5ccc(F)cc5)CCC4)ccc32)CC1] | N-(4-fluorophenyl)-1-[1-(1-methylcyclopropane-1-carbonyl)-1,2,3,4-tetrahydroquinolin-6-yl]cyclobutane-1-carboxamide | Calc'd 407, found 407 | 3.5 |
| 105 | Isomer 1 | N-(4-fluorophenyl)-1-{1-[(2S)-oxane-2-carbonyl]-1,2,3,4-tetrahydroquinolin-6-yl}cyclobutane-1-carboxamide | Calc'd 437, found 437 | 1.9 |
| 106 | Isomer 2 | N-(4-fluorophenyl)-1-{1-[(2R)-oxane-2-carbonyl]-1,2,3,4-tetrahydroquinolin-6-yl}cyclobutane-1-carboxamide | Calc'd 437, found 437 | 1.2 |
| 107 | 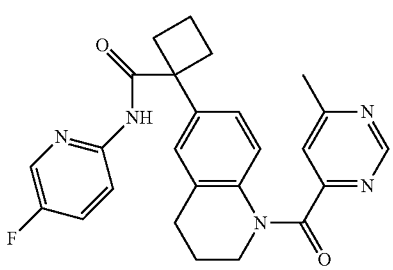 [SMILES: Cc1cc(C(=O)N2CCCc3cc(C4(C(=O)Nc5ccc(F)cn5)CCC4)ccc32)ncn1] | N-(5-fluoropyridin-2-yl)-1-[1-(6-methylpyrimidine-4-carbonyl)-1,2,3,4-tetrahydroquinolin-6-yl]cyclobutane-1-carboxamide | Calc'd 446, found 446 | 12.8 |
| 108 | 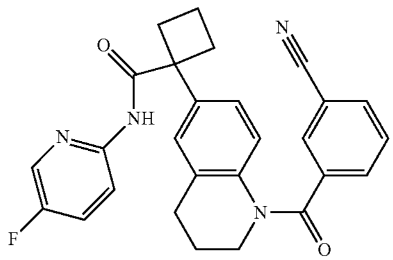 [SMILES: N#Cc1cccc(C(=O)N2CCCc3cc(C4(C(=O)Nc5ccc(F)cn5)CCC4)ccc32)c1] | 1-[1-(3-cyanobenzene-1-carbonyl)-1,2,3,4-tetrahydroquinolin-6-yl]-N-(5-fluoropyridin-2-yl)cyclobutane-1-carboxamide | Calc'd 455, found 455 | 4.9 |

-continued

| Ex. # | Structure | Chemical Name | Mass [M + H]+ | Hela IC$_{50}$, nM |
|---|---|---|---|---|
| 109 | 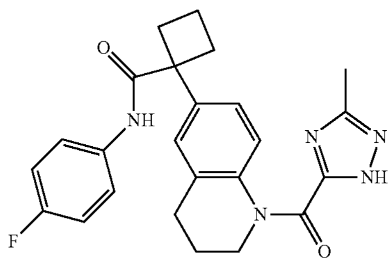 [SMILES: Cc1n[nH]c(C(=O)N2CCCc3cc(C4(C(=O)Nc5ccc(F)cc5)CCC4)ccc32)n1] | N-(4-fluorophenyl)-1-[1-(3-methyl-1H-1,2,4-triazole-5-carbonyl)-1,2,3,4-tetrahydroquinolin-6-yl]cyclobutane-1-carboxamide | Calc'd 434, found 434 | 16.2 |
| 110 | 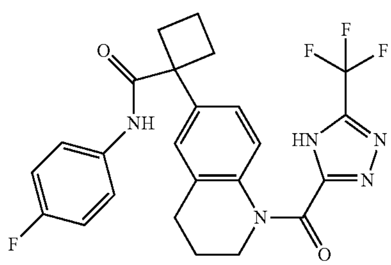 [SMILES: O=C(c1nnc(C(F)(F)F)[nH]1)N1CCCc2cc(C3(C(=O)Nc4ccc(F)cc4)CCC3)ccc21] | N-(4-fluorophenyl)-1-{1-[5-(trifluoromethyl)-4H-1,2,4-triazole-3-carbonyl]-1,2,3,4-tetrahydroquinolin-6-yl}cyclobutane-1-carboxamide | Calc'd 488, found 488 | 247.7 |
| 111 | 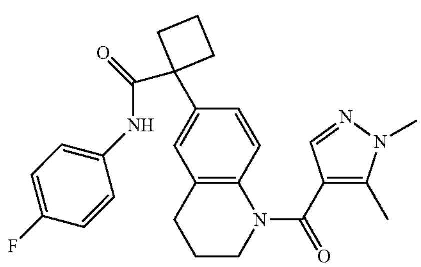 [SMILES: Cc1c(C(=O)N2CCCc3cc(C4(C(=O)Nc5ccc(F)cc5)CCC4)ccc32)cnn1C] | 1-[1-(1,5-dimethyl-1H-pyrazole-4-carbonyl)-1,2,3,4-tetrahydroquinolin-6-yl]-N-(4-fluorophenyl)cyclobutane-1-carboxamide | Calc'd 447, found 447 | 65.5 |
| 112 | 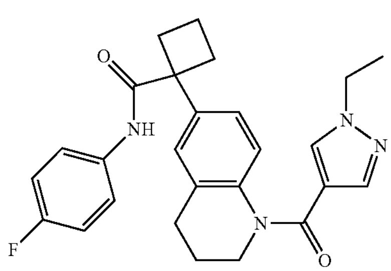 [SMILES: CCn1cc(C(=O)N2CCCc3cc(C4(C(=O)Nc5ccc(F)cc5)CCC4)ccc32)cn1] | 1-[1-(1-ethyl-1H-pyrazole-4-carbonyl)-1,2,3,4-tetrahydroquinolin-6-yl]-N-(4-fluorophenyl)cyclobutane-1-carboxamide | Calc'd 447, found 447 | 2.7 |
| 113 | 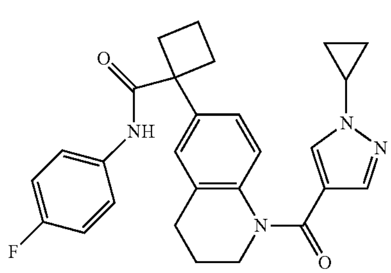 [SMILES: O=C(c1cnn(C2CC2)c1)N1CCCc2cc(C3(C(=O)Nc4ccc(F)cc4)CCC3)ccc21] | 1-[1-(1-cyclopropyl-1H-pyrazole-4-carbonyl)-1,2,3,4-tetrahydroquinolin-6-yl]-N-(4-fluorophenyl)cyclobutane-1-carboxamide | Calc'd 459, found 459 | 65.8 |

-continued

| Ex. # | Structure | Chemical Name | Mass [M + H]+ | Hela IC$_{50}$, nM |
|---|---|---|---|---|
| 114 | 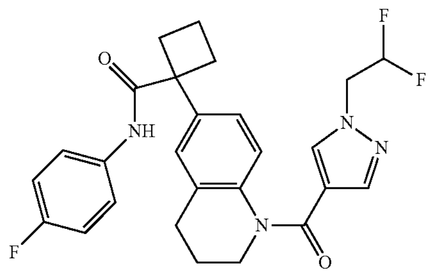 [SMILES: O=C(c1cnn(CC(F)F)c1)N1CCCc2cc(C3(C(=O)Nc4ccc(F)cc4)CCC3)ccc21] | 1-{1-[1-(2,2-difluoroethyl)-1H-pyrazole-4-carbonyl]-1,2,3,4-tetrahydroquinolin-6-yl}-N-(4-fluorophenyl)cyclobutane-1-carboxamide | Calc'd 483, found 483 | 86.1 |
| 115 | 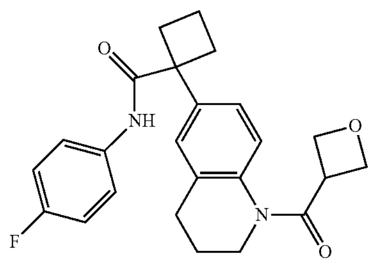 [SMILES: O=C(C1COC1)N1CCCc2cc(C3(C(=O)Nc4ccc(F)cc4)CCC3)ccc21] | N-(4-fluorophenyl)-1-[1-(oxetane-3-carbonyl)-1,2,3,4-tetrahydroquinolin-6-yl]cyclobutane-1-carboxamide | Calc'd 409, found 409 | 20.0 |
| 116 | 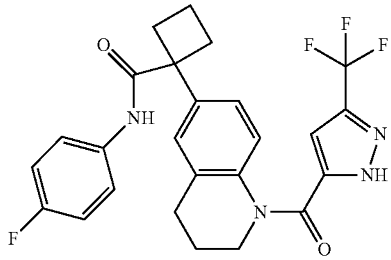 [SMILES: O=C(c1cc(C(F)(F)F)n[nH]1)N1CCCc2cc(C3(C(=O)Nc4ccc(F)cc4)CCC3)ccc21] | N-(4-fluorophenyl)-1-{1-[3-(trifluoromethyl)-1H-pyrazole-5-carbonyl]-1,2,3,4-tetrahydroquinolin-6-yl}cyclobutane-1-carboxamide | Calc'd 487, found 487 | 51.4 |
| 117 | 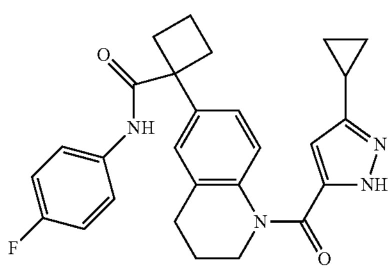 [SMILES: O=C(c1cc(C2CC2)n[nH]1)N1CCCc2cc(C3(C(=O)Nc4ccc(F)cc4)CCC3)ccc21] | 1-[1-(3-cyclopropyl-1H-pyrazole-5-carbonyl)-1,2,3,4-tetrahydroquinolin-6-yl]-N-(4-fluorophenyl)cyclobutane-1-carboxamide | Calc'd 459, found 459 | 17.7 |
| 118 | 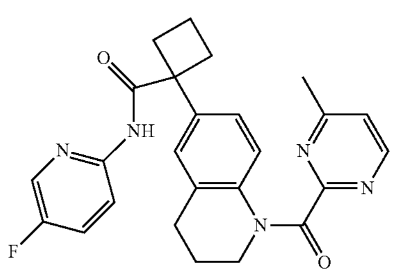 [SMILES: Cc1ccnc(C(=O)N2CCCc3cc(C4(C(=O)Nc5ccc(F)cn5)CCC4)ccc32)n1] | N-(5-fluoropyridin-2-yl)-1-[1-(4-methylpyrimidine-2-carbonyl)-1,2,3,4-tetrahydroquinolin-6-yl]cyclobutane-1-carboxamide | Calc'd 446, found 446 | 1.5 |

-continued

| Ex. # | Structure | Chemical Name | Mass [M + H]+ | Hela IC$_{50}$, nM |
|---|---|---|---|---|
| 119 | 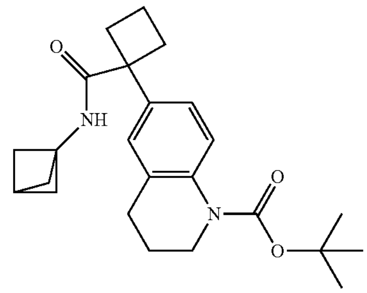 [SMILES: CC(C)(C)OC(=O)N1CCCc2cc(C3(C(=O)NC45CC(C4)C5)CCC3)ccc21] | tert-butyl 6-{1-[(bicyclo[1.1.1]pentan-1-yl)carbamoyl]cyclobutyl}-3,4-dihydroquinoline-1(2H)-carboxylate | Calc'd 397, found 397 | 87.6 |
| 120 | 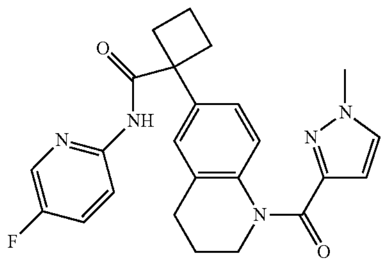 [SMILES: Cn1ccc(C(=O)N2CCCc3cc(C4(C(=O)Nc5ccc(F)cn5)CCC4)ccc32)n1] | N-(5-fluoropyridin-2-yl)-1-[1-(1-methyl-1H-pyrazole-3-carbonyl)-1,2,3,4-tetrahydroquinolin-6-yl]cyclobutane-1-carboxamide | Calc'd 434, found 434 | 1.4 |
| 121 | 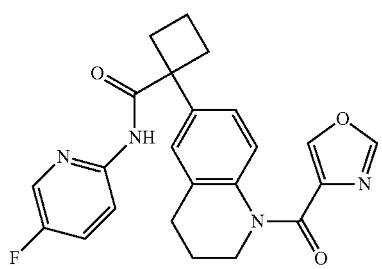 [SMILES: O=C(c1cocn1)N1CCCc2cc(C3(C(=O)Nc4ccc(F)cn4)CCC3)ccc21] | N-(5-fluoropyridin-2-yl)-1-[1-(1,3-oxazole-4-carbonyl)-1,2,3,4-tetrahydroquinolin-6-yl]cyclobutane-1-carboxamide | Calc'd 421, found 421 | 4.1 |
| 122 | 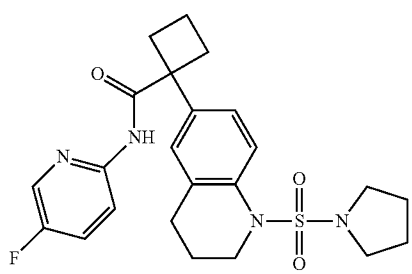 [SMILES: O=C(Nc1ccc(F)cn1)C1(c2ccc3c(c2)CCCN3S(=O)(=O)N2CCCC2)CCC1] | N-(5-fluoropyridin-2-yl)-1-{1-[(pyrrolidin-1-yl)sulfonyl]-1,2,3,4-tetrahydroquinolin-6-yl}cyclobutane-1-carboxamide | Calc'd 459, found 459 | 67.1 |
| 123 | 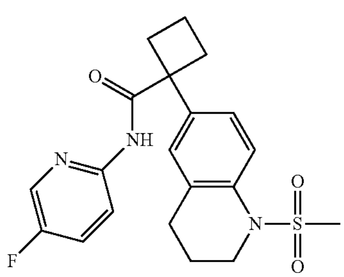 [SMILES: CS(=O)(=O)N1CCCc2cc(C3(C(=O)Nc4ccc(F)cn4)CCC3)ccc21] | N-(5-fluoropyridin-2-yl)-1-[1-(methylsulfonyl)-1,2,3,4-tetrahydroquinolin-6-yl]cyclobutane-1-carboxamide | Calc'd 404, found 404 | 34.1 |

| Ex. # | Structure | Chemical Name | Mass [M + H]+ | Hela IC$_{50}$, nM |
|---|---|---|---|---|
| 124 | 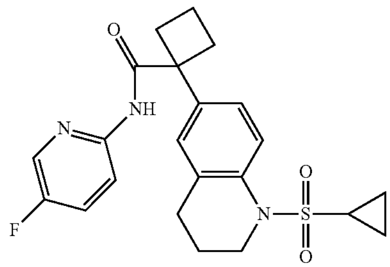 [SMILES: O=C(Nc1ccc(F)cn1)C1(c2ccc3c(c2)CCCN3S(=O)(=O)C2CC2)CCC1] | 1-[1-(cyclopropylsulfonyl)-1,2,3,4-tetrahydroquinolin-6-yl]-N-(5-fluoropyridin-2-yl)cyclobutane-1-carboxamide | Calc'd 430, found 430 | 26.2 |

Example 125. 4-chloro-N-(1-(5-(cyclopropanecarbonyl)-5,6,7,8-tetrahydro-1,5-naphthyridin-2-yl)ethyl)benzamide

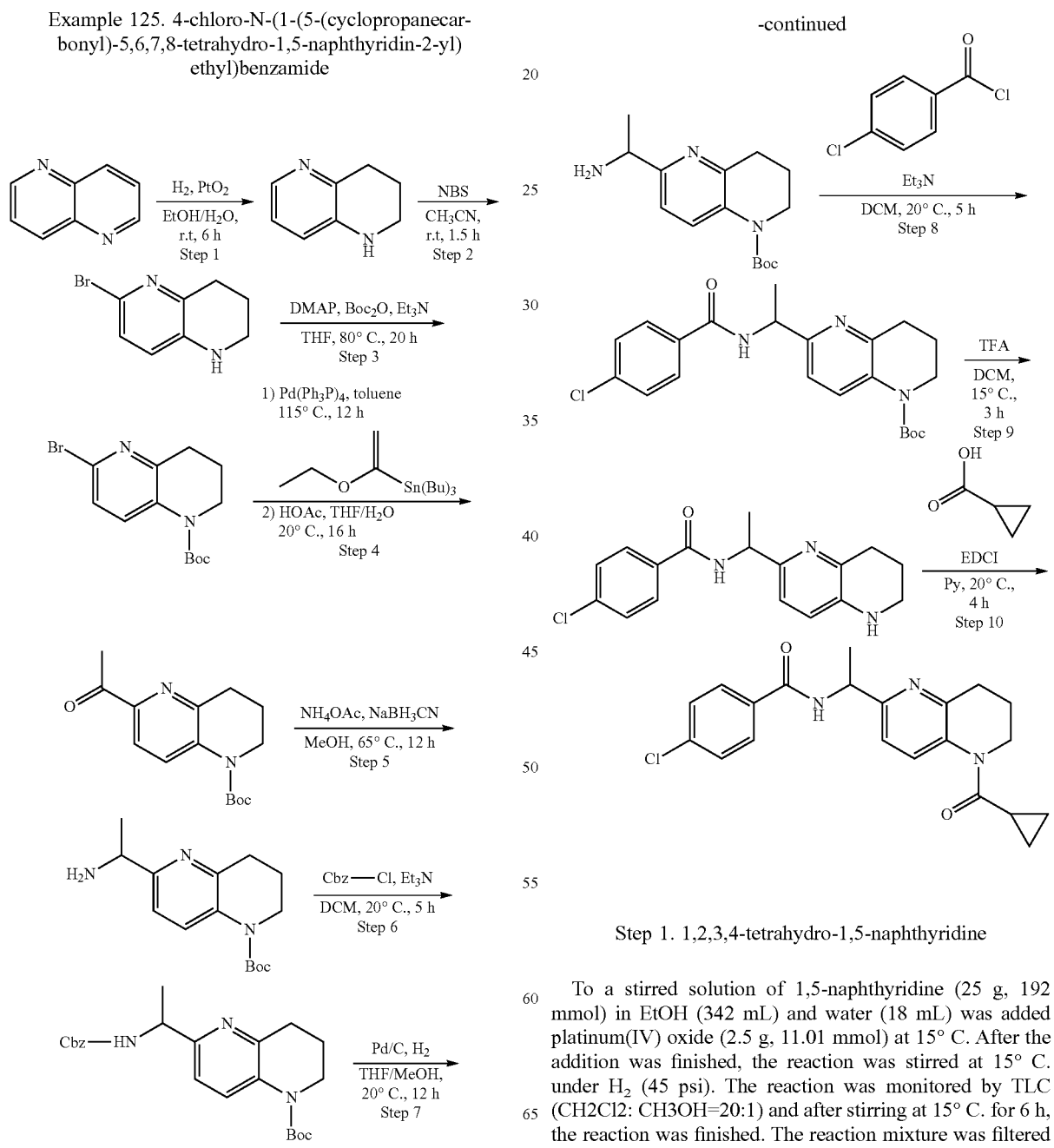

Step 1. 1,2,3,4-tetrahydro-1,5-naphthyridine

To a stirred solution of 1,5-naphthyridine (25 g, 192 mmol) in EtOH (342 mL) and water (18 mL) was added platinum(IV) oxide (2.5 g, 11.01 mmol) at 15° C. After the addition was finished, the reaction was stirred at 15° C. under H$_2$ (45 psi). The reaction was monitored by TLC (CH2Cl2: CH3OH=20:1) and after stirring at 15° C. for 6 h, the reaction was finished. The reaction mixture was filtered through a pad of Celite, and washed with methanol (200 mL). The filtrate was concentrated under reduced pressure to give the title compound as a solid.

Step 2.
6-bromo-1,2,3,4-tetrahydro-1,5-naphthyridine

To a solution of 1,2,3,4-tetrahydro-1,5-naphthyridine (15 g, 112 mmol) in acetonitrile (150 mL) was added NBS (20.10 g, 113 mmol) at 0° C. After the addition was finished, the reaction was stirred at RT and monitored by TLC (pure EtOAc). After stirring at 15° C. for 1.5 h, the reaction was finished. The reaction mixture was concentrated under reduced pressure. The residue was diluted with DCM (200 mL), and washed with sat. $Na_2SO_3$ aqueous solution (50 mL×2). The organic layers was collected and dried over anhydrous sodium sulfate, filtered and concentrated under reduced pressure. The residue was purified by silica gel column chromatography using (Petroleum ether/ethyl acetate=100:1-4:1 as eluent) to give the title compound as a solid.

Step 3. tert-butyl 6-bromo-3,4-dihydro-1,5-naphthyridine-1(2H)-carboxylate

To a stirred solution of 6-bromo-1,2,3,4-tetrahydro-1,5-naphthyridine (20 g, 94 mmol) in THF (60 mL) was added $Et_3N$ (39.2 mL, 282 mmol), DMAP (3.33 g, 27.2 mmol) and $Boc_2O$ (43.5 mL, 188 mmol) at 15° C. After the addition was finished, the reaction was stirred at 80° C. and monitored by TLC (Pet. ether/EtOAc=5:1). After stirring at 80° C. for 8 h, the other batch of $Boc_2O$ (43.5 mL, 188 mmol) was added at 80° C., and after stirring at 80° C. for additional 12 h, the reaction was finished. The mixture was concentrated under reduced pressure. The residue was purified by silica gel column chromatography using (Petroleum ether/ethyl acetate=100:1-20:1 as eluent) to give the title compound as a solid.

Step 4. tert-butyl 6-acetyl-3,4-dihydro-1,5-naphthyridine-1(2H)-carboxylate

To a solution of tert-butyl 6-bromo-3,4-dihydro-1,5-naphthyridine-1(2H)-carboxylate (20 g, 63.9 mmol) in toluene (300 mL) were added tributyl(1-ethoxyvinyl)stannane (38.49 g, 107 mmol) and $Pd(PPh_3)_4$ (7.38 g, 6.39 mmol) at 20° C. After the addition was finished, the mixture was stirred at 115° C. for 12 h, then cooled to 20° C., then KF (344 mL, 1721 mmol) (5 M in water) was added. After the reaction mixture was stirred at 20° C. for 2 h, the salt was filtered off and the filtrate was extracted with EtOAc (400 mL×2), the organic layer was concentrated under reduced pressure, the residue was re-dissolved in THF (50 mL) and water (25 mL) and acetic acid (25 mL, 437 mmol) was added at 20° C. After the addition was finished, the reaction was stirred at 20° C. The reaction was monitored by TLC (Pet. ether/EtOAc=5:1, Rf=0.4) and after stirring at 20° C. for 16 h, the reaction was finished. The mixture was quenched with water (200 mL), extracted with EtOAc (300 mL×2), and the organic layers were concentrated under reduced pressure. The residue was purified by silica gel column chromatography using (Petroleum ether/ethyl acetate=100:1-5:1 as eluent) to give the title compound as a solid.

Step 5. tert-butyl 6-(1-aminoethyl)-3,4-dihydro-1,5-naphthyridine-1(2H)-carboxylate To a stirred solution of tert-butyl 6-acetyl-3,4-dihydro-1,5-naphthyridine-1(2H)-carboxylate (5 g, 18.09 mmol) in MeOH (25 mL) was added $NH_4OAc$ (16.74 g, 217 mmol) at 20° C. After the addition was finished, the reaction was stirred at 20° C. for 1h and to the mixture was added NaBH3CN (4.55 g, 72.4 mmol) at 20° C. After the addition, the reaction was stirred at 65° C. and monitored by TLC (pet. ether/EtOAc=5:1). The reaction was complete after stirring at 65° C. for 12 h. The mixture was neutralized by $NaHCO_3$ to pH=8, and diluted with water (100 mL), extracted with $CH_2Cl_2$ (100 mL×2), the organic layer was washed with brine (ca. 30 mL), dried over $Na_2SO_4$, and concentrated under reduced pressure. The residue was purified by silica gel column chromatography using ($CH_2Cl_2$/MeOH=100:1-1:1 as eluent) to give the title compound as an oil. MS (ESI) m/z: 278.2 [M+H+].

Step 6. tert-butyl 6-(1-(((benzyloxy)carbonyl)amino)ethyl)-3,4-dihydro-1,5-naphthyridine-1(2H)-carboxylate To a stirred solution of tert-butyl 6-(1-aminoethyl)-3,4-dihydro-1,5-naphthyridine-1(2H)-carboxylate (12.5 g, 45.1 mmol) in DCM (125 mL) was added $Et_3N$ (18 mL, 129 mmol) at 20° C., then to the mixture was added Cbz-Cl (9 mL, 63.0 mmol) at 0° C. After the addition, the reaction was stirred at 20° C. and was monitored by TLC ($CH_2Cl_2$/MeOH=10:1, Rf=0.9). After stirring at 20° C. for 5 h, the reaction was finished. The mixture was diluted with water (150 mL), extracted with DCM (150 mL×2). The organic layer was washed with brine (ca. 130 mL), dried over $Na_2SO_4$, and concentrated under reduced pressure. The residue was purified by silica gel column chromatography using (Petroleum ether/EtOAc=100:1-5:1 as eluent) to give the title compound as an oil. MS (ESI) m/z: 412.2 [M+H+]

This intermediate was separated under following conditions. All final compounds were made using material collected under peak 1 unless specified under comments field.

Column: AS (250 mm×50 mm×10 um); Mobile phase: Supercritical CO2/EtOH (0.1% NH3.H2O)=65/35; Flow rate: 200 mL/min; Column Temp: 38° C.; Nozzle Pressure: 100Bar; Nozzle Temp: 60° C.; Evaporator Temp: 20° C.; Trimmer Temp: 25° C.; Wavelength: 220 nm Peak 1: ESI MS m/z: 412.2 [M+H+]. 1H NMR (400 MHz, CDCl3) δ 8.01 (br d, J=8.3 Hz, 1H), 7.29-7.41 (m, 5H), 7.01 (br d, J=8.3 Hz, 1H), 6.14 (br d, J=6.6 Hz, 1H), 5.07-5.17 (m, 2H), 4.85 (br t, J=6.8 Hz, 1H), 3.65-3.80 (m, 2H), 2.92 (t, J=6.6 Hz, 2H), 1.95-2.04 (m, 2H), 1.53 (s, 9H), 1.45 (d, J=7.0 Hz, 3H).

Peak 2: ESI MS m/z: 412.7 [M+H+]. 1H NMR (400 MHz, $CDCl_3$), δ 8.00 (br d, J=7.0 Hz, 1H), 7.28-7.40 (m, 5H), 7.00 (br d, J=8.8 Hz, 1H), 6.12 (br s, 1H), 5.07-5.15 (m, 2H), 4.84 (br t, J=6.8 Hz, 1H), 3.64-3.78 (m, 2H), 2.91 (t, J=6.6 Hz, 2H), 1.94-2.02 (m, 2H), 1.52 (s, 9H), 1.44 (br d, J=6.6 Hz, 3H).

Step 7. tert-butyl 6-(1-aminoethyl)-3,4-dihydro-1,5-naphthyridine-1(2H)-carboxylate To a stirred solution of tert-butyl 6-(1-(((benzyloxy)carbonyl)amino)ethyl)-3,4-dihydro-1,5-naphthyridine-1(2H)-carboxylate (1 g, 2.430 mmol) in THF (10 mL) and MeOH (10 mL) was added Pd/C (0.259 g, 0.243 mmol) (10%) at 20° C. After the addition, the reaction was stirred at 20° C. under $H_2$ (15 psi) and was monitored by TLC (Petroleum ether/EtOAc=1:1). The reaction was finished after stirring at 20° C. for 12 h. The mixture was filtered and the filtrate was concentrated under reduced pressure to give the title compound as an oil. MS (ESI) m/z: 278.2 [M+H⁺]

Step 8. tert-butyl 6-(1-(4-chlorobenzamido)ethyl)-3,4-dihydro-1,5-naphthyridine-1(2H)-carboxylate To a stirred solution of tert-butyl 6-(1-aminoethyl)-3,4-dihydro-1,5-naphthyridine-1(2H)-carboxylate (120 mg, 0.433 mmol) in DCM (2 mL) was added Et₃N (0.15 mL, 1.076 mmol) at 20° C. After stirring for 15 min, 4-chlorobenzoyl chloride (98 mg, 0.562 mmol) was added at 0° C. under nitrogen. After the addition, the reaction was stirred at 20° C. under nitrogen. The reaction was monitored by TLC (Petroleum ether/EtOAc=1:1) and the reaction was finished. After stirring at 20° C. for 5 h, to the mixture was added NaHCO₃ to adjust pH 7-8, diluted with water (15 mL), and extracted with DCM (10 mL×2). The organic layer was washed with brine (ca. 10 mL), dried over Na₂SO₄, and concentrated under reduced pressure. The residue was purified by silica gel column chromatography using (Petroleum ether/ethyl acetate=10:1-3:1 as eluent) to give the title compound as an oil. MS (ESI) m/z: 416.2 [M+H⁺].

Step 9. 4-chloro-N-(1-(5,6,7,8-tetrahydro-1,5-naphthyridin-2-yl)ethyl)benzamide

To a stirred solution of tert-butyl 6-(1-(4-chlorobenzamido)ethyl)-3,4-dihydro-1,5-naphthyridine-1(2H)-carboxylate (133 mg, 0.320 mmol) in DCM (3 mL) was added TFA (0.5 mL, 6.49 mmol) at 15° C. After the addition, the reaction was stirred at 15° C. and was monitored by LC-MS. The reaction was complete after stirring at 15° C. for 3 h. Then the mixture was concentrated under reduced pressure to give the title compound as an oil. MS (ESI) m/z: 316.1 [M+H⁺];

Step 10. 4-chloro-N-(1-(5-(cyclopropanecarbonyl)-5,6,7,8-tetrahydro-1,5-naphthyridin-2-yl)ethyl)benzamide To a stirred solution of 4-chloro-N-(1-(5,6,7,8-tetrahydro-1,5-naphthyridin-2-yl)ethyl)benzamide (100 mg, 0.317 mmol) in pyridine (2 mL) was added cyclopropanecarboxylic acid (36 mg, 0.418 mmol) and EDCI (182 mg, 0.950 mmol) at 20° C. After the addition, the reaction was stirred at 20° C. and was monitored by LC-MS. The reaction was complete after stirring at 20° C. for 4 h. Water (10 mL) was added and extracted by EtOAc (15 mL×2), the organic layers were collected, washed with brine (10 mL), and dried over Na₂SO₄. The mixture was filtered and the filtrate was concentrated in vacuo. The residue was purified by reversed phase HPLC with Agela ASB 150×25 mm×5 um using water (0.1% TFA)-CH₃CN as eluents (Mobile phase A water (0.1% TFA), Mobile phase B acetonitrile, Detection wavelength 220 nm) and concentration to give the title compound as an oil. ¹H NMR (400 MHz, CD3OD), δ 8.50 (br s, 1H), 7.88 (d, J=8.6 Hz, 2H), 7.59 (d, J=9.1 Hz, 1H), 7.51 (d, J=8.6 Hz, 2H), 5.25 (q, J=7.0 Hz, 1H), 4.03 (t, J=6.1 Hz, 2H), 3.09-3.21 (m, 2H), 2.13-2.20 (m, 2H), 2.03-2.10 (m, 1H), 1.66 (d, J=7.1 Hz, 3H), 0.92-1.10 (m, 4H). MS (ESI) m/z: 284.2 [M+H⁺]

The compounds in the following table were prepared in a similar manner as Example 125. Also, unless a chiral separation method is mentioned, all compounds were made from peak 1 material made in Step G.

| Ex. # | Structure | Chemical Name | Mass [M + H⁺] | Hela IC₅₀, nM |
|---|---|---|---|---|
| 125 | 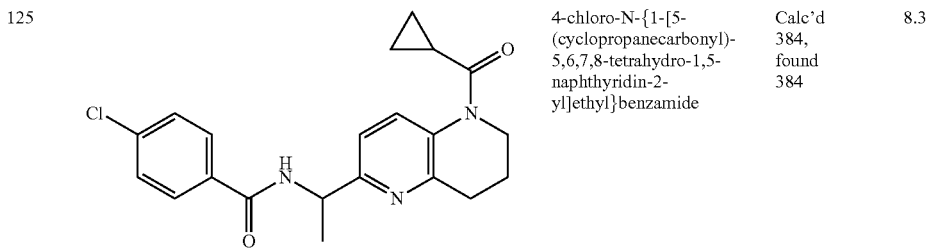<br>Isomer 1 | 4-chloro-N-{1-[5-(cyclopropanecarbonyl)-5,6,7,8-tetrahydro-1,5-naphthyridin-2-yl]ethyl}benzamide | Calc'd 384, found 384 | 8.3 |
| 126 | 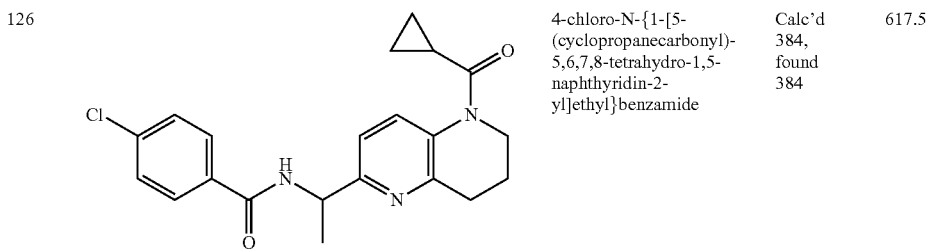<br>Isomer 2 | 4-chloro-N-{1-[5-(cyclopropanecarbonyl)-5,6,7,8-tetrahydro-1,5-naphthyridin-2-yl]ethyl}benzamide | Calc'd 384, found 384 | 617.5 |

-continued

| Ex. # | Structure | Chemical Name | Mass [M + H⁺] | Hela IC$_{50}$, nM |
|---|---|---|---|---|
| 127 | Racemic | 4-chloro-N-{1-[5-(3-chlorobenzene-1-carbonyl)-5,6,7,8-tetrahydro-1,5-naphthyridin-2-yl]ethyl}benzamide | Calc'd 454, found 454 | 4.6 |
| 128 | Isomer 1 | 4-chloro-N-{1-[5-(3-chlorobenzene-1-carbonyl)-5,6,7,8-tetrahydro-1,5-naphthyridin-2-yl]ethyl}benzamide | Calc'd 454, found 454 | 1.3 |
| 129 | Isomer 2 | 4-chloro-N-{1-[5-(3-chlorobenzene-1-carbonyl)-5,6,7,8-tetrahydro-1,5-naphthyridin-2-yl]ethyl}benzamide | Calc'd 454, found 454 | 15.4 |
| 130 | 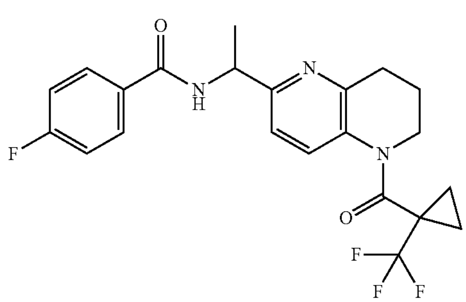 [SMILES: CC(NC(=O)c1ccc(F)cc1)c1ccc2c(n1)CCCN2C(=O)C1(C(F)(F)F)CC1] | 4-fluoro-N-(1-{5-[1-(trifluoromethyl)cyclopropane-1-carbonyl]-5,6,7,8-tetrahydro-1,5-naphthyridin-2-yl}ethyl)benzamide | Calc'd 436, found 436 | 20.1 |
| 131 | 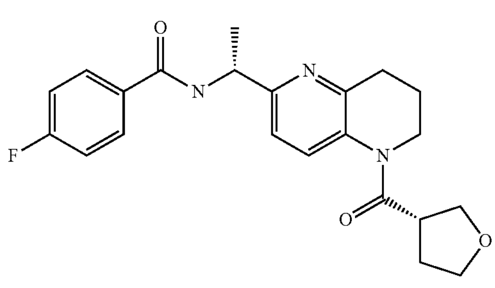 [SMILES: C[C@@H](NC(=O)c1ccc(F)cc1)c1ccc2c(n1)CCCN2C(=O)[C@H]1CCOC1] | 4-fluoro-N-((R)-1-(5-((S)-tetrahydrofuran-3-carbonyl)-5,6,7,8-tetrahydro-1,5-naphthyridin-2-yl)ethyl)benzamide | Calc'd 398, found 398 | 356.0 |

| Ex. # | Structure | Chemical Name | Mass [M + H⁺] | Hela IC$_{50}$, nM |
|---|---|---|---|---|
| 132 | 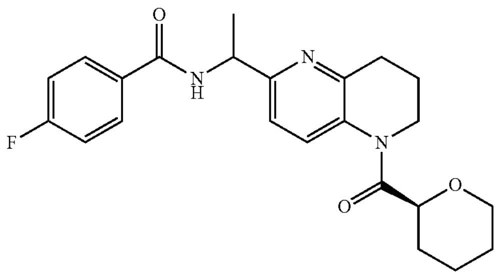 [SMILES: CC(NC(=O)c1ccc(F)cc1)c1ccc2c(n1)CCCN2C(=O)[C@@H]1CCCCO1] | 4-fluoro-N-(1-(5-((S)-tetrahydro-2H-pyran-2-carbonyl)-5,6,7,8-tetrahydro-1,5-naphthyridin-2-yl)ethyl)benzamide | Calc'd 412, found 412 | 48.7 |
| 133 | 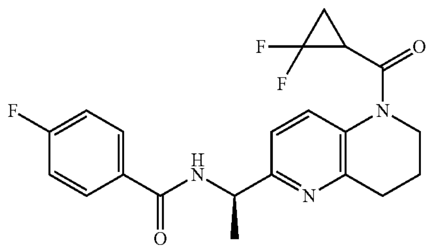 [SMILES: C[C@@H](NC(=O)c1ccc(F)cc1)c1ccc2c(n1)CCCN2C(=O)C1CC1(F)F] | N-{(1R)-1-[5-(2,2-difluorocyclopropane-1-carbonyl)-5,6,7,8-tetrahydro-1,5-naphthyridin-2-yl]ethyl}-4-fluorobenzamide | Calc'd 404, found 404 | 63.6 |
| 134 | Isomer 1 | N-[(1R)-1-{5-[(1R)-2,2-difluorocyclopropane-1-carbonyl]-5,6,7,8-tetrahydro-1,5-naphthyridin-2-yl}ethyl]-4-fluorobenzamide | Calc'd 404, found 404 | 24.0 |
| 135 | Isomer 2 | N-[(1R)-1-{5-[(1S)-2,2-difluorocyclopropane-1-carbonyl]-5,6,7,8-tetrahydro-1,5-naphthyridin-2-yl}ethyl]-4-fluorobenzamide | Calc'd 404, found 404 | 414.2 |
| 136 | Racemic | 4-fluoro-N-{1-[5-(2-methyloxane-2-carbonyl)-5,6,7,8-tetrahydro-1,5-naphthyridin-2-yl]ethyl}benzamide | Calc'd 426, found 426 | 540.2 |

| Ex. # | Structure | Chemical Name | Mass [M + H⁺] | Hela IC₅₀, nM |
|---|---|---|---|---|
| 137 | 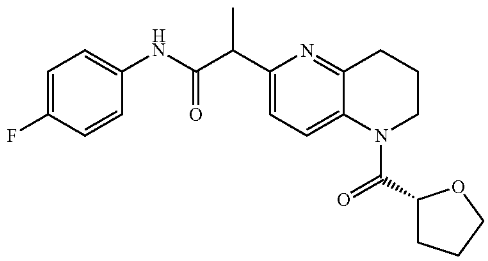 [SMILES: CC(C(=O)Nc1ccc(F)cc1)c1ccc2c(n1)CCCN2C(=O)[C@H]1CCCO1] | N-(4-fluorophenyl)-2-(5-((R)-tetrahydrofuran-2-carbonyl)-5,6,7,8-tetrahydro-1,5-naphthyridin-2-yl)propanamide | Calc'd 398, found 398 | 12.0 |
| 138 | 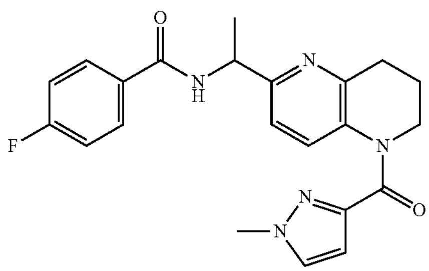 [SMILES: CC(NC(=O)c1ccc(F)cc1)c1ccc2c(n1)CCCN2C(=O)c1ccn(C)n1] | 4-fluoro-N-{1-[5-(1-methyl-1H-pyrazole-3-carbonyl)-5,6,7,8-tetrahydro-1,5-naphthyridin-2-yl]ethyl}benzamide | Calc'd 408, found 408 | 6.3 |
| 139 | Isomer 1 | 4-fluoro-N-(1-{5-[(2S)-2-methyloxane-2-carbonyl]-5,6,7,8-tetrahydro-1,5-naphthyridin-2-yl}ethyl)benzamide | Calc'd 426, found 426 | 348.0 |
| 140 | Isomer 2 | 4-fluoro-N-(1-{5-[(2R)-2-methyloxane-2-carbonyl]-5,6,7,8-tetrahydro-1,5-naphthyridin-2-yl}ethyl)benzamide | Calc'd 426, found 426 | 1616.0 |
| 141 | 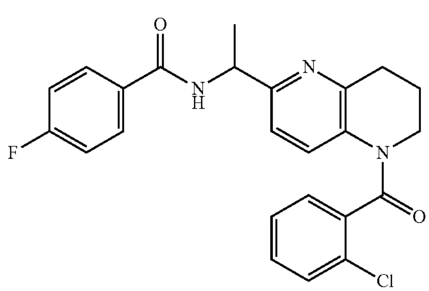 [SMILES: CC(NC(=O)c1ccc(F)cc1)c1ccc2c(n1)CCCN2C(=O)c1ccccc1Cl] | N-{1-[5-(2-chlorobenzene-1-carbonyl)-5,6,7,8-tetrahydro-1,5-naphthyridin-2-yl]ethyl}-4-fluorobenzamide | Calc'd 438, found 438 | 1.7 |

-continued

| Ex. # | Structure | Chemical Name | Mass [M + H⁺] | Hela IC$_{50}$, nM |
|---|---|---|---|---|
| 142 | 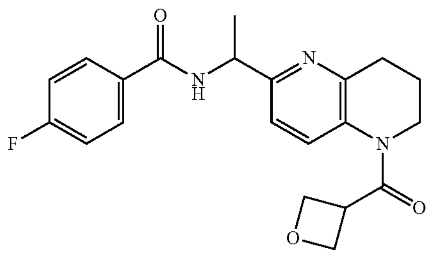 [SMILES: CC(NC(=O)c1ccc(F)cc1)c1ccc2c(n1)CCCN2C(=O)C1COC1] | 4-fluoro-N-{1-[5-(oxetane-3-carbonyl)-5,6,7,8-tetrahydro-1,5-naphthyridin-2-yl]ethyl}benzamide | Calc'd 384, found 384 | 1542.0 |
| 143 | 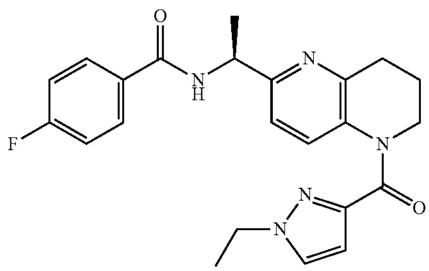 [SMILES: CCn1ccc(C(=O)N2CCCc3nc([C@H](C)NC(=O)c4ccc(F)cc4)ccc32)n1] | N-{(1R)-1-[5-(1-ethyl-1H-pyrazole-3-carbonyl)-5,6,7,8-tetrahydro-1,5-naphthyridin-2-yl]ethyl}-4-fluorobenzamide | Calc'd 422, found 422 | 11.5 |
| 144 | 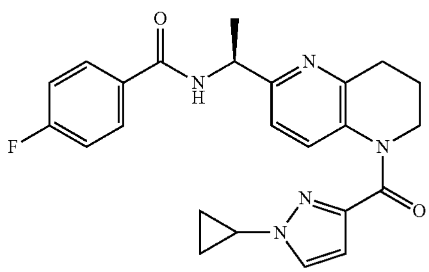 [SMILES: C[C@H](NC(=O)c1ccc(F)cc1)c1ccc2c(n1)CCCN2C(=O)c1ccn(C2CC2)n1] | N-{(1R)-1-[5-(1-cyclopropyl-1H-pyrazole-3-carbonyl)-5,6,7,8-tetrahydro-1,5-naphthyridin-2-yl]ethyl}-4-fluorobenzamide | Calc'd 434, found 434 | 18.1 |
| 145 | 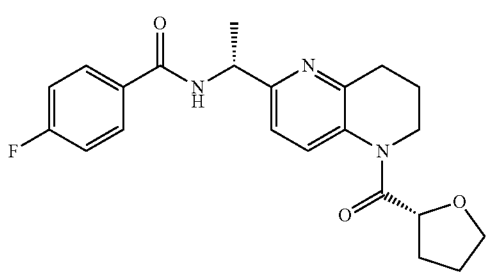 [SMILES: C[C@@H](NC(=O)c1ccc(F)cc1)c1ccc2c(n1)CCCN2C(=O)[C@H]1CCCO1] | 4-fluoro-N-[(1R)-1-{5-[(2R)-oxolane-2-carbonyl]-5,6,7,8-tetrahydro-1,5-naphthyridin-2-yl}ethyl]benzamide | Calc'd 398, found 398 | 8.0 |
| 146 | 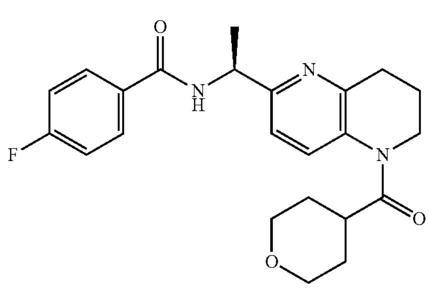 [SMILES: C[C@H](NC(=O)c1ccc(F)cc1)c1ccc2c(n1)CCCN2C(=O)C1CCOCC1] | 4-fluoro-N-{(1R)-1-[5-(oxane-4-carbonyl)-5,6,7,8-tetrahydro-1,5-naphthyridin-2-yl]ethyl}benzamide | Calc'd 412, found 412 | 35.5 |

-continued

| Ex. # | Structure | Chemical Name | Mass [M + H⁺] | Hela IC₅₀, nM |
|---|---|---|---|---|
| 147 | 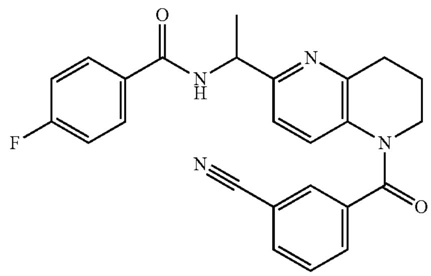 [SMILES: CC(NC(=O)c1ccc(F)cc1)c1ccc2c(n1)CCCN2C(=O)c1cccc(C#N)c1] | N-{1-[5-(3-cyanobenzene-1-carbonyl)-5,6,7,8-tetrahydro-1,5-naphthyridin-2-yl]ethyl}-4-fluorobenzamide | Calc'd 429, found 429 | 1.7 |
| 148 | 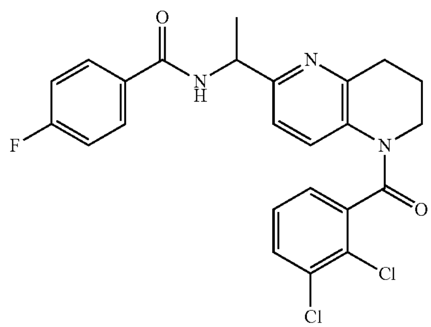 [SMILES: CC(NC(=O)c1ccc(F)cc1)c1ccc2c(n1)CCCN2C(=O)c1cccc(Cl)c1Cl] | N-{1-[5-(2,3-dichlorobenzene-1-carbonyl)-5,6,7,8-tetrahydro-1,5-naphthyridin-2-yl]ethyl}-4-fluorobenzamide | Calc'd 472, found 472 | 2.5 |
| 149 | 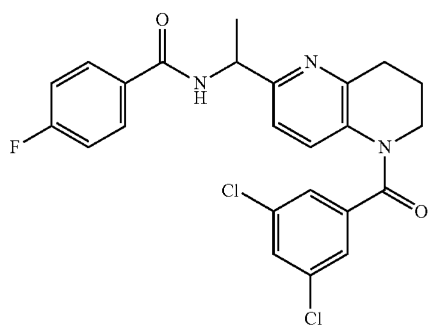 [SMILES: CC(NC(=O)c1ccc(F)cc1)c1ccc2c(n1)CCCN2C(=O)c1cc(Cl)cc(Cl)c1] | N-{1-[5-(3,5-dichlorobenzene-1-carbonyl)-5,6,7,8-tetrahydro-1,5-naphthyridin-2-yl]ethyl}-4-fluorobenzamide | Calc'd 472, found 472 | 3.2 |
| 150 | 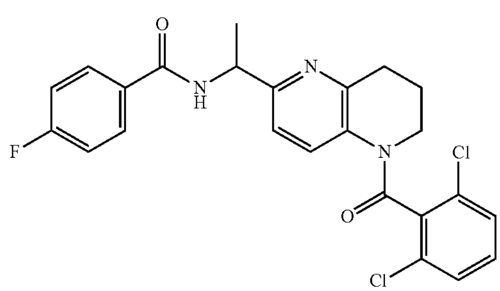 [SMILES: CC(NC(=O)c1ccc(F)cc1)c1ccc2c(n1)CCCN2C(=O)c1c(Cl)cccc1Cl] | N-{1-[5-(2,6-dichlorobenzene-1-carbonyl)-5,6,7,8-tetrahydro-1,5-naphthyridin-2-yl]ethyl}-4-fluorobenzamide | Calc'd 472, found 472 | 7.3 |
| 151 | 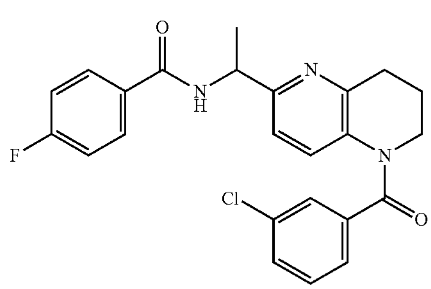 [SMILES: CC(NC(=O)c1ccc(F)cc1)c1ccc2c(n1)CCCN2C(=O)c1cccc(Cl)c1] | 2-[5-(3-chlorobenzene-1-carbonyl)-5,6,7,8-tetrahydro-1,5-naphthyridin-2-yl]-N-(4-fluorophenyl)propanamide | Calc'd 438, found 438 | 0.9 |

Example 152. 4-chloro-N-(1-(1-(3-chlorobenzoyl)-1,2,3,4-tetrahydro-1,7-naphthyridin-6-yl)ethyl)benzamide

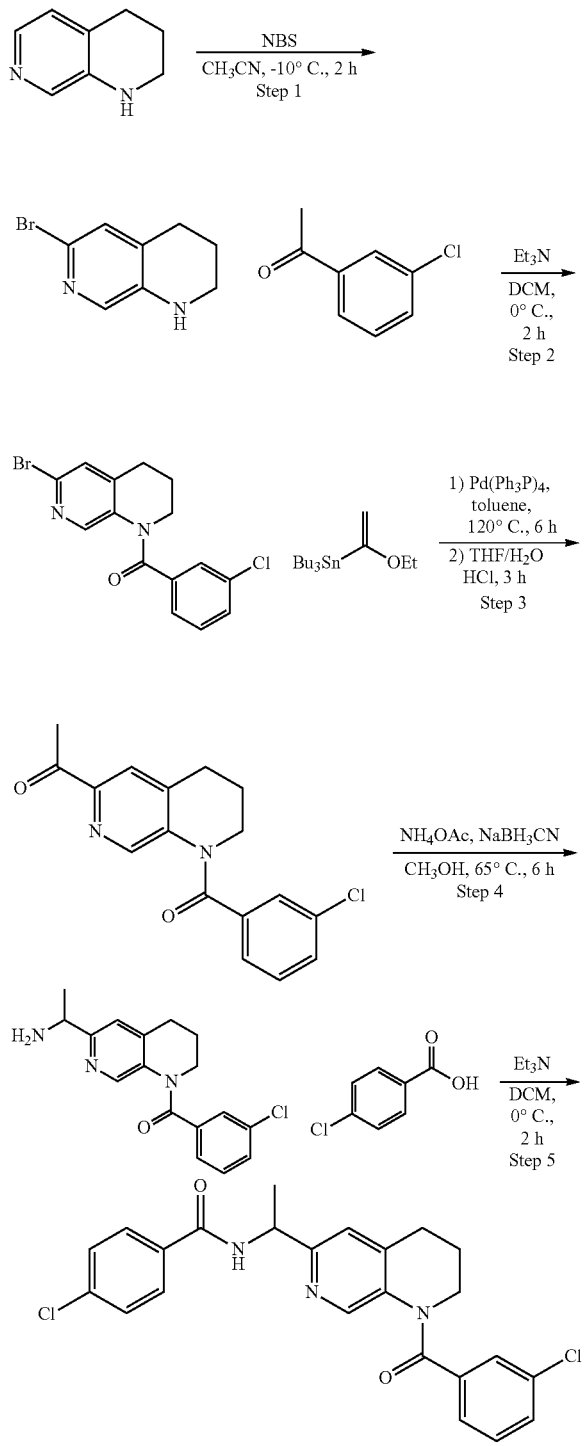

Step 1. 6-bromo-1,2,3,4-tetrahydro-1,7-naphthyridine

To a solution of 1,2,3,4-tetrahydro-1,7-naphthyridine (1.0 g, 7.45 mmol) in CH₃CN (50 mL) was added NBS (1459 mg, 8.20 mmol). Then the mixture was stirred at −10° C. and the reaction was monitored by TLC (Pet. ether/EtOAc=5:1). The reaction was complete after stirring at −10° C. for 2 h. The reaction mixture was diluted with DCM (100 mL), washed with sat. Na₂SO₃ aqueous solution (50 mL), dried over anhydrous sodium sulfate, filtered and concentrated in vacuo. The residue was purified by column chromatography (SiO₂, Pet. ether/EtOAc=5:1) to give the title compound as a solid. MS (ESI) m/z: 214.9 [M+H⁺]

Step 2. (6-bromo-3,4-dihydro-1,7-naphthyridin-1(2H)-yl)(3-chlorophenyl)methanone To a solution of 6-bromo-1,2,3,4-tetrahydro-1,7-naphthyridine (240 mg, 1.126 mmol) and Et₃N (0.50 ml, 3.59 mmol) in DCM (6 mL) was added a solution of 3-chlorobenzoyl chloride (296 mg, 1.690 mmol) in DCM (4.0 mL) dropwise at 0° C. After the addition was finished, the mixture was stirred at 0° C. and was monitored by TLC (Pet. ether/EtOAc=3:1). The reaction was complete after stirring for 2 h at 0° C. Then the reaction was diluted with DCM (20 mL), washed with sat. NaHCO₃ aqueous solution (15 mL×2) and brine (10 mL). The organic phase was dried over anhydrous sodium sulfate, filtered and concentrated under reduced pressure to give the title compound as an oil which was used in the next step directly. MS (ESI) m/z: 353.0 [M+H⁺]

Step 3. 1-(1-(3-chlorobenzoyl)-1,2,3,4-tetrahydro-1,7-naphthyridin-6-yl)ethanone To a solution of (6-bromo-3,4-dihydro-1,7-naphthyridin-1(2H)-yl)(3-chlorophenyl)methanone (395 mg, 1.123 mmol) in toluene (8 mL) were added tributyl(1-ethoxyvinyl)stannane (1950 mg, 5.40 mmol), Pd(PPh₃)₄ (1298 mg, 1.123 mmol) at 20° C. Then the mixture was stirred at 120° C. under nitrogen atmosphere and was monitored by LC-MS. After stirring at 120° C. for 6 h, the solvent was removed under reduced pressure, the residue was dissolved in THF (6 mL), and 3.0 M HCl (1.2 mL, 3.60 mmol) was added at 15° C. Then the mixture was stirred at 15° C. for 3 h, diluted with DCM (30 mL), and washed with sat. NaHCO₃ (30 mL) and brine (10 mL). The organic phase was dried over anhydrous sodium sulfate, filtered and concentrated under reduced pressure to give the title compound as an oil which was used directly. MS (ESI) m/z: 315.0 [M+H⁺]

Step 4. (6-(1-aminoethyl)-3,4-dihydro-1,7-naphthyridin-1(2H)-yl)(3-chlorophenyl)methanone To a solution of 1-(1-(3-chlorobenzoyl)-1,2,3,4-tetrahydro-1,7-naphthyridin-6-yl)ethanone (50 mg, 0.159 mmol) in MeOH (2 ml) were added NH₄OAc (122 mg, 1.588 mmol) and NaBH₃CN (39.9 mg, 0.635 mmol) at 20° C. Then the mixture was stirred at 65° C. and the reaction was monitored by LC-MS. The reaction was complete after stirring at 65° C. for 6 h. The reaction mixture was diluted with DCM (20 mL), and washed with sat. NaHCO₃ (10 mL) and brine (10 mL). The organic phase was dried over anhydrous sodium sulfate, filtered and concentrated under reduced pressure to give the title compound as an oil which was used directly in the next step. MS (ESI) m/z: 316.1 [M+H⁺]

Step 5. 4-chloro-N-(1-(1-(3-chlorobenzoyl)-1,2,3,4-tetrahydro-1,7-naphthyridin-6-yl)ethyl)benzamide To a mixture of (6-(1-aminoethyl)-3,4-dihydro-1,7-naphthyridin-1(2H)-yl)(3-chlorophenyl)methanone (50 mg, 0.158 mmol), Et₃N (0.10 ml, 0.717 mmol) in DCM (3 mL) was added 4-chlorobenzoyl chloride (41 mg, 0.234 mmol) at 0° C. Then the mixture was stirred at 0° C. and the reaction was monitored by TLC (Pet. ether/EtOAc=3:1). The reaction was complete after stirring at 0° C. for 2 h. Then the reaction was diluted with DCM (10 mL), washed with brine (10 mL), dried over anhydrous sodium sulfate, and filtered and concentrated under reduced pressure. The residue was purified by pre-HPLC (Column Xtimate C18 150×25 mm×5 um, Condition: water (10 mM NH₄HCO₃)—CH₃CN, Begin B: 48, End B: 68, Gradient Time (min): 15, 100% B Hold Time (min): 2, FlowRate (ml/min): 25) to give the title compound as a solid. $^1$H NMR (400 MHz, CDCl₃) δ 8.21 (brs, 1H), 7.71 (d, J=8.4 Hz, 2H), 7.38 (d, J=4.8 Hz, 1H), 7.31-7.37 (m, 4H), 7.21-7.27 (m, 2H), 7.06 (s, 1H), 5.16-5.22 (m, 1H), 3.78-3.87 (m, 2H), 2.84 (t, J=6.4 Hz, 2H), 1.99 (s, 2H), 1.47 (d, J=6.4 Hz, 3H). MS (ESI) m/z: 454.1 [M+H⁺]

After SFC separation, two chiral isomers were obtained; Column: AD (250 mm×30 mm×10 um, Eluent: 0.1% NH₃H₂O IPA; Begin B: 45%, End B: 45%; FlowRate (ml/min): 80; Injections: 40

The compounds in the following table were prepared in a similar manner as Example 152.

| Ex. # | Structure | Chemical Name | Mass [M + H]+ | Hela IC₅₀, nM |
|---|---|---|---|---|
| 152 | 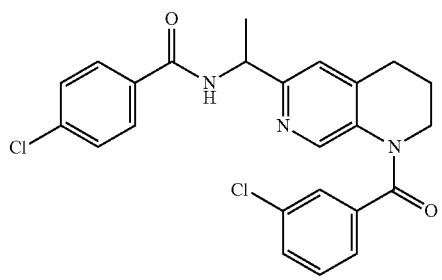 Racemic | 4-chloro-N-(1-(1-(3-chlorobenzoyl)-1,2,3,4-tetrahydro-1,7-naphthyridin-6-yl)ethyl)benzamide | Calc'd 454.0, found 454.0 | 8.9 |
| 153 | 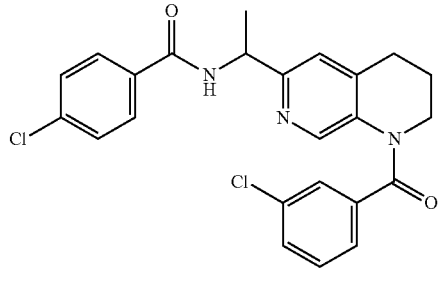 Isomer 1 | 4-chloro-N-(1-(1-(3-chlorobenzoyl)-1,2,3,4-tetrahydro-1,7-naphthyridin-6-yl)ethyl)benzamide | Calc'd 454.0, found 454.0 | 977.0 |
| 154 | 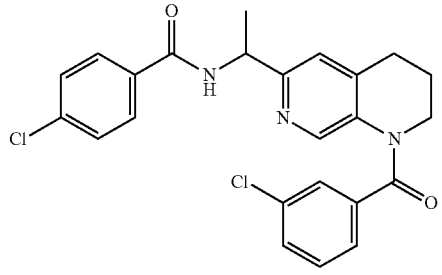 Isomer 2 | 4-chloro-N-(1-(1-(3-chlorobenzoyl)-1,2,3,4-tetrahydro-1,7-naphthyridin-6-yl)ethyl)benzamide | Calc'd 454.0, found 454.0 | 7.8 |

Example 155. 2-(1-(cyclopropanecarbonyl)-1,2,3,4-tetrahydroquinolin-6-yl)-N-(5-fluoropyridin-2-yl)-2-methoxyacetamide

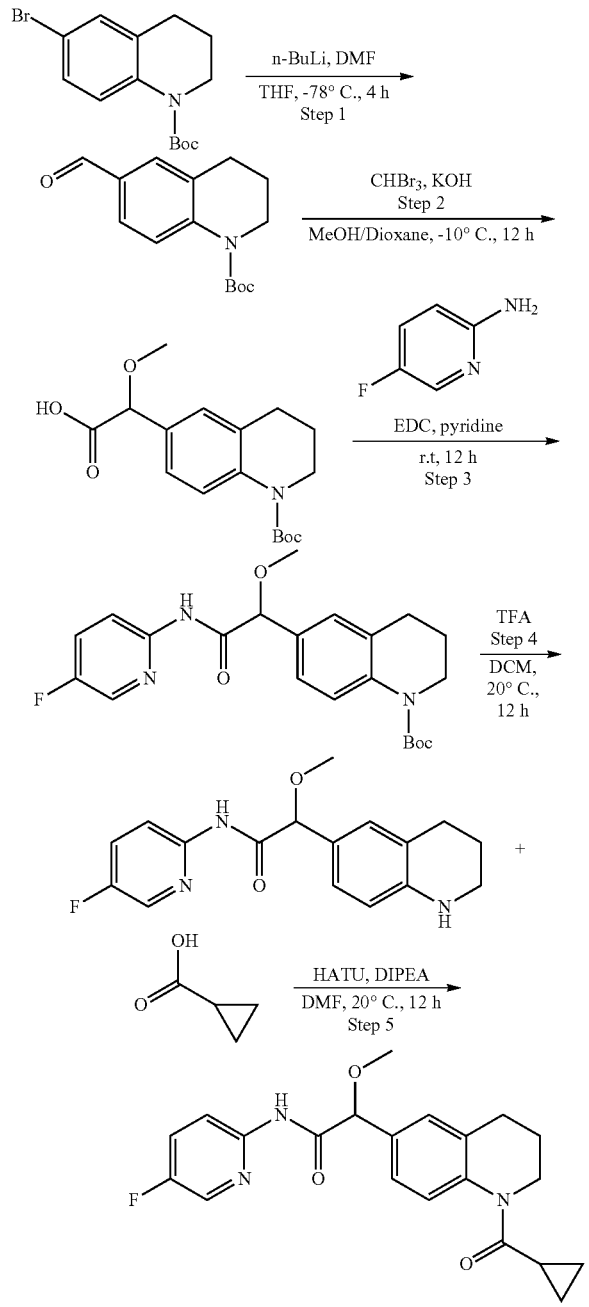

Step 1. tert-butyl 6-formyl-3,4-dihydroquinoline-1(2H)-carboxylate

To a stirred solution of tert-butyl 6-bromo-3,4-dihydroquinoline-1(2H)-carboxylate (600 mg, 1.92 mmol) in THF (20 mL) at −78° C. under nitrogen atmosphere, n-butyllithium (0.85 mL, 2.13 mmol) was added dropwise. After stirring for 1 h at −78° C., DMF (0.24 mL, 3.10 mmol) was added at −78° C. and the reaction was monitored by LCMS and TLC (Pet. ether:EtOAc=5:1). It was found that the reaction was finished after stirring for 4 h at −78° C. and 2 h at 20° C. The mixture was quenched with aq. NH$_4$Cl (10 mL), and diluted with EtOAc (40 mL). The organic layer was separated, and the aqueous layer was extracted with EtOAc (30 mL×2), the combined organic layers were washed with brine (30 mL), dried over Na$_2$SO$_4$, filtered and concentrated. The residue was purified by column chromatography (SiO$_2$, EtOAc in Pet. ether: 0 to 7%) to give the title compound as an oil. ESI MS m/z 262.1 [M+H$^+$].

Step 2. 2-(1-(tert-butoxcarbonyl)-1,2,3,4-tetrahydroquinolin-6-yl)-2-methoxyacetic acid To a solution of tert-butyl 6-formyl-3,4-dihydroquinoline-1(2H)-carboxylate (154 mg, 0.45 mmol) in anhydrous MeOH (0.4 mL) and anhydrous 1,4-dioxane (0.4 mL) at −15 to −10° C. was added bromoform (0.05 mL, 0.58 mmol). Then a solution of KOH (127 mg, 2.27 mmol) in methanol (0.4 mL) was added over a period of 20 min. Then the mixture was stirred for 1 h at the same temperature and slowly warmed to RT. The reaction was monitored by LCMS and TLC (DCM:MeOH=10:1). After stirring for 12 h, the reaction was finished. The reaction was then diluted with water, acidified to pH=1 with 6 M HCl, extracted with EtOAc (20 mL×3), the combined organic layers were washed with brine, dried over Na$_2$SO$_4$ and concentrated in vacuo to give the title compound as an oil. ESI MS m/z 344.0 [M+Na$^+$].

Step 3. tert-butyl 6-(2-((5-fluoropyridin-2-yl)amino)-1-methoxy-2-oxoethyl)-3,4-dihydroquinoline-1(2H)-carboxylate To a stirred solution of 2-(1-(tert-butoxycarbonyl)-1,2,3,4-tetrahydroquinolin-6-yl)-2-methoxyacetic acid (160 mg, 0.40 mmol) in pyridine (4 mL) were added 5-fluoropyridin-2-amine (56 mg, 0.50 mmol) and EDC (250 mg, 1.30 mmol) at 20° C. After the addition was finished, the reaction was stirred at 20° C. and was monitored by LCMS. The reaction was finished after stirring for 16 h. Then it was concentrated in vacuo and the residue was purified by prep-TLC (Pet. ether/EtOAc=2:1) to give the title compound as a solid. ESI MS m/z 416.0 [M+H$^+$].

Step 4. N-(5-fluoropyridin-2-yl)-2-methoxy-2-(1,2,3,4-tetrahydroquinolin-6-Yl)acetamide To a stirred solution of tert-butyl 6-(2-((5-fluoropyridin-2-yl)amino)-1-methoxy-2-oxoethyl)-3,4-dihydroquinoline-1(2H)-carboxylate (101 mg, 0.24 mmol) in DCM (3 mL) was added TFA (0.5 mL, 6.48 mmol), the resulting mixture was stirred at 20° C. The reaction was monitored by LCMS and TLC (DCM:MeOH=10:1). After stirring for 12 h, the reaction was finished. The mixture was concentrated in vacuo to give the title compound as an oil, which was used in next step without further purification. ESI MS m/z 316.0 [M+H$^+$].

Step 5. 2-(1-(cyclopropanecarbonyl)-1,2,3,4-tetrahydroquinolin-6-yl)-N-(5-fluoropyridin-2-yl)-2-methoxyacetamide To a stirred solution of N-(5-fluoropyridin-2-yl)-2-methoxy-2-(1,2,3,4-tetrahydroquinolin-6-yl)acetamide (114 mg, 0.24 mmol), cyclopropanecarboxylic acid (30 mg, 0.35 mmol) and HATU (111 mg, 0.29 mmol) in DMF (4 mL) was added DIPEA (0.3 mL, 0.24 mmol) at 0° C. After the addition was finished, the resulting mixture was stirred at 20° C. The reaction was monitored by LCMS, the starting material was consumed and desired mass was detected. After stirring for 12 h, the reaction was complete. The mixture was diluted with water (40 mL), extracted with EtOAc (10 mL×3), and the combined organic layers were washed with brine (20 mL×2), dried over $Na_2SO_4$, filtered and concentrated. The residue was purified by HPLC(Column: Agela ASB 150×25 mm×5 um; Condition: water (0.1% TFA)-$CH_3CN$; Begin B: 30; End B: 50; Gradient Time (min): 10; 100% B Hold Time (min): 2; FlowRate (mL/min): 25) to give the title compound as a solid. $^1$H-NMR (400 MHz, $CDCl^3$) δ (400 MHz): 9.68 (br s, 1H), 8.33 (dd, J=3.8, 9.2 Hz, 1H), 8.16 (d, J=2.8 Hz, 1H), 7.51-7.58 (m, 1H), 7.41 (br d, J=8.8 Hz, 1H), 7.29 (br s, 2H), 4.76 (s, 1H), 3.75-3.87 (m, 2H), 3.47 (s, 3H), 2.76 (br t, J=6.4 Hz, 2H), 1.97 (quin, J=6.5 Hz, 3H), 1.16 (br t, J=3.8 Hz, 2H), 0.82 (br dd, J=4.0, 7.39 Hz, 2H). ESI MS m/z 384.0 [M+H$^+$]

After SFC separation, two chiral isomers were obtained —Column: OD (250 mm×30 mm, 5 um); Condition: 0.1% $NH_3H_2O$ IPA; Begin B: 30%; End B: 30%; FlowRate (ml/min): 50; Injections: 90

The compounds in the following table were prepared in a similar manner as Example 155.

| Ex. # | Structure | Chemical Name | Mass [M + H]+ | Hela IC$_{50}$, nM |
|---|---|---|---|---|
| 155 | Racemic | 2-(1-(cyclopropanecarbonyl)-1,2,3,4-tetrahydroquinolin-6-yl)-N-(5-fluoropyridin-2-yl)-2-methoxyacetamide | Calc'd 384, found 384 | 272.7 |
| 156 | Isomer 1 | 2-(1-(cyclopropanecarbonyl)-1,2,3,4-tetrahydroquinolin-6-yl)-N-(5-fluoropyridin-2-yl)-2-methoxyacetamide | Calc'd 384, found 384 | 793.5 |
| 157 | Isomer 2 | 2-(1-(cyclopropanecarbonyl)-1,2,3,4-tetrahydroquinolin-6-yl)-N-(5-fluoropyridin-2-yl)-2-methoxyacetamide | Calc'd 384, found 384 | 153.7 |

Example 158. N-(4-fluorophenyl)-2-(5-(tetrahydro-2H-pyran-2-carbonyl)-5,6,7,8-tetrahydro-1,5-naphthyridin-2-yl)propanamide

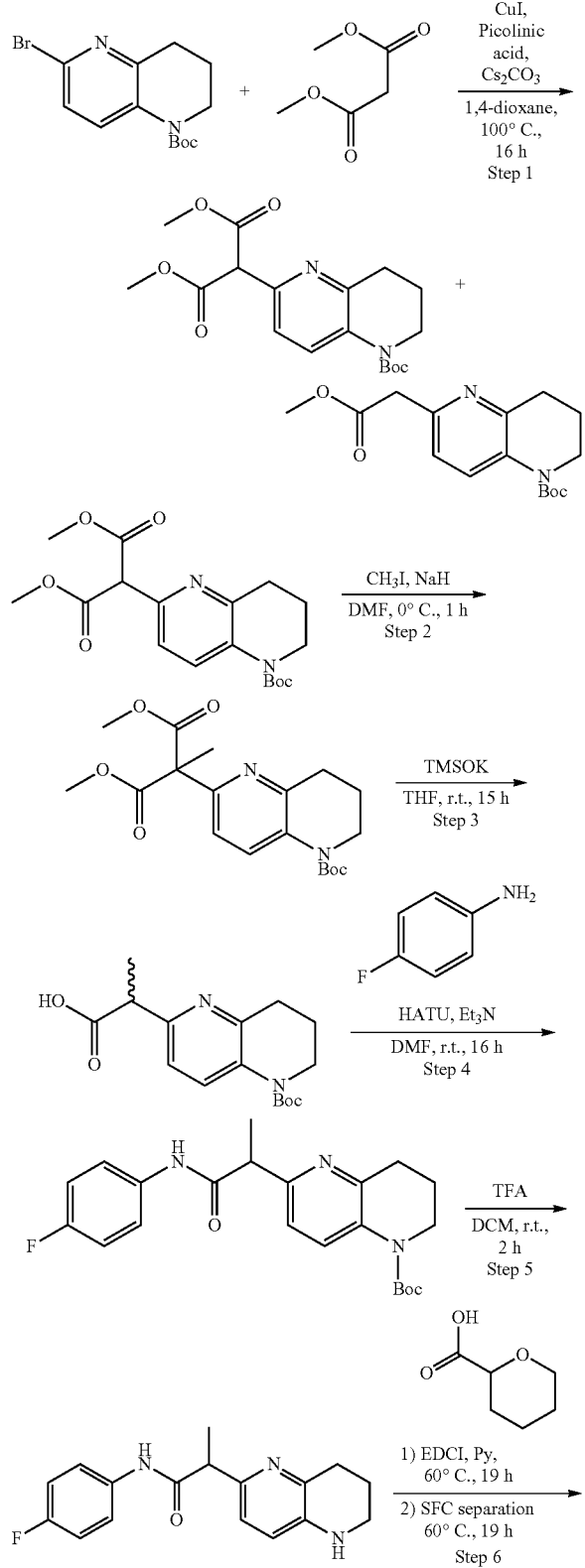

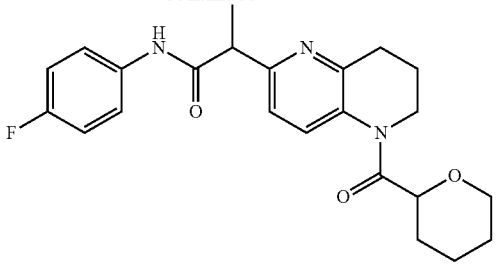

Step 1. dimethyl 2-(5-tert-butoxycarbonyl)-5,6,7,8-tetrahydro-1,5-napththyridin-2-yl)malonate To a solution of tert-butyl 6-bromo-3,4-dihydro-1,5-naphthyridine-1(2H)-carboxylate (10.0 g, 31.9 mmol) and picolinic acid (3.14 g, 25.5 mmol) in 1,4-dioxane (100 mL) were added copper(I) iodide (0.608 g, 3.19 mmol) and $Cs_2CO_3$ (31.2 g, 96 mmol) at RT. After the addition, dimethyl malonate (16.87 g, 128 mmol) was added to the solution at 20° C. Then the mixture was stirred at 100° C. and the reaction was monitored by LC-MS. After stirring at 100° C. for 16 h overnight, the reaction was finished and was cooled to RT. EtOAc (200 mL) was added to the mixture and the salt was removed by filtration. The filtrate was concentrated in vacuo. The residue was purified by flash silica gel chromatography (ISCO®; Agela® Flash Column Silica-CS (80 g), Eluent of 0-15% Ethyl acetate/Petroleum ether gradient @ 60 mL/min) to give the title compound as a solid. MS (ESI) m/z: 365.2 [M+H$^+$]

Step 2. dimethyl 2-(5-(tert-butoxycarbonyl)-5,6,7,8-tetrahydro-1,5-naphthyridin-2-yl)-2-methylmalonate To a solution of dimethyl 2-(5-(tert-butoxycarbonyl)-5,6,7,8-tetrahydro-1,5-naphthyridin-2-yl)malonate (3.0 g, 8.23 mmol) in DMF (25 mL) was added NaH (0.4 g, 10.00 mmol) (60%) at 0° C. After the addition was finished, the mixture was stirred at 0° C. for 10 min, then MeI (0.62 mL, 9.87 mmol) was added at 0° C. After the addition was finished, the reaction was stirred at 0° C. The reaction was monitored by TLC. After stirring at 0° C. for 1 h, TLC (Ethyl acetate/Petroleum ether=1:1) showed the reaction was finished. Then the mixture was quenched by sat. $NH_4Cl$ (120 mL), extracted by EtOAc (50 mL×3), the organic layers were collected, washed with brine, and dried over $Na_2SO_4$. After filtration, the filtrate was concentrated in vacuo. The residue was purified by flash silica gel chromatography (ISCO®; Agela® Flash Column Silica-CS (20 g), Eluent of 030% Ethyl acetate/Petroleum ether gradient @ 35 mL/min) to give the title compound as a solid. MS (ESI) m/z: 379.1 [M+H$^+$]

Step 3. 2-(5-(tert-butoxycarbonyl)-5,6,7,8-tetrahydro-1,5-naphthyridin-2-yl)propanoic acid To a solution of dimethyl 2-(5-(tert-butoxycarbonyl)-5,6,7,8-tetrahydro-1,5-naphthyridin-2-yl)-2-methylmalonate (1000 mg, 2.64 mmol) in THF (20 mL) was added TMSOK (1356 mg, 10.57 mmol) at RT. After the addition was complete, the mixture was stirred at RT and the reaction was monitored by LC-MS. After stirring at RT for 15 h, LC-MS showed the reaction was finished. The pH of the mixture was adjusted to 6-7 with acetic acid, then diluted with water (30 mL), extracted by EtOAc (30 mL×2), the organic layers were collected, washed with brine, and dried over $Na_2SO_4$.

The reaction mixture was filtered and the filtrate was concentrated in vacuo to give the title compound as an oil, which was used directly in the next step without further purification. MS (ESI) m/z: 307.1 [M+H+]

Step 4. tert-butyl 6-(1-((4-fluorophenyl)amino)-1-oxopropan-2-yl)-3,4-dihydro-1,5-naphthyridine-1(2H)-carboxylate To a stirred solution of 2-(5-(tert-butoxycarbonyl)-5,6,7,8-tetrahydro-1,5-naphthyridin-2-yl)propanoic acid (390 mg, 1.273 mmol) in THF (15 mL) were added HATU (581 mg, 1.528 mmol), 4-fluoroaniline (170 mg, 1.528 mmol) and triethylamine (0.56 mL, 4.02 mmol) at RT. After the addition was finished, the reaction was stirred at 25° C. The reaction was monitored by LC-MS and after stirring at 25° C. for 16 h, the reaction was finished. Then the mixture was diluted with water (30 mL), extracted by EtOAc (20 mL×3), the organic layers were collected, washed with brine, dried over Na$_2$SO$_4$ and was filtered. The filtrate was concentrated in vacuo. The residue was purified by silica gel chromatography (SiO$_2$, eluenting with petroleum ether/ethyl acetate=10:1-4:1) to give the title compound as a an oil. MS (ESI) m/z: 400.2 [M+H$^+$].

Step 5. N-(4-fluorophenyl)-2-(5,6,7,8-tetrahydro-1,5-naphthyridin-2-yl)propanamide To a stirred solution of tert-butyl 6-(1-((4-fluorophenyl)amino)-1-oxopropan-2-yl)-3,4-dihydro-1,5-naphthyridine-1(2H)-carboxylate (380 mg, 0.951 mmol) in DCM (5 mL) was added TFA (2 mL, 26.0 mmol) at RT. After the addition was finished, the reaction was stirred at 25° C. The reaction was monitored by LC-MS, after stirring at 25° C. for 2 h, the reaction was finished. Then water (10 mL) was added and the mixture was basified to pH ~8 with sat. NaHCO$_3$ solution, extracted by DCM (10 mL×3), the organic layers were collected, washed with brine, and dried over Na$_2$SO$_4$. After filtration, the filtrate was concentrated in vacuo to give the title compound as an oil, which was used directly in the next step without further purification. MS (ESI) m/z:300.0 [M+H$^+$].

Step 6. N-(4-fluorophenyl)-2-(5-(tetrahydro-2H-pyran-2-carbonyl)-5,6,7,8-tetrahydro-1,5-naphthyridin-2-yl)propanamide To a stirred solution of N-(4-fluorophenyl)-2-(5,6,7,8-tetrahydro-1,5-naphthyridin-2-yl)propanamide (100 mg, 0.334 mmol) in pyridine (2 mL) were added tetrahydro-2H-pyran-2-carboxylic acid (65 mg, 0.499 mmol) and EDCI (192 mg, 1.002 mmol) at RT. After the addition, the reaction was stirred at 60° C. and the reaction was monitored by LC-MS. The reaction was complete after stirring at 60° C. for 19 h. Then the mixture was cooled to RT and the solvent was removed off by concentration. The formed residue was purified by reversed phase HPLC on a GILSON 281 instrument fitted with a Agela ASB 150×25 mm×5 um using water (0.225% FA) and acetonitrile as eluents (Mobile phase A water (0.225% FA), Mobile phase B acetonitrile, Detection wavelength: 220 nm) followed by freeze-drying to give the title compound as a solid. $^1$H NMR (400 MHz, CD$_3$OD) δ 8.17 (br s, 1H), 7.55 (dd, J=8.6, 4.8 Hz, 2H), 7.38 (br d, J=8.8 Hz, 1H), 7.03 (t, J=8.8 Hz, 2H), 4.34 (br d, J=8.8 Hz, 1H), 3.92-4.06 (m, 3H), 3.71 (br s, 1H), 3.49-3.61 (m, 1H), 3.02 (br t, J=6.7 Hz, 2H), 2.02-2.14 (m, 2H), 1.93 (br s, 1H), 1.69-1.81 (m, 2H), 1.54-1.66 (m, 6H). MS (ESI) m/z: 412.1 [M+H$^+$].

After SFC separation, 4 isomers were obtained —SFC conditions: Column: Column: Chiralpak (C2 250 mm×30 mm, 10 um); Eluent: 0.1% NH3-H2O EtOH, Begin B 25%, End B 25%, Flow Rate (ml/min):60 Injections: 30

The compounds in the following table were prepared in a similar manner as Example 158.

| Ex. # | Structure | Chemical Name | Mass [M + H]+ | Hela IC$_{50}$, nM |
|---|---|---|---|---|
| 158 | Isomer 1 | N-(4-fluorophenyl)-2-[5-(oxane-2-carbonyl)-5,6,7,8-tetrahydro-1,5-naphthyridin-2-yl]propanamide | Calc'd 412, found 412 | 38.1 |
| 159 | Isomer 2 | N-(4-fluorophenyl)-2-[5-(oxane-2-carbonyl)-5,6,7,8-tetrahydro-1,5-naphthyridin-2-yl]propanamide | Calc'd 412, found 412 | 1.5 |

| Ex. # | Structure | Chemical Name | Mass [M + H]+ | Hela IC$_{50}$, nM |
|---|---|---|---|---|
| 160 | Isomer 3 | N-(4-fluorophenyl)-2-[5-(oxane-2-carbonyl)-5,6,7,8-tetrahydro-1,5-naphthyridin-2-yl]propanamide | Calc'd 412, found 412 | 8.2 |
| 161 | Isomer 4 | N-(4-fluorophenyl)-2-[5-(oxane-2-carbonyl)-5,6,7,8-tetrahydro-1,5-naphthyridin-2-yl]propanamide | Calc'd 412, found 412 | 5.6 |
| 162 | Racemic | N-(4-fluorophenyl)-2-{5-[(2R)-oxolane-2-carbonyl]-5,6,7,8-tetrahydro-1,5-naphthyridin-2-yl}propanamide | Calc'd 398, found 398 | 2.7 |
| 163 | Isomer 1 | N-(4-fluorophenyl)-2-{5-[(2R)-oxolane-2-carbonyl]-5,6,7,8-tetrahydro-1,5-naphthyridin-2-yl}propanamide | Calc'd 398, found 398 | 21.8 |
| 164 | Isomer 2 | N-(4-fluorophenyl)-2-{5-[(2R)-oxolane-2-carbonyl]-5,6,7,8-tetrahydro-1,5-naphthyridin-2-yl}propanamide | Calc'd 398, found 398 | 1.1 |

-continued

| Ex. # | Structure | Chemical Name | Mass [M + H]+ | Hela IC$_{50}$, nM |
|---|---|---|---|---|
| 165 | Racemic | N-(4-fluorophenyl)-2-[5-(oxane-4-carbonyl)-5,6,7,8-tetrahydro-1,5-naphthyridin-2-yl]propanamide | Calc'd 412, found 412 | 2.7 |
| 166 | Isomer 1 | N-(4-fluorophenyl)-2-[5-(oxane-4-carbonyl)-5,6,7,8-tetrahydro-1,5-naphthyridin-2-yl]propanamide | Calc'd 412, found 412 | 16.7 |
| 167 | Isomer 2 | N-(4-fluorophenyl)-2-[5-(oxane-4-carbonyl)-5,6,7,8-tetrahydro-1,5-naphthyridin-2-yl]propanamide | Calc'd 412, found 412 | 5.1 |

Example 168. N-(1-(5-(cyclopropanecarbonyl)-5,6,7,8-tetrahydro-1,5-naphthyridin-2-yl)cyclopropyl)-4-fluorobenzamide

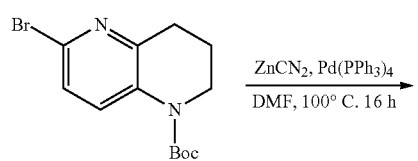

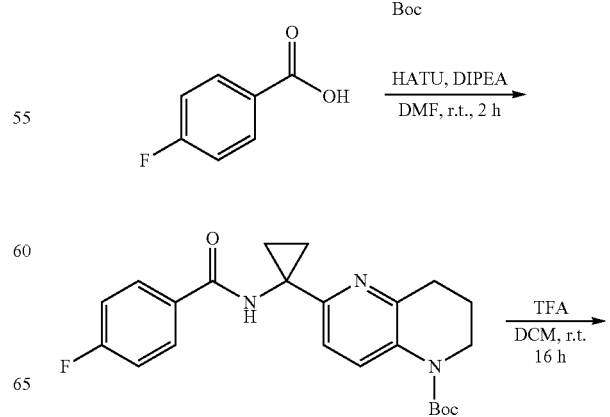

-continued

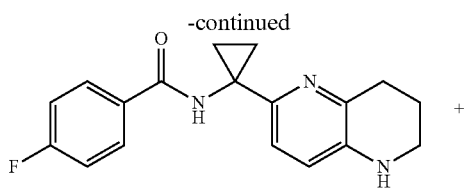

+

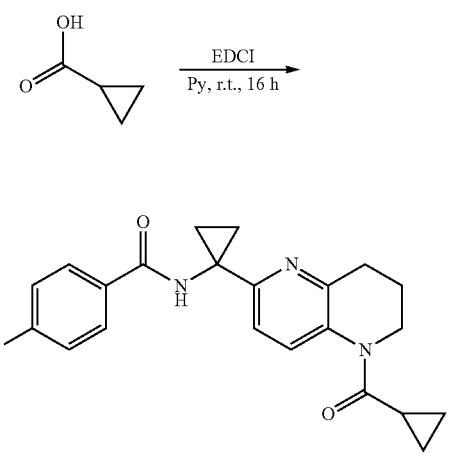

Step 1. tert-butyl 6-cyano-3,4-dihydro-1,5-naphthyridine-1(2H)-carboxylate

To a stirred solution of tert-butyl 6-bromo-3,4-dihydro-1,5-naphthyridine-1(2H)-carboxylate (500 mg, 1.596 mmol) in DMF (10 mL) were added cyanozinc (680 mg, 7.44 mmol) and Pd(PPh$_3$)$_4$ (184 mg, 0.160 mmol) at 20° C. After the addition, the reaction was stirred at 100° C. The reaction was monitored by LC-MS and found the reaction was finished after stirring at 100° C. for 16 h. The reaction mixture was cooled to RT, extracted by EtOAc (80 mL×3), the organic layers were collected, washed with brine (50 mL), and dried over Na$_2$SO$_4$. After filtration, the filtrate was concentrated in vacuo. The residue was purified by flash silica gel chromatography (ISCO®; Agela® Flash Column Silica-CS (12 g) Eluent of 030% Ethyl acetate/Petroleum ether gradient @ 30 mL/min) to give the title compound as a solid. MS (ESI) m/z: 260.1 (M+H$^+$)

Step 2. tert-butyl 6-(1-aminocyclopropyl)-3,4-dihydro-1,5-naphthyridine-1(2H)-carboxylate To a solution of tert-butyl 6-cyano-3,4-dihydro-1,5-naphthyridine-1(2H)-carboxylate (350 mg, 1.350 mmol) and Ti(i-PrO)$_4$ (422 mg, 1.485 mmol) in THF (10 mL) was added ethylmagnesium bromide (0.9 mL, 2.70 mmol) dropwise with stirring at −70° C. under nitrogen atmosphere. After the addition, the reaction mixture was stirred at −70° C. for 30 min and then at 20° C. for 1 h. BF$_3$.Et2O (0.35 mL, 2.76 mmol) was added slowly. The reaction mixture was stirred at 20° C. for 14 h. The reaction was monitored by LC-MS and after stirring at 20° C. for 14 h, the reaction was finished. The mixture was quenched by the addition of water (100 mL), and extracted by EtOAc (80 mL×3). The organic layers were collected, washed with brine (50 mL), and dried over Na$_2$SO$_4$. After filtration, the filtrate was concentrated in vacuo to give the title compound as an oil which was used in the next step without any further purification. MS (ESI) m/z: 290.2 (M+H$^+$)

Step 3. tert-butyl 6-(1-(4-fluorobenzamido)cyclopropyl)-3,4-dihydro-1,5-naphthyridine-1(2H)-carboxylate To a stirred solution of tert-butyl 6-(1-aminocyclopropyl)-3,4-dihydro-1,5-naphthyridine-1(2H)-carboxylate (350 mg, 0.605 mmol) in DMF (5 mL) were added 4-fluorobenzoic acid (85 mg, 0.605 mmol), HATU (30 mg, 0.605 mmol) and DIEA (0.32 mL, 1.832 mmol) at 20° C. After the addition, the reaction was stirred at 20° C. and the reaction was monitored by LC-MS. After stirring at 20° C. for 2 h, the reaction was finished. To the mixture was added water (200 mL), and extracted by EtOAc (80 mL×3). The organic layers were collected, washed with brine (50 mL), and dried over Na$_2$SO$_4$. After filtration, the filtrate was concentrated in vacuo. The residue was purified by flash silica gel chromatography (ISCO®; Agela® Flash Column Silica-CS (12 g), Eluent of 030% Ethyl acetate/Petroleum ether gradient @45 mL/min) to give the title compound as an oil. MS (ESI) m/z: 412.1 [M+H$^+$],

Step 4. 4-fluoro-N-(1-(5,6,7,8-tetrahydro-1,5-naphthyridin-2-yl)cyclopropyl)benzamide To a stirred solution of tert-butyl 6-(1-(4-fluorobenzamido)cyclopropyl)-3,4-dihydro-1,5-naphthyridine-1(2H)-carboxylate (85 mg, 0.207 mmol) in DCM (5 mL) was added TFA (1 mL, 12.98 mmol) at 15° C. After the addition, the reaction was stirred at 15° C. The reaction was monitored by LC-MS. After stirring at 15° C. for 16 h, the reaction was complete. The mixture was concentrated under reduced pressure to give the title compound as an oil. MS (ESI) m/z: 312.1 [M+H$^+$]

Step 5. N-(1-(5-(cyclopropanecarbonyl)-5,6,7,8-tetrahydro-1,5-naphthyridin-2-yl)cyclopropyl)-4-fluorobenzamide To a stirred solution of 4-fluoro-N-(1-(5,6,7,8-tetrahydro-1,5-naphthyridin-2-yl)cyclopropyl)benzamide (30 mg, 0.096 mmol) in pyridine (5 mL) was added cyclopropanecarboxylic acid (11 mg, 0.128 mmol) and N1-((ethylimino)methylene)-N3,N3-dimethylpropane-1,3-diamine hydrochloride (46 mg, 0.240 mmol) at 20° C. After the addition, the reaction was stirred at 20° C. The reaction was monitored by LC-MS and after stirring at 20° C. for 16 h, the reaction was finished. Water (30 mL) was added and extracted by EtOAc (25 mL×2). The organic layers were collected, washed with brine (20 mL), and dried over Na2SO4. The solid was removed by filtration and the filtrate was concentrated in vacuo. The residue was purified by prep-HPLC (Method Column Phenomenex Synergi C18 150×30 mm×4 um Condition water (0.225% FA)-ACN Begin B 35 End B 55 Gradient Time (min) 11 100% B Hold Time (min) 2 FlowRate (ml/min) 25 Injections 4) to give the title compound as a solid. $^1$H NMR (400 MHz, CD$_3$OD) δ 8.00-7.91 (m, 2H), 7.76 (br d, J=7.7 Hz, 1H), 7.27-7.17 (m, 3H), 3.84 (br s, 2H), 2.89 (t, J=6.7 Hz, 2H), 2.08-1.94 (m, 3H), 1.70-1.61 (m, 2H), 1.35-1.29 (m, 2H), 1.06-0.98 (m, 2H), 0.91-0.82 (m, 2H); MS (ESI) m/z: 380.1 [M+H$^+$]

The compounds in the following table were prepared in a similar manner as Example 168.

| Ex. # | Structure | Chemical Name | Mass [M + H⁺] | Hela IC₅₀, nM |
|---|---|---|---|---|
| 168 | 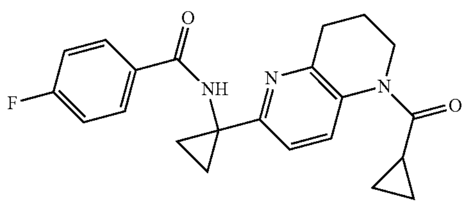 [SMILES: O=C(NC1(c2ccc3c(n2)CCCN3C(=O)C2CC2)CC1)c1ccc(F)cc1] | N-{1-[5-(cyclopropanecarbonyl)-5,6,7,8-tetrahydro-1,5-naphthyridin-2-yl]cyclopropyl}-4-fluorobenzamide | Calc'd 380, found 380 | 25.7 |
| 169 | 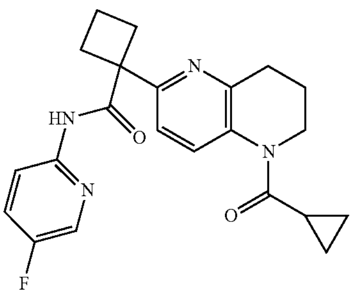 [SMILES: O=C(C1CC1)N1CCCc2nc(C3(C(=O)Nc4ccc(F)cn4)CCC3)ccc21] | 1-[5-(cyclopropanecarbonyl)-5,6,7,8-tetrahydro-1,5-naphthyridin-2-yl]-N-(5-fluoropyridin-2-yl)cyclobutane-1-carboxamide | Calc'd 395, found 395 | 55.7 |
| 170 | 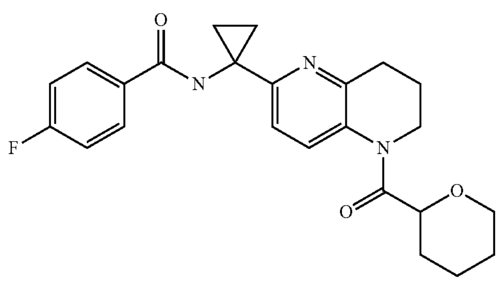 [SMILES: O=C(NC1(c2ccc3c(n2)CCCN3C(=O)C2CCCCO2)CC1)c1ccc(F)cc1] | 4-fluoro-N-{1-[5-(oxane-2-carbonyl)-5,6,7,8-tetrahydro-1,5-naphthyridin-2-yl]cyclopropyl}benzamide | Calc'd 424, found 424 | 2.4 |
| 171 | 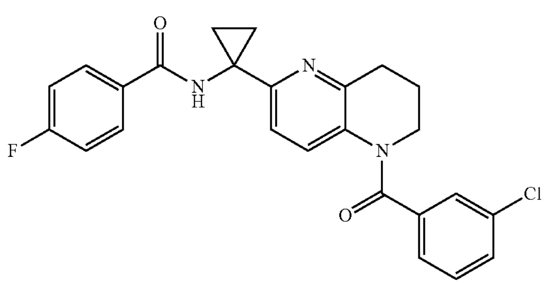 [SMILES: O=C(NC1(c2ccc3c(n2)CCCN3C(=O)c2cccc(Cl)c2)CC1)c1ccc(F)cc1] | N-{1-[5-(3-chlorobenzene-1-carbonyl)-5,6,7,8-tetrahydro-1,5-naphthyridin-2-yl]cyclopropyl}-4-fluorobenzamide | Calc'd 450, found 450 | 2.3 |
| 172 | 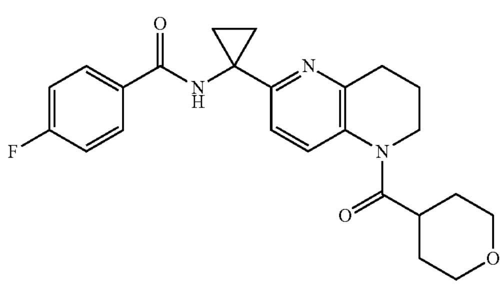 [SMILES: O=C(NC1(c2ccc3c(n2)CCCN3C(=O)C2CCOCC2)CC1)c1ccc(F)cc1] | 4-fluoro-N-{1-[5-(oxane-4-carbonyl)-5,6,7,8-tetrahydro-1,5-naphthyridin-2-yl]cyclopropyl}benzamide | Calc'd 424, found 424 | 16.1 |

-continued

| Ex. # | Structure | Chemical Name | Mass [M + H+] | Hela IC50, nM |
|---|---|---|---|---|
| 173 | 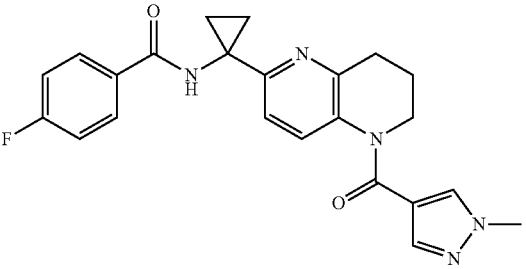 [SMILES: Cn1cc(C(=O)N2CCCc3nc(C4(NC(=O)c5ccc(F)cc5)CC4)ccc32)cn1] | 4-fluoro-N-{1-[5-(1-methyl-1H-pyrazole-4-carbonyl)-5,6,7,8-tetrahydro-1,5-naphthyridin-2-yl]cyclopropyl}benzamide | Calc'd 420, found 420 | 39.9 |
| 174 | 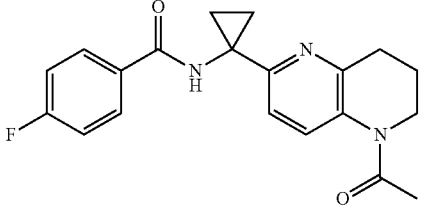 [SMILES: CC(=O)N1CCCc2nc(C3(NC(=O)c4ccc(F)cc4)CC3)ccc21] | N-[1-(5-acetyl-5,6,7,8-tetrahydro-1,5-naphthyridin-2-yl)cyclopropyl]-4-fluorobenzamide | Calc'd 354, found 354 | 266.1 |
| 175 | 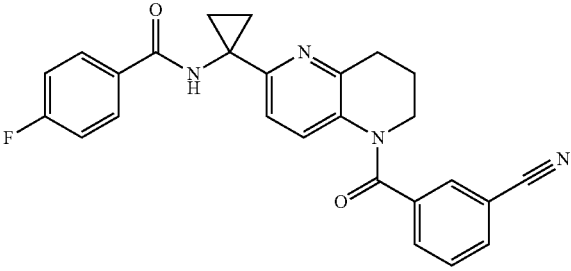 [SMILES: N#Cc1cccc(C(=O)N2CCCc3nc(C4(NC(=O)c5ccc(F)cc5)CC4)ccc32)c1] | N-{1-[5-(3-cyanobenzene-1-carbonyl)-5,6,7,8-tetrahydro-1,5-naphthyridin-2-yl]cyclopropyl}-4-fluorobenzamide | Calc'd 441, found 441 | 4.9 |
| 176 | 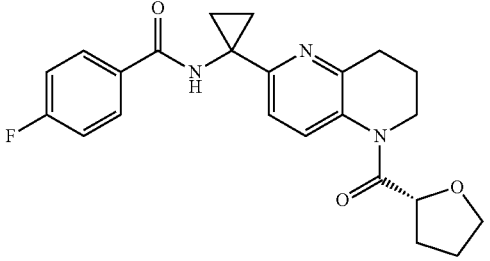 [SMILES: O=C(NC1(c2ccc3c(n2)CCCN3C(=O)[C@H]2CCCO2)CC1)c1ccc(F)cc1] | 4-fluoro-N-(1-{5-[(2R)-oxolane-2-carbonyl]-5,6,7,8-tetrahydro-1,5-naphthyridin-2-yl}cyclopropyl)benzamide | Calc'd 410, found 410 | 9.7 |
| 177 | 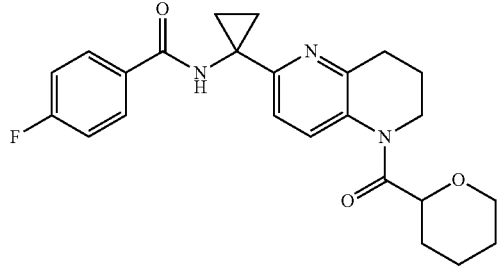 [SMILES: O=C(NC1(c2ccc3c(n2)CCCN3C(=O)C2CCCCO2)CC1)c1ccc(F)cc1] | 4-fluoro-N-{1-[5-(oxane-2-carbonyl)-5,6,7,8-tetrahydro-1,5-naphthyridin-2-yl]cyclopropyl}benzamide | Calc'd 424, found 424 | 7.5 |

Example 178. N-(4-fluorophenyl)-1-(5-(tetrahydro-2H-pyran-2-carbonyl)-5,6,7,8-tetrahydro-1,5-naphthyridin-2-yl)cyclobutanecarboxamide

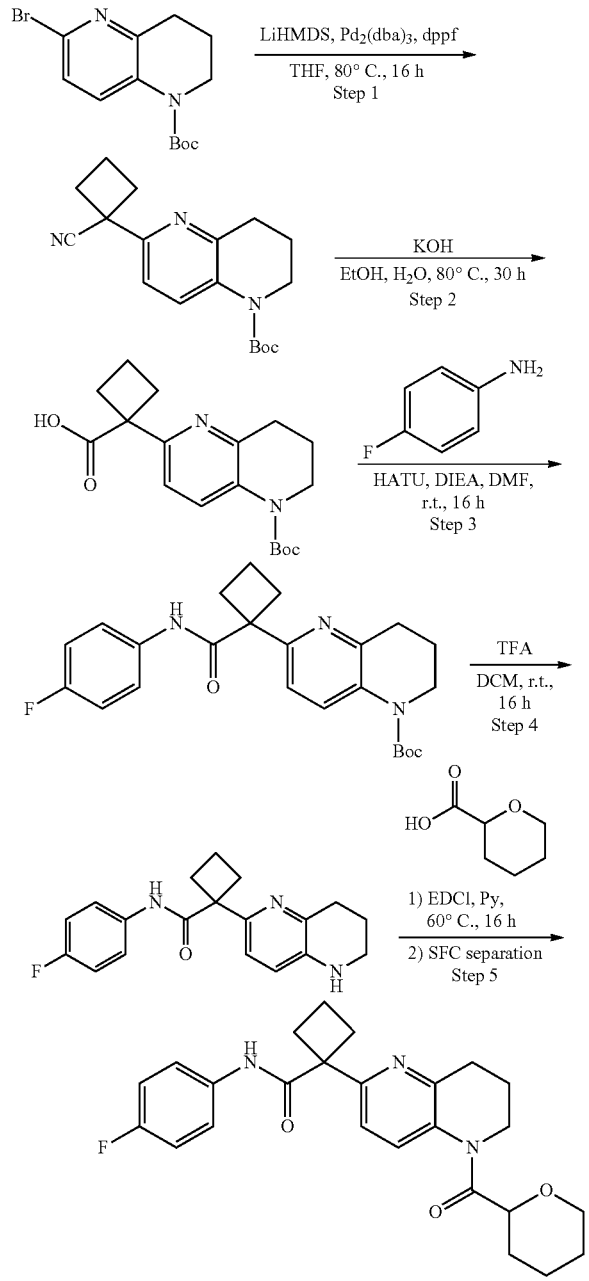

Step 1. tert-butyl 6-(1-cyanocyclobutyl)-3,4-dihydro-1,5-naphthyridine-1(2H)-carboxylate To a solution of tert-butyl 6-bromo-3,4-dihydro-1,5-naphthyridine-1(2H)-carboxylate (10 g, 31.9 mmol) in THF (150 mL) was added dppf (1.770 g, 3.19 mmol), $Pd_2(dba)_3$ (1.462 g, 1.596 mmol), cyclobutanecarbonitrile (5.18 g, 63.9 mmol), and LiHMDS (63.9 mL, 63.9 mmol) (1 M in THF) at RT. After the addition was finished, the resulting mixture was stirred at 80° C. The reaction was monitored by TLC (Pet. ether/EtOAc=5:1) and after stirring at 80° C. for 16 h, the reaction was finished. The reaction was cooled to RT, quenched with sat. $NH_4Cl$ (400 mL), and extracted with ethyl acetate (500 mL×2). The organic layers were collected, washed with brine (300 mL), and dried over anhydrous $Na_2SO_4$. The solid was removed by filtration and the filtrate was concentrated in vacuo. The residue was purified by column chromatography on silica gel ($SiO_2$) (eluting with Petroleum ether/ethyl acetate=20:1 to 8:1) to give the title compound as a an oil. MS (ESI) m/z:314.1 [M+H$^+$]

Step 2. 1-(5-(tert-butoxycarbonyl)-5,6,7,8-tetrahydro-1,5-naphthyridin-2-yl)cyclobutanecarboxylic acid To a stirred solution of tert-butyl 6-(1-cyanocyclobutyl)-3,4-dihydro-1,5-naphthyridine-1(2H)-carboxylate (4.2 g, 13.40 mmol) in ethanol (80 mL) and water (40 mL) was added potassium hydroxide (2.63 g, 46.9 mmol) at 15° C. After the addition, the reaction was stirred at 80° C. and the reaction was monitored by LC-MS. After stirring at 80° C. for 30 h, the reaction was finished and was cooled to RT. Aqueous HCl (1M) was added to adjust pH~6 and the reaction mixture was extracted by EtOAc (200 mL×3). The organic layers were collected, washed with brine, and dried over $Na_2SO_4$. After filtration, the filtrate was concentrated in vacuo and the residue was purified by silica gel chromatography ($SiO_2$, $CH_2C2$/MeOH=20:1 to 10:1) to give the title compound as an oil. MS (ESI) m/z:333.2 [M+H$^+$]

Step 3. tert-butyl 6-(1-((4-fluorophenyl)carbamoyl)cyclobutyl)-3,4-dihydro-1,5-naphthyridine-1(2H)-carboxylate To a stirred solution of 1-(5-(tert-butoxycarbonyl)-5,6,7,8-tetrahydro-1,5-naphthyridin-2-yl)cyclobutanecarboxylic acid (500 mg, 1.504 mmol) in DCM (5 mL) were added HATU (858 mg, 2.256 mmol) and $Et_3N$ (2 mL, 14.35 mmol) at 20° C. After the addition, the reaction was stirred at 20° C. and was monitored by LCMS. After stirring at 20° C. for 2 h, the reaction was finished. The reaction was diluted with water (200 mL) and extracted by ethyl acetate (100 mL×3). The organic layers were collected, combined and washed with brine (ca. 200 mL), and dried over $Na_2SO_4$. After filtration, the filtrate was concentrated in vacuo to give the title compound as a an oil. ESI MS m/z 426.2 [M+H$^+$]

Step 4. N-(4-fluorophenyl)-1-(5,6,7,8-tetrahydro-1,5-naphthyridin-2-yl)cyclobutanecarboxamide To a stirred solution of tert-butyl 6-(1-((4-fluorophenyl)carbamoyl)cyclobutyl)-3,4-dihydro-1,5-naphthyridine-1(2H)-carboxylate (400 mg, 0.940 mmol) in DCM (5 mL) was added TFA (1 mL, 12.98 mmol) at 20° C. After the addition, the reaction was stirred at 20° C. for 16 h and the reaction was finished. Then the reaction was diluted with water (60 mL), extracted by DCM (20 mL×3), the organic layers were collected, washed with brine, and dried over $Na_2SO_4$. After filtration, the filtrate was concentrated in vacuo to give the title compound as an oil, which was used in the next step without further purification. ESI MS m/z: 326.1[M+H$^+$]

Step 5. N-(4-fluorophenyl)-1-(5-(tetrahydro-2H-pyran-2-carbonyl)-5,6,7,8-tetrahydro-1,5-naphthyridin-2-yl)cyclobutanecarboxamide To a stirred solution of N-(4-fluorophenyl)-1-(5,6,7,8-tetrahydro-1,5-naphthyridin-2-yl)cyclobutanecarboxamide (40 mg, 0.123 mmol) in pyridine (2 mL) was added EDCI (71 mg, 0.370 mmol) and tetrahydro-2H-pyran-2-carboxylic acid (24.00 mg, 0.184 mmol) at 16° C. After the addition, the reaction was stirred at 60° C. for 16 h. Then the solvent was removed in vacuo, the residue was purified by prep-HPLC to give the title compound as a solid. $^1$H NMR (400 MHz, CD$_3$OD) δ 8.04 (br s, 1H) 7.46-7.54 (m, 2H) 7.30 (br d, J=8.4 Hz, 1H) 7.00 (t, J=8.7 Hz, 2H) 4.32 (br d, J=9.0 Hz, 1H) 3.97 (br d, J=10.4 Hz, 2H) 3.47-3.74 (m, 2H) 3.01 (t, J=6.8 Hz, 2H) 2.81-2.91 (m, 2H) 2.60-2.76 (m, 2H) 1.85-2.16 (m, 5H) 1.47-1.83 (m, 5H); ESI MS m/z=438.3[M+H$^+$]

After SFC separation, two chiral isomers were obtained —Column OJ (250 mm×30 mm, 5 um), Condition 0.1% NH$_3$H$_2$O ETOH begin B 25%, End B 25%; Gradient Time (min), 100% B Hold Time (min); FlowRate (ml/min) 60, Injections 120

Example 178 (Peak 1): $^1$H NMR (400 MHz, CD3OD) δ 8.05 (br s, 1H) 7.46-7.55 (m, 2H) 7.30 (d, J=8.4 Hz, 1H) 7.01 (t, J=8.8 Hz, 2H) 4.34 (br d, J=8.8 Hz, 1H) 3.98 (br d, J=10.8 Hz, 2H) 3.50-3.74 (m, 2H) 3.02 (t, J=6.9 Hz, 2H) 2.81-2.91 (m, 2H) 2.64-2.75 (m, 2H) 1.87-2.14 (m, 5H) 1.50-1.82 (m, 5H). ESI MS m/z=438.1[M+H$^+$].

Example 179 (Peak 2): $^1$H NMR (400 MHz, CD3OD) δ 7.94 (br s, 1H) 7.35-7.47 (m, 2H) 7.21 (d, J=8.6 Hz, 1H) 6.86-6.98 (m, 2H) 4.24 (br d, J=9.7 Hz, 1H) 3.88 (br d, J=10.8 Hz, 2H) 3.38-3.66 (m, 2H) 2.93 (t, J=6.9 Hz, 2H) 2.71-2.83 (m, 2H) 2.51-2.66 (m, 2H) 1.76-2.08 (m, 5H) 1.43-1.74 (m, 5H), ESI MS m/z=438.1 [M+H$^+$]

The compounds in the following table were prepared in a similar manner as Example 178.

| Ex. # | Structure | Chemical name | Mass [M + H]+ | Hela IC$_{50}$, nM |
|---|---|---|---|---|
| 178 | 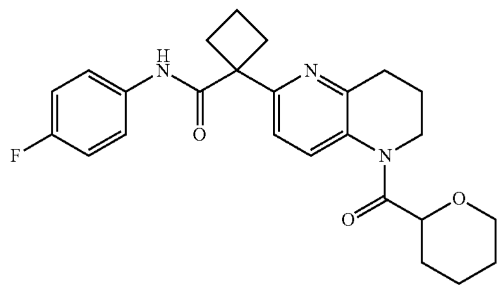 [SMILES: O=C(C1CCCCO1)N1CCCc2nc(C3(C(=O)Nc4ccc(F)cc4)CCC3)ccc21] | N-(4-fluorophenyl)-1-[5-(oxane-2-carbonyl)-5,6,7,8-tetrahydro-1,5-naphthyridin-2-yl]cyclobutane-1-carboxamide | Calc'd 438, found 438 | 1.6 |
| 179 | 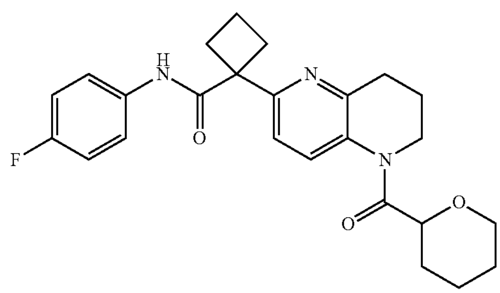 [SMILES: O=C(C1CCCCO1)N1CCCc2nc(C3(C(=O)Nc4ccc(F)cc4)CCC3)ccc21] | N-(4-fluorophenyl)-1-[5-(oxane-2-carbonyl)-5,6,7,8-tetrahydro-1,5-naphthyridin-2-yl]cyclobutane-1-carboxamide | Calc'd 438, found 438 | 1.8 |
| 180 | 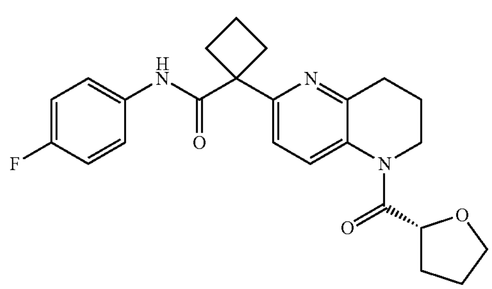 [SMILES: O=C([C@H]1CCCO1)N1CCCc2nc(C3(C(=O)Nc4ccc(F)cc4)CCC3)ccc21] | N-(4-fluorophenyl)-1-{5-[(2R)-oxolane-2-carbonyl]-5,6,7,8-tetrahydro-1,5-naphthyiridin-2-yl}cyclobutane-1-carboxamide | Calc'd 424, found 424 | 1.9 |
| 181 | 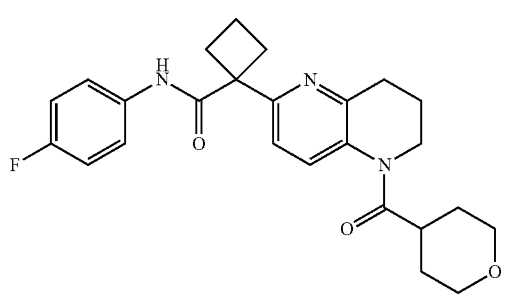 [SMILES: O=C(C1CCOCC1)N1CCCc2nc(C3(C(=O)Nc4ccc(F)cc4)CCC3)ccc21] | N-(4-fluorophenyl)-1-[5-(oxane-4-carbonyl)-5,6,7,8-tetrahydro-1,5-naphthyridin-2-yl]cyclobutane-1-carboxamide | Calc'd 438, found 438 | 3.1 |

| Ex. # | Structure | Chemical name | Mass [M + H]+ | Hela IC$_{50}$, nM |
|---|---|---|---|---|
| 182 | 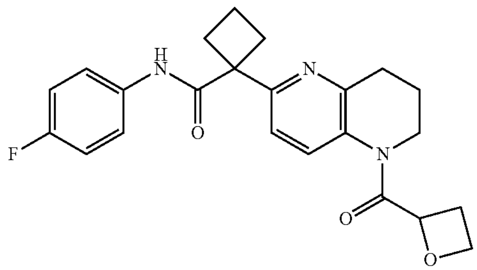 [SMILES: O=C(C1CCO1)N1CCCc2nc(C3(C(=O)Nc4ccc(F)cc4)CCC3)ccc21] | N-(4-fluorophenyl)-1-[5-(oxetane-2-carbonyl)-5,6,7,8-tetrahydro-1,5-naphthyridin-2-yl]cyclobutane-1-carboxamide | Calc'd 410, found 410 | 5.2 |
| 183 | 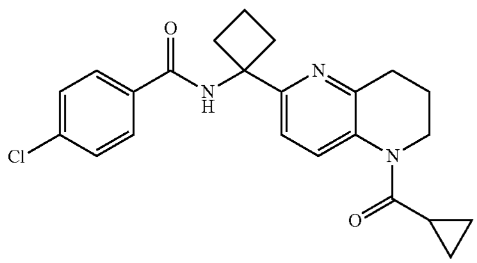 [SMILES: O=C(NC1(c2ccc3c(n2)CCCN3C(=O)C2CC2)CCC1)c1ccc(Cl)cc1] | 4-chloro-N-{1-[5-(cyclopropanecarbonyl)-5,6,7,8-tetrahydro-1,5-naphthyridin-2-yl]cyclobutyl}benzamide | Calc'd 410, found 410 | 5.2 |

Example 184. 2-(5-(cyclopropanecarbonyl)-5,68-tetrahydro-5-naphthyridin-2-yl)-N-(4-fluorophenyl)-2-methylpropanamide

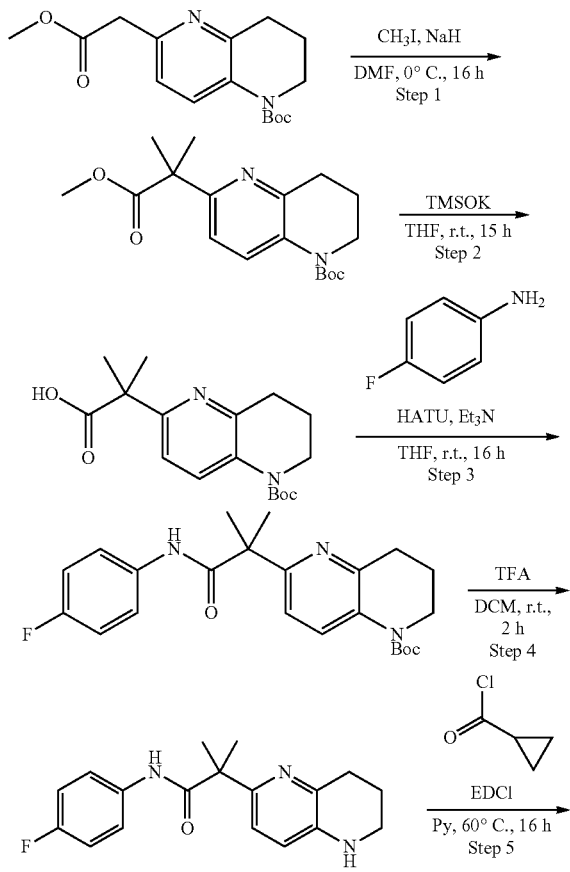

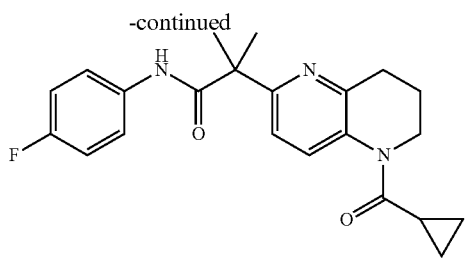

Step 1. tert-butyl 6-(1-methoxy-2-methyl-1-oxopropan-2-yl)-3,4-dihydro-1,5-naphthyridine-1(2H)-carboxylate To a solution of tert-butyl 6-(2-methoxy-2-oxoethyl)-3,4-dihydro-1,5-naphthyridine-1(2H)-carboxylate (800 mg, 2.61 mmol) in DMF (5 mL) was added sodium hydride (230 mg, 5.74 mmol) (60%) at 0° C. After the addition, the mixture was stirred at 0° C. for 10 min and iodomethane (0.41 mL, 6.53 mmol) was added. The mixture was stirred at 0° C. for 2 h and gradually warmed to RT and stirred for 16 h. LC-MS showed the reaction was finished. Then the mixture was quenched with a sat. solution of NH$_4$Cl (10 mL), water (20 mL) was added, and extracted with EtOAc (20 mL×3). The organic layers were collected and combined, washed with brine, and dried over Na$_2$SO$_4$. The mixture was filtered and the filtrate was concentrated in vacuo. The resulting residue was purified by flash silica gel chromatography (ISCO®; Agela® Flash Column Silica-CS (4 g), Eluent of 0-25% EA/Petroleum ether gradient @ 30 mL/min) to give the title compound as an oil. MS (ESI) m/z: 335.3 [M+H$^+$].

Step 2. 2-(5-(tert-butoxcarbonyl)-5,6,7,8-tetrahydro-1,5-naphthyridin-2-yl)-2-methylpropanoic acid To a solution of tert-butyl 6-(1-methoxy-2-methyl-1-oxopropan-2-yl)-3,4-dihydro-1,5-naphthyridine-1(2H)-carboxylate (400 mg, 1.196 mmol) in THF (20 mL) was added TMSOK (614 mg, 4.78 mmol) at RT. After the addition, the mixture was stirred at RT for 15 h. Then the mixture was acidified to pH 6-7 with acetic acid, diluted with water (20 mL), and extracted by EtOAc (30 mL×2). The organic layers were collected, washed with brine, and dried over $Na_2SO_4$. The solvent was removed in vacuo to give the title compound as an oil, which was used quickly in the next step without further purification. MS (ESI) m/z: 321.1 $[M+H^+]$.

Step 3. tert-butyl 6-(1-((4-fluorophenyl)amino)-2-methyl-1-oxopropan-2-yl)-3,4-dihydro-1,5-naphthyridine-1(2H)-carboxylate To a stirred solution of 2-(5-(tert-butoxycarbonyl)-5,6,7,8-tetrahydro-1,5-naphthyridin-2-yl)-2-methylpropanoic acid (383 mg, 1.195 mmol) in THF (10 mL) were added HATU (545 mg, 1.435 mmol), 4-fluoroaniline (159 mg, 1.435 mmol) and TEA (0.5 mL, 3.59 mmol) at RT. After the addition, the reaction was stirred at 25° C. for 16 h and the mixture was concentrated in vacuo. The residue was purified by flash silica gel chromatography ($SiO_2$, eluting with Petroleum ether/ethyl acetate=3:1) to give the title compound as an oil. MS (ESI) m/z: 414.4 $[M+H^+]$ Step 4. N-(4-fluorophenyl)-2-methyl-2-(5,6,7,8-tetrahydro-1,5-naphthyridin-2-yl)propanamide To a stirred solution of tert-butyl 6-(1-((4-fluorophenyl)amino)-2-methyl-1-oxopropan-2-yl)-3,4-dihydro-1,5-naphthyridine-1(2H)-carboxylate (400 mg, 0.967 mmol) in DCM (2 mL) was added TFA (1 mL, 12.98 mmol) at RT. After the addition, the reaction was stirred at 25° C. for 2 h. LC-MS showed the reaction was finished. Then water (10 mL) was added and the mixture was basified to pH ~8 with sat. $NaHCO_3$ solution, and extracted with DCM (10 mL×3). The organic layers were collected, washed with brine, and dried over $Na_2SO_4$. The solvent was removed in vacuo to give the title compound as an oil, which was used directly in the next step without further purification.

Step 5. 2-(5-(cyclopropanecarbonyl)-5,6,7,8-tetrahydro-1,5-naphthyridin-2-yl)-N-(4-fluorophenyl)-2-methylpropanamide To a stirred solution of N-(4-fluorophenyl)-2-methyl-2-(5,6,7,8-tetrahydro-1,5-naphthyridin-2-yl)propanamide (37 mg, 0.118 mmol) in pyridine (2 mL) were added cyclopropanecarboxylic acid (16 mg, 0.186 mmol) and EDCI (68 mg, 0.355 mmol) at RT. The reaction was stirred at 60° C. for 16h. LC-MS showed the reaction was finished. Then the mixture was cooled to RT and the mixture was concentrated in vacuo. The residue was purified using reversed phase HPLC to give the title compound as a solid. $^1$H NMR (400 MHz, $CD_3OD$) δ 7.90 (br d, J=8.2 Hz, 1H), 7.43-7.51 (m, 2H), 7.33 (d, J=8.4 Hz, 1H), 6.96-7.06 (m, 2H), 3.89 (br t, J=5.9 Hz, 2H), 3.00 (t, J=6.7 Hz, 2H), 1.95-2.12 (m, 3H), 1.66 (s, 6H), 1.00-1.06 (m, 2H), 0.84-0.93 (m, 2H). MS (ESI) m/z: 382.1 $[M+H^+]$.

The compounds in the following table were prepared in a similar manner as Example 184.

| Ex. # | Structure | Chemical name | Mass [M + H]+ | Hela $IC_{50}$, nM |
|---|---|---|---|---|
| 184 | 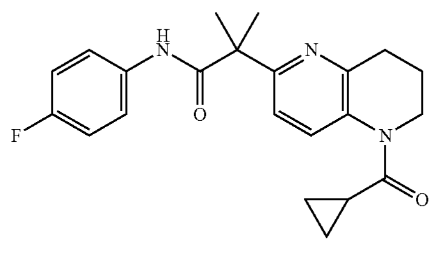 [SMILES: CC(C)(C(=O)Nc1ccc(F)cc1)c1ccc2c(n1)CCCN2C(=O)C1CC1] | 2-[5-(cyclopropanecarbonyl)-5,6,7,8-tetrahydro-1,5-naphthyridin-2-yl]-N-(4-fluorophenyl)-2-methylpropanamide | Calc'd 382, found 382 | 10.8 |
| 185 | 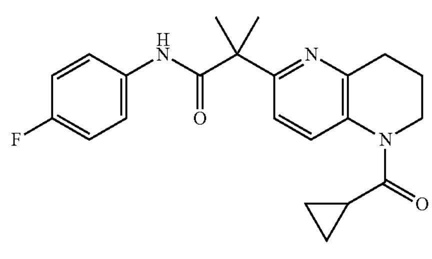 [SMILES: CC(C)(C(=O)Nc1ccc(F)cc1)c1ccc2c(n1)CCCN2C(=O)C1CC1] | N-{2-[5-(cyclopropanecarbonyl)-5,6,7,8-tetrahydro-1,5-naphthyridin-2-yl]propan-2-yl}-4-fluorobenzamide | Calc'd 382, found 382 | 104.4 |
| 186 | 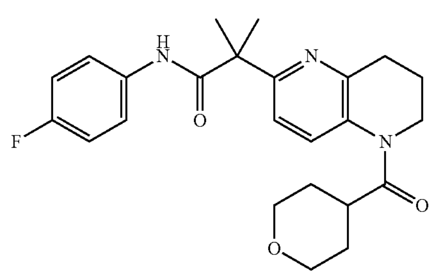 [SMILES: CC(C)(C(=O)Nc1ccc(F)cc1)c1ccc2c(n1)CCCN2C(=O)C1CCOCC1] | N-(4-fluorophenyl)-2-methyl-2-[5-(oxane-4-carbonyl)-5,6,7,8-tetrahydro-1,5-naphthyridin-2-yl]propanamide | Calc'd 426, found 426 | 5.9 |

-continued
| Ex. # | Structure | Chemical name | Mass [M + H]+ | Hela IC$_{50}$, nM |
|---|---|---|---|---|
| 187 | 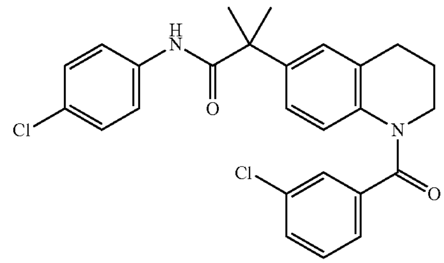 [SMILES: CC(C)(C(=O)Nc1ccc(Cl)cc1)c1ccc2c(c1)CCCN2C(=O)c1cccc(Cl)c1] | 2-[1-(3-chlorobenzene-1-carbonyl)-1,2,3,4-tetrahydroquinolin-6-yl]-N-(4-chlorophenyl)-2-methylpropanamide | Calc'd 467, found 467 | 4.5 |
| 188 | 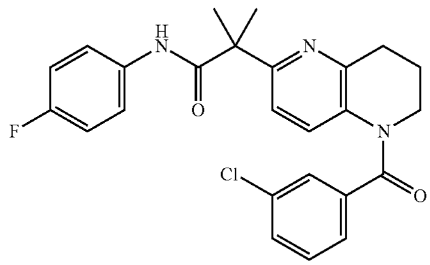 [SMILES: CC(C)(C(=O)Nc1ccc(F)cc1)c1ccc2c(n1)CCCN2C(=O)c1cccc(Cl)c1] | 2-[5-(3-chlorobenzene-1-carbonyl)-5,6,7,8-tetrahydro-1,5-naphthyridin-2-yl]-N-(4-fluorophenyl)-2-methylpropanamide | Calc'd 452, found 452 | 5.7 |
Example 189. 4-chloro-N-(1-(1-(3-chlorobenzol)-4,4-difluoro-1,2,3,4-tetrahydroquinolin-6-yl)ethyl)benzamide
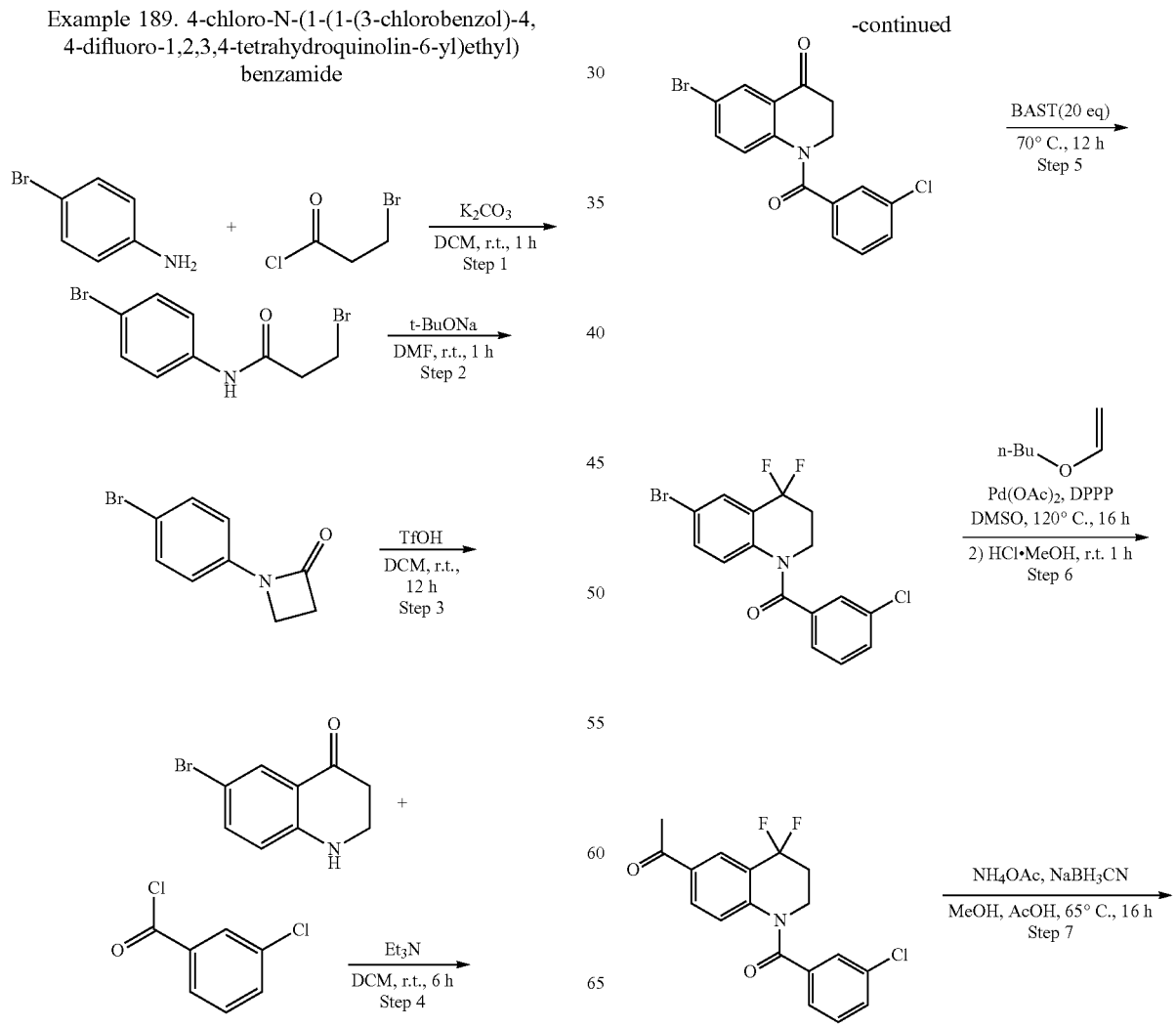

-continued

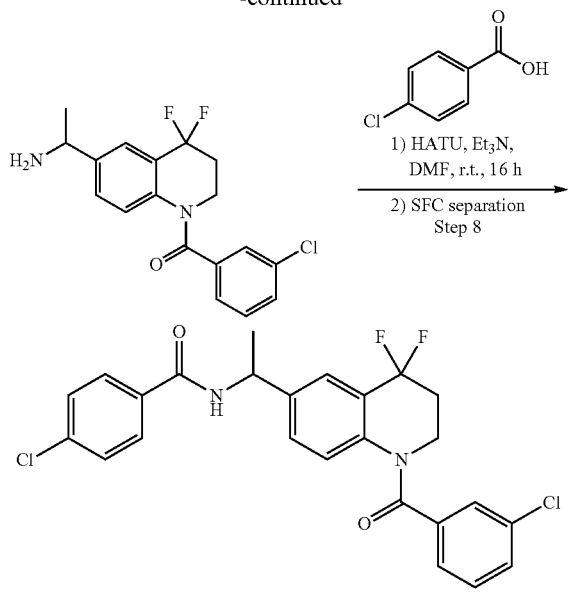

Step 1. 3-bromo-N-(4-bromophenyl)propanamide

To a stirred solution of 4-bromoaniline (10 g, 58.1 mmol) and potassium carbonate (16.07 g, 116 mmol) in DCM (180 mL) was added a solution of 3-bromopropanoyl chloride (7.1 mL, 70.5 mmol) in DCM (20 mL) under nitrogen atmosphere at RT. After the addition was finished, the resulting mixture was stirred at 10° C. The reaction was monitored by TLC (DCM:MeOH=15:1) and after stirring at 10° C. for 1 h, the reaction was finished. The mixture was diluted with water (300 mL), and extracted with DCM (200 mL×2). The combined organic layers were washed with brine (ca. 100 mL), dried over $Na_2SO_4$, and filtered and concentrated under reduced pressure to give the title compound as a solid. MS (ESI) m/z: 307.8 [M+H$^+$].

Step 2. 6-1-(4-bromophenyl)azetidin-2-one

To a stirred solution of 3-bromo-N-(4-bromophenyl)propanamide (17.85 g, 58.1 mmol) in DMF (220 mL) was added t-BuONa (5.87 g, 61.1 mmol) in DMF (40 mL) under nitrogen atmosphere at RT. After the addition, the resulting mixture was stirred at 10° C. for 1 h and the reaction was found to be complete by LCMS. The reaction was diluted with water (2 L), and extracted by ethyl acetate (300 mL×2). The organic layers were collected, washed with brine (ca. 100 mL), dried over $Na_2SO_4$, and the solvent was removed in vacuo. The residue was purified by silica gel chromatography ($SiO_2$, pet. ether: ethyl acetate=30:1 to 5:1) to give the title compound as a solid. MS (ESI) m/z: 227.9 [M+H$^+$].

Step 3. 6-bromo-2,3-dihydroquinolin-4(1H)-one

To a stirred solution of 1-(4-bromophenyl)azetidin-2-one (3.5 g, 15.48 mmol) in DCM (10 mL) under nitrogen atmosphere at 20° C. were added trifluoromethanesulfonic acid (5.0 mL, 56.9 mmol). After the addition was finished, the resulting mixture was stirred at 20° C. for 12 h and the reaction was complete as shown by LCMS. The reaction was quenched with the addition of water (100 mL) and $K_2CO_3$ (3.0 g). The organic layer was washed with sat. NaHCO$_3$ (100 mL) and brine (80 mL), dried over $Na_2SO_4$, and was concentrated under reduced pressure. The residue was purified by silica gel chromatography ($SiO_2$, Pet. ether/Ethyl acetate=100/0 to 10/1) to give the title compound as a solid. MS (ESI) m/z: 225.9 [M+H$^+$].

Step 4. 6-bromo-1-(3-chlorobenzoyl)-2,3-dihydroquinolin-4(1H)-one

To a stirred solution of 6-bromo-2,3-dihydroquinolin-4(1H)-one (1.4 g, 6.19 mmol) in DCM (5 mL) was added Et$_3$N (2.6 mL, 18.65 mmol) at 20° C. After stirring at 20° C. for 15 min, 3-chlorobenzoyl chloride (1.453 g, 8.30 mmol) was added at 0° C. under nitrogen. After the addition, the reaction was stirred at 20° C. under nitrogen for 6 h. Then sat. NaHCO$_3$ was added to adjust pH=7-8, diluted with water (15 mL), and extracted with DCM (10 mL×2). The organic layer was washed with brine (ca. 10 mL), dried over Na$_2$SO$_4$ and concentrated under reduced pressure. The residue was purified by silica gel column chromatography using (petroleum ether/ethyl acetate=100:1-10:1 as eluent) to give the title compound as a solid.

Step 5. (6-bromo-4,4-difluoro-3,4-dihydroquinolin-1(2H)-yl)(3-chlorophenyl)methanone A solution of 6-bromo-1-(3-chlorobenzoyl)-2,3-dihydroquinolin-4(1H)-one (200 mg, 0.549 mmol) in BAST (2 mL, 10.85 mmol) was stirred at 70° C. The reaction was monitored by TLC (petroleum ether/Ethyl acetate=5:1). After stirring at 70° C. for 12 h, the reaction was finished. The mixture was quenched with sat. NaHCO$_3$ (20 mL), and extracted with ethyl acetate (20 mL×2). The organic layer was washed with brine (10 mL), dried over Na$_2$SO$_4$ and was concentrated under reduced pressure. The residue was purified by prep-TLC (SiO$_2$, petroleum ether/EtOAc=7:1) to give the title compound as a solid. MS (ESI) m/z: 388.0 [M+H$^+$].

Step 6. 1-(1-(3-chlorobenzoyl)-4,4-difluoro-1,2,3,4-tetrahydroquinolin-6-yl)ethanone To a stirred solution of (6-bromo-4,4-difluoro-3,4-dihydroquinolin-1(2H)-yl)(3-chlorophenyl)methanone (100 mg, 0.259 mmol) in DMSO (10 mL) and 3-butyl-1-methyl-1h-imidazol-3-ium tetrafluoroborate (0.1 mL, 0.535 mmol) were added 1-(vinyloxy)butane (39 mg, 0.389 mmol), 1,3-bis(diphenylphosphino)propane (32 mg, 0.078 mmol), diisopropylamine (33 mg, 0.326 mmol) and Pd(OAc)$_2$ (9 mg, 0.040 mmol) at 15° C. After the addition, the reaction was stirred at 120° C. under nitrogen atmosphere for 16 h. After being cooled to RT, the mixture was diluted with water (50 mL), and extracted with ethyl acetate (50 mL×3). The organic layers were collected, washed with brine, dried over Na$_2$SO$_4$, and concentrated in vacuo. The residue was purified by prep-TLC (pet. ether/Ethyl acetate=3:1) to give the title compound as a solid. MS (ESI) m/z: 349.1 [M+H$^+$].

Step 7. (6-(1-aminoethyl)-4,4-difluoroquinolin-1(4H)-yl)(3-chlorophenyl)methanone To a stirred solution of 1-(1-(3-chlorobenzoyl)-4,4-difluoro-1,4-dihydroquinolin-6-yl)ethanone (70 mg, 0.201 mmol) in MeOH (10 mL) and AcOH (1 mL) was added ammonium acetate (155 mg, 2.013 mmol) at 20° C. After the addition, the reaction was stirred at 20° C. under nitrogen atmosphere for 2 h. Then sodium cyanoborohydride (48 mg, 0.764 mmol) was added. After the addition was finished, the reaction was stirred at 70° C. under nitrogen for 3 h and LCMS showed the reaction was finished. After cooling to RT, the mixture was added aq. NaOH (50 mL, 6M), and extracted by ethyl acetate (50 mL×3). The organic layers were collected, washed with brine, dried over $Na_2SO_4$ and was concentrated in vacuo to give the title compound as an oil which was used in next step directly without further purification. MS (ESI) m/z: 334.1 [M-16].

Step 8. N-4-chloro-N-(1-(1-(3-chlorobenzoyl)-4,4-difluoro-1,2,3,4-tetrahydroquinolin-6-yl)ethyl)benzamide To a stirred solution of (6-(1-aminoethyl)-4,4-difluoro-3,4-dihydroquinolin-1(2H)-yl)(3-chlorophenyl)methanone (45 mg, 0.128 mmol) in DMF (2 mL) were added 4-chlorobenzoic acid (40 mg, 0.255 mmol), HATU (98 mg, 0.257 mmol) and DIPEA (0.12 mL, 0.687 mmol) at 20° C. The reaction was stirred at 20° C. for 16 h and the solvent was removed under vacuum. Then the residue was purified by reverse phase HPLC to give the title compound as a solid. $^1$H NMR (400 MHz, $CD_3OD$) δ 7.81 (d, J=8.33 Hz, 2H), 7.73 (s, 1H), 7.42-7.53 (m, 4H), 7.33-7.41 (m, 2H), 7.31 (br d, J=8.4 Hz, 1H), 7.12 (br d, J=8.8 Hz, 1H), 5.21 (q, J=7.2 Hz, 1H), 4.00-4.08 (m, 2H), 2.49-2.63 (m, 2H), 1.54 (d, J=7.6 Hz, 3H); MS (ESI) m/z: 511.2 [M+Na$^+$].

After SFC separation, two chiral isomers were obtained-Column OD (250 mm×30 mm×5 um), Condition 0.1% $NH_3H_2O$ EtOH Begin B 45%, End B 45%; Gradient Time (min), 100% B FlowRate (mL/min) 60; Injections 120

The compounds in the following table were prepared in a similar manner as Example 189.

| Ex. # | Structure | Chemical Name | Mass [M + H]+ | Hela IC$_{50}$, nM |
|---|---|---|---|---|
| 189 | 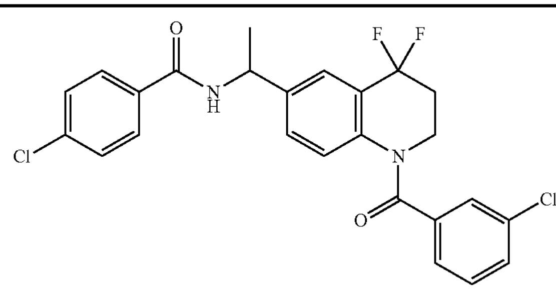 | 4-chloro-N-(1-(1-(3-chlorobenzoyl)-4,4-difluoro-1,2,3,4-tetrahydroquinolin-6-yl)ethyl)benzamide Racemic | Calc'd 489, found 489 | 7.0 |
| 190 | 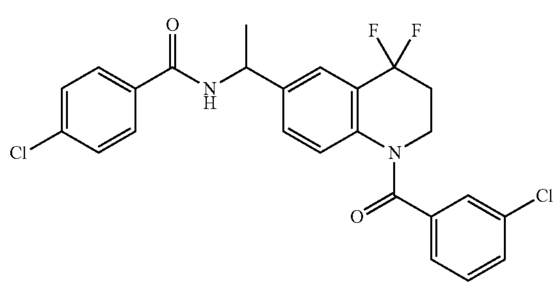 | 4-chloro-N-(1-(1-(3-chlorobenzoyl)-4,4-difluoro-1,2,3,4-tetrahydroquinolin-6-yl)ethyl)benzamide Isomer 1 | Calc'd 489, found 489 | 506.7 |
| 191 | 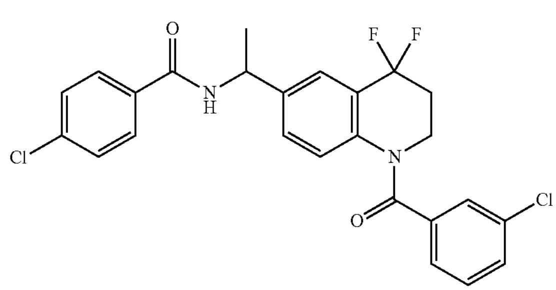 | 4-chloro-N-(1-(1-(3-chlorobenzoyl)-4,4-difluoro-1,2,3,4-tetrahydroquinolin-6-yl)ethyl)benzamide Isomer 2 | Calc'd 489, found 489 | 5.1 |

| Ex. # | Structure | Chemical Name | Mass [M + H]+ | Hela IC$_{50}$, nM |
|---|---|---|---|---|
| 192 | 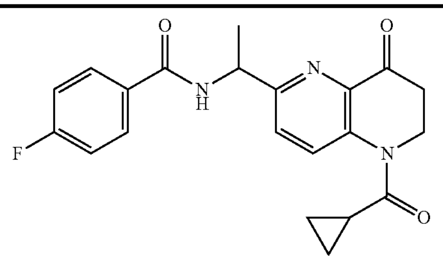 | N-(1-(5-(cyclo-propanecarbonyl)-8-oxo-5,6,7,8-tetrahydro-1,5-naphthyridin-2-yl)ethyl)-4-fluorobenzamide | Calc'd 382, found 382 | 825.2 |

Example 193. N-(1-(5-(cyclopropanecarbonyl)-8,8-difluoro-5,6,7,8-tetrahydro-1,5-naphthyridin-2-yl)ethyl)-4-fluorobenzamide

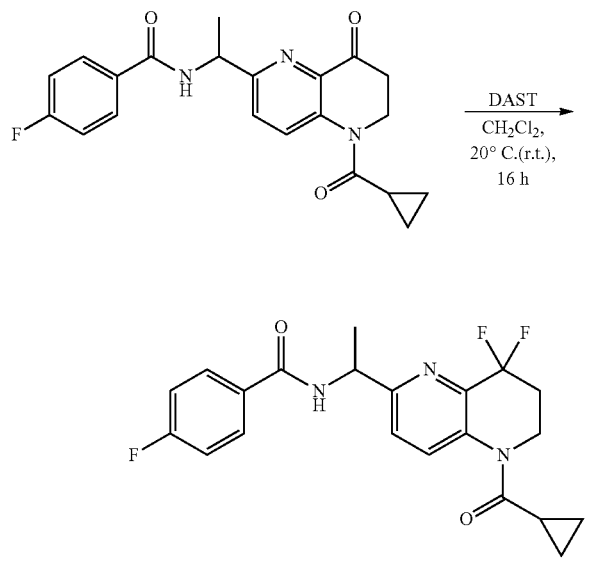

Step 1 N-(1-(5-(cyclopropanecarbonyl)-8,8-difluoro-5,6,7,8-tetrahydro-1,5-naphthyridin-2-yl)ethyl)-4-fluorobenzamide To a stirred solution of N-(1-(5-(cyclopropanecarbonyl)-8-oxo-5,6,7,8-tetrahydro-1,5-naphthyridin-2-yl)ethyl)-4-fluorobenzamide (90 mg, 0.236 mmol) in DCM (3 mL) was added DAST (1 mL, 0.236 mmol) at −78° C. The reaction mixture was stirred at 20° C. for 16 h. LCMS showed the reaction was complete. Then the reaction was diluted with water (10 m), and extracted by DCM (5 mL×3). The organic layers were collected, washed with brine (5 mL), dried over Na$_2$SO$_4$ and was concentrated in vacuo. The residue was purified by a reverse phase HPLC to give the title compound as a solid. $^1$H NMR (400 MHz, CD$_3$OD) δ 8.15 (d, J=8.3 Hz, 1 H), 7.87-7.97 (m, 2H), 7.52 (d, J=8.8 Hz, 1H), 7.14-7.25 (m, 2H), 5.30 (q, J=7.0 Hz, 1H), 4.12-4.21 (m, 2H), 2.51-2.65 (m, 2H), 2.00-2.09 (m, 1H), 1.60 (d, J=7.0 Hz, 3H), 1.04-1.09 (m, 2H), 0.93-1.00 (m, 2H); MS (ESI) m/z: 404.0 (M+H$^+$)

After SFC separation, two chiral isomers were obtained- Column AD (250 mm×30 mm×5 um) Condition 0.1% NH$_3$H$_2$O EtOH Begin B 35%, End B 35% Gradient Time (min); 100% B Hold Time (min) FlowRate (mL/min) 60

Peak 1: 1H NMR (400 MHz, CD3OD) δ 8.16 (d, J=8.8 Hz, 1H), 7.90-7.97 (m, 2H), 7.53 (d, J=8.8 Hz, 1H), 7.17-7.24 (m, 2H), 5.30 (q, J=7.0 Hz, 1H), 4.18 (q, J=5.3 Hz, 2H), 2.51-2.65 (m, 2H), 2.01-2.10 (m, 1H), 1.61 (d, J=7.02 Hz, 3H), 1.04-1.11 (m, 2H), 0.93-1.01 (m, 2H)

Peak 2: 1H NMR (400 MHz, CD3OD) δ 8.16 (d, J=8.8 Hz, 1H), 7.87-7.98 (m, 2H), 7.52 (d, J=8.8 Hz, 1H), 7.16-7.25 (m, 2H), 5.30 (q, J=7.0 Hz, 1H), 4.09-4.24 (m, 2H), 2.48-2.68 (m, 2H), 2.00-2.10 (m, 1H), 1.60 (d, J=7.0 Hz, 3H), 1.07 (quin, J=3.7 Hz, 2H), 0.93-1.01 (m, 2H)

The compounds in the following table were prepared in a similar manner as Example 193.

| Ex. # | Structure | Chemical Name | Mass [M + H]+ | Hela IC$_{50}$, nM |
|---|---|---|---|---|
| 193 | Racemic | N-(1-(5-(cyclopropanecarbonyl)-8,8-difluoro-5,6,7,8-tetrahydro-1,5-naphthyridin-2-yl)ethyl)-4-fluorobenzamide | Calc'd 404, found 404 | 5287.0 |

| Ex. # | Structure | Chemical Name | Mass [M + H]+ | Hela IC50, nM |
|---|---|---|---|---|
| 194 | Isomer 1 | N-(1-(5-(cyclopropanecarbonyl)-8,8-difluoro-5,6,7,8-tetrahydro-1,5-naphthyridin-2-yl)ethyl)-4-fluorobenzamide | Calc'd 404, found 404 | 2655.0 |
| 195 | Isomer 2 | N-(1-(5-(cyclopropanecarbonyl)-8,8-difluoro-5,6,7,8-tetrahydro-1,5-naphthyridin-2-yl)ethyl)-4-fluorobenzamide | Calc'd 404, found 404 | 9543.0 |
Example 196. N-(1-(5-(cyclopropanecarbonyl)-8-hydroxy-5,6,78-tetrahydro-1,5-naphthyridin-2-yl)ethyl)-4-fluorobenzamide
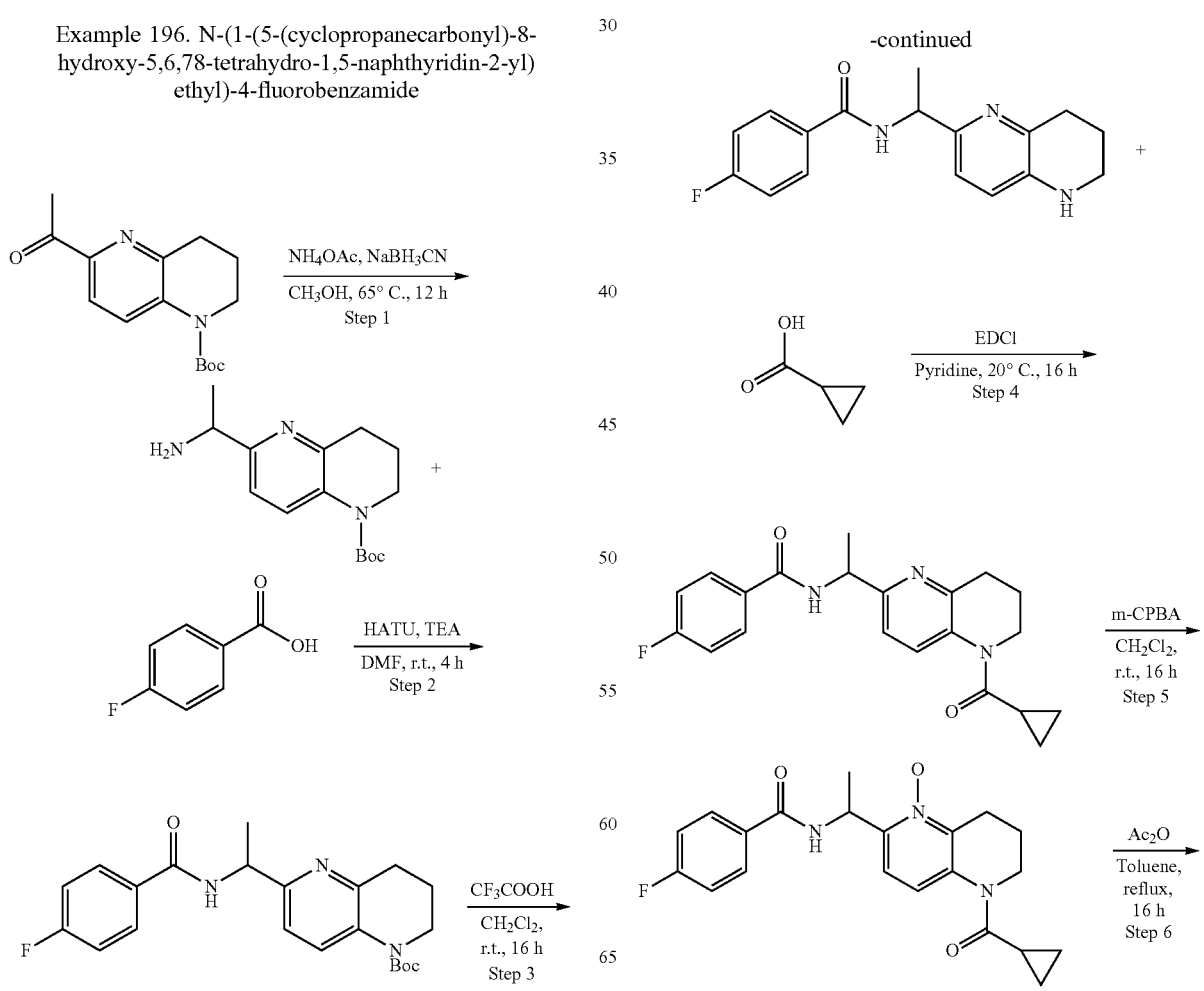

169

-continued

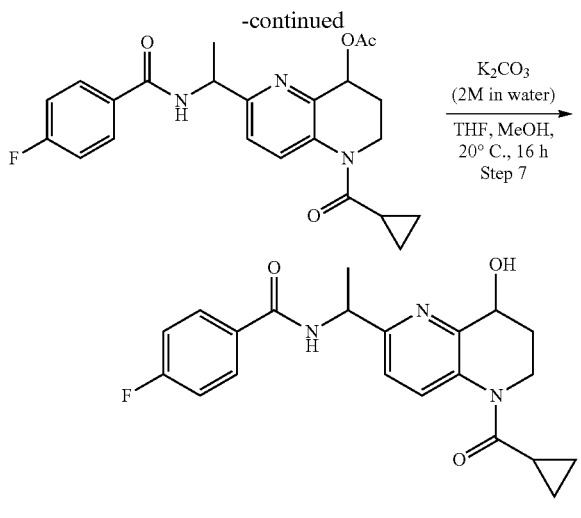

Step 1. tert-butyl 6-(1-aminoethyl)-3,4-dihydro-1,5-naphthyridine-1(2H)-carboxylate To a stirred solution of tert-butyl 6-acetyl-3,4-dihydro-1,5-naphthyridine-1(2H)-carboxylate (3 g, 10.86 mmol) in MeOH (25 mL) was added $NH_4OAc$ (10.04 g, 130 mmol) at 20° C. After stirring at 20° C. for 1 h, $NaBH_3CN$ (2.73 g, 43.4 mmol) was added at 20° C. After the addition, the reaction was stirred at 65° C. for 12 h and the reaction was found to be complete by LCMS. The mixture was neutralized by $NaHCO_3$ to pH=8, diluted with water (100 mL), and extracted with DCM (100 mL×2). The organic layer was washed with brine (30 mL), dried over $Na_2SO_4$, and concentrated under reduced pressure. The residue was purified by silica gel column chromatography using ($CH_2Cl_2$/$CH_3OH$=100:1-1:1 as eluent) to give the title compound as an oil. MS (ESI) m/z:278.1 [M+H$^+$]

Step 2. tert-butyl 6-(1-(4-fluorobenzamido)ethyl)-3,4-dihydro-1,5-naphthyridine-1(2H)-carboxylate To a stirred solution of tert-butyl 6-(1-aminoethyl)-3,4-dihydro-1,5-naphthyridine-1(2H)-carboxylate (1.5 g, 5.41 mmol) in DMF (8 mL) were added 4-fluorobenzoic acid (0.758 g, 5.41 mmol), HATU (2.262 g, 5.95 mmol) and TEA (2.3 mL, 16.50 mmol) at 15° C. The formed reaction mixture was stirred at RT for 16 h and the reaction was quenched by the addition of water (25 mL). Then it was extracted by EtOAc (20 mL×3), the organic layers were collected, washed with brine (10 mL), and dried over $Na_2SO_4$. After filtration, the filtrate was concentrated in vacuo. The residue was purified by silica gel chromatography ($SiO_2$, Pet. ether/ethyl acetate=50:1 to 10:1) to give the title compound as an oil. MS (ESI) m/z: 400.1 [M+H$^+$]

Step 3. 4-fluoro-N-(1-(5,6,7,8-tetrahydro-1,5-naphthyridin-2-yl)ethyl)benzamide To a stirred solution of tert-butyl 6-(1-(4-fluorobenzamido)ethyl)-3,4-dihydro-1,5-naphthyridine-1(2H)-carboxylate (1.6 g, 4.01 mmol) in DCM (3 mL) was added TFA (3 mL, 4.01 mmol) at 20° C. The reaction mixture was stirred at 20° C. for 16 h and the solvent was removed in vacuo to give the title compound as an oil, which was used directly in next step without further purification. MS (ESI) m/z: 300.1 [M+H$^+$]

170

Step 4. N-(1-(5-(cyclopropanecarbonyl)-5,6,7,8-tetrahydro-1,5-naphthyridin-2-yl)ethyl)-4-fluorobenzamide To a stirred solution of 4-fluoro-N-(1-(5,6,7,8-tetrahydro-1,5-naphthyridin-2-yl)ethyl)benzamide (1.1 g, 3.67 mmol) in pyridine (20 mL) was added cyclopropanecarboxylic acid (0.411 g, 4.78 mmol) and EDCI (1.8 g, 9.39 mmol) at 20° C. The reaction was monitored by LC-MS and after stirring at 20° C. for 16 h, the reaction was finished. Then the reaction was quenched by the addition of water (30 mL), and extracted with ethyl acetate (25 mL×2). The organic layers were collected, washed with brine (20 mL) and dried over $Na_2SO_4$. The solvent was removed in vacuo and the residue was purified by flash silica gel chromatography (ISCO®; Agela® Flash Column Silica-CS (20 g), Eluent of 080% Ethyl acetate/Petroleum ether gradient @ 40 mL/min) to give the title compound as a solid. MS (ESI) m/z: 368.2 [M+H$^+$]

Step 5. 5-(cyclopropanecarbonyl)-2-(1-(4-fluorobenzamido)ethyl)-5,6,7,8-tetrahydro-1,5-naphthyridinel-oxide To a stirred solution of N-(1-(5-(cyclopropanecarbonyl)-5,6,7,8-tetrahydro-1,5-naphthyridin-2-yl)ethyl)-4-fluorobenzamide (1.2 g, 3.27 mmol) in DCM (20 mL) was added 3-chlorobenzoperoxoic acid (1.127 g, 6.53 mmol) at 20° C. After the addition was finished, the reaction was stirred at 20° C. for 16 h. Then the reaction was quenched by the addition of water (35 mL), and extracted by DCM (40 mL×3). The organic layers were collected, washed with brine (20 mL), and dried over $Na_2SO_4$. After the filtration, the filtrate was concentrated in vacuo to give the title compound as a solid, which was used directly in next step without further purification. MS (ESI) m/z: 384.2 [M+H$^+$]

Step 6. 1-(cyclopropanecarbonyl)-6-(1-(4-fluorobenzamido)ethyl)-1,2,3,4-tetrahydro-1,5-naphthyridin-4-yl acetate To a stirred solution of 5-(cyclopropanecarbonyl)-2-(1-(4-fluorobenzamido)ethyl)-5,6,7,8-tetrahydro-1,5-naphthyridine 1-oxide (1.2 g, 3.13 mmol) in toluene (8 mL) was added acetic anhydride (11 mL, 3.13 mmol) at 20° C. After the addition, the reaction was stirred at 110° C. for 16 h and the reaction was found to be complete by TLC ($SiO_2$, Pet. ether/ethyl acetate=1:1). Then the reaction was quenched by the addition of water (15 mL), and extracted by ethyl acetate (30 mL×3). The organic layers were collected, washed with brine (20 mL), and dried over $Na_2SO_4$. After filtration, the filtrate was concentrated in vacuo and the residue was purified by flash silica gel chromatography (ISCO®; Agela® Flash Column Silica-CS (20 g), Eluent of 080% Ethyl acetate/Petroleum ether gradient @ 40 mL/min) to give the title compound as an oil. MS (ESI) m/z: 426.1 [M+H$^+$]

Step 7. N-(1-(5-(cyclopropanecarbonyl)-8-hydroxy-5,6,7,8-tetrahydro-1,5-naphthyridin-2-yl)ethyl)-4-fluorobenzamide To a stirred solution of 1-(cyclopropanecarbonyl)-6-(1-(4-fluorobenzamido)ethyl)-1,2,3,4-tetrahydro-1,5-naphthyridin-4-yl acetate (1.1 g, 2.59 mmol) in MeOH (15 mL) and THF (15 mL) was added potassium carbonate (3.8 mL, 7.60 mmol) at 20° C. The formed reaction mixture was stirred at 20° C. for 16 h, the reaction was finished as shown by LCMS. 6N HCl was added to adjust pH~7, then the solvent was removed by concentration. The residue was diluted with water (30 mL), and extracted by ethyl acetate (25 mL×3). The organic layers were collected, washed with brine (15 mL), dried over $Na_2SO_4$ and the solvent was concentrated in vacuo. The residue was purified by flash silica gel chromatography (ISCO®; Agela® Flash Column Silica-CS (20 g), Eluent of 0100% Ethyl acetate/Petroleum ether gradient @ 50 mL/min) to give the title compound as a solid. MS (ESI) m/z: 384.2 [M+H$^+$]

After SFC separation, four chiral isomers were obtained-Column AD (250 mm×30 mm, 10 um); Condition 0.1% $NH_3H_2O$ IPA Begin B 30% End B 30%; Gradient Time (min) 100% B Hold Time (min); FlowRate (ml/min) 60 mL/min Example 197 and Example 199(RT=5.243) $^1$H NMR (400 MHz, $CD_3OD$) δ 8.39 (brd, J=8.8 Hz, 1H), 7.91-7.98 (m, 2H), 7.55 (d, J=8.6 Hz, 1H), 7.21 (t, J=8.7 Hz, 2H), 5.35 (q, J=6.9 Hz, 1H), 4.86-4.89 (m, 1H), 4.18 (ddd, J=12.5, 7.4, 4.7 Hz, 1H), 3.92 (ddd, J=12.6, 8.2, 4.4 Hz, 1H), 2.24-2.35 (m, 1H), 2.00-2.15 (m, 2H), 1.64 (d, J=7.1 Hz, 3H), 1.08-1.14 (m, 1H), 0.89-1.03 (m, 3H)

Example 198 and Example 200(RT=5.831) $^1$H NMR (400 MHz, $CD_3OD$) δ 8.40 (brd, J=8.6 Hz, 1H), 7.88-7.99 (m, 2H), 7.56 (d, J=8.8 Hz, 1H) 7.21 (t, J=8.8 Hz, 2H), 5.35 (q, J=7.1 Hz, 1H), 4.93 (brs, 1H), 4.19 (ddd, J=12.6, 7.5, 4.6 Hz, 1H), 3.91 (ddd, J=12.7, 8.2, 4.4 Hz, 1H), 2.26-2.37 (m, 1H), 2.02-2.13 (m, 2H), 1.64 (d, J=7.1 Hz, 3H), 1.06-1.15 (m, 1H), 0.89-1.04 (m, 3H)

| Ex. # | Structure | Chemical Name | Mass [M + H]+ | Hela IC$_{50}$, nM |
|---|---|---|---|---|
| 196 | 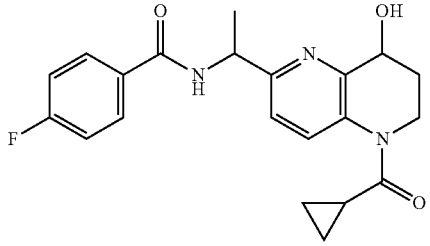 | N-(1-(5-(cyclopropanecarbonyl)-8-hydroxy-5,6,7,8-tetrahydro-1,5-naphthyridin-2-yl)ethyl)-4-fluorobenzamide | Calc'd 384, found 384 | 342.0 |
| 197 | 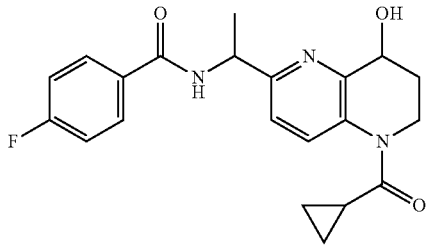
Isomer 1 | N-(1-(5-(cyclopropanecarbonyl)-8-hydroxy-5,6,7,8-tetrahydro-1,5-naphthyridin-2-yl)ethyl)-4-fluorobenzamide | Calc'd 384, found 384 | 290.4 |
| 198 | 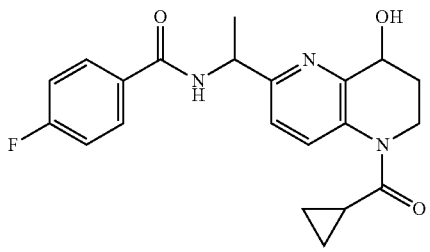 [SMILES: CC(NC(=O)c1ccc(F)cc1)c1ccc2c(n1)C(O)CCN2C(=O)C1CC1]
Isomer 2 | N-(1-(5-(cyclopropanecarbonyl)-8-hydroxy-5,6,7,8-tetrahydro-1,5-naphthyridin-2-yl)ethyl)-4-fluorobenzamide | Calc'd 384, found 384 | 393.2 |

-continued

| Ex. # | Structure | Chemical Name | Mass [M + H]+ | Hela IC$_{50}$, nM |
|---|---|---|---|---|
| 199 | 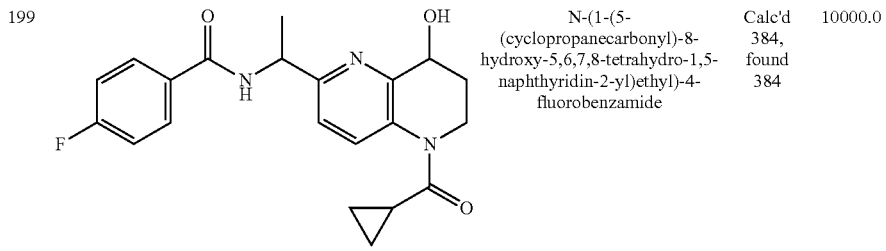<br>Isomer 3 | N-(1-(5-(cyclopropanecarbonyl)-8-hydroxy-5,6,7,8-tetrahydro-1,5-naphthyridin-2-yl)ethyl)-4-fluorobenzamide | Calc'd 384, found 384 | 10000.0 |
| 200 | 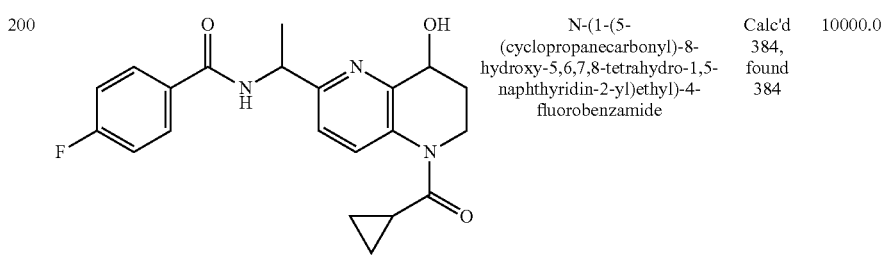<br>Isomer 4 | N-(1-(5-(cyclopropanecarbonyl)-8-hydroxy-5,6,7,8-tetrahydro-1,5-naphthyridin-2-yl)ethyl)-4-fluorobenzamide | Calc'd 384, found 384 | 10000.0 |

Example 201. N-(1-(5-(cyclopropanecarbonyl)-8-fluoro-5,6,7,8-tetrahydro-1,5-naphthyridin-2-yl)ethyl)-4-fluorobenzamide

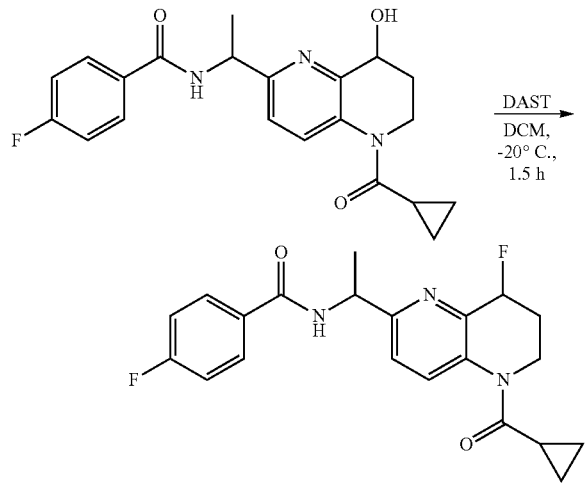

Step 1. N-(1-(5-(cyclopropanecarbonyl)-8-fluoro-5,6,7,8-tetrahydro-1,5-naphthyridin-2-yl)ethyl)-4-fluorobenzamide To a stirred solution of N-(1-(5-(cyclopropanecarbonyl)-8-hydroxy-5,6,7,8-tetrahydro-1,5-naphthyridin-2-yl)ethyl)-4-fluorobenzamide (100 mg, 0.261 mmol) in DCM (6 mL) was added DAST (126 mg, 0.782 mmol) at −78° C. After the addition, the reaction was stirred at −20° C. for 1.5 h. Then the reaction was quenched by the addition of water (10 mL), and extracted with DCM (10 mL×2). The organic layers were collected, washed with brine (5 mL), and dried over Na$_2$SO$_4$. After filtration, the filtrate was concentrated in vacuo. The formed residue was purified by reverse phase HPLC to give the title compound as a solid. MS (ESI) m/z:386.1 [M+H-]

After SFC separation, 4 isomers were obtained-Column Chiralpak AS-H 250×30 5u; Condition 0.1% NH$_3$H$_2$O IPA Begin B 40% End B 40%; Flow Rate (ml/min) 50

Peak 1. $^1$H NMR (400 MHz, CD3OD) δ 8.25 (br d, J=8.6 Hz, 1H), 7.93 (dd, J=8.8, 5.3 Hz, 2H), 7.47-7.54 (m, 1H), 7.21 (t, J=8.7 Hz, 2H), 5.54-5.75 (m, 1H), 5.27 (q, J=7.3 Hz, 1H), 4.49 (dt, J=13.1, 4.2 Hz, 1H), 3.53-3.68 (m, 1H), 2.48 (ddd, J=18.6, 15.4, 3.2 Hz, 1H), 2.00-2.33 (m, 2H), 1.62 (d, J=7.1 Hz, 3H), 1.09-1.21 (m, 1H), 0.84-1.06 (m, 3H)

Peak 2. $^1$H NMR (400 MHz, CD3OD) δ 8.22 (br d, J=8.8 Hz, 1H), 7.88-8.02 (m, 2H), 7.49 (br d, J=8.4 Hz, 1H), 7.20 (t, J=8.7 Hz, 2H), 5.49-5.70 (m, 1H), 5.29 (q, J=6.9 Hz, 1H), 4.46 (dt, J=13.1, 4.2 Hz, 1H), 3.63 (td, J=12.7, 2.7 Hz, 1H), 2.47 (ddd, J=18.6, 15.3, 3.1 Hz, 1H), 1.99-2.34 (m, 2H), 1.61 (d, J=7.3 Hz, 3H), 1.10-1.22 (m, 1H), 0.82-1.06 (m, 3H)

Peak 3. $^1$HNMR (400 MHz, CD3OD) δ 8.28 (d, J=8.8 Hz, 1H), 7.90-8.00 (m, 2H), 7.52 (dd, J=8.7, 1.7 Hz, 1H), 7.14-7.27 (m, 2H), 5.51-5.74 (m, 1H), 5.22-5.35 (m, 1H), 4.39-4.54 (m, 1H), 3.56-3.71 (m, 1H), 2.48 (ddq, J=18.7, 15.3, 3.3, 3.3, 3.3 Hz, 1H), 1.95-2.34 (m, 2H), 1.61 (d, J=7.1 Hz, 3H), 1.09-1.18 (m, 1H), 0.83-1.06 (m, 3H)

Peak 4. $^1$HNMR (400 MHz, CD3D) 68.25 (d, J=8.8 Hz, 1H), 7.87-7.97 (m, 2H), 7.51 (dd, J=8.6, 1.5 Hz, 1H), 7.13-7.24 (m, 2H), 5.52-5.72 (m, 1H), 5.26 (q, J=7.0 Hz, 1H), 4.48 (d, J=12.8, 4.1 Hz, 1H), 3.53-3.68 (m, 1H), 2.47 (ddd, J=18.9, 15.6, 3.3 Hz, 1H), 1.97-2.34 (m, 2H), 1.61 (d, J=7.0 Hz, 3H), 1.07-1.21 (m, 1H), 0.83-1.06 (m, 3H)

| Ex. # | Structure | Chemical Name | Mass [M + H]+ | Hela IC$_{50}$, nM |
|---|---|---|---|---|
| 201 | Isomer 1 | N-(1-(5-(cyclopropanecarbonyl)-8-fluoro-5,6,7,8-tetrahydro-1,5-naphthyridin-2-yl)ethyl)-4-fluorobenzamide | Calc'd 386, found 386 | 186.2 |
| 202 | Isomer 2 | N-(1-(5-(cyclopropanecarbonyl)-8-fluoro-5,6,7,8-tetrahydro-1,5-naphthyridin-2-yl)ethyl)-4-fluorobenzamide | Calc'd 386, found 386 | 396.4 |
| 203 | Isomer 3 | N-(1-(5-(cyclopropanecarbonyl)-8-fluoro-5,6,7,8-tetrahydro-1,5-naphthyridin-2-yl)ethyl)-4-fluorobenzamide | Calc'd 386, found 386 | 7510.0 |
| 204 | Isomer 4 | N-(1-(5-(cyclopropanecarbonyl)-8-fluoro-5,6,7,8-tetrahydro-1,5-naphthyridin-2-yl)ethyl)-4-fluorobenzamide | Calc'd 386, found 386 | 227.5 |

Example 205. 2-methoxyethyl 6-(1-(4-fluorobenzamido)ethyl)-3,4-dihydro-1,5-naphthyridine-1(2H)-carboxylate

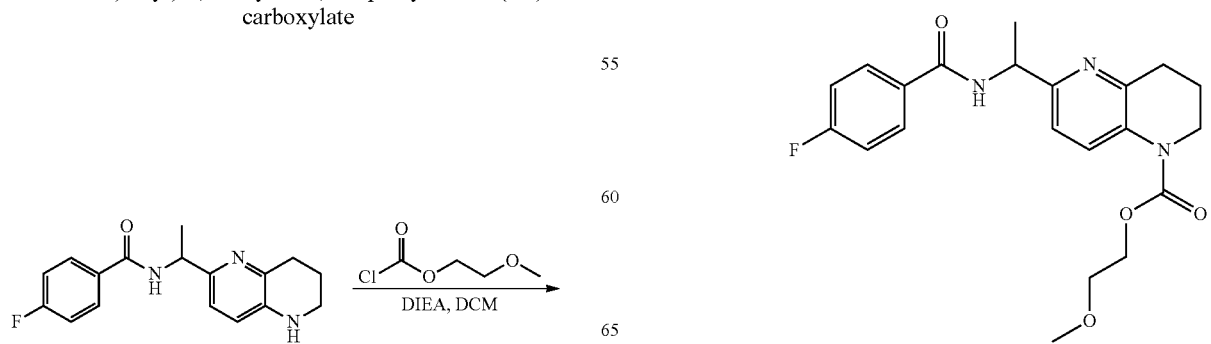

-continued

To a solution of 4-fluoro-N-(1-(5,6,7,8-tetrahydro-1,5-naphthyridin-2-yl)ethyl)benzamide (made from peak 1 from chiral separation, 50.0 mg, 0.149 mmol) in DCM (1.5 ml) was added DIEA (76 mg, 0.596 mmol) at 25° C., and then was added dropwise 2-methoxyethyl carbonochloridate (41.3 mg, 0.298 mmol) at 0° C. The reaction mixture was stirred at 25° C. for 12 h and water was added thereto. The mixture was extracted with ethyl acetate twice. The organic layers were combined and washed with water, a 2N aqueous hydrochloric acid solution, a sat. aqueous sodium hydrogen carbonate solution, and brine then dried over anhydrous sodium sulfate. The resulting solvent was evaporated under reduced pressure. The crude material was purified by mass-directed reversed phase chromatography (MeCN/water gradient with 0.1% TFA modifier) to give the title compound. MS (ESI) calc'd for C21H24FN3O4 [M+H]+, 402; found, 402. $^1$H NMR (499 MHz, DMSO-d$_6$) δ 8.93 (d, J=6.8 Hz, 1H), 8.21 (s, 1H), 8.08-7.90 (m, 2H), 7.38 (d, J=8.0 Hz, 1H), 7.32 (t, J=8.6 Hz, 2H), 5.29-4.92 (m, 1H), 4.25 (s, 2H), 3.75 (s, 2H), 3.58 (d, J=4.1 Hz, 2H), 3.28 (s, 3H), 3.06-2.77 (m, 2H), 2.04-1.90 (m, 2H), 1.51 (d, J=6.9 Hz, 3H).

The compounds in the following table were prepared in a similar manner as Example 205 using appropriate precursors.

| Ex. # | Structure | Chemical Name | Mass [M + H]+ | Hela IC$_{50}$, nM |
|---|---|---|---|---|
| 205 | 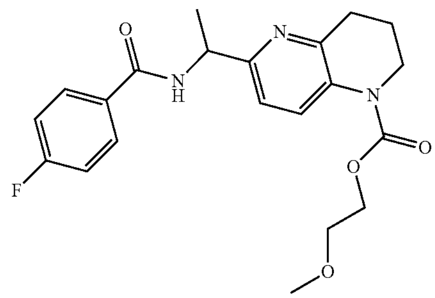 [SMILES: COCCOC(=O)N1CCCc2nc(C(C)NC(=O)c3ccc(F)cc3)ccc21] | 2-methoxyethyl 6-{1-[(4-fluorobenzene-1-carbonyl)amino]ethyl}-3,4-dihydro-1,5-naphthyridine-1(2H)-carboxylate | Calc'd 402, found 402 | 10.4 |
| 206 | 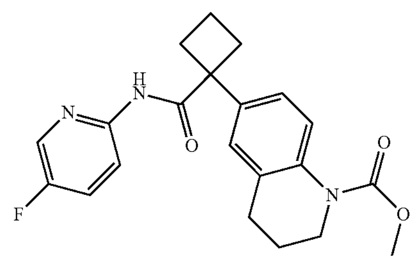 [SMILES: COC(=O)N1CCCc2cc(C3(C(=O)Nc4ccc(F)cn4)CCC3)ccc21] | methyl 6-{1-[(5-fluoropyridin-2-yl)carbamoyl]cyclobutyl}-3,4-dihydroquinoline-1(2H)-carboxylate | Calc'd 384, found 384 | 1.5 |
| 207 | 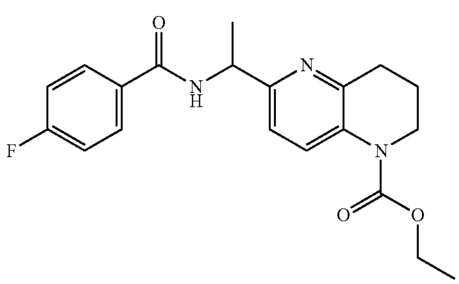 [SMILES: CCOC(=O)N1CCCc2nc(C(C)NC(=O)c3ccc(F)cc3)ccc21] | ethyl 6-{1-[(4-fluorobenzene-1-carbonyl)amino]ethyl}-3,4-dihydro-1,5-naphthyridine-1(2H)-carboxylate | Calc'd 372, found 372 | 3.1 |
| 208 | 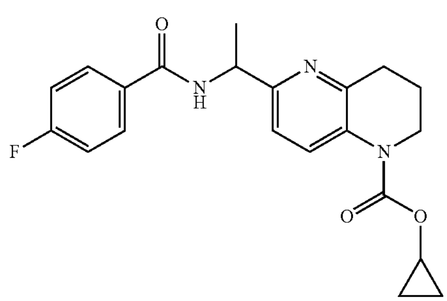 [SMILES: CC(NC(=O)c1ccc(F)cc1)c1ccc2c(n1)CCCN2C(=O)OC1CC1] | cyclopropyl 6-{1-[(4-fluorobenzene-1-carbonyl)amino]ethyl}-3,4-dihydro-1,5-naphthyridine-1(2H)-carboxylate | Calc'd 384, found 384 | 2.0 |

-continued

| Ex. # | Structure | Chemical Name | Mass [M + H]+ | Hela IC$_{50}$, nM |
|---|---|---|---|---|
| 209 | 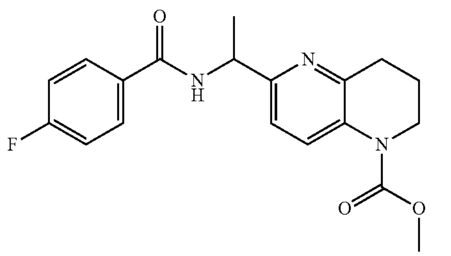 [SMILES: COC(=O)N1CCCc2nc(C(C)NC(=O)c3ccc(F)cc3)ccc21] | methyl 6-{1-[(4-fluorobenzene-1-carbonyl)amino]ethyl}-3,4-dihydro-1,5-naphthyridine-1(2H)-carboxylate | Calc'd 358, found 358 | 21.9 |
| 210 | 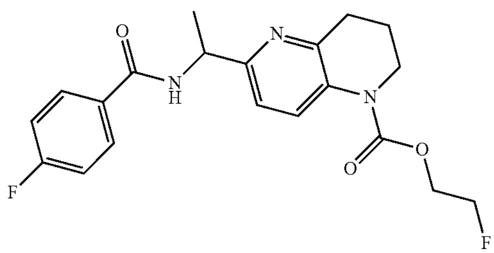 [SMILES: CC(NC(=O)c1ccc(F)cc1)c1ccc2c(n1)CCCN2C(=O)OCCF] | 2-fluoroethyl 6-{1-[(4-fluorobenzene-1-carbonyl)amino]ethyl}-3,4-dihydro-1,5-naphthyridine-1(2H)-carboxylate | Calc'd 390, found 390 | 5.5 |
| 211 | 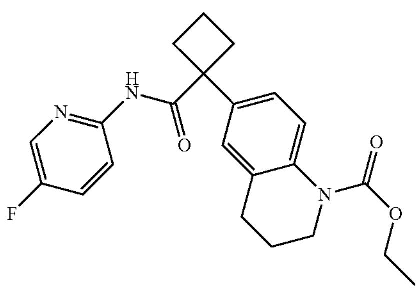 [SMILES: CCOC(=O)N1CCCc2cc(C3(C(=O)Nc4ccc(F)cn4)CCC3)ccc21] | ethyl 6-{1-[(5-fluoropyridin-2-yl)carbamoyl]-cyclobutyl}-3,4-dihydroquinoline-1(2H)-carboxylate | Calc'd 398, found 398 | 2.2 |
| 212 | 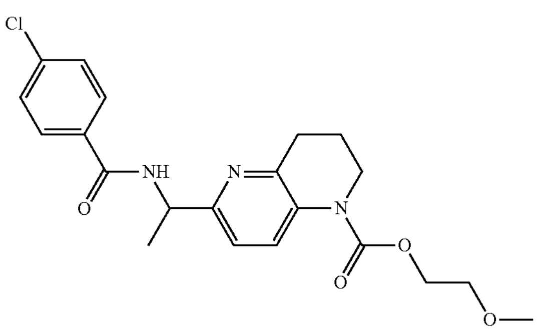 [SMILES: COCCOC(=O)N1CCCc2nc(C(C)NC(=O)c3ccc(Cl)cc3)ccc21] | 2-methoxyethyl 6-{1-[(4-chlorobenzene-1-carbonyl)amino]ethyl}-3,4-dihydro-1,5-naphthyridine-1(2H)-carboxylate | Calc'd 418, found 418 | 3.0 |
| 213 | 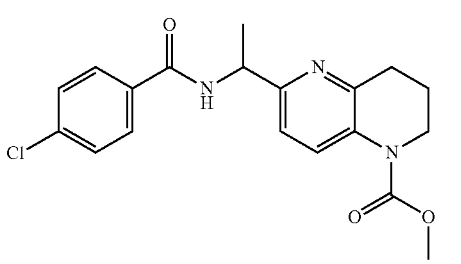 [SMILES: COC(=O)N1CCCc2nc(C(C)NC(=O)c3ccc(Cl)cc3)ccc21] | methyl 6-{1-[(4-chlorobenzene-1-carbonyl)amino]ethyl}-3,4-dihydro-1,5-naphthyridine-1(2H)-carboxylate | Calc'd 374, found 374 | 6.3 |

-continued

| Ex. # | Structure | Chemical Name | Mass [M + H]+ | Hela IC$_{50}$, nM |
|---|---|---|---|---|
| 214 | 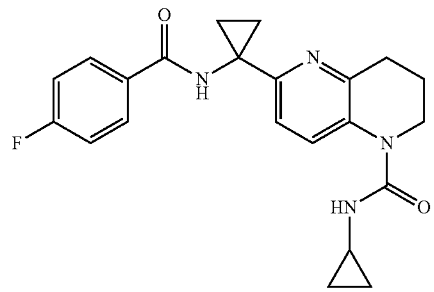 [SMILES: O=C(NC1(c2ccc3c(n2)CCCN3C(=O)NC2CC2)CC1)c1ccc(F)cc1] | N-cyclopropyl-6-{1-[(4-fluorobenzene-1-carbonyl)amino]cyclopropyl}-3,4-dihydro-1,5-naphthyridine-1(2H)-carboxamide | Calc'd 395, found 395 | 159.0 |
| 215 | 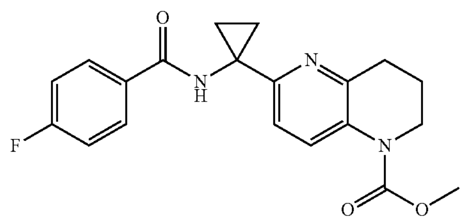 [SMILES: COC(=O)N1CCCc2nc(C3(NC(=O)c4ccc(F)cc4)CC3)ccc21] | methyl 6-{1-[(4-fluorobenzene-1-carbonyl)amino]cyclopropyl}-3,4-dihydro-1,5-naphthyridine-1(2H)-carboxylate | Calc'd 370, found 370 | 57.0 |
| 216 | 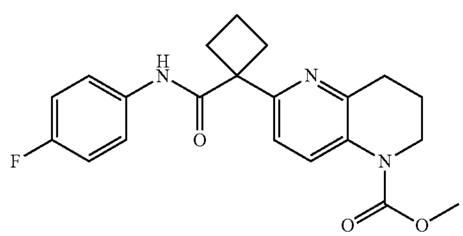 [SMILES: COC(=O)N1CCCc2nc(C3(C(=O)Nc4ccc(F)cc4)CCC3)ccc21] | methyl 6-{1-[(4-fluorophenyl)carbamoyl]cyclobutyl}-3,4-dihydro-1,5-naphthyridine-1(2H)-carboxylate | Calc'd 384, found 384 | 1.5 |
| 217 | 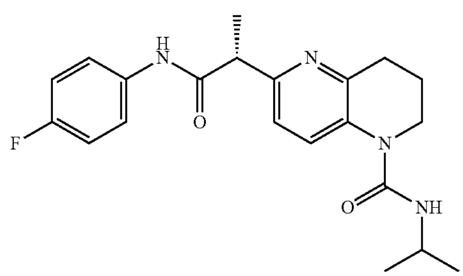 [SMILES: CC(C)NC(=O)N1CCCc2nc([C@@H](C)C(=O)Nc3ccc(F)cc3)ccc21] | 6-{(2R)-1-[(4-fluorophenyl)amino]-1-oxopropan-2-yl}-N-(propan-2-yl)-3,4-dihydro-1,5-naphthyridine-1(2H)-carboxamide | Calc'd 385, found 385 | 24.6 |
| 218 | 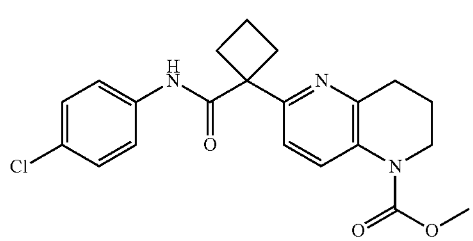 [SMILES: COC(=O)N1CCCc2nc(C3(C(=O)Nc4ccc(Cl)cc4)CCC3)ccc21] | methyl 6-{1-[(4-chlorophenyl)carbamoyl]cyclobutyl}-3,4-dihydro-1,5-naphthyridine-1(2H)-carboxylate | Calc'd 400, found 400 | 5.1 |
| 219 | 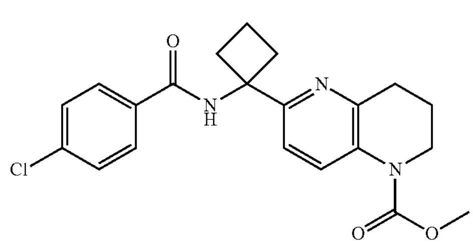 [SMILES: COC(=O)N1CCCc2nc(C3(NC(=O)c4ccc(Cl)cc4)CCC3)ccc21] | methyl 6-{1-[(4-chlorobenzene-1-carbonyl)amino]cyclobutyl}-3,4-dihydro-1,5-naphthyridine-1(2H)-carboxylate | Calc'd 400, found 400 | 9.9 |

| Ex. # | Structure | Chemical Name | Mass [M + H]+ | Hela IC$_{50}$, nM |
|---|---|---|---|---|
| 220 | 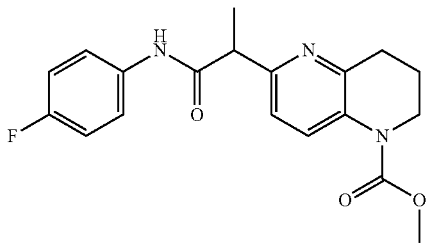 [SMILES: COC(=O)N1CCCc2nc(C(C)C(=O)Nc3ccc(F)cc3)ccc21] | methyl 6-{1-[(4-fluorophenyl)amino]-1-oxopropan-2-yl}-3,4-dihydro-1,5-naphthyridine-1(2H)-carboxylate | Calc'd 358, found 358 | 1.9 |
| 221 | 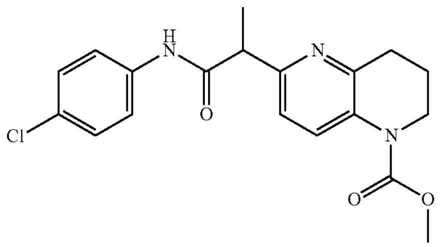 [SMILES: COC(=O)N1CCCc2nc(C(C)C(=O)Nc3ccc(Cl)cc3)ccc21] | methyl 6-{1-[(4-chlorophenyl)amino]-1-oxopropan-2-yl}-3,4-dihydro-1,5-naphthyridine-1(2H)-carboxylate | Calc'd 374, found 374 | 19.8 |
| 222 | 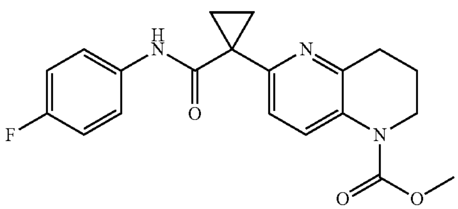 [SMILES: COC(=O)N1CCCc2nc(C3(C(=O)Nc4ccc(F)cc4)CC3)ccc21] | methyl 6-{1-[(4-fluorophenyl)carbamoyl]cyclopropyl}-3,4-dihydro-1,5-naphthyridine-1(2H)-carboxylate | Calc'd 370, found 370 | 21.8 |
| 223 | 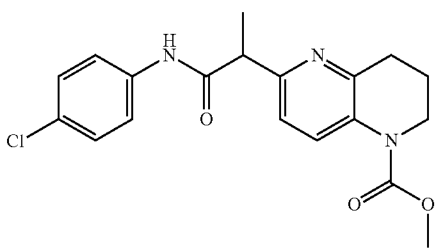 [SMILES: COC(=O)N1CCCc2nc(C(C)C(=O)Nc3ccc(Cl)cc3)ccc21] | methyl 6-{1-[(4-chlorophenyl)amino]-1-oxopropan-2-yl}-3,4-dihydro-1,5-naphthyridine-1(2H)-carboxylate | Calc'd 374, found 374 | 10.8 |

Example 224. 2-(1-(3-chlorobenzyl)-1,2,3,4-tetrahydroquinolin-6-yl)-N-(4-fluorophenyl)propanamide

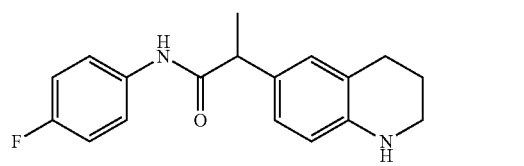

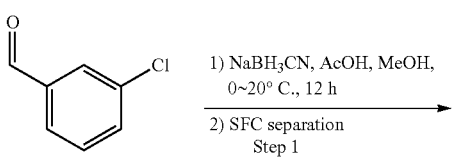

1) NaBH$_3$CN, AcOH, MeOH, 0~20° C., 12 h
2) SFC separation
Step 1

-continued

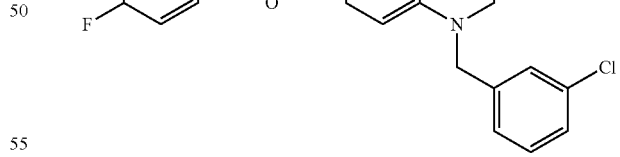

Step 1. 2-(1-(3-chlorobenzyl)-1,2,3,4-tetrahydroquinolin-6-yl)-N-(4-fluorophenyl)propanamide To a mixture of N-(4-fluorophenyl)-2-(1,2,3,4-tetrahydroquinolin-6-yl)propanamide (45 mg, 0.127 mmol) and 3-chlorobenzaldehyde (25 mg, 0.178 mmol) in MeOH (3 mL) was added acetic acid (10 µL, 0.175 mmol) at RT. Then the reaction mixture was cooled to 0° C. and stirred for 0.5 h. NaBH₃CN (30 mg, 0.477 mmol) was added to the reaction portion wise at 0° C. After the addition was finished, the resulting mixture was stirred at RT for 12 h and the reaction was finished as checked by LCMS. The mixture was purified by preparative HPLC to give the title compound (racemic) as a solid. 1H-NMR (400 MHz, CDCl₃) δ 7.38 (br dd, J=4.9, 8.8 Hz, 2H), 7.31 (br d, J=4.6 Hz, 2H), 7.23 (br s, 2H), 7.02-7.10 (m, 2H), 6.99 (br t, J=8.5 Hz, 2H), 6.77 (br d, J=8.6 Hz, 1H), 4.49 (s, 2H), 3.61-3.70 (m, 1H), 3.40-3.48 (m, 2H), 2.88 (br t, J=6.2 Hz, 2H), 2.09 (br d, J=5.7 Hz, 2H), 1.57 (br d, J=7.1 Hz, 3H); MS (ESI) m/z: 423.1 [M+H⁺]

After SFC separation, two chiral isomers were obtained-Column: AD (250 mm×30 mm×10 um); Eluent: 0.1% NH3.H2O IPA; Begin B: 40%; End B: 40%; FlowRate (mL/min): 80; Injections: 40

The compounds in the following table were prepared in a similar manner as Example 224.

| Ex. # | Structure | Chemical Name | Mass [M + H]+ | Hela IC₅₀, nM |
|---|---|---|---|---|
| 224 | racemic | 2-{1-[(3-chlorophenyl)methyl]-1,2,3,4-tetrahydroquinolin-6-yl}-N-(4-fluorophenyl)propanamide | Calc'd 423, found 423 | 7.9 |
| 225 | isomer 1 | 2-{1-[(3-chlorophenyl)methyl]-1,2,3,4-tetrahydroquinolin-6-yl}-N-(4-fluorophenyl)propanamide | Calc'd 423, found 423 | 4.7 |
| 226 | isomer 2 | 2-{1-[(3-chlorophenyl)methyl]-1,2,3,4-tetrahydroquinolin-6-yl}-N-(4-fluorophenyl)propanamide | Calc'd 423, found 423 | 43.6 |
| 227 | 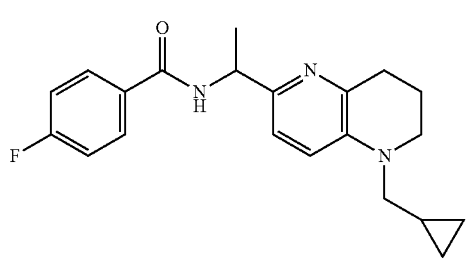 [SMILES: CC(NC(=O)c1ccc(F)cc1)c1ccc2c(n1)CCCN2CC1CC1] | N-{1-[5-(cyclopropylmethyl)-5,6,7,8-tetrahydro-1,5-naphthyridin-2-yl]ethyl}-4-fluorobenzamide | Calc'd 354, found 354 | 70.5 |

| Ex. # | Structure | Chemical Name | Mass [M + H]+ | Hela IC$_{50}$, nM |
|---|---|---|---|---|
| 228 | 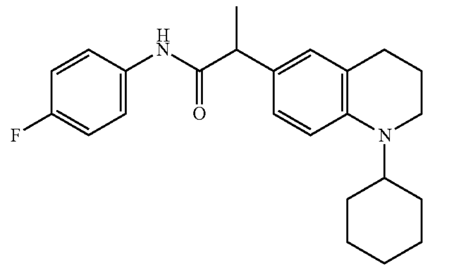 [SMILES: CC(C(=O)Nc1ccc(F)cc1)c1ccc2c(c1)CCCN2C1CCCCC1] | 2-(1-cyclohexyl-1,2,3,4-tetrahydroquinolin-6-yl)-N-(4-fluorophenyl)propanamide | Calc'd 381, found 381 | 4147.0 |
| 229 | 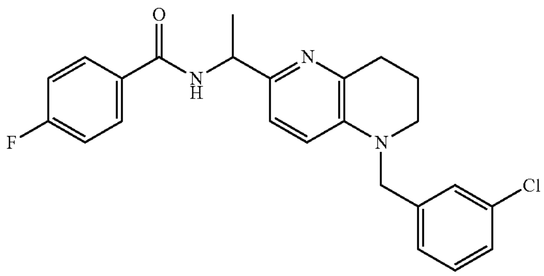 [SMILES: CC(NC(=O)c1ccc(F)cc1)c1ccc2c(n1)CCCN2Cc1cccc(Cl)c1] | N-(1-{5-[(3-chlorophenyl)methyl]-5,6,7,8-tetrahydro-1,5-naphthyridin-2-yl}ethyl)-4-fluorobenzamide | Calc'd 424, found 424 | 3.5 |
| 230 | 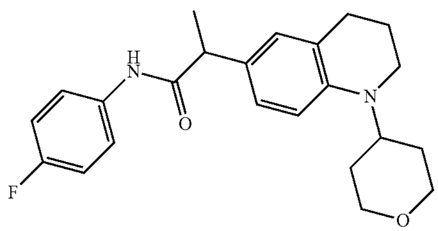 [SMILES: CC(C(=O)Nc1ccc(F)cc1)c1ccc2c(c1)CCCN2C1CCOCC1] | N-(4-fluorophenyl)-2-[1-(oxan-4-yl)-1,2,3,4-tetrahydroquinolin-6-yl]propanamide | Calc'd 383, found 383 | 5791.0 |
| 231 | 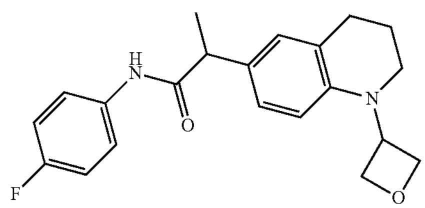 [SMILES: CC(C(=O)Nc1ccc(F)cc1)c1ccc2c(c1)CCCN2C1COC1] | N-(4-fluorophenyl)-2-[1-(oxetan-3-yl)-1,2,3,4-tetrahydroquinolin-6-yl]propanamide | Calc'd 355, found 355 | 91.1 |

Example 232. 1-[1-(1-ethyl-H-pyrazol-3-yl)-1,2,3,4-tetrahydroquinolin-6-yl]-N-(5-fluoropyridin-2-yl)cyclobutane-11-carboxamide

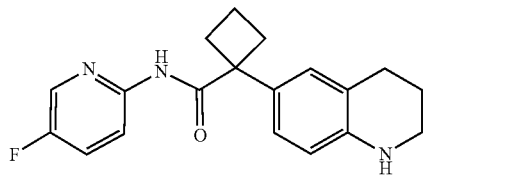

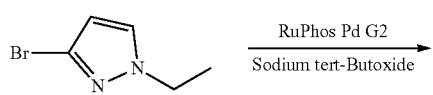

A mixture of N-(5-fluoropyridin-2-yl)-1-(1,2,3,4-tetrahydroquinolin-6 yl)cyclobutanecarboxamide, HCl salt (made from peak 1 intermediate from the chiral separation. 113 mg, 0.312 mmol), 3-bromo-1-ethyl-H-pyrazole (82 mg, 0.468 mmol), RuPhos Pd G2 (CAS 1375325-68-0, 36.3 mg, 0.047 mmol) and sodium tert-butoxide (90 mg, 0.936 mmol) was flushed with nitrogen three time. THF (1 ml) was added and the mixture was stirred at 80° C. for 10h. Then the mixture was concentrated under vacuum and the residue was purified using preparative HPLC to give the title product. LC-MS 420.3 (M+1). $^1$H NMR (499 MHz, DMSO-d$_6$) δ 9.76 (s, 1H), 8.27 (d, J=2.7 Hz, 1H), 8.08 (dd, J=9.2, 4.1 Hz, 1H), 7.71 (td, J=8.8, 2.9 Hz, 1H), 7.63 (d, J=1.8 Hz, 1H), 7.18-7.05 (m, 3H), 5.99 (d, J=1.9 Hz, 1H), 4.08-3.99 (m, 2H), 3.62-3.54 (m, 2H), 2.81-2.69 (m, 4H), 2.46-2.32 (m, 2H), 1.95-1.86 (m, 2H), 1.78 (dt, J=13.6, 6.8 Hz, 2H), 1.35 (t, J=7.2 Hz, 3H).

The compounds in the following table were prepared in a similar manner as Example 232.

| Ex. # | Structure | Chemical Name | Mass [M + H]+ | Hela IC$_{50}$, nM |
|---|---|---|---|---|
| 232 | 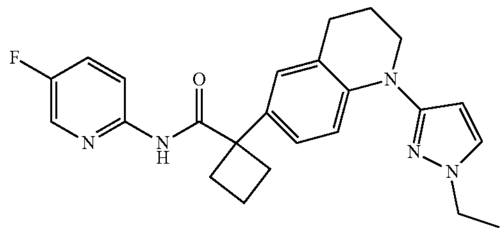 [SMILES: CCn1ccc(N2CCCc3cc(C4(C(=O)Nc5ccc(F)cn5)CCC4)ccc32)n1] | 1-[1-(1-ethyl-1H-pyrazol-3-yl)-1,2,3,4-tetrahydroquinolin-6-yl]-N-(5-fluoropyridin-2-yl)cyclobutane-1-carboxamide | Calc'd 420, found 420 | 5.4 |
| 233 | 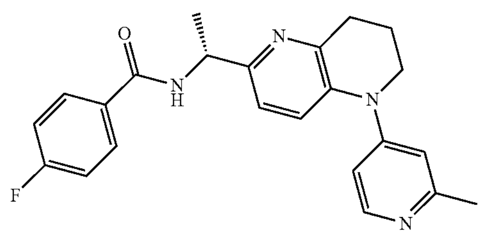 [SMILES: Cc1cc(N2CCCc3nc([C@@H](C)NC(=O)c4ccc(F)cc4)ccc32)ccn1] | 4-fluoro-N-{(1S)-1-[5-(2-methylpyridin-4-yl)-5,6,7,8-tetrahydro-1,5-naphthyridin-2-yl]ethyl}benzamide | Calc'd 391, found 391 | 57.3 |
| 234 | 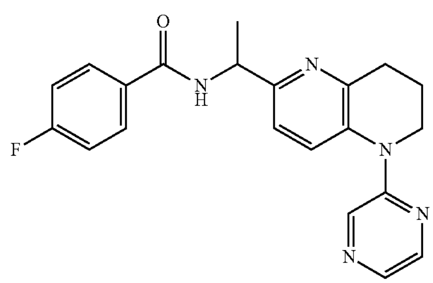 [SMILES: CC(NC(=O)c1ccc(F)cc1)c1ccc2c(n1)CCCN2c1cnccn1] | 4-fluoro-N-{1-[5-(pyrazin-2-yl)-5,6,7,8-tetrahydro-1,5-naphthyridin-2-yl]ethyl}benzamide | Calc'd 378, found 378 | 30.6 |
| 235 | 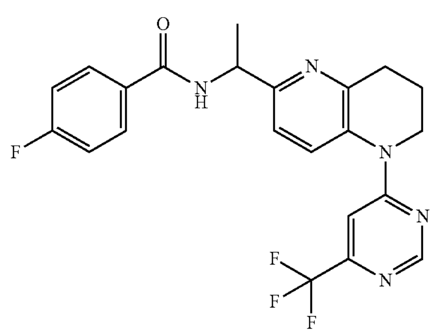 | 4-fluoro-N-(1-{5-[6-(trifluoromethyl)pyrimidin-4-yl]-5,6,7,8-tetrahydro-1,5-naphthyridin-2-yl}ethyl)benzamide Isomer 1 | Calc'd 446, found 446 | 17.0 |

-continued

| Ex. # | Structure | Chemical Name | Mass [M + H]+ | Hela IC$_{50}$, nM |
|---|---|---|---|---|
| 236 | Isomer 2 | 4-fluoro-N-(1-{5-[2-(trifluoromethyl)pyrimidin-4-yl]-5,6,7,8-tetrahydro-1,5-naphthyridin-2-yl}ethyl)benzamide | Calc'd 446, found 446 | 1.9 |
| 237 | 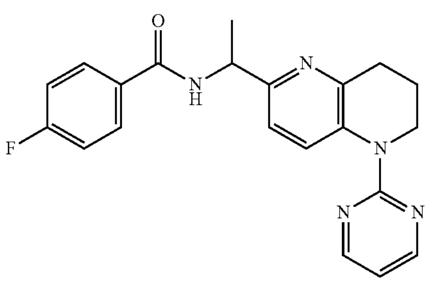 [SMILES: CC(NC(=O)c1ccc(F)cc1)c1ccc2c(n1)CCCN2c1ncccn1] | 4-fluoro-N-{1-[5-(pyrimidin-2-yl)-5,6,7,8-tetrahydro-1,5-naphthyridin-2-yl]ethyl}benzamide | Calc'd 378, found 378 | 35.2 |
| 238 | 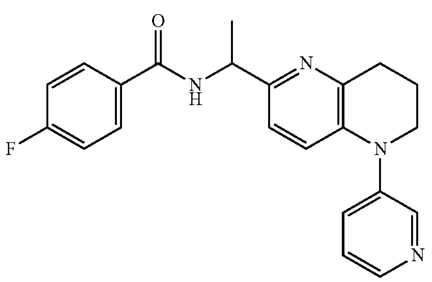 [SMILES: CC(NC(=O)c1ccc(F)cc1)c1ccc2c(n1)CCCN2c1cccnc1] | 4-fluoro-N-{1-[5-(pyridin-3-yl)-5,6,7,8-tetrahydro-1,5-naphthyridin-2-yl]ethyl}benzamide | Calc'd 377, found 377 | 304.0 |
| 239 | Isomer 1 | 4-chloro-N-[1-(6'-fluoro[3,4-dihydro-2H-[1,4'-biquinoline]]-6-yl)ethyl]benzamide | Calc'd 460, found 460 | 11.3 |
| 240 | Isomer 2 | 4-chloro-N-[1-(6'-fluoro[3,4-dihydro-2H-[1,4'-biquinoline]]-6-yl)ethyl]benzamide | Calc'd 460, found | 4779.0 |

-continued

| Ex. # | Structure | Chemical Name | Mass [M + H]+ | Hela IC$_{50}$, nM |
|---|---|---|---|---|
| 241 | 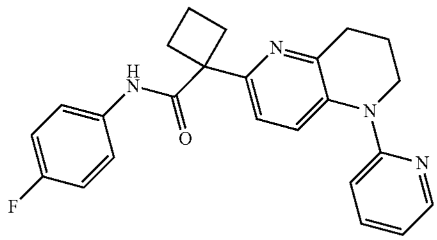 [SMILES: O=C(Nc1ccc(F)cc1)C1(c2ccc3c(n2)CCCN3c2ccccn2)CCC1] | N-(4-fluorophenyl)-1-[1-(pyridin-2-yl)-1,2,3,4-tetrahydroquinolin-6-yl]cyclobutane-1-carboxamide | Calc'd 402, found 402 | 1.7 |
| 242 | 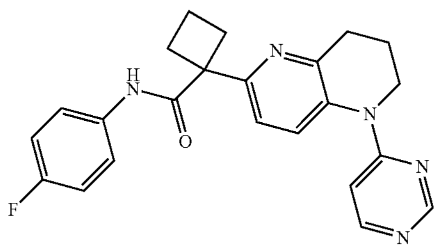 [SMILES: O=C(Nc1ccc(F)cc1)C1(c2ccc3c(n2)CCCN3c2ccncn2)CCC1] | N-(4-fluorophenyl)-1-[1-(pyrimidin-4-yl)-1,2,3,4-tetrahydroquinolin-6-yl]cyclobutane-1-carboxamide | Calc'd 403, found 403 | 1.7 |
| 243 | 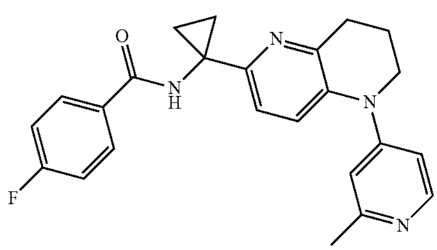 [SMILES: Cc1cc(N2CCCc3nc(C4(NC(=O)c5ccc(F)cc5)CC4)ccc32)ccn1] | 4-fluoro-N-{1-[5-(2-methylpyridin-4-yl)-5,6,7,8-tetrahydro-1,5-naphthyridin-2-yl]cyclopropyl}benzamide | Calc'd 403, found 403 | 14.3 |

Example 244. 4-fluoro-N-(1-(5-(2-methylpyrimidin-4-yl)-5,6,7,8-tetrahydro-1,5-naphthyridin-2-yl)cyclopropyl)benzamide Step 1. 4-fluoro-N-(1-(5,6,7,8-tetrahydro-1,5-naphthyridin-2-yl)cyclopropyl)benzamide hydrochloride

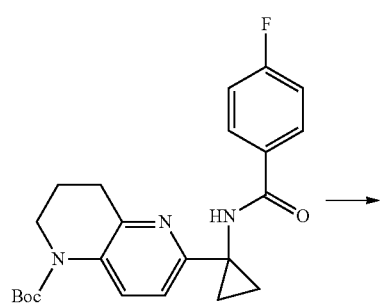

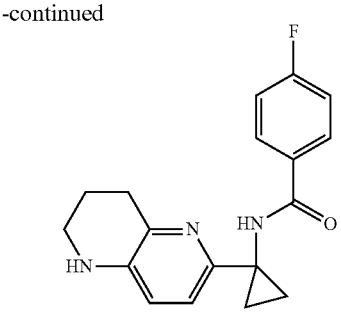

To a solution of tert-butyl 6-(1-(4-fluorobenzamido)cyclopropyl)-3,4-dihydro-1,5-naphthyridine-1(2H)-carboxylate (692 mg, 1.68 mmol) in dioxane (5 ml) was added HCl 4M in dioxane (4.20 ml, 16.8 mmol). The mixture was stirred at RT for 14h. The mixture was concentrated to afford 4-fluoro-N-(1-(5,6,7,8-tetrahydro-1,5-naphthyridin-2-yl)cyclopropyl)benzamide hydrochloride as a light brown solid, which was used for next step directly.

Step 2. 4-fluoro-N-(1-(5-(2-methylpyrimidin-4-yl)-5,6,7,8-tetrahydro-1,5-naphthyridin-2-yl)cyclopropyl)benzamide Method A:

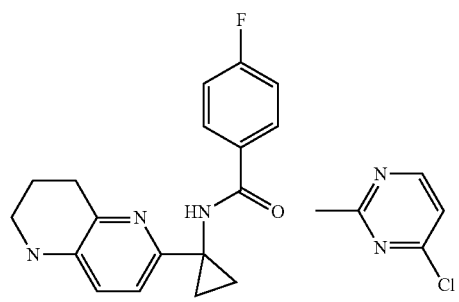

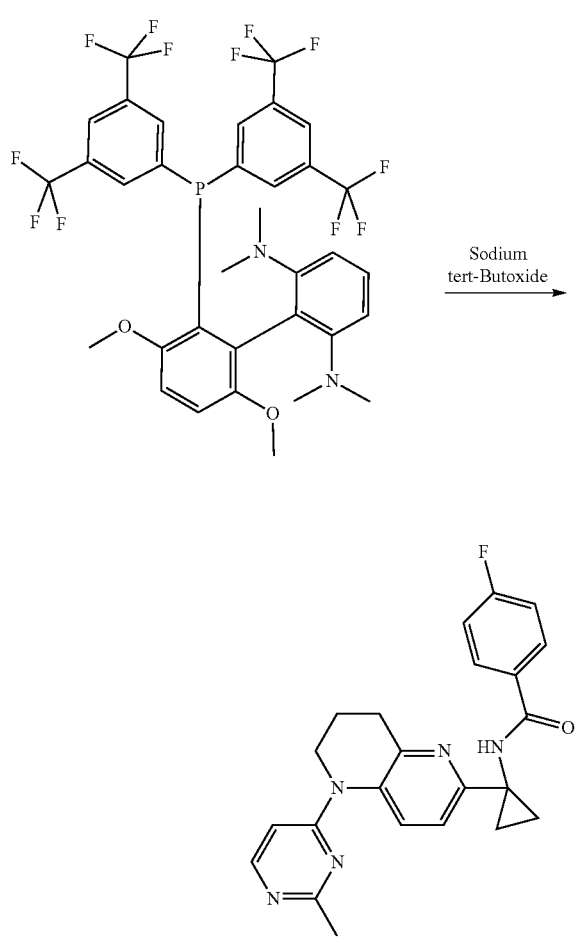

A mixture of 4-fluoro-N-(1-(5,6,7,8-tetrahydro-1,5-naphthyridin-2-yl)cyclopropyl)benzamide hydrochloride (585 mg, 1.68 mmol), 4-bromo-2-methylpyrimidine (727 mg, 4.2 mmol), 2'-(bis(3,5-bis(trifluoromethyl)phenyl)phosphino)-3',6'-dimethoxy-N2,N2,N6,N6-tetramethyl-[1,1'-biphenyl]-2,6-diamine (191 mg, 0.252 mmol), methanesulfonato (2-bis (3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium(II) (287 mg, 0.252 mmol) and sodium tert-butoxide (485 mg, 5.0 mmol) was evacuated and refilled with nitrogen for 3 times, followed by the addition of CPME (8.40 mL). The reaction mixture was heated at 80° C. for 14 h. The reaction mixture was cooled down, filtered, diluted with EtOAc and water. The organic layer was separated, washed with brine, dried over MgSO$_4$, and concentrated. The residue was purified by flash chromatography (0-50% 3:1 ethyl acetate:ethanol/hexanes, 24 gold silica column) to give the title compound as a solid. LC-MS 404.2 (M+1). $^1$H NMR (600 MHz, DMSO-d$_6$) δ 9.27 (s, 1H), 8.19 (d, J=6.1 Hz, 1H), 8.01 (dd, J=8.3, 5.7 Hz, 2H), 7.79 (d, J=8.5 Hz, 1H), 7.33 (t, J=8.7 Hz, 2H), 7.14 (d, J=8.5 Hz, 1H), 6.80 (d, J=6.1 Hz, 1H), 3.86 (t, J=5.9 Hz, 2H), 2.81 (t, J=6.5 Hz, 2H), 2.41 (s, 3H), 1.95 (m, 2H), 1.52 (m, 2H), 1.23 (m, 2H).

Method B:

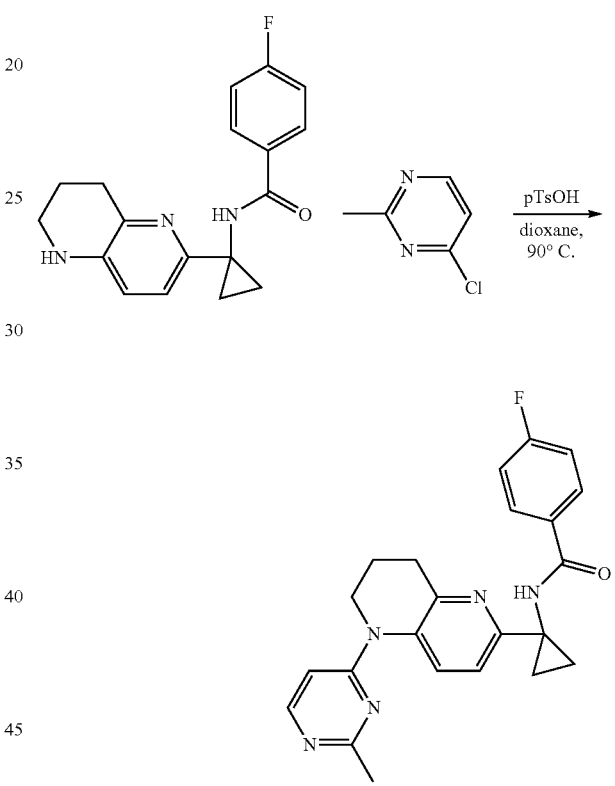

To a flask containing 4-fluoro-N-(1-(5,6,7,8-tetrahydro-1,5-naphthyridin-2-yl)cyclopropyl) benzamide (8.5 g, 27.3 mmol), 4-chloro-2-methylpyrimidine (7.02 g, 54.6 mmol) and 4-methylbenzenesulfonic acid (5.17 g, 30.0 mmol) was added dioxane (137 ml). The mixture was heated at 100° C. for 14h. The mixture was cooled down, neutralized with sat aq. NaHCO$_3$, and extracted with DCM. The combined organics were was dried over MgSO$_4$, and concentrated. The residue was purified by flash chromatography[0~100% (1:3EtOH/EtOAt)/hexanes] to give desired product which was contaminated by some minor impurities. The material was dissolved in minimum amount of DCM, then EtOAc was added until precipitate came out. The mixture was left sitting at rt for 1h and the precipitate was collected by filteration and rinsing with EtOAc to give the title compound as a white solid.

The compounds in the following table were prepared in a similar manner as Example 244.

| Ex. # | Chemical Name | Structure | Mass [M + H]+ | Hela IC$_{50}$, nM |
|---|---|---|---|---|
| 244 | 4-fluoro-N-(1-(5-(2-methylpyrimidin-4-yl)-5,6,7,8-tetrahydro-1,5-naphthyridin-2-yl)cyclopropyl)benzamide | | Calc'd 404, found 404 | 1.4 |
| 245 | 4-fluoro-N-(1-(5-(6-methylpyridin-2-yl)-5,6,7,8-tetrahydro-1,5-naphthyridin-2-yl)cyclopropyl)benzamide | | Calc'd 403, found 403 | 2.7 |
| 246 | 4-fluoro-N-(1-(5-(pyrimidin-4-yl)-5,6,7,8-tetrahydro-1,5-naphthyridin-2-yl)cyclopropyl)benzamide | | Calc'd 390, found 390 | 9.3 |
| 247 | 4-fluoro-N-(1-(5-(pyridin-2-yl)-5,6,7,8-tetrahydro-1,5-naphthyridin-2-yl)cyclopropyl)benzamide | | Calc'd 389, found 389 | 13.9 |
| 248 | 4-fluoro-N-(1-(5-(2-(trifluoromethyl)pyrimidin-4-yl)-5,6,7,8-tetrahydro-1,5-naphthyridin-2-yl)cyclopropyl)benzamide | | Calc'd 458, found 458 | 1.1 |
| 249 | 4-chloro-N-(1-(5-(2-methylpyrimidin-4-yl)-5,6,7,8-tetrahydro-1,5-naphthyridin-2-yl)cyclopropyl)benzamide | | Calc'd 420, found 420 | 0.7 |

| Ex. # | Chemical Name | Structure | Mass [M + H]+ | Hela IC$_{50}$, nM |
|---|---|---|---|---|
| 250 | 4-chloro-N-(1-(5-(2-methylpyrimidin-4-yl)-5,6,7,8-tetrahydro-1,5-naphthyridin-2-yl)ethyl)benzamide | | Calc'd 408, found 408 | 2.0 |
| 251 | 4-fluoro-N-(1-(5-(2-methylpyrimidin-4-yl)-5,6,7,8-tetrahydro-1,5-naphthyridin-2-yl)ethyl)benzamide | | Calc'd 392, found 392 | 3.6 |
Example 253. N-(1-(1-benzoyl-2,3-dihydro-H-pyrido[2,3-b][1,4]oxazin-6-yl)ethyl)-4-chlorobenzamide
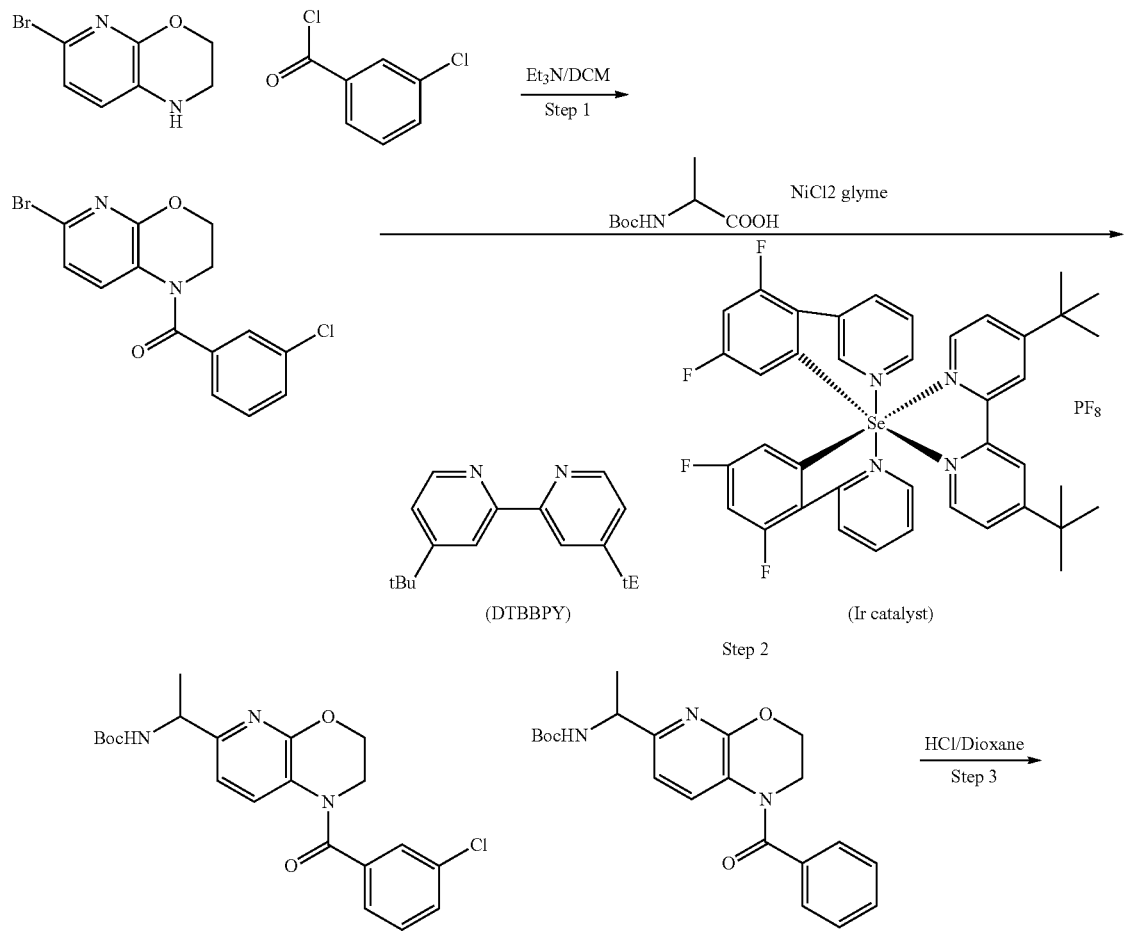

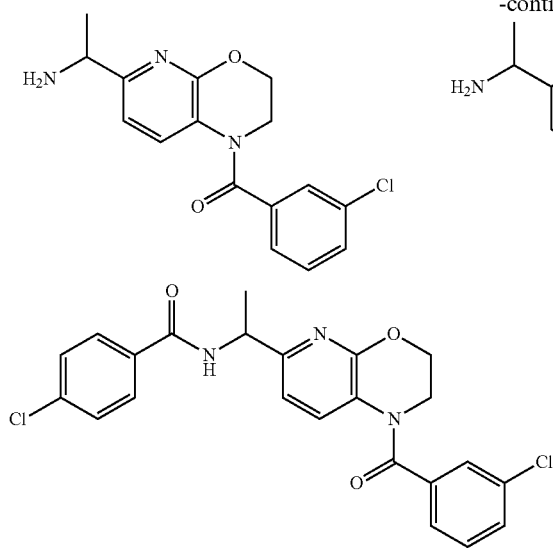
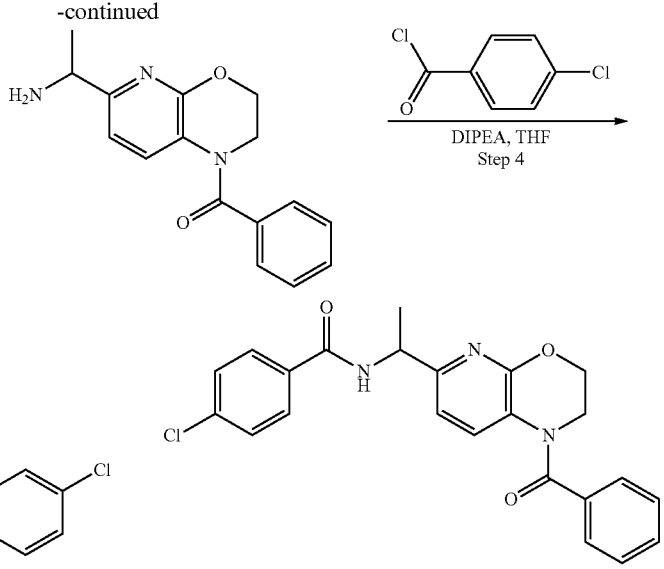

Step 1. 6-bromo-2,3-dihydro-1H-pyrido[2,3-b][1,4]oxazin-1-yl)(3-chlorophenyl)methanone To a solution of 6-bromo-2,3-dihydro-1H-pyrido[2,3-b][1,4]oxazine (500 mg, 2.32 mmol) in DCM (4.6 ml) at RT was added Et$_3$N (648 μl, 4.65 mmol) and 3-chlorobenzoyl chloride (448 mg, 2.56 mmol). After the mixture was stirred at RT for 2 h, it was diluted with sat. NaHCO$_3$ and extracted with EtOAc. The organic layer was separated, washed with brine, dried over MgSO$_4$, and concentrated. The residue was purified by flash chromatography [0-100% (1:3EtOAc/EtOH)/hexanes] to give the title compound. LCMS m/z (M+H$^+$) calc'd: 355; found: 355

Step 2. tert-butyl (1-(1-(3-chlorobenzoyl)-2,3-dihydro-1H-pyrido[2,3-b][1,4]oxazin-6-yl) ethyl) carbamate and tert-butyl (1-(1-benzoyl-2,3-dihydro-1H-pyrido[2,3-b][1,4]oxazin-6-yl)ethyl)carbamate A mixture of DTBBPY (57 mg, 0.21 mmol) and nickel glyme adduct (47 mg, 0.21 mmol) in DMSO (2.8 ml) was bubbled with nitrogen for 10 min and the resulting solution was added to a 20 ml reaction vial containing a mixture of 2-((tert-butoxycarbonyl)amino)propanoic acid (401 mg, 2.12 mmol), cesium carbonate (921 mg, 2.83 mmol), (6-bromo-2,3-dihydro-1H-pyrido[2,3-b][1,4]oxazin-1-yl)(3-chlorophenyl)methanone (500 mg, 1.41 mmol), and Iridium catalyst (139 mg, 0.14 mmol). The resulting mixture was bubbled with nitrogen for 10 min. The reaction mixture was sealed and irradiated using Merck Photo-reactor for 10 h. The reaction mixture was diluted with EtOAc and water. The organic layer was separated and washed with water and brine, dried over MgSO$_4$, and concentrated. The crude material was purified by flash column chromatography [hexanes/(1:3 ethyl acetate/EtOH), 0-100%] to give a mixture of the title compound along with de-Cl-byproduct, ratio~1:1.3. LCMS m/z (M+H$^+$) calc'd: 418, 384; found: 418, 384. This mixture was used for next step.

Step 3 (6-(1-aminoethyl)-2,3-dihydro-1H-pyrido[2,3-b][1,4]oxazin-1-yl)(3-chlorophenyl)methanone and (6-(1-aminoethyl)-2,3-dihydro-1H-pyrido[2,3-b][1,4]oxazin-1-yl)(phenyl)methanone To a solution of the mixture from the previous step in dioxanes (1 ml) containing both tert-butyl (3-((4-(4-((S)-4-fluorobicyclo[4.2.0]octa-1(6), 2,4-trien-7-yl)-5-oxo-4,5-dihydro-1,2,4-oxadiazol-3-yl)-1,2,5-oxadiazol-3-yl)thio)-2-hydroxypropyl) carbamate and tert-butyl (1-(1-benzoyl-2,3-dihydro-1H-pyrido[2,3-b][1,4]oxazin-6-yl)ethyl)carbamate (~270 mg) was added HCl (4.0 M in dioxane, 2 ml). The mixture was stirred at RT for 5 h. The reaction mixture was concentrated and the resulting residue was used directly for next step. LCMS m/z (M+H$^+$) calc'd: 318, 284; found: 318, 284. This mixture was used for the next step.

Step 4. tert-butyl 4-chloro-N-(1-(1-(3-chlorobenzoyl)-2,3-dihydro-1H-pyrido[2,3-b][1,4]oxazin-6-yl)ethyl)benzamide and N-(1-(1-benzoyl-2,3-dihydro-1H-pyrido[2,3-b][1,4]oxazin-6-yl)ethyl)-4-chlorobenzamide To a mixture containing both (6-(1-aminoethyl)-2,3-dihydro-1H-pyrido[2,3-b][1,4]oxazin-1-yl)(3-chlorophenyl)methanone and (6-(1-aminoethyl)-2,3-dihydro-1H-pyrido[2,3-b][1,4]oxazin-1-yl)(phenyl)methanone (~270 mg from the previous step) in THF (1.3 mL) at RT was added DIPEA (550 μl, 3.2 mmol) and 4-chlorobenzoyl chloride (138 mg, 0.79 mmol). The mixture was stirred at RT for 1 h. The reaction mixture was diluted with sat. NaHCO$_3$ and extracted with EtOAc. The organic layer was separated, washed with brine, dried over MgSO$_4$, and concentrated. The residue was purified by flash chromatography [0-100% (1:3EtOAc/EtOH)/hexanes] to give a pure racemic N-(1-(1-benzoyl-2,3-dihydro-1H-pyrido[2,3-b][1,4]oxazin-6-yl)ethyl)-4-chlorobenzamide and impure racemic 4-chloro-N-(1-(1-(3-chlorobenzoyl)-2,3-dihydro-1H-pyrido[2,3-b][1,4]oxazin-6-yl)ethyl)benzamide respectively.

The impure racemic material was separated through chiral separation to give two separated enantiomers. Chiral separation conditions: Chiralpak, OJ-H, 21×250 (mm); Modifier: Methanol +0.25% Dimethyl Ethyl Amine; % modifier in CO$_2$: 20. Peak 1: 5.0 min (tR), peak 2: 5.9 min (tR).

Spectra data for N-(1-(1-benzoyl-2,3-dihydro-1H-pyrido[2,3-b][1,4]oxazin-6-yl)ethyl)-4-chlorobenzamide (racemic): $^1$HNMR (500 MHz, DMSO-d$_6$): 8.86 (d, 1H, J=7.5 Hz), 7.65-8.00 (m, 3H), 7.42-7.60 (m, 7H), 6.92 (d, 1H, J=7.5 Hz), 5.04 (t, 1H, J=7.0 Hz), 4.39 (s, 2H), 3.85 (s, 2H), 1.45 (d, 3H, J=7.0 Hz). LCMS m/z (M+H$^+$) calc'd: 422; found: 422

Spectra data for 4-chloro-N-(1-(1-(3-chlorobenzoyl)-2,3-dihydro-1H-pyrido[2,3-b][1,4]oxazin-6-yl)ethyl)benzamide (enantiomer 1): $^1$HNMR (500 MHz, DMSO-$d_6$): 8.88 (d, 1H, J=7.0 Hz), 7.95 (d, 2H, J=7.0 Hz) 7.42-7.70 (m, 7H), 6.96 (brs, 1H), 5.05 (t, 1H, J=7.0 Hz), 4.43 (s, 2H), 3.85 (s, 2H), 1.47 (d, 3H, J=7.0 Hz). LCMS m/z (M+H$^+$) calc'd: 456; found: 456

4-Chloro-N-(1-(1-(3-chlorobenzoyl)-2,3-dihydro-1H-pyrido[2,3-b][1,4]oxazin-6-yl)ethyl)benzamide (enantiomer 2): $^1$HNMR (500 MHz, DMSO-$d_6$): 8.88 (d, 1H, J=7.0 Hz), 7.95 (d, 2H, J=7.0 Hz) 7.42-7.70 (m 7H), 6.96 (brs, 1H), 5.05 (t, 1H, J=7.0 Hz), 4.43 (s, 2H), 3.85 (s, 2H), 1.47 (d, 3H, J=7.0 Hz). LCMS m/z (M+H$^+$) calc'd: 456; found: 456

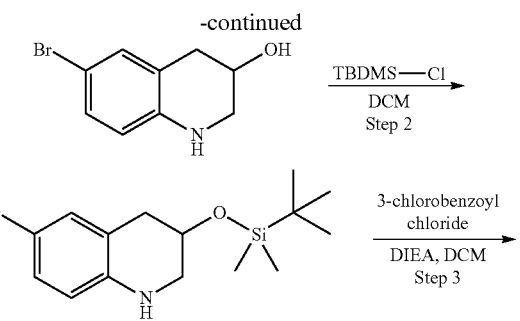

| Ex. # | Structure | Chemical Name | Mass [M + H]+ | Hela IC$_{50}$, nM |
|---|---|---|---|---|
| 253 | (Racemic) | N-(1-(1-benzoyl-2,3-dihydro-1H-pyrido[2,3-b][1,4]oxazin-6-yl)ethyl)-4-chlorobenzamide | Calc'd 422, found 422 | 3.5 |
| 254 | (Isomer 1) | N-(1-(1-benzoyl-2,3-dihydro-1H-pyrido[2,3-b][1,4]oxazin-6-yl)ethyl)-4-chlorobenzamide | Calc'd 456, found 456 | 3.7 |
| 255 | (Isomer 2) | N-(1-(1-benzoyl-2,3-dihydro-1H-pyrido[2,3-b][1,4]oxazin-6-yl)ethyl)-4-chlorobenzamide | Calc'd 456, found 456 | 74.6 |

Example 256. 2-(1-(3-chlorobenzol)-3-fluoro-1,2,3,4-tetrahydroquinolin-6-yl)-N-(4-chlorophenyl)propanamide

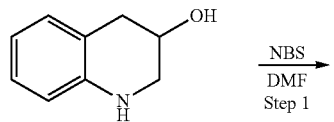

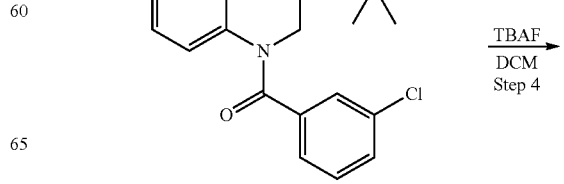

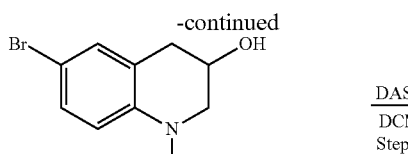

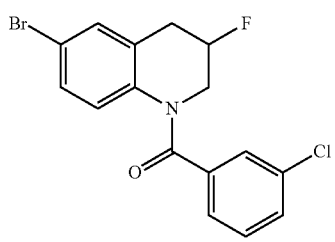

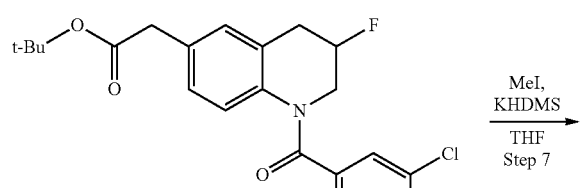

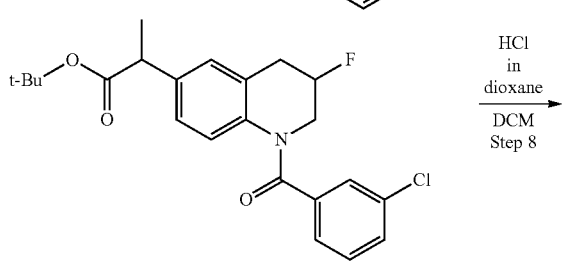

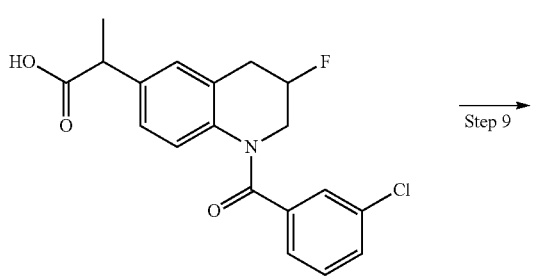

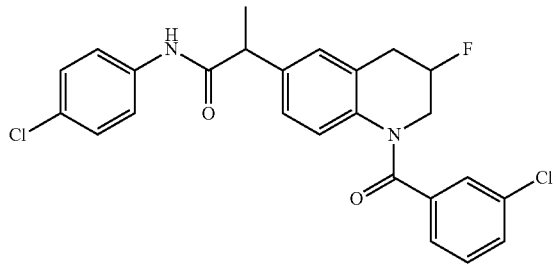

Step 1: 6-bromo-1,2,3,4-tetrahydroquinolin-3-ol

To 1,2,3,4-tetrahydroquinolin-3-ol (1.50 g, 10.05 mmol) in DMF (20.11 ml) at 0° C. was added a solution of NBS (2.147 g, 12.07 mmol) in DMF (3 ml). The mixture was stirred at 0° C. for 1h, then at RT for 14h. LC showed both the mono and di-bromo products. The mixture was diluted with sat. NaHCO₃, and extracted with EtOAc. The organic layer was separated, washed with brine, dried over anhydrous MgSO₄, filtered, and concentrated. The residue was purified by flash chromatography (0-50% EtOAc/hexanes) to give the title compound as a solid. LCMS m/z (M+H⁺) calc'd: 228, found 228.1 and 230

Step 2: 6-bromo-3-((tert-butyldimethylsilyl)oxy)-1,2,3,4-tetrahydroquinoline

To 6-bromo-1,2,3,4-tetrahydroquinolin-3-ol (1.71 g, 7.50 mmol) in DCM (12.00 ml) at 0° C. was added a solution of TBDMS-Cl (1.695 g, 11.25 mmol) in DMF (3 ml). The mixture was stirred at 0° C. for 30 min, then at RT for 20 min. The mixture was diluted with sat. NaHCO₃, and extracted with EtOAc. The organic layer was separated, washed with brine, dried over anhydrous MgSO₄, filtered, and concentrated. The residue was purified by flash chromatography (0-50% EtOAc/hexanes) to give the title compound as an oil. LCMS m/z (M+H) calc'd: 343, found 344/345

Step 3: (6-bromo-3-((tert-butyldimethylsilyl)oxy)-3,4-dihydroquinolin-1(2H)-yl)(3-chlorophenyl)methanone To 6-bromo-3-((tert-butyldimethylsilyl)oxy)-1,2,3,4-tetrahydroquinoline (2.45 g, 7.16 mmol) and DIEA (3.75 ml, 21.47 mmol) in DCM (5 ml) at 0° C. was added 3-chlorobenzoyl chloride (1.566 g, 8.95 mmol). After the addition, the reaction mixture was warmed up to RT and allowed to stir for 30 min. The reaction mixture was concentrated, extracted with ethyl acetate, washed with brine, dried over anhydrous MgSO₄, filtered, and excess solvent was removed under reduced pressure. This was purified on a silica gel column using 20% ethyl acetate-hexane. Appropriate fractions were pooled together, excess solvent was removed under reduced pressure, and vacuum dried to give the title compound as an oil. LCMS m/z (M+H⁺) calc'd: 480, found 480.0 and 482.0

Step 4: (6-bromo-3-hydroxy-3,4-dihydroquinolin-1(2H)-yl)(3-chlorophenyl)methanone To (6-bromo-3-((tert-butyldimethylsilyl)oxy)-3,4-dihydroquinolin-1(2H)-yl)(3-chlorophenyl)methanone (1.00 g, 2.079 mmol) in CH₂Cl₂ (5 ml) at 0° C. was added TBAF (4.16 ml, 4.16 mmol). After the addition, the reaction mixture was stirred at 0° C. for approx. 60 min. The reaction mix was quenched and purified on a silica gel column using ethyl acetate-hex. Appropriate fractions were pooled together, and excess solvent was removed under reduced pressure to give the title compound as a solid (racemic mixture). LCMS m/z (M+H⁺) calc'd: 366, found 366 and 368.

Step 5: (6-bromo-3-fluoro-3,4-dihydroquinolin-1 (2H)-yl)(3-chlorophenyl)methanone To (6-bromo-3-hydroxy-3,4-dihydroquinolin-1(2H)-yl) (3-chlorophenyl)methanone (150.00 mg, 0.409 mmol) in DCM (0.50 ml) at 0° C., DAST (0.065 ml, 0.491 mmol) was added and allowed to stir for 1.5 h. The reaction mixture was quenched with aq. NaHCO$_3$ solution, and diluted with excess DCM. The organic layer was separated, washed with brine, dried over anhydrous MgSO$_4$, filtered, and excess solvent was removed under reduced pressure to give an oil. This was purified on a silica gel column using 20% ethyl acetate/hexane. Appropriate fractions were pooled together, excess solvent was removed under reduced pressure, and vacuum dried to give the title compound as a solid. LCMS m/z (M+H$^+$) calc'd: 368, found 368.0 and 370

Step 6: 4-chloro-N-(1-(5-(2-methylpyrimidin-4-yl)-5,6,7,8-tetrahydro-1,5-naphthyridin-2-yl)ethyl)benzamide A microwave vial was charged with (6-bromo-3-((tert-butyldimethylsilyl)oxy)-3,4-dihydroquinolin-1(2H)-yl)(cyclopropyl)methanone and Pd$_2$(dba)$_3$ (19.38 mg, 0.021 mmol), 2-(dicyclohexylphosphino)-2',4',6'-triisopropylbiphenyl (20.17 mg, 0.042 mmol), and THF (1.00 ml). The vial was thoroughly flushed with nitrogen and then 2-tert-butoxy-2-oxoethylzinc chloride (1.763 ml, 0.882 mmol) was added. The reaction mixture was allowed to stir at 65° C. for 4 h. Additional 4 mL of Zn reagent was added and this was allowed to stir for 3 more h. The reaction was quenched with ammonium chloride and diluted with excess ethyl acetate, excess solvent was removed in-vacuo to remove THF, and then diluted with ethyl acetate. The organic phase was separated, dried over anhydrous MgSO$_4$, filtered, and concentrated in-vacuo. The oil obtained was purified on a silica gel column using 15% ethyl acetate-hex. Appropriate fractions were pooled together, excess solvent was removed under reduced pressure, and vacuum dried to give the title compound as an oil (mixture). LCMS m/z (M+H$^+$) calc'd: 404, found 404.1

Step 7: tert-butyl 2-(1-(3-chlorobenzoyl)-3-fluoro-1,2,3,4-tetrahydroquinolin-6-yl)propanoate To tert-butyl 2-(1-(3-chlorobenzoyl)-3-fluoro-1,2,3,4-tetrahydroquinolin-6-yl)acetate (97 mg, 0.240 mmol) in THF (3 ml) at –78° C. was added potassium hexamethyldisilazide (0.288 ml, 0.288 mmol). This was allowed to sir for 30 min and then iodomethane (0.024 ml, 0.384 mmol) was added. The reaction mixture was allowed to stir at –78° C. for 45 min, warmed to RT and allowed to stir for 1 h. TLC showed no starting material. The reaction mixture was quenched with sat. NH$_4$Cl solution, and diluted with EA. Excess solvent was removed in vacuo. This was diluted with ethyl acetate and brine. The organic layer was separated, dried over anhydrous MgSO$_4$, filtered, and excess solvent was removed in vacuo. The crude oil obtained was purified on a silica gel column using 30% ethyl acetate-hex. Appropriate fractions were pooled together, excess solvent was removed in vacuo, and vacuum dried. The mono and bis-methylated compounds were difficult to separate and deprotected as a mixture in the next step. The title compound was obtained as a solid. LCMS m/z (M+H$^+$) calc'd: 418, found 418.1

Step 8: 2-(1-(3-chlorobenzol)-3-fluoro-1,2,3,4-tetrahydroquinolin-6-yl)propanoic acid To tert-butyl 2-(1-(3-chlorobenzoyl)-3-fluoro-1,2,3,4-tetrahydroquinolin-6-yl)-2-methylpropanoate (97 mg, 0.225 mmol) in DCM (3 ml) at 0° C. was added HCl (0.056 ml, 0.225 mmol). The reaction mixture was allowed to stir at RT for 5 h. Excess solvent was removed under reduced pressure and this was co-evaporated three times with ethyl ether and then vacuum dried to give the title compound as a solid. LCMS m/z (M+H$^+$) calc'd: 362, found 362.0

Step 9: 2-(1-(3-chlorobenzol)-3-fluoro-1,2,3,4-tetrahydroquinolin-6-yl)-N-(4-chlorophenyl)propanamide (Racemic)

To 2-(1-(3-chlorobenzoyl)-3-fluoro-1,2,3,4-tetrahydroquinolin-6-yl)propanoic acid (45.0 mg, 0.124 mmol), HATU (95 mg, 0.249 mmol)) and DIEA (0.065 ml, 0.373 mmol) in DMF (1.00 ml) was added 4-chloroaniline (23.80 mg, 0.187 mmol) at 0° C. The reaction mixture was allowed to stir for 30 min. The reaction mixture was then warmed to RT and allowed to stir for 1 h. The reaction mixture was partitioned into ethyl acetate and aq. NaHCO$_3$ solution. The aq. layer was extracted twice (2×25 mL). The organic layer was separated, washed with water and brine, dried over anhydrous MgSO$_4$, filtered, and excess solvent was removed under reduced pressure. An oil was obtained and purified on HPLC. Appropriate fractions were pooled together, excess solvent was removed under reduced pressure, and vacuum dried to give a title compound as a solid (racemic mixture). $^1$H NMR (499 MHz, DMSO-d$_6$) δ 10.16 (s, 1H), 7.72-7.59 (m, 2H), 7.53-7.44 (m, 1H), 7.34 (t, J=26.1 Hz, 6H), 7.16-6.94 (m, 2H), 5.53-5.26 (m, 1H), 4.28-4.08 (m, 1H), 3.89-3.66 (m, 2H), 3.17-2.99 (m, 3H), 1.37 (d, J=6.8 Hz, 3H). LCMS m/z (M+H$^+$) calc'd: 471, found 471.1

The racemic mixture was resolved using Chiral SFC to afford 2-(1-(3-chlorobenzoyl)-3-fluoro-1,2,3,4-tetrahydroquinolin-6-yl)-N-(4-chlorophenyl)propanamide the four chiral stereoisomers using 1:1 MeOH/CH$_3$CN with Modifier Isopropanol w/0.25% DMEA. The Retention time (min): 3.5, 4.2, 4.8, 6.8.

Isomer 1, first eluting $^1$H NMR (499 MHz, DMSO-d$_6$) δ 10.22 (s, 1H), 7.61 (d, J=8.6 Hz, 2H), 7.50 (s, 1H), 7.43-7.21 (m, 6H), 7.05-6.79 (m, 2H), 5.35 (d, J=49.6 Hz, 1H), 4.32-4.03 (m, 1H), 3.86-3.63 (m, 2H), 3.30-3.06 (m, 2H), 1.37 (d, J=6.8 Hz, 3H). LCMS m/z (M+H$^+$) 471, found 471.1

Isomer 2, second eluting 1H NMR (499 MHz, DMSO-d$_6$) δ 10.24 (s, 1H), 7.61 (d, J=8.6 Hz, 2H), 7.50 (d, J=7.5 Hz, 1H), 7.43-7.22 (m, 6H), 7.14-6.80 (m, 2H), 5.35 (d, J=49.3 Hz, 1H), 4.28-4.08 (m, 1H), 3.98-3.67 (m, 2H), 3.26-3.06 (m, 2H), 1.37 (d, J=6.7 Hz, 3H). LCMS m/z (M+H$^+$) 471, found 471.1

Isomer 3, 3rd eluting 1H NMR (499 MHz, DMSO-d$_6$) δ 10.22 (s, 1H), 7.61 (d, J=8.6 Hz, 2H), 7.50 (d, J=7.6 Hz, 1H), 7.41-7.24 (m, 6H), 7.08-6.78 (m, 2H), 5.35 (d, J=49.8 Hz, 1H), 4.28-4.08 (m, 1H), 3.85-3.68 (m, 2H), 3.25-3.04 (m, 2H), 1.37 (d, J=6.8 Hz, 3H). LCMS m/z (M+H$^+$) 471, found 471.1

Isomer 4, 4th eluting 1H NMR (499 MHz, DMSO-d6) δ 10.22 (s, 1H), 7.61 (d, J=8.6 Hz, 2H), 7.50 (d, J=7.6 Hz, 1H), 7.41-7.24 (m, 61H), 7.08-6.78 (m, 2H), 5.35 (d, J=49.8 Hz, 1H), 4.28-4.08 (m, 11H), 3.85-3.68 (m, 2H), 3.25-3.04 (m, 2H), 1.37 (d, J=6.8 Hz, 3H). LCMS m/z (M+H$^+$) 471, found 471.1

| Ex. # | Structure | Chemical name | Mass [M + H]+ | Hela IC$_{50}$, nM |
|---|---|---|---|---|
| 256 | Isomer 1 | 2-(1-(3-chlorobenzoyl)-3-fluoro-1,2,3,4-tetrahydroquinolin-6-yl)-N-(4-chlorophenyl)propanamide | Calc'd 471, found 471 | 2.37 |
| 257 | Isomer 2 | 2-(1-(3-chlorobenzoyl)-3-fluoro-1,2,3,4-tetrahydroquinolin-6-yl)-N-(4-chlorophenyl)propanamide | Calc'd 471, found 471 | 1.34 |
| 258 | Isomer 3 | 2-(1-(3-chlorobenzoyl)-3-fluoro-1,2,3,4-tetrahydroquinolin-6-yl)-N-(4-chlorophenyl)propanamide | Calc'd 471, found 471 | 5.86 |
| 259 | Isomer 4 | 2-(1-(3-chlorobenzoyl)-3-fluoro-1,2,3,4-tetrahydroquinolin-6-yl)-N-(4-chlorophenyl)propanamide | Calc'd 471, found 471 | 2.51 |

Example 260. 2-(5-(cyclopropanecarbonyl)-5,6,7,8-tetrahydro-1,5-naphthyridin-2-yl)-2-cyclopropyl-N-(4-fluorophenyl)acetamide -continued

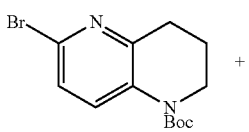

+

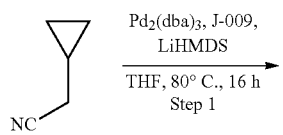

Pd$_2$(dba)$_3$, J-009, LiHMDS

THF, 80° C., 16 h
Step 1

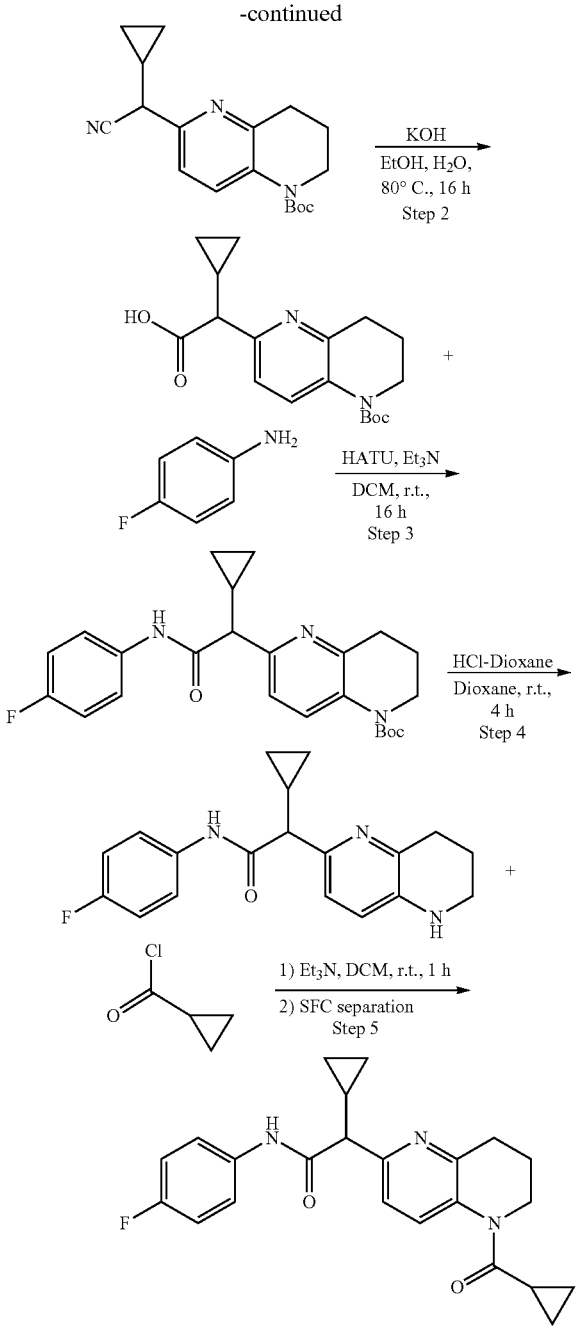

Step 1. tert-butyl 6-(cyano(cyclopropyl)methyl)-3,4-dihydro-1,5-naphthyridine-1(2H)-carboxylate To a stirred solution of tert-butyl 6-bromo-3,4-dihydro-1,5-naphthyridine-1(2H)-carboxylate (800 mg, 2.55 mmol) in THF (15 mL) were added 2-cyclopropylacetonitrile (420 mg, 5.18 mmol), LiHMDS (5.1 mL, 5.10 mmol), Pd$_2$(dba)$_3$ (110 mg, 0.12 mmol), and (R)-(−)-1-[(S)-2-(dicyclohexylphosphino)ferrocenyl]ethyldi-t-butylphosphine (140 mg, 0.25 mmol). After the addition, the mixture was stirred at 80° C. for 16 h. Then the reaction was cooled to RT, quenched with water (50 mL), and extracted with ethyl acetate (50 mL×4). The organic layers were collected, washed with brine, and dried over Na$_2$SO$_4$. After filtration, the filtrate was concentrated in vacuo. The residue was purified by flash silica gel chromatography (ISCO®; Agela® Flash Column Silica-CS (20 g), Eluent of 20-100% ethyl acetate/petroleum ether gradient @ 40 mL/min) to give the title compound as a solid. ESI mass m/z: 314.2 [M+H$^+$]

Step 2. tert-butyl 6-(cyano(cyclopropyl)methyl)-3,4-dihydro-1,5-naphthyridine-1(2H)-carboxylate To a stirred solution of tert-butyl 6-(cyano(cyclopropyl)methyl)-3,4-dihydro-1,5-naphthyridine-1(2H)-carboxylate (260 mg, 0.83 mmol) in EtOH (10 mL) and water (2 mL) was added KOH (230 mg, 4.15 mmol). After the addition, the mixture was stirred at 90° C. The reaction was monitored by LCMS and after stirring at 90° C. for 16 h, the reaction was finished. Then the reaction was cooled to RT and the pH was adjusted to ~5 using sat. citric acid, and extracted with ethyl acetate (50 mL×4). The organic layers were collected, washed with brine, and dried over Na$_2$SO$_4$. After filtration, the filtrate was concentrated in vacuo to give the title compound as a solid which was used directly in the next step without further purification. ESI mass m/z: 333.2 [M+H$^+$].

Step 3. tert-butyl 6-(1-cyclopropyl-2-((4-fluorophenyl)amino)-2-oxoethyl)-3,4-dihydro-1,5-naphthyridine-1(2H)-carboxylate To a stirred solution of 2-(5-(tert-butoxycarbonyl)-5,6,7,8-tetrahydro-1,5-naphthyridin-2-yl)-2-cyclopropylacetic acid (200 mg, 0.60 mmol) in DCM (10 mL) were added 4-fluoroaniline (67 mg, 0.60 mmol), HATU (230 mg, 0.60 mmol) and Et$_3$N (0.25 mL, 1.79 mmol). The mixture was stirred at RT for 16 h. The reaction was finished and was quenched with water (50 mL), and extracted with ethyl acetate (50 mL×3). The organic layers were collected, washed with brine, and dried over Na$_2$SO$_4$. After filtration, the filtrate was concentrated in vacuo. The residue was purified by flash silica gel chromatography (ISCO®; Agela® Flash Column Silica-CS (20 g), Eluent of 1060% Ethyl acetate/Petroleum ether gradient @ 40 mL/min) to give the title compound as a solid. ESI mass m/z: 426.3 [M+H$^+$].

Step 4. 2-cyclopropyl-N-(4-fluorophenyl)-2-(5,6,7,8-tetrahydro-1,5-naphthyridin-2-yl)acetamide To a stirred solution of tert-butyl 6-(1-cyclopropyl-2-((4-fluorophenyl)amino)-2-oxoethyl)-3,4-dihydro-1,5-naphthyridine-1(2H)-carboxylate (120 mg, 0.28 mmol) in dioxane (2 mL) was added 4 M HCl (1 mL, 4.0 mmol) (4 M in dioxane) at RT. The reaction was stirred at RT for 2 h and was concentrated to give the title compound as a solid which was used directly in the next step without further purification. ESI mass m/z: 326.2 [M+H$^+$].

Step 5. 2-(5-(cyclopropanecarbonyl)-5,6,7,8-tetrahydro-1,5-naphthyridin-2-yl)-2-cyclopropyl-N-(4-fluorophenyl)acetamide To a stirred solution of 2-cyclopropyl-N-(4-fluorophenyl)-2-(5,6,7,8-tetrahydro-1,5-naphthyridin-2-yl)acetamide (40 mg, 0.123 mmol) in DCM (2 mL) were added Et$_3$N (0.1 mL, 0.717 mmol) and cyclopropanecarbonyl chloride (32 mg, 0.306 mmol) at 0° C. After the addition was finished, the reaction was stirred at RT for 2 h and the reaction was finished. The solvent was removed in vacuo, and the residue was purified by reverse phase HPLC followed by SFC separation to give the title compound as a solid. ESI mass m/z: 394.2 [M+H]. $^1$H NMR (400 MHz, CD$_3$OD) δ 7.81 (d, J=8.4 Hz, 2H), 7.73 (s, 1H), 7.42-7.53 (m, 4H), 7.33-7.41 (m, 2H), 7.31 (br d, J=8.4 Hz, 1H), 7.12 (br d, J=8.8 Hz, 1H), 5.21 (q, J=7.2 Hz, 1H), 4.00-4.08 (m, 2H), 2.49-2.63 (m, 2H), 1.54 (d, J=7.6 Hz, 3H).

Column Chiralpak AS-H 250*30 5u; Condition 0.1% NH₃H₂O EtOH Begin B 25% End B 25% Gradient Time (min) 100% B Hold Time (min); FlowRate (mL/min) 60; Injections 120 Racemic; peak 1: retention time: 2.75 min; peak 2: retention time: 3.83 min

| Ex. # | Structure | Chemical name | Mass [M + H]+ | Hela IC$_{50}$, nM |
|---|---|---|---|---|
| 260 | Racemic | 2-(5-(cyclopropanecarbonyl)-5,6,7,8-tetrahydro-1,5-naphthyridin-2-yl)-2-cyclopropyl-N-(4-fluorophenyl)acetamide | Calc'd 394, found 394 | 34 |
| 261 | Isomer 1 | 2-(5-(cyclopropanecarbonyl)-5,6,7,8-tetrahydro-1,5-naphthyridin-2-yl)-2-cyclopropyl-N-(4-fluorophenyl)acetamide | Calc'd 394, found 394 | 24 |
| 262 | Isomer 2 | 2-(5-(cyclopropanecarbonyl)-5,6,7,8-tetrahydro-1,5-naphthyridin-2-yl)-2-cyclopropyl-N-(4-fluorophenyl)acetamide | Calc'd 394, found 394 | 11 |

Example 263. 2-(5-(cyclopropanecarbonyl)-5,6,7,8-tetrahydro-1,5-naphthyridin-2-yl)-N-(4-fluorophenyl)-3-methylbutanamide

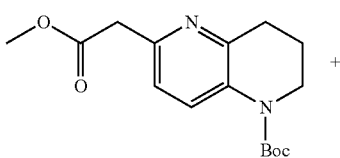

+

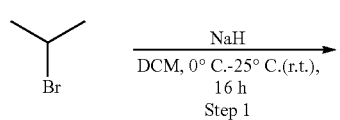

NaH
DCM, 0° C.-25° C.(r.t), 16 h
Step 1

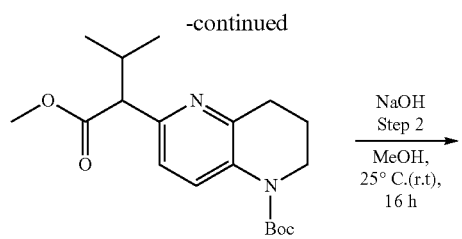

NaOH
Step 2
MeOH, 25° C.(r.t), 16 h

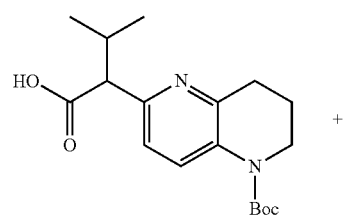

+

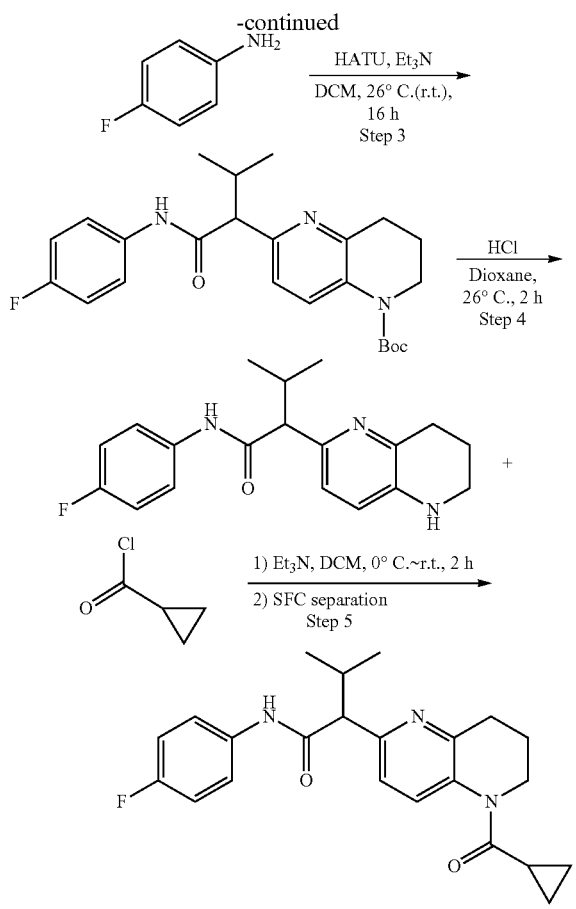

Step 1. tert-butyl 6-(1-methoxy-3-methyl-1-oxobutan-2-yl)-3,4-dihydro-1,5-naphthyridine-1(2H)-carboxylate To a stirred solution of tert-butyl 6-(2-methoxy-2-oxoethyl)-3,4-dihydro-1,5-naphthyridine-1(2H)-carboxylate (150 mg, 0.489 mmol) in DCM (10 mL) was added sodium hydride (23.50 mg, 0.587 mmol, 60%) and 2-bromopropane (72.26 mg, 0.587 mmol) at 0° C. After the addition was finished, the reaction was stirred at RT for 16 h. The mixture was quenched with water (100 mL), and extracted with DCM (100 mL×3). The organic layers were collected, washed with brine, and dried over $Na_2SO_4$. The residue was purified by silica gel column chromatography using ($SiO_2$, Petroleum.ether/ethyl acetate=100% to 50% as eluent) to give the title compound as an oil. ESI MS m/z: 349.2 [M+H$^+$]

Step 2. 2-(5-(tert-butoxycarbonyl)-5,6,7,8-tetrahydro-1,5-naphthyridin-2-yl)-3-methylbutanoic acid To a stirred solution of tert-butyl 6-(1-methoxy-3-methyl-1-oxobutan-2-yl)-3,4-dihydro-1,5-naphthyridine-1(2H)-carboxylate (110.00 mg, 0.315 mmol) in MeOH (3 mL) was added sodium hydroxide (0.5 mL, 1.50 mmol, 3M in water) at RT. The reaction was stirred at RT for 16 h. The mixture was quenched with 1M HCl (aq., 1 M, in water) until pH~6 and then extracted with ethyl acetate (30 mL×3). The organic layers were collected, washed with brine, and dried over $Na_2SO_4$. After filtration, the filtrate was concentrated in vacuo to give the title compound as an oil, which was used in the next step without further purification. ESI MS m/z: 335.2 [M+H$_+$]

Step 3. tert-butyl 6-(1-((4-fluorophenyl)amino)-3-methyl-1-oxobutan-2-yl)-3,4-dihydro-1,5-naphthyridine-1(2H)-carboxylate To a stirred solution of 2-(5-(tert-butoxycarbonyl)-5,6,7,8-tetrahydro-1,5-naphthyridin-2-yl)-3-methylbutanoic acid (100 mg, 0.299 mmol) in DCM (10 mL) were added 4-fluoroaniline (50 mg, 0.449 mmol), HATU (170 mg, 0.447 mmol) and TEA (0.12 mL, 0.889 mmol) at RT. The reaction mixture was stirred at RT for 16 h. The mixture was quenched with water (100 mL), and extracted with DCM (40 mL×3). The organic layers were collected, washed with brine, and dried over $Na_2SO_4$. After filtration, the filtrate was concentrated in vacuo, and the residue was purified by silica gel column chromatography using ($SiO_2$, Petroleum.ether/ethyl acetate=100% to 50% as eluent) to give the title compound as an oil. ESI MS m/z: 428.3 [M+H$^+$]

Step 4. N-(4-fluorophenyl)-3-methyl-2-(5,6,7,8-tetrahydro-1,5-naphthyridin-2-yl) butanamide hydrochloride To a solution of tert-butyl 6-(1-((4-fluorophenyl)amino)-3-methyl-1-oxobutan-2-yl)-3,4-dihydro-1,5-naphthyridine-1(2H)-carboxylate (60 mg, 0.14 mmol) in dioxane (2 mL) was added 4 M HCl (2 mL, 8 mmol, 4 M, in dioxane) at RT. After stirring at RT for 2 h, the reaction was complete. Then the solvent was removed under reduced pressure to give the title compound, which was used directly in the next step without any further purification. ESI MS m/z: 328.2[M+H$^+$]

Step 5. 2-(5-(cyclopropanecarbonyl)-5,6,7,8-tetrahydro-1,5-naphthyridin-2-yl)-N-(4-fluorophenyl)-3-methylbutanamide To a solution of N-(4-fluorophenyl)-3-methyl-2-(5,6,7,8-tetrahydro-1,5-naphthyridin-2-yl)butanamide hydrochloride (51 mg, 0.14 mmol) in DCM (10 mL) were added TEA (0.08 mL, 0.573 mmol) and cyclopropanecarbonyl chloride at RT. After the reaction was stirred at RT for 2 h, the reaction was quenched with water (20 mL) and extracted with DCM (30 mL×2). The organic layers were collected, washed with brine (20 mL), and dried over $Na_2SO_4$. After filtration, the filtrate was concentrated in vacuo. The residue was purified by preparative HPLC on a GILSON 281 instrument fitted with a Waters Xbridge Prep OBD C18 100×19 mm×5 um using water (0.225% FA)-ACN, Mobile phase B ACN, Detective wavelength: 220 nm, followed by SFC separation to give the title compound as a solid. $^1$H NMR (400 MHz, CDCl$_3$) δ 7.5 (br d, J=4.82 Hz, 2H) 7.0 (t, J=8.77 Hz, 2H) 3.9 (br s, 2H) 3.1 (br s, 2H) 2.4 (br s, 1H) 2.1-2.2 (m, 2H) 1.8-1.9 (m, 1H) 1.7-1.8 (m, 1H) 1.1-1.2 (m, 5H) 0.9 (brs, 2H) 0.8 (d, J=6.58 Hz, 3H). ESI MS m/z: 396.2 [M+H$^+$]

Column Chiralpak AS-H (250 mm×30 mm×5 um); Mobile phase: Supercritical $CO_2$/EtOH (0.1% $NH_3$—$H_2O$)=65/35 at 60 mL/min; Column Temp: 38° C.; Nozzle Pressure: 100Bar; Nozzle Temp: 60° C.; Evaporator Temp: 20° C.; Trimmer Temp: 25° C.; Wavelength: 220 nm.

| Ex. # | Structure | Chemical Name | Mass [M + H]+ | Hela IC$_{50}$, nM |
|---|---|---|---|---|
| 263 | 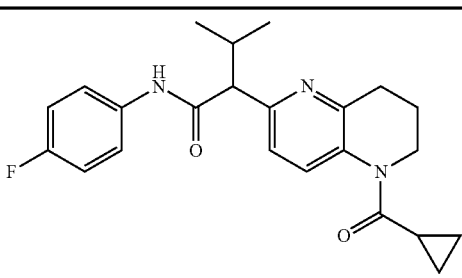 Racemic | 2-(5-(cyclopropanecarbonyl)-5,6,7,8-tetrahydro-1,5-naphthyridin-2-yl)-N-(4-fluorophenyl)-3-methylbutanamide | Calc'd 396, found 396 | 34.9 |
| 264 | 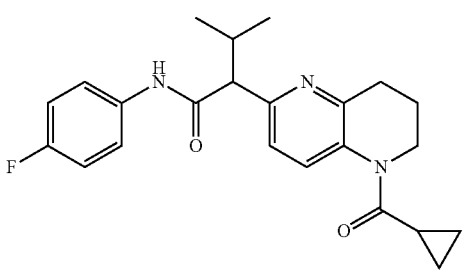 Isomer 1 | 2-(5-(cyclopropanecarbonyl)-5,6,7,8-tetrahydro-1,5-naphthyridin-2-yl)-N-(4-fluorophenyl)-3-methylbutanamide | Calc'd 396, found 396 | 30.9 |
| 265 | 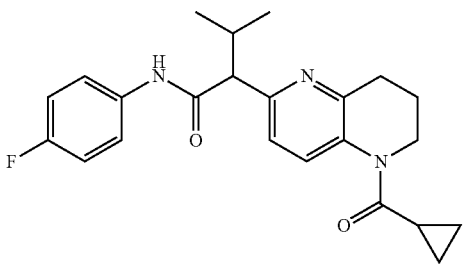 Isomer 2 | 2-(5-(cyclopropanecarbonyl)-5,6,7,8-tetrahydro-1,5-naphthyridin-2-yl)-N-(4-fluorophenyl)-3-methylbutanamide | Calc'd 396, found 396 | 15.7 |

Example 266. cyclopropyl 6-(3-((4-fluorophenyl)carbamoyl)oxetan-3-yl)-3,4-dihydro-1,5-naphthyridine-1(2H)-carboxylate

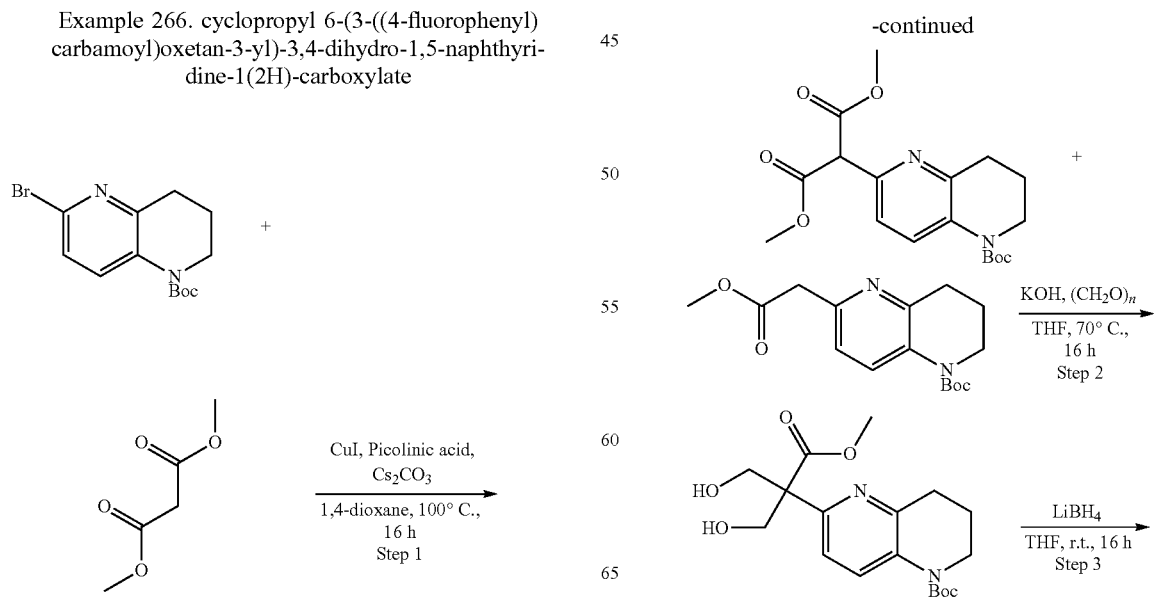

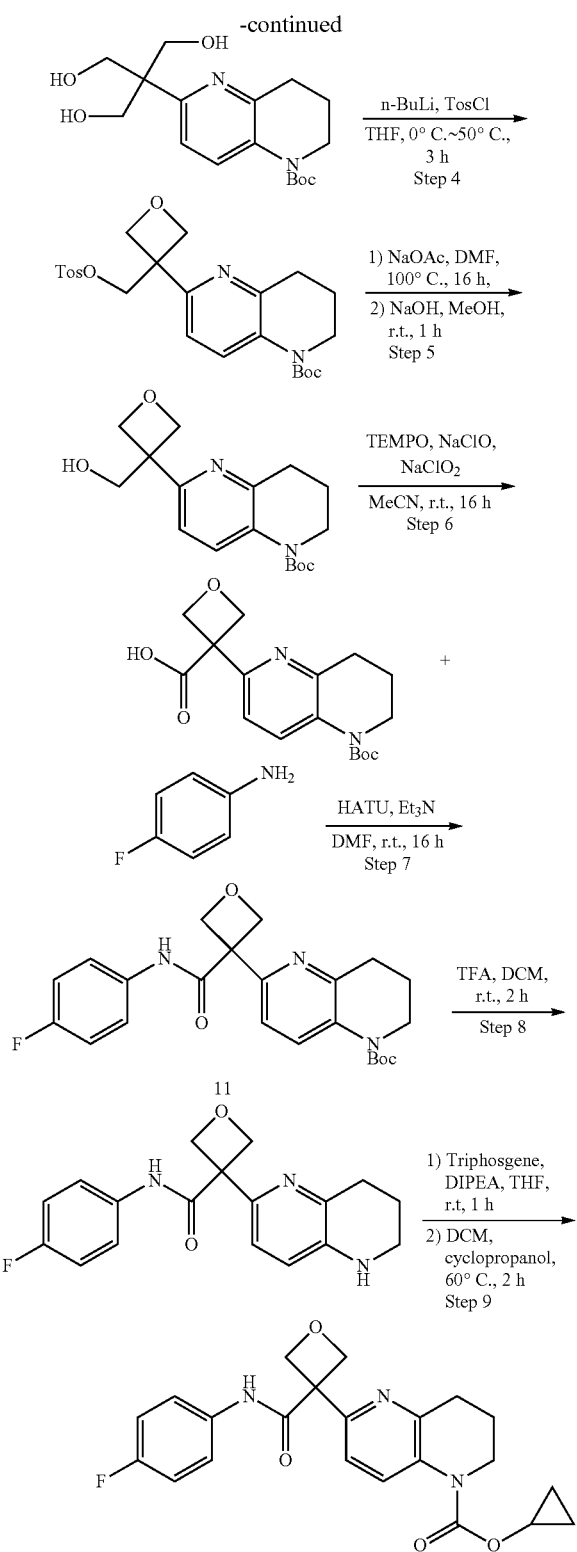

Step 1. tert-butyl 6-(2-methoxy-2-oxoethyl)-3,4-dihydro-1,5-naphthyridine-1(2H)-carboxylate To a solution of tert-butyl 6-bromo-3,4-dihydro-1,5-naphthyridine-1(2H)-carboxylate (10.0 g, 31.9 mmol) and picolinic acid (3.14 g, 25.5 mmol) in 1,4-dioxane (100 mL) were added copper(I) iodide (0.608 g, 3.19 mmol) and $Cs_2CO_3$ (31.2 g, 96 mmol) at RT. Then dimethyl malonate (16.87 g, 128 mmol) was added to the above solution at RT. The mixture was stirred at 100° C. and the reaction was monitored by LC-MS. After stirring at 100° C. for 16 h, the reaction was finished. After cooled to RT, 200 mL of EtOAc was added to the mixture, filtered, and the filtrate was concentrated in vacuo. The residue was purified by flash silica gel chromatography (ISCO®; Agela® Flash Column Silica-CS (80 g), Eluent of 0-15% ethyl acetate/Petroleum ether gradient @ 60 mL/min) to give dimethyl 2-(5-(tert-butoxycarbonyl)-5,6,7,8-tetrahydro-1,5-naphthyridin-2-yl)malonate as a solid and tert-butyl 6-(2-methoxy-2-oxoethyl)-3,4-dihydro-1,5-naphthyridine-1(2H)-carboxylate as an oil.

MS (ESI) m/z: 307.2 [M+H+] tR=0.923 min; MS (ESI) m/z: 365.2 [M+H+] tR=1.123 min.

Step 2. tert-butyl 6-(3-hydroxy-2-(hydroxymethyl)-1-methoxy-1-oxopropan-2-yl)-3,4-dihydro-1,5-naphthyridine-1(2H)-carboxylate To a solution of tert-butyl 6-(2-methoxy-2-oxoethyl)-3,4-dihydro-1,5-naphthyridine-1(2H)-carboxylate (1.8 g, 5.88 mmol) and KOH (0.033 g, 0.588 mmol) in THF (20 mL) was added paraformaldehyde (0.705 g, 23.50 mmol) at RT. After the addition was finished, the reaction was stirred at 60° C. and the reaction was monitored by LC-MS. After stirring at 60° C. for 18 h, the reaction was finished. After cooling to RT, 25 mL of aqueous $NH_4Cl$ was added, and extracted by EtOAc (30 mL×2). The organic layers were collected, washed with brine (20 mL), and dried over $Na_2SO_4$. After filtration, the filtrate was concentrated. The residue was purified by flash silica gel chromatography (ISCO®; Agela® Flash Column Silica-CS (12 g), Eluent of 030% Ethyl acetate/Petroleum ether gradient @ 25 mL/min) to give the title compound as an oil. MS (ESI) m/z: 367.2 [M+H+]

Step 3. tert-butyl 6-(1,3-dihydroxy-2-(hydroxymethyl)propan-2-yl)-3,4-dihydro-1,5-naphthyridine-1(2H)-carboxylate To a stirred solution of tert-butyl 6-(3-hydroxy-2-(hydroxymethyl)-1-methoxy-1-oxopropan-2-yl)-3,4-dihydro-1,5-naphthyridine-1(2H)-carboxylate (2.0 g, 5.46 mmol) in THF (20 mL) was added $LiBH_4$ (0.357 g, 16.38 mmol) at 0° C. After the addition was finished, the reaction was stirred at RT and monitored by LC-MS. After stirring at 20° C. for 18 h, desired compound was detected. The reaction was quenched with 5 mL of MeOH, and the solvent was removed in vacuo. The residue was purified by flash silica gel chromatography (ISCO®; Agela® Flash Column Silica-CS (12 g), Eluent of 010% MeOH/DCM gradient @ 30 mL/min) to give the title compound as a solid. MS (ESI) m/z: 339.2 [M+H+]

Step 4. tert-butyl 6-(3-((tosyloxy)methyl)oxetan-3-yl)-3,4-dihydro-1,5-naphthyridine-1(2H)-carboxylate To a stirred solution of tert-butyl 6-(1,3-dihydroxy-2-(hydroxymethyl) propan-2-yl)-3,4-dihydro-1,5-naphthyridine-1(2H)-carboxylate (1.7 g, 5.02 mmol) in THF (40 mL) was added n-butyllithium (4 mL, 10.04 mmol) (2.5M) dropwise at 0° C. After the addition was finished, the mixture was stirred at RT for 30 min. Then a solution of 4-methylbenzene-1-sulfonyl chloride (1.915 g, 10.05 mmol)

in 5 mL of THF was added at 0° C. After the addition, the reaction was stirred at 0° C. for 1 h, then n-BuLi (2.0 mL, 5.0 mmol) (2.5M) was added to the above mixture at 0° C. and the mixture was stirred at 0° C. for 0.5 h. Then the mixture was heated to 50° C. The r and monitored by LC-MS. After stirring at 50° C. for 0.5 h, the reaction was finished. After cooling to RT, the reaction was quenched with aq. NH$_4$Cl solution (40 mL), and extracted by EtOAc (40 mL×2). The organic layers were collected, washed with brine (40 mL), and dried over Na$_2$SO$_4$. After filtration, the filtrate was concentrated in vacuo. The residue was purified by flash silica gel chromatography (ISCO®; Agela® Flash Column Silica-CS (12 g), Eluent of 030% Ethyl acetate/Petroleum ether gradient @ 30 mL/min) to give the title compound as an oil. MS (ESI) m/z: 475.1 [M+H+]

Step 5. tert-butyl 6-(3-(hydroxymethyl)oxetan-3-yl)-3,4-dihydro-1,5-naphthyridine-1(2H)-carboxylate To a stirred solution of tert-butyl 6-(3-((tosyloxy)methyl) oxetan-3-yl)-3,4-dihydro-1,5-naphthyridine-1(2H)-carboxylate (700 mg, 1.475 mmol) in DMF (10 mL) was added NaOAc (292 mg, 4.43 mmol) at RT. After the addition was finished, the reaction was stirred at 100° C. and monitored by LC-MS. After stirring at 100° C. for 16 h, the reaction was finished. After cooling to RT, 5 mL of MeOH was added to the reaction mixture, then NaOH (177 mg, 4.43 mmol) was added to the above mixture. After the addition was finished, the reaction was stirred at RT and monitored by LC-MS. After stirring at 20° C. for 1 h, the reaction was finished. The mixture was diluted with water (50 mL), extracted by EtOAc (25 mL×2). The organic layers were collected, washed with brine (25 mL), and dried over Na$_2$SO$_4$. After filtration, the filtrate was concentrated in vacuo. The residue was purified by prep-TLC (Petroleum ether/EtOAc=1:1) to give the title compound as a solid. MS (ESI) m/z: 321.1 [M+H+]

Step 6. 3-(5-(tert-butoxycarbonyl)-5,6,7,8-tetrahydro-1,5-naphthyridin-2-yl)oxetane-3-carboxylic acid To a stirred solution of tert-butyl 6-(3-(hydroxymethyl) oxetan-3-yl)-3,4-dihydro-1,5-naphthyridine-1(2H)-carboxylate (150 mg, 0.468 mmol) in MeCN (5 mL) were added TEMPO (15 mg, 0.096 mmol), sodium chlorite (85 mg, 0.936 mmol) in 0.5 ml of water and chlorosylsodium (0.5 ml, 0.468 mmol) (10% in water) successively at RT. After the addition was finished, the reaction was stirred at 20° C. and monitored by LC-MS. After stirring at 20° C. for 16 h, the reaction was finished. The reaction was treated with 2M NaOH to pH=10, 10% sodium thiosulfate (2 mL) was added and the mixture was partitioned between ethyl acetate (20 mL) and water (10 mL). The aqueous phase was then acidified with citric acid to pH=4 and extracted with ethyl acetate (15 mL×2). The organic phase was then dried over magnesium sulfate, filtered and concentrated in vacuo. The residue was purified by prep-TLC (DCM/MeOH=8:1) to give the title compound as an oil. MS (ESI) m/z: 335.1 [M+H$^+$]

Step 7. tert-butyl 6-(3-((4-fluorophenyl)carbamoyl) oxetan-3-yl)-3,4-dihydro-1,5-naphthyridine-1(2H)-carboxylate To a stirred solution of 3-(5-(tert-butoxycarbonyl)-5,6,7,8-tetrahydro-1,5-naphthyridin-2-yl)oxetane-3-carboxylic acid (90 mg, 0.269 mmol) in DMF (5 mL) were successively added Et$_3$N (0.1 mL, 0.717 mmol), HATU (154 mg, 0.404 mmol), and 4-fluoroaniline (45 mg, 0.405 mmol) at RT. After the addition was finished, the reaction was stirred at 20° C. The reaction was monitored by LC-MS, after stirring at 20° C. for 16 h, the reaction was finished. Then 20 mL of water was added to the mixture, and extracted with EtOAc (15 mL×2). The organic layers were collected, washed with brine (10 mL), and dried over Na$_2$SO$_4$. After filtration, the filtrate was concentrated in vacuo. The residue was purified by prep-TLC (Petroleum ether/EtOAc=1:1) to give the title compound as an oil. MS (ESI) m/z: 428.2 [M+H+]

Step 8. N-(4-fluorophenyl)-3-(5,6,7,8-tetrahydro-1, 5-naphthyridin-2-yl)oxetane-3-carboxamide To a solution of tert-butyl 6-(3-((4-fluorophenyl)carbamoyl)oxetan-3-yl)-3,4-dihydro-1,5-naphthyridine-1(2H)-carboxylate (80 mg, 0.187 mmol) in DCM (5 mL) was added TFA (1 mL) at RT. After the addition was finished, the reaction was stirred at 26° C. and the reaction monitored by LCMS. After stirring at 26° C. for 6 h, the reaction was finished. The mixture was basified with 1N NaOH to pH=7-8. DCM (10 mL) and water (10 mL) were added to the mixture and the mixture was extracted with DCM (10 mL×2). The combined organic phases were washed with brine (10 mL), then dried over anhydrous Na$_2$SO$_4$, filtered and concentrated in vacuo to give the title compound as an oil. MS(ESI0 m/z 328.1 [M+H+]

Step 9. cyclopropyl 6-(3-((4-fluorophenyl)carbamoyl)oxetan-3-yl)-3,4-dihydro-1,5-naphthyridine-1 (2H)-carboxylate To a stirred solution of N-(4-fluorophenyl)-3-(5,6,7,8-tetrahydro-1,5-naphthyridin-2-yl)oxetane-3-carboxamide (60 mg, 0.183 mmol) in DCM (5 mL) were successively added DIEA (0.096 ml, 0.550 mmol) and bis(trichloromethyl) carbonate (109 mg, 0.367 mmol) at 0° C. After the addition was finished, the reaction was stirred at 0° C. and monitored by LC-MS. After stirring at 0° C. for 1 h, the reaction was finished. The mixture was added sat. NaHCO$_3$ solution to adjust pH~8, and water (10 mL) was added. The mixture was extracted with DCM (10 mL×2), the organic layers were collected, washed with brine (10 mL), and dried over Na$_2$SO$_4$. After filtration, the filtrate was concentrated in vacuo to give 6-(3-((4-fluorophenyl)carbamoyl)oxetan-3-yl)-3,4-dihydro-1,5-naphthyridine-1(2H)-carbonyl chloride as an oil. MS (ESI) m/z:390.1 [M+H+].

To a stirred solution of 6-(3-((4-fluorophenyl)carbamoyl) oxetan-3-yl)-3,4-dihydro-1,5-naphthyridine-1(2H)-carbonyl chloride (60 mg, 0.154 mmol) and K$_2$CO3 (63.8 mg, 0.462 mmol) in CH$_2$Cl$_2$ (2 mL) was added cyclopropanol (89 mg, 1.539 mmol) at RT. After the addition was finished, the reaction was stirred at 60° C. The reaction was monitored by LC-MS, after stirring at 60° C. for 16 h, the reaction was finished. After cooling to RT, the mixture was concentrated under reduced pressure. The residue was purified by p-HPLC (Column Agela ASB 150×25 mm×5 mm, Condition water (0.1% TFA)-MeCN Begin B 35, End B 55 Gradient Time (min) 10, 100% B Hold Time (min) 2, FlowRate (mL/min) 25 Injections 4) to give cyclopropyl 6-(3-((4-fluorophenyl)carbamoyl)oxetan-3-yl)-3,4-dihydro-1,5-naphthyridine-1(2H)-carboxylate as a solid. $^1$H NMR (400 MHz, CD$_3$OD) δ 8.26 (br d, J=8.6 Hz, 1H), 7.51-7.58 (m, 2H), 7.34 (d, J=8.6 Hz, 1H), 7.01-7.09 (m, 2H), 5.26 (d, J=6.4 Hz, 2H), 5.11 (d, J=6.2 Hz, 2H), 4.12-4.20 (m, 1H), 3.73-3.80 (m, 2H), 3.01 (t, J=6.5 Hz, 2H), 1.99-2.06 (m, 2H), 0.72-0.78 (m, 4H); MS (ESI) m/z: 412.0 [M+H+]

The compounds in the following table were prepared in a similar manner as Example 266.

| Ex. # | Structure | Chemical Name | Mass [M + H]+ | Hela IC$_{50}$, nM |
|---|---|---|---|---|
| 266 | 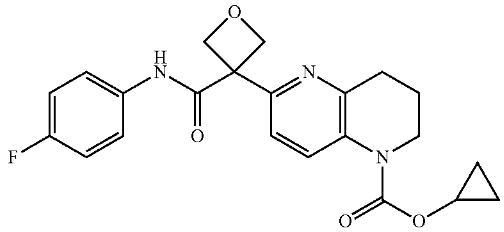 [SMILES: O=C(OC1CC1)N1CCCc2nc(C3(C(=O)Nc4ccc(F)cc4)COC3)ccc21] | cyclopropyl 6-(3-((4-fluorophenyl)carbamoyl)oxetan-3-yl)-3,4-dihydro-1,5-naphthyridine-1(2H)-carboxylate | Calc'd 412, found 412 | 2.8 |
| 267 | 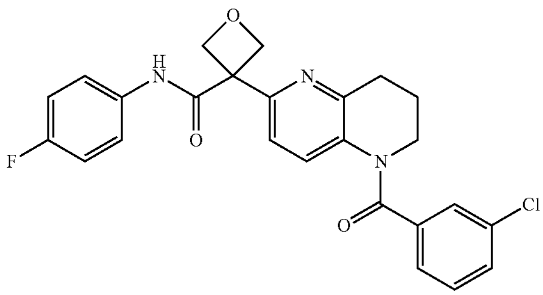 [SMILES: O=C(c1cccc(Cl)c1)N1CCCc2nc(C3(C(=O)Nc4ccc(F)cc4)COC3)ccc21] | 3-(5-(3-chlorobenzoyl)-5,6,7,8-tetrahydro-1,5-naphthyridin-2-yl)-N-(4-fluorophenyl)oxetane-3-carboxamide | Calc'd 466, found 466 | 2.2 |

Example 268. 1-[1-(cyclopropanecarbonyl-2,3-dihydro-1H-pyrrolo[3,2-b]pyridin-5-yl]-N-(4-fluorophenyl)cyclobutane-1-carboxamide

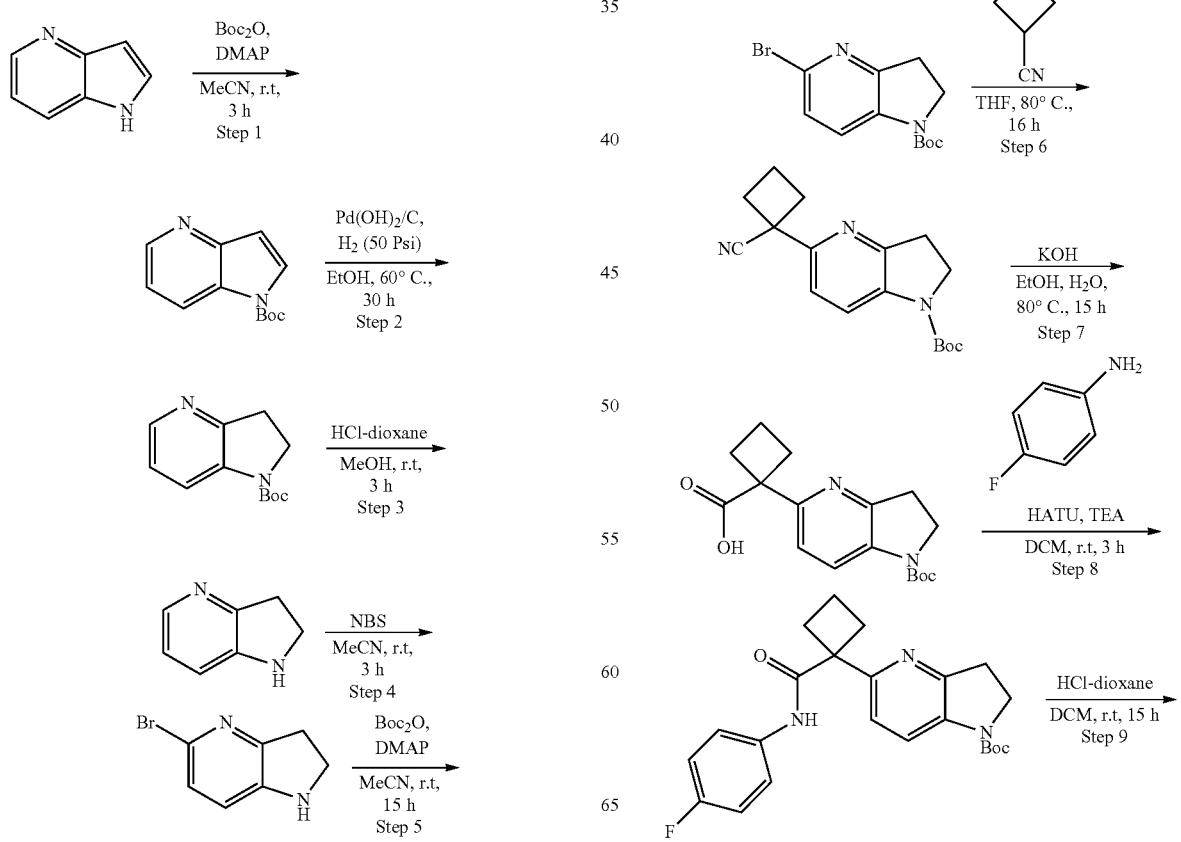

-continued

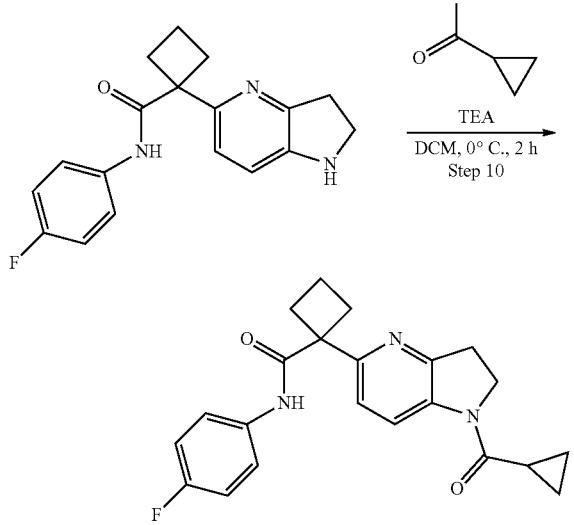

Step 1. tert-butyl 1H-pyrrolo[3,2-b]pyridine-1-carboxylate

To a stirred solution of 1H-pyrrolo[3,2-b]pyridine (10 g, 85 mmol) in ACN (200 mL) were added DMAP (1.034 g, 8.46 mmol) and Boc$_2$O (23.58 mL, 102 mmol) at RT. After the addition was finished, the reaction was stirred at 20° C. and the reaction was monitored by TLC (Petroleum ether/EtOAc=1:1). After stirring at 20° C. for 3 h, the reaction was finished and the solvent was removed. The residue was purified by column chromatography on silica gel (SiO$_2$) (eluting with Petroleum ether/ethyl acetate 20:1 to 10:1) to give the title compound as a solid. MS (ESI) m/z: 219. [M+H+].

Step 2. tert-butyl 2,3-dihydro-1H-pyrrolo[3,2-b]pyridine-1-carboxylate

To a stirred solution of tert-butyl 1H-pyrrolo[3,2-b]pyridine-1-carboxylate (3 g, 13.75 mmol) in EtOH (40 mL) was added Pd(OH)$_2$/C (1 g, 1.424 mmol)(20%). Then the reaction was stirred at 60° C. under H$_2$ (50 psi). The reaction was monitored by TLC (Petroleum ether/EtOAc=5:1) and after stirring at 60° C. for 30 h, the reaction was finished. The reaction mixture was filtered through a pad of Celite and was washed with EtOH (10 mL×3). The filtrate was concentrated under reduced pressure to give the title compound as an oil, which was used directly in the next step without further purification. MS (ESI) m/z: 221.1[M+H+]

Step 3. 2,3-dihydro-1H-pyrrolo[3,2-b]pyridine

To a solution of tert-butyl 2,3-dihydro-H-pyrrolo[3,2-b]pyridine-1-carboxylate (3.0 g, 13.62 mmol) in MeOH (5 mL) and DCM (10 mL) was added 4 N HCl (20 mL, 80 mmol, in EtOAc). After the addition was finished, the reaction was stirred at 20° C. The reaction was monitored by TLC (Petroleum ether/EtOAc=2:1) and after stirring at 20° C. for 15 h, the reaction was finished. The solvent was removed, diluted with water (20 mL), basified with 2N NaOH to pH ~10, extracted with ethyl acetate (20 mL×5), washed with brine (20 mL), dried over sodium sulfate, filtered, and concentrated in vacuo to give the title compound as an oil, which was used in the next step without further purification.

Step 4. 5-bromo-2,3-dihydro-1H-pyrrolo[3,2-b]pyridine

To a solution of 2,3-dihydro-1H-pyrrolo[3,2-b]pyridine (1.60 g, 13.32 mmol) in ACN (20 mL) was added NBS (2.370 g, 13.32 mmol) at 0° C. After the addition was finished, the reaction was stirred at 0° C. and the reaction was monitored by TLC (Petroleum ether/EtOAc=1:1). After stirring at 0° C. for 5 h, the reaction was finished. The solvent was removed, diluted with water (30 mL), and extracted by EtOAc (20 mL×3). The organic layers were collected, washed with brine (20 mL), and dried over Na$_2$SO$_4$. After filtration, the filtrate was concentrated in vacuo. The residue was purified by silica gel chromatography (SiO$_2$, Petroleum ether/EtOAc=20:1 to 10:1) to give the title compound as a solid. ESI MS(ESI) m/z 199.0 [M+H+].

Step 5. tert-butyl 5-bromo-2,3-dihydro-1H-pyrrolo[3,2-b]pyridine-1-carboxylate To a solution of 5-bromo-2,3-dihydro-1H-pyrrolo[3,2-b]pyridine (1.06 g, 5.33 mmol) in ACN (20 mL) were added (Boc)$_2$O (1.84 mL, 7.92 mmol) and DMAP (66 mg, 0.540 mmol) at 0° C. After the addition was finished, the reaction was stirred at RT and the reaction was monitored by TLC (Petroleum ether/EtOAc=5:1). After stirring at 20° C. for 15 h, the reaction was finished. The solvent was removed and purified by silica gel chromatography (SiO$_2$, Petroleum ether/EtOAc=20:1) to give the title compound as a solid.

Step 6. tert-butyl 5-(1-cyanocyclobutyl)-2,3-dihydro-1H-pyrrolo[3,2-b]pyridine-1-carboxylate To a mixture of tert-butyl 5-bromo-2,3-dihydro-1H-pyrrolo[3,2-b]pyridine-1-carboxylate (500 mg, 1.671 mmol), cyclobutanecarbonitrile (271 mg, 3.34 mmol), Pd$_2$(dba)$_3$ (77 mg, 0.084 mmol), NiXantphos (92 mg, 0.167 mmol) in THF (13.5 mL) was added LiHMDS (3.34 mL, 3.34 mmol) (1 M) at 20° C. in glove box. After the addition was finished, the reaction was stirred at 80° C. and the reaction was monitored by LCMS. After stirring at 80° C. for 15 h, the reaction was finished. The reaction was diluted with water (20 mL), extracted with EtOAc (10 mL×3), the organic layers were collected, washed with brine (10 mL), and dried over Na$_2$SO$_4$. After filtration, the filtrate was concentrated in vacuo. The residue was purified by silica gel chromatography (SiO$_2$, Petroleum ether/EtOAc=20:1) to give the title compound as a solid. MS(ESI) m/z: 300.1 [M+H+].

Step 7. 1-(1-(tert-butoxycarbonyl)-2,3-dihydro-1H-pyrrolo[3,2-b]pyridin-5-yl)cyclobutane-carboxylic acid To a solution of tert-butyl 5-(1-cyanocyclobutyl)-2,3-dihydro-1H-pyrrolo[3,2-b]pyridine-1-carboxylate (50 mg, 0.167 mmol) in EtOH (5 mL) was added KOH (93 mg, 1.67 mmol) in water (1 mL) at 20° C. After the addition was finished, the reaction was stirred at 80° C. The reaction was monitored by LCMS. After stirring at 80° C. for 15 h, the reaction was finished. The solvent was removed, diluted with water (20 mL), acidified with HCl (3 M) to pH ~6, and extracted with EtOAc (15 mL×3). The organic layers were collected, washed with brine (ca. 20 mL), and dried over Na₂SO₄. After filtration, the filtrate was concentrated in vacuo to give the title compound as an oil, which was directly used in the next step without further purification. ESI MS m/z 319.2 [M+H⁺]

Step 8. tert-butyl 5-(1-((4-fluorophenyl)carbamoyl)cyclobutyl)-2,3-dihydro-1H-pyrrolo[3,2-b]pyridine-1-carboxylate To a solution of 1-(1-(tert-butoxycarbonyl)-2,3-dihydro-1H-pyrrolo[3,2-b]pyridin-5-yl)cyclobutanecarboxylic acid (35 mg, 0.110 mmol) in DCM (2 mL) were added HATU (46 mg, 0.121 mmol), 4-fluoroaniline (15 mg, 0.135 mmol) and DIEA (43 mg, 0.333 mmol) at RT. After the addition was finished, the reaction was stirred at RT. After stirring at 20° C. for 1 h, LCMS showed that the reaction was finished. The solvent was removed, purified by pre-TLC (Petroleum ether/EtOAc=2:1) to give the title compound as an oil. ESI MS m/z 412.2 [M+H⁺]

Step 9. 1-(2,3-dihydro-1H-pyrrolo[3,2-b]pyridin-5-yl)-N-(4-fluorophenyl)cyclobutanecarboxamide hydrochloride To a solution of tert-butyl 5-(1-((4-fluorophenyl)carbamoyl)cyclobutyl)-2,3-dihydro-1H-pyrrolo[3,2-b]pyridine-1-carboxylate (15 mg, 0.036 mmol) in DCM (1 mL) was added HCl (0.5 mL, 4M in dioxane) at 0° C. After the addition was finished, the reaction was stirred at RT for 15 h and LCMS showed that the reaction was finished. The solvent was removed to give the title compound as an oil, which was directly used in the next step without further purification. MS(ESI) m/z 312.1 [M+H⁺]

Step 10. 1-(1-(cyclopropanecarbonyl)-2,3-dihydro-1H-pyrrolo[3,2-b]pyridin-5-yl)-N-(4-fluorophenyl)cyclobutanecarboxamide To a solution of 1-(2,3-dihydro-H-pyrrolo[3,2-b]pyridin-5-yl)-N-(4-fluorophenyl)cyclobutanecarboxamide hydrochloride (12 mg, 0.035 mmol) in DCM (3 mL) was added triethylamine (11 mg, 0.109 mmol) at 0° C. After stirring at 0° C. for 0.5 h, cyclopropanecarbonyl chloride (7 mg, 0.067 mmol) was added and after stirring at 0° C. for 2 h, the reaction was finished. The solvent was removed, purified by reversed phase HPLC on a GILSON 281 instrument fitted with a Phenomenex Synergi C18 150×30 mm×4 um using water (0.1% TFA)-ACN as eluents, followed by lyophilization to give the title compound as a solid. ¹H NMR (400 MHz, CDCl₃) δ 9.50 (br s, 1H), 8.60 (br d, J=7.0 Hz, 1H), 7.56-7.64 (m, 2H), 7.38 (d, J=8.4 Hz, 1H), 6.93-7.02 (m, 2H), 4.44 (br t, J=8.6 Hz, 2H), 3.63 (br t, J=8.5 Hz, 2H), 3.04-3.11 (m, 2H), 2.64-2.73 (m, 2H), 2.07-2.17 (m, 1H), 1.87-1.97 (m, 1H), 1.73-1.81 (m, 1H), 1.15-1.19 (m, 2H), 0.97-1.02 (m, 2H); MS(ESI) m/z 380.2 [M+H⁺]

The compounds in the following table were prepared in a similar manner as Example 268.

| Ex. # | Structure | Chemical Name | Mass [M + H]+ | Hela IC$_{50}$, nM |
|---|---|---|---|---|
| 268 | 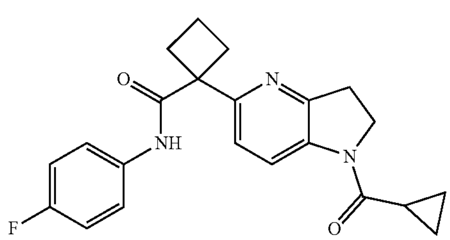 [SMILES: O=C(C1CC1)N1CCc2nc(C3(C(=O)Nc4ccc(F)cc4)CCC3)ccc21] | 1-[1-(cyclopropanecarbonyl)-2,3-dihydro-1H-pyrrolo[3,2-b]pyridin-5-yl]-N-(4-fluorophenyl)cyclobutane-1-carboxamide | Calc'd 380, found 380 | 7.9 |
| 269 | 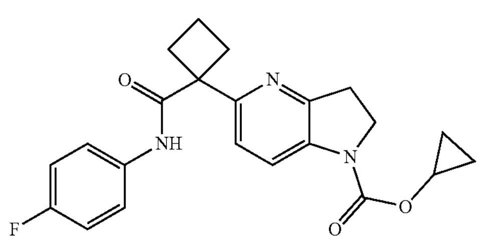 [SMILES: O=C(OC1CC1)N1CCc2nc(C3(C(=O)Nc4ccc(F)cc4)CCC3)ccc21] | cyclopropyl 5-(1-((4-fluorophenyl)carbamoyl)cyclobutyl) 2,3-dihydro-1H-pyrrolo[3,2-b]pyridine-1-carboxylate | Calc'd 396, found 396 | 2.2 |
| 270 | 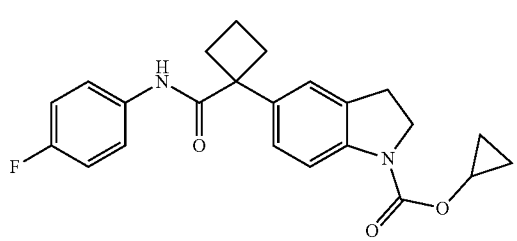 [SMILES: O=C(OC1CC1)N1CCc2cc(C3(C(=O)Nc4ccc(F)cc4)CCC3)ccc21] | cyclopropyl 5-{1-[(4-fluorophenyl)carbamoyl]cyclobutyl}-2,3-dihydro-1H-indole-1-carboxylate | Calc'd 395, found 395 | 1.2 |

| Ex. # | Structure | Chemical Name | Mass [M + H]+ | Hela IC$_{50}$, nM |
|---|---|---|---|---|
| 271 | 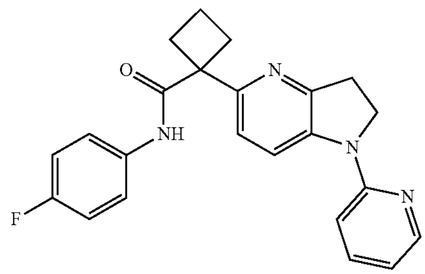 [SMILES: O=C(Nc1ccc(F)cc1)C1(c2ccc3c(n2)CCN3c2ccccn2)CCC1] | N-(4-fluorophenyl)-1-[1-(pyridin-2-yl)-2,3-dihydro-1H-pyrrolo[3,2-b]pyridin-5-yl]cyclobutane-1-carboxamide | Calc'd 389, found 389 | 10.9 |
| 272 | 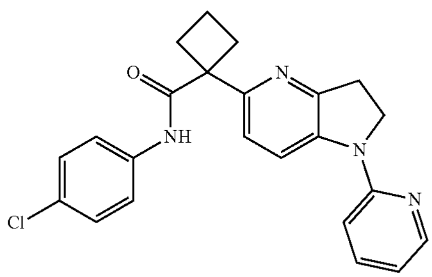 [SMILES: O=C(Nc1ccc(Cl)cc1)C1(c2ccc3c(n2)CCN3c2ccccn2)CCC1] | N-(4-chlorophenyl)-1-[1-(pyridin-2-yl)-2,3-dihydro-1H-pyrrolo[3,2-b]pyridin-5-yl]cyclobutane-1-carboxamide | Calc'd 405, found 405 | 1.9 |
| 273 | 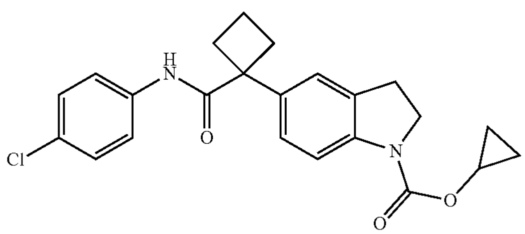 [SMILES: O=C(OC1CC1)N1CCc2cc(C3(C(=O)Nc4ccc(Cl)cc4)CCC3)ccc21] | cyclopropyl 5-{1-[(4-chlorophenyl)carbamoyl]cyclobutyl}-2,3-dihydro-1H-indole-1-carboxylate | Calc'd 411, found 411 | 2.0 |
| 274 | 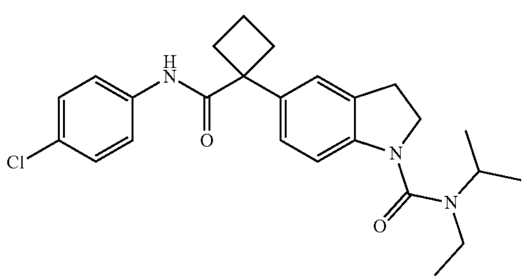 [SMILES: CCN(C(=O)N1CCc2cc(C3(C(=O)Nc4ccc(Cl)cc4)CCC3)ccc21)C(C)C] | 5-{1-[(4-chlorophenyl)carbamoyl]cyclobutyl}-N-ethyl-N-(propan-2-yl)-2,3-dihydro-1H-indole-1-carboxamide | Calc'd 440, found 440 | 3.3 |
| 275 | 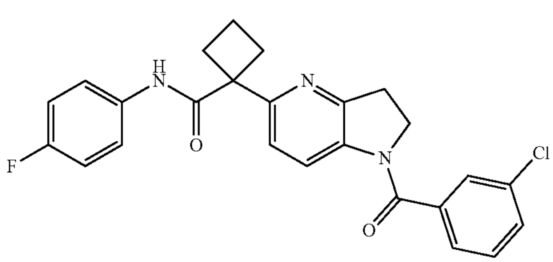 [SMILES: O=C(c1cccc(Cl)c1)N1CCc2nc(C3(C(=O)Nc4ccc(F)cc4)CCC3)ccc21] | 1-[1-(3-chlorobenzene-1-carbonyl)-2,3-dihydro-1H-pyrrolo[3,2-b]pyridin-5-yl]-N-(4-fluorophenyl)cyclobutane-1-carboxamide | Calc'd 450, found 450 | 3.0 |

The compounds in the following table were synthesized using the general procedure described in Step 9 of Example #125 using either 4-chloro-N-(1-(5,6,7,8-tetrahydro-1,5-naphthyridin-2-yl)ethyl)benzamide or 4-fluoro-N-(1-(5,6,7,8-tetrahydro-1,5-naphthyridin-2-yl)ethyl)benzamide as a common intermediate and the corresponding carboxylic acid.

| Ex. # | Structure | Chemical Name | Mass [M + H+] | Hela IC50, nM |
|---|---|---|---|---|
| 277 | 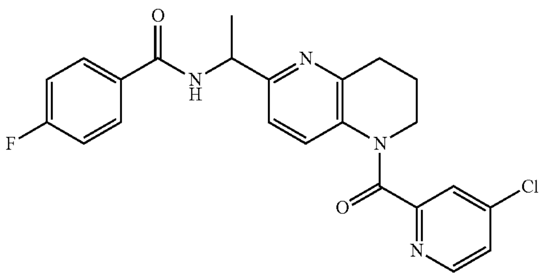 [SMILES: CC(NC(=O)c1ccc(F)cc1)c1ccc2c(n1)CCCN2C(=O)c1cc(Cl)ccn1] | N-(1-(5-(4-chloropicolinoyl)-5,6,7,8-tetrahydro-1,5-naphthyridin-2-yl)ethyl)-4-fluorobenzamide | Calc'd 438, found 439.7 | 2.3 |
| 278 | 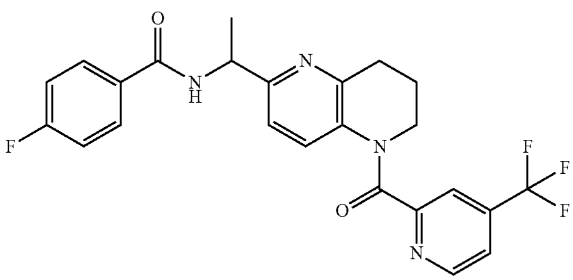 [SMILES: CC(NC(=O)c1ccc(F)cc1)c1ccc2c(n1)CCCN2C(=O)c1cc(C(F)(F)F)ccn1] | 4-fluoro-N-(1-(5-(4-(trifluoromethyl)picolinoyl)-5,6,7,8-tetrahydro-1,5-naphthyridin-2-yl)ethyl)benzamide | Calc'd 438, found 439.7 | 472 |
| 279 | 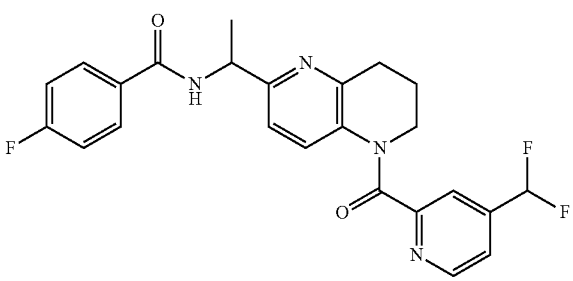 [SMILES: CC(NC(=O)c1ccc(F)cc1)c1ccc2c(n1)CCCN2C(=O)c1cc(C(F)F)ccn1] | N-(1-(5-(4-(difluoromethyl)picolinoyl)-5,6,7,8-tetrahydro-1,5-naphthyridin-2-yl)ethyl)-4-fluorobenzamide | Calc'd 454, found 455.1 | 7.3 |
| 280 | 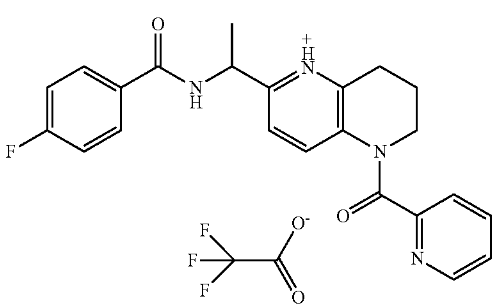 | 2-(1-(4-fluorobenzamido)ethyl)-5-picolinoyl-5,6,7,8-tetrahydro-1,5-naphthyridin-1-ium 2,2,2-trifluoroacetate | Calc'd 404, found 405.1 | 7.0 |
| 281 | 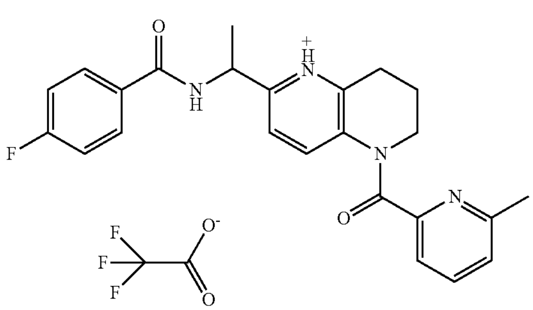 | 2-(1-(4-fluorobenzamido)ethyl)-5-(6-methylpicolinoyl)-5,6,7,8-tetrahydro-1,5-naphthyridin-1-ium 2,2,2-trifluoroacetate | Calc'd 418, found 419.7 | 3.0 |

-continued

| Ex. # | Structure | Chemical Name | Mass [M + H+] | Hela IC50, nM |
|---|---|---|---|---|
| 282 | 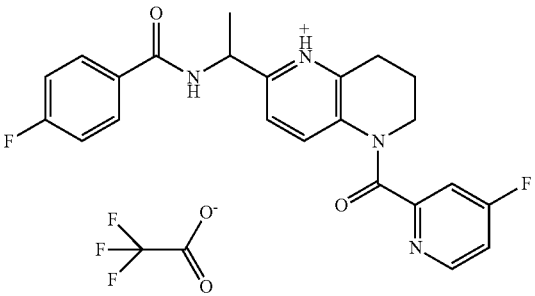 | 2-(1-(4-fluorobenzamido)ethyl)-5-(4-fluoropicolinoyl)-5,6,7,8-tetrahydro-1,5-naphthyridin-1-ium 2,2,2-trifluoroacetate | Calc'd 422, found 423.1 | 2.8 |
| 283 | 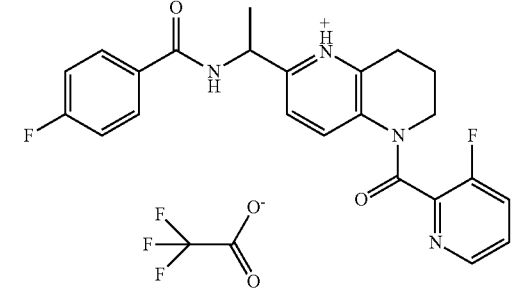 | 2-(1-(4-fluorobenzamido)ethyl)-5-(3-fluoropicolinoyl)-5,6,7,8-tetrahydro-1,5-naphthyridin-1-ium 2,2,2-trifluoroacetate | Calc'd 422, found 423.1 | 2.2 |
| 284 | 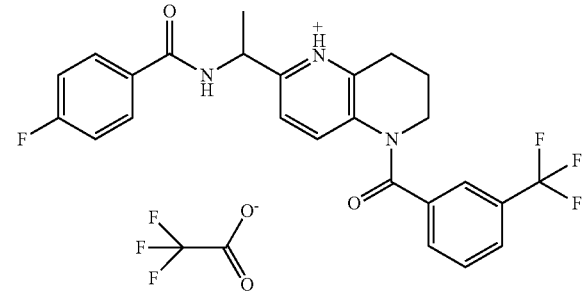 | 2-(1-(4-fluorobenzamido)ethyl)-5-(3-(trifluoromethyl)benzoyl)-5,6,7,8-tetrahydro-1,5-naphthyridin-1-ium 2,2,2-trifluoroacetate | Calc'd 471, found 472 | 1.2 |
| 285 | 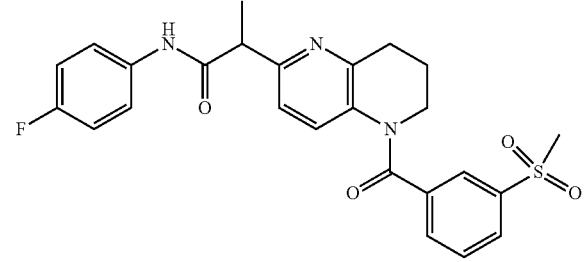 [SMILES: CC(C(=O)Nc1ccc(F)cc1)c1ccc2c(n1)CCCN2C(=O)c1cccc(S(C)(=O)=O)c1] | N-(4-fluorophenyl)-2-(5-(3-(methylsulfonyl)benzoyl)-5,6,7,8-tetrahydro-1,5-naphthyridin-2-yl)propanamide | Calc'd 481, found 482.1 | 4000 |
| 286 | 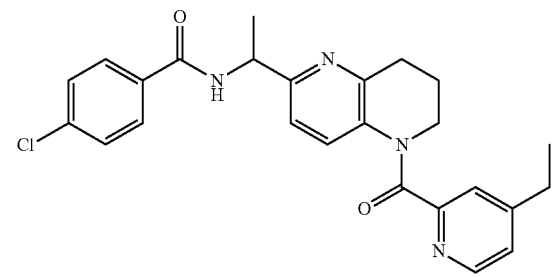 [SMILES: CCc1ccnc(C(=O)N2CCCc3nc(C(C)NC(=O)c4ccc(Cl)cc4)ccc32)c1] | 4-chloro-N-(1-(5-(4-ethylpicolinoyl)-5,6,7,8-tetrahydro-1,5-naphthyridin-2-yl)ethyl)benzamide | Calc'd 448, found 449.1 | 1.2 |

-continued

| Ex. # | Structure | Chemical Name | Mass [M + H+] | Hela IC50, nM |
|---|---|---|---|---|
| 287 | 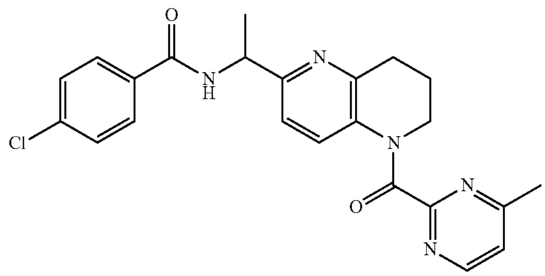 [SMILES: Cc1ccnc(C(=O)N2CCCc3nc(C(C)NC(=O)c4ccc(Cl)cc4)ccc32)n1] | 4-chloro-N-(1-(5-(4-methylpyrimidine-2-carbonyl)-5,6,7,8-tetrahydro-1,5-naphthyridin-2-yl)ethyl)benzamide | Calc'd 435.9, found 436.1 | 1.8 |
| 288 | 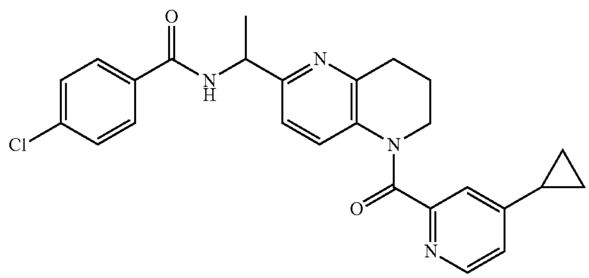 [SMILES: CC(NC(=O)c1ccc(Cl)cc1)c1ccc2c(n1)CCCN2C(=O)c1cc(C2CC2)ccn1] | 4-chloro-N-(1-(5-(4-cyclopropylpicolinoyl)-5,6,7,8-tetrahydro-1,5-naphthyridin-2-yl)ethyl)benzamide | Calc'd 460.9, found 461.1 | 3.2 |
| 289 | 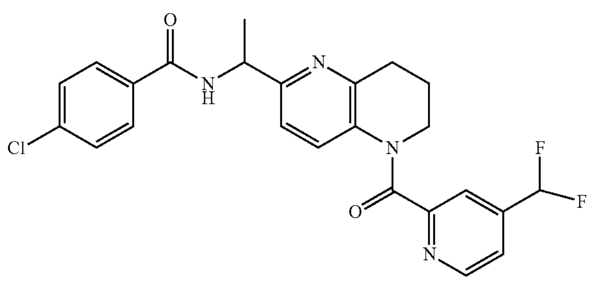 [SMILES: CC(NC(=O)c1ccc(Cl)cc1)c1ccc2c(n1)CCCN2C(=O)c1cc(C(F)F)ccn1] | 4-chloro-N-(1-(5-(4-(difluoromethyl)picolinoyl)-5,6,7,8-tetrahydro-1,5-naphthyridin-2-yl)ethyl)benzamide | Calc'd 470.8, found 471.1 | 2.7 |
| 292 | 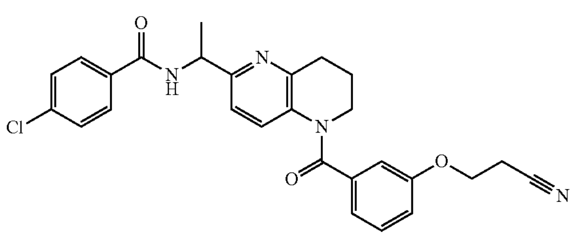 [SMILES: CC(NC(=O)c1ccc(Cl)cc1)c1ccc2c(n1)CCCN2C(=O)c1cccc(OCCC#N)c1] | 4-chloro-N-(1-(5-(3-(2-cyanoethoxy)benzoyl)-5,6,7,8-tetrahydro-1,5-naphthyridin-2-yl)ethyl)benzamide | Calc'd 448.2, found 489 | 10000 |

The compounds listed in the following table were prepared in a similar manner as described for Example #244 using either Method A or Method B

| Ex. # | Chemical Name | Structure | Mass [M + H+] | Hela IC50, nM |
|---|---|---|---|---|
| 296 | 4-fluoro-N-(1-(5-(6-methylpyrazin-2-yl)-5,6,7,8-tetrahydro-1,5-naphthyridin-2-yl)cyclopropyl)benzamide | | Calc'd 403.4, found 404.4 | 1.51 |

-continued

| Ex. # | Chemical Name | Structure | Mass [M + H⁺] | Hela IC₅₀, nM |
|---|---|---|---|---|
| 297 | 4-fluoro-N-(1-(5-(6-(2-hydroxypropan-2-yl)pyridin-2-yl)-5,6,7,8-tetrahydro-1,5-naphthyridin-2-yl)cyclopropyl)benzamide | 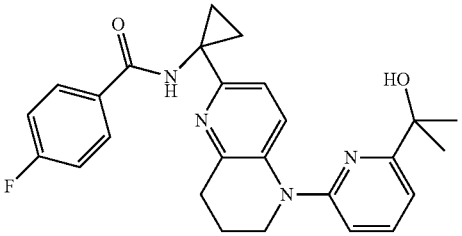 [SMILES: CC(C)(O)c1cccc(N2CCCc3nc(C4(NC(=O)c5ccc(F)cc5)CC4)ccc32)n1] | Calc'd 446.7, found 447.5 | 46.4 |
| 298 | 4-fluoro-N-(1-(5-(4-methoxypyrimidin-2-yl)-5,6,7,8-tetrahydro-1,5-naphthyridin-2-yl)cyclopropyl)benzamide | 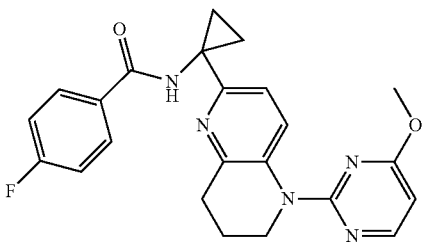 [SMILES: COc1ccnc(N2CCCc3nc(C4(NC(=O)c5ccc(F)cc5)CC4)ccc32)n1] | Calc'd 419.5, found 420.5 | 14.5 |
| 299 | 4-chloro-N-(1-(5-(2-methylpyrimidin-4-yl)-5,6,7,8-tetrahydro-1,5-naphthyridin-2-yl)cyclopropyl)benzamide | 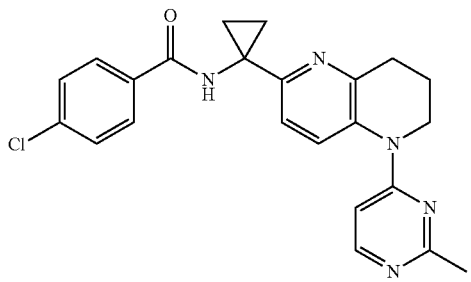 [SMILES: Cc1nccc(N2CCCc3nc(C4(NC(=O)c5ccc(Cl)cc5)CC4)ccc32)n1] | Calc'd 419.2, found 420.5 | 0.74 |
| 300 | 6-chloro-N-(1-(5-(2-methylpyrimidin-4-yl)-5,6,7,8-tetrahydro-1,5-naphthyridin-2-yl)cyclopropyl)nicotinamide | 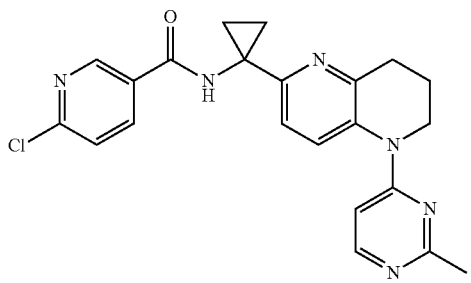 [SMILES: Cc1nccc(N2CCCc3nc(C4(NC(=O)c5ccc(Cl)nc5)CC4)ccc32)n1] | Calc'd 420.1, found 421. | 1.9 |
| 301 | 4-bromo-N-(1-(5-(2-methylpyrimidin-4-yl)-5,6,7,8-tetrahydro-1,5-naphthyridin-2-yl)cyclopropyl)benzamide | 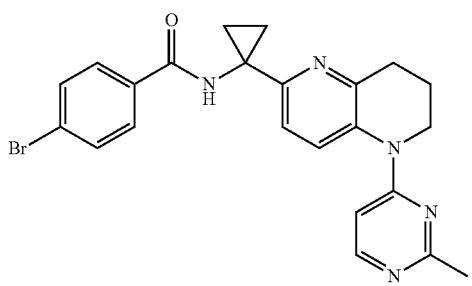 | Calc'd 463.1, found 464 | 1.69 |

-continued

| Ex. # | Chemical Name | Structure | Mass [M + H+] | Hela IC50, nM |
|---|---|---|---|---|
| 302 | 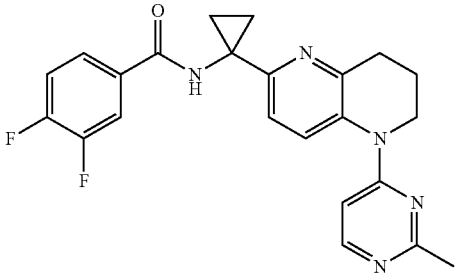 [SMILES: Cc1nccc(N2CCCc3nc(C4(NC(=O)c5ccc(F)c(F)c5)CC4)ccc32)n1] | 3,4-difluoro-N-(1-(5-(2-methylpyrimidin-4-yl)-5,6,7,8-tetrahydro-1,5-naphthyridin-2-yl)cyclopropyl)benzamide | Calc'd 421.2, found 422 | 2.92 |
| 303 | 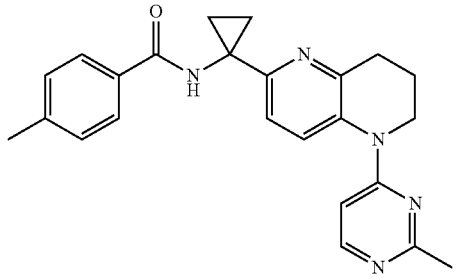 | 4-methyl-N-(1-(5-(2-methylpyrimidin-4-yl)-5,6,7,8-tetrahydro-1,5-naphthyridin-2-yl)cyclopropyl)benzamide | Calc'd 399.2, found 400.1 | 2.15 |
| 304 | 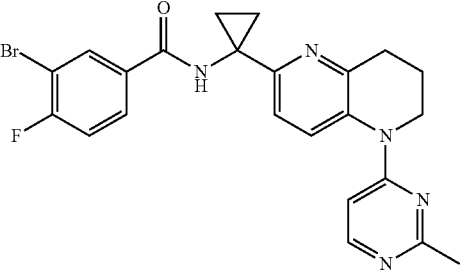 | 3-bromo-4-fluoro-N-(1-(5-(2-methylpyrimidin-4-yl)-5,6,7,8-tetrahydro-1,5-naphthyridin-2-yl)cyclopropyl)benzamide | Calc'd 481.1, found 482 | 2.79 |
| 307 | 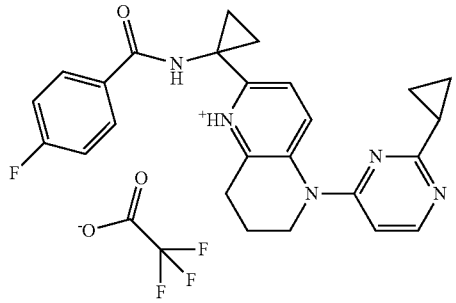 | 5-(2-cyclopropylpyrimidin-4-yl)-2-(1-(4-fluorobenzamido)cyclopropyl)-5,6,7,8-tetrahydro-1,5-naphthyridin-1-ium 2,2,2-trifluoroacetate | Calc'd 429, found 430.2 | 0.89 |

The examples listed in the following table from 309 to 341 were prepared following procedures described for Example #205 using the corresponding chloroformate.

| Ex. # | Chemical Name | Structure | Mass [M + H⁺] | Hela IC$_{50}$, nM |
|---|---|---|---|---|
| 309 | 2,2-difluoroethyl 6-(1-(4-fluorobenzamido)ethyl)-3,4-dihydro-1,5-naphthyridine-1(2H)-carboxylate | | Calc'd 407.3 found 408.1 | 24.55 |
| 310 | 2,2-difluoroethyl 6-(1-(4-fluorobenzamido)ethyl)-3,4-dihydro-1,5-naphthyridine-1(2H)-carboxylate | | Calc'd 441.8 found 442.0 | 1.61 |
| 311 | cyclobutyl 6-(1-(4-fluorobenzamido)ethyl)-3,4-dihydro-1,5-naphthyridine-1(2H)-carboxylate | | Calc'd 415.19 found 416.2 | 1.24 |
| 312 | 1,1,1-trifluoro-2-methylpropan-2-yl 6-(1-4-fluorobenzamido)ethyl)-3,4-dihydro-1,5-naphthyridine-1(2H)-carboxylate | | Calc'd 453.17 found 454.1 | 9.87 |
| 313 | oxetan-2-ylmethyl 6-(1-(4-fluorobenzamido)ethyl)-3,4-dihydro-1,5-naphthyridine-1(2H)-carboxylate | | Calc'd 413.18 found 414.1 | 45.34 |
| 314 | cyclopentyl 6-(1-(4-fluorobenzamido)ethyl)-3,4-dihydro-1,5-naphthyridine-1(2H)-carboxylate | | Calc'd 411.2 found 412.1 | 0.65 |

-continued

| Ex. # | Chemical Name | Structure | Mass [M + H⁺] | Hela IC$_{50}$, nM |
|---|---|---|---|---|
| 315 | (R)-1-methoxypropan-2-yl 6-(1-(4-fluorobenzamido)ethyl)-3,4-dihydro-1,5-naphthyridine-1(2H)-carboxylate | | Calc'd 415.2 found 416.1 | 2.9 |
| 316 | oxetan-3-yl 6-(1-(4-fluorobenzamido)ethyl)-3,4-dihydro-1,5-naphthyridine-1(2H)-carboxylate | | Calc'd 399.16 found 400.1 | 19.2 |
| 317 | (1-methyl-1H-pyrazol-3-yl)methyl 6-(1-(4-fluorobenzamido)ethyl)-3,4-dihydro-1,5-naphthyridine-1(2H)-carboxylate | | Calc'd 437.15 found 438.1 | 21.15 |
| 318 | 1-(pyridin-3-yl)ethyl 6-(1-(4-fluorobenzamido)ethyl)-3,4-dihydro-1,5-naphthyridine-1(2H)-carboxylate | | Calc'd 448.19 found 449.1 | 19.82 |
| 319 | 2-(2,2-difluorocyclopropyl)ethyl 6-(1-(4-fluorobenzamido)ethyl)-3,4-dihydro-1,5-naphthyridine-1(2H)-carboxylate | | Calc'd 447.18 found 448.1 | 9.87 |
| 320 | (3,5-dimethyl-1H-pyrazol-1-yl)methyl 6-(1-(4-fluorobenzamido)ethyl)-3,4-dihydro-1,5-naphthyridine-1(2H)-carboxylate | | Calc'd 451.2 found 452.2 | 69.22 |

-continued

| Ex. # | Chemical Name | Structure | Mass [M + H+] | Hela IC50, nM |
|---|---|---|---|---|
| 321 | (3,5-dimethyl-1H-pyrazol-1-yl)methyl 6-(1-(4-fluorobenzamido)ethyl)-3,4-dihydro-1,5-naphthyridine-1(2H)-carboxylate | 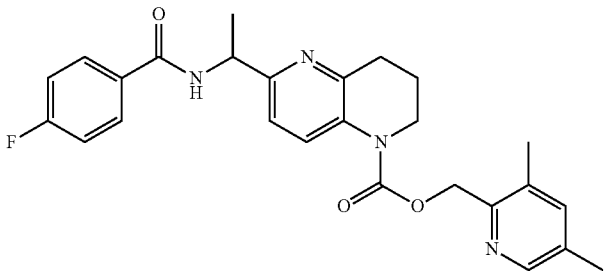 [SMILES: Cc1cnc(COC(=O)N2CCCc3nc(C(C)NC(=O)c4ccc(F)cc4)ccc32)c(C)c1] | Calc'd 470.16 found 471.1 | 2.7 |
| 322 | 3-(pyridin-4-yl)propyl 6-(1-(4-fluorobenzamido)ethyl)-3,4-dihydro-1,5-naphthyridine-1(2H)-carboxylate | 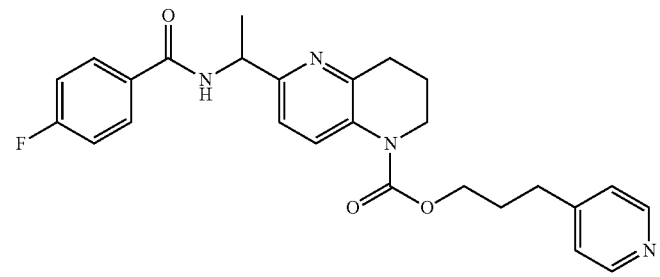 [SMILES: CC(NC(=O)c1ccc(F)cc1)c1ccc2c(n1)CCCN2C(=O)OCCCc1ccncc1] | Calc'd 462.53 found 463.0 | 453 |
| 323 | 2-propoxyethyl 6-(1-(4-fluorobenzamido)ethyl)-3,4-dihydro-1,5-naphthyridine-1(2H)-carboxylate | 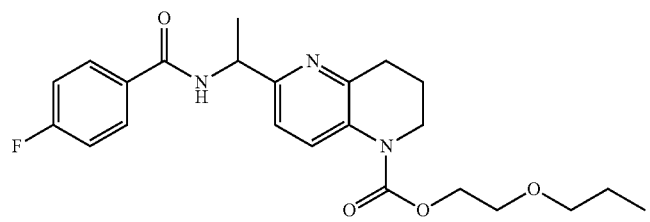 [SMILES: CCCOCCOC(=O)N1CCCc2nc(C(C)NC(=O)c3ccc(F)cc3)ccc21] | Calc'd 429.2 found 430.2 | 4.4 |
| 324 | 2-(diethylamino)ethyl 6-(1-(4-fluorobenzamido)ethyl)-3,4-dihydro-1,5-naphthyridine-1(2H)-carboxylate | 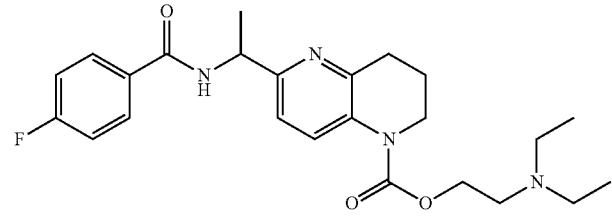 [SMILES: CCN(CC)CCOC(=O)N1CCCc2nc(C(C)NC(=O)c3ccc(F)cc3)ccc21] | Calc'd 442.2 found 443.1 | 3400 |
| 325 | 3-(1H-imidazol-1-yl)propyl 6-(1-(4-fluorobenzamido)ethyl)-3,4-dihydro-1,5-naphthyridine-1(2H)-carboxylate | 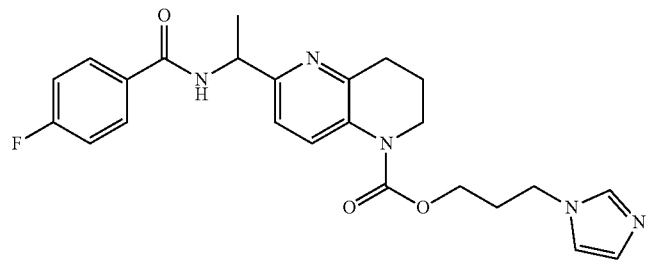 [SMILES: CC(NC(=O)c1ccc(F)cc1)c1ccc2c(n1)CCCN2C(=O)OCCCn1ccnc1] | Calc'd 451.2 found 452.1 | 1300 |
| 326 | 3,4-dichlorophenethyl 6-(1-(4-fluorobenzamido)ethyl)-3,4-dihydro-1,5-naphthyridine-1(2H)-carboxylate | 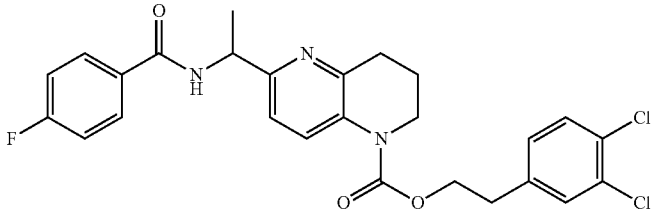 [SMILES: CC(NC(=O)c1ccc(F)cc1)c1ccc2c(n1)CCCN2C(=O)OCCc1ccc(Cl)c(Cl)c1] | Calc'd 515.2 found 516.1 | 24.3 |

-continued

| Ex. # | Chemical Name | Structure | Mass [M + H$^+$] | Hela IC$_{50}$, nM |
|---|---|---|---|---|
| 327 | 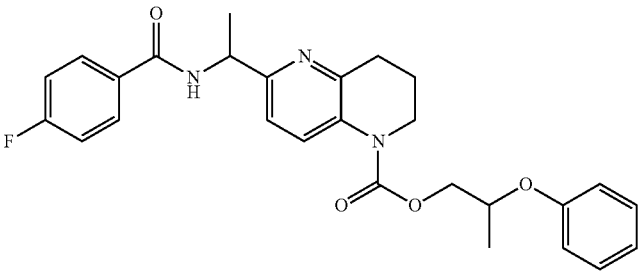 [SMILES: CC(COC(=O)N1CCCc2nc(C(C)NC(=O)c3ccc(F)cc3)ccc21)Oc1ccccc1] | 2-phenoxypropyl 6-(1-(4-fluorobenzamido)ethyl)-3,4-dihydro-1,5-naphthyridine-1(2H)-carboxylate | Calc'd 477.2 found 478.1 | 14.4 |
| 328 | 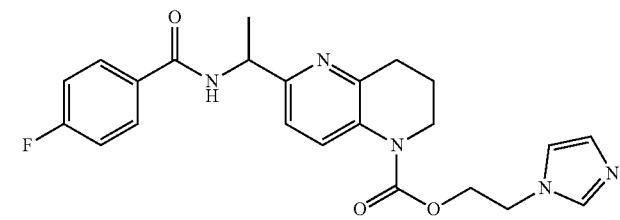 [SMILES: CC(NC(=O)c1ccc(F)cc1)c1ccc2c(n1)CCCN2C(=O)OCCn1ccnc1] | 2-(1H-imidazol-1-yl)ethyl 6-(1-(4-fluorobenzamido)ethyl)-3,4-dihydro-1,5-naphthyridine-1(2H)-carboxylate | Calc'd 437.1 found 438.2 | 479 |
| 329 | 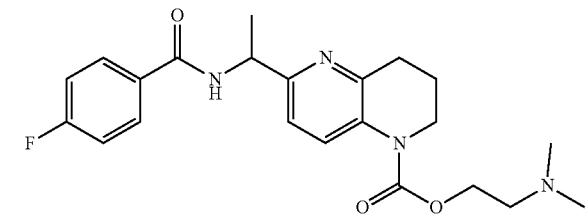 [SMILES: CC(NC(=O)c1ccc(F)cc1)c1ccc2c(n1)CCCN2C(=O)OCCN(C)C] | 2-(dimethylamino)ethyl 6-(1-(4-fluorobenzamido)ethyl)-3,4-dihydro-1,5-naphthyridine-1(2H)-carboxylate | Calc'd 414.2 found 415.2 | 2200 |
| 330 | 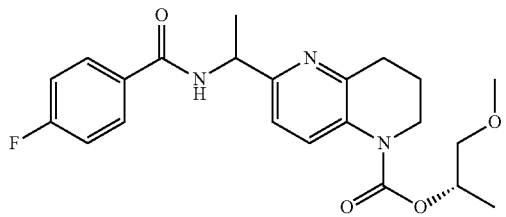 [SMILES: COC[C@H](C)OC(=O)N1CCCc2nc(C(C)NC(=O)c3ccc(F)cc3)ccc21] | (S)-1-methoxypropan-2-yl 6-(1-(4-chlorobenzamido)ethyl)-3,4-dihydro-1,5-naphthyridine-1(2H)-carboxylate | Calc'd 431.2 found 432.2 | 1.1 |
| 331 | 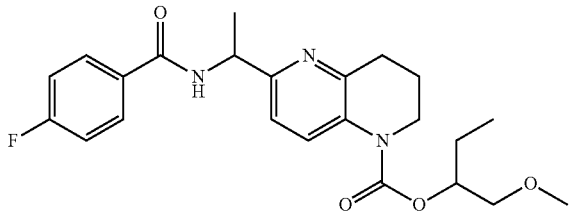 [SMILES: CCC(COC)OC(=O)N1CCCc2nc(C(C)NC(=O)c3ccc(F)cc3)ccc21] | 1-methoxybutan-2-yl 6-(1-(4-fluorobenzamido)ethyl)-3,4-dihydro-1,5-naphthyridine-1(2H)-carboxylate | Calc'd 429.2 found 430.2 | 2.02 |
| 334 | 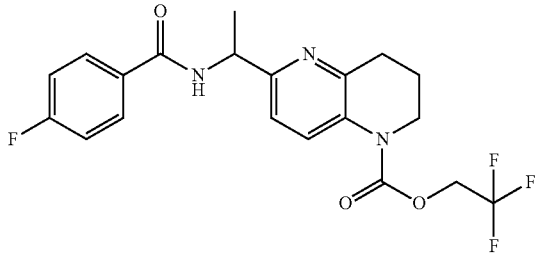 [SMILES: CC(NC(=O)c1ccc(F)cc1)c1ccc2c(n1)CCCN2C(=O)OCC(F)(F)F] | 2,2,2-trifluoroethyl 6-(1-(4-fluorobenzamido)ethyl)-3,4-dihydro-1,5-naphthyridine-1(2H)-carboxylate | Calc'd 425 found 426 | 279 |

| Ex. # | Chemical Name | Structure | Mass [M + H⁺] | Hela IC₅₀, nM |
|---|---|---|---|---|
| 335 | cyclopropyl 6-(1-(3-cyanobenzamido)ethyl)-3,4-dihydro-1,5-naphthyridine-1(2H)-carboxylate | | Calc'd 390 found 391 | 5700 |
| 336 | cyclopropyl 6-(1-(3-methoxybenzamido)ethyl)-3,4-dihydro-1,5-naphthyridine-1(2H)-carboxylate | | Calc'd 395 found 396 | 973 |
| 337 | cyclopropyl 6-(1-(4-cyanobenzamido)ethyl)-3,4-dihydro-1,5-naphthyridine-1(2H)-carboxylate | | Calc'd 390 found 391 | 88.2 |
| 338 | cyclopropyl 6-(1-(4-methoxybenzamido)ethyl)-3,4-dihydro-1,5-naphthyridine-1(2H)-carboxylate | | Calc'd 395.2 found 396.1 | 161.4 |
| 340 | 2-methoxyethyl 6-(1-(4-bromobenzamido)ethyl)-3,4-dihydro-1,5-naphthyridine-1(2H)-carboxylate Isomer 1 | | Calc'd 461.1 found 461.9 | 1.03 |
| 341 | 2-methoxyethyl 6-(1-(4-bromobenzamido)ethyl)-3,4-dihydro-1,5-naphthyridine-1(2H)-carboxylate Isomer 2 | | Calc'd 462.3 found 463 | 58.72 |

Compounds listed in the following table were synthesized following a similar procedure as that of Example #244, using the common intermediates 4-fluoro-N-(1-(5,6,7,8-tetrahydro-1,5-naphthyridin-2-yl)ethyl)benzamide or 4-chloro-N-(1-(5,6,7,8-tetrahydro-1,5-naphthyridin-2-yl)ethyl)benzamide. The final step was done using the corresponding halo heterocycle following the procedure described in Step 2, Example #244 using either Method A or Method B.

| Ex. # | Structure | Chemical Name | Mass [M + H$^+$] | Hela IC$_{50}$, nM |
|---|---|---|---|---|
| 345 | 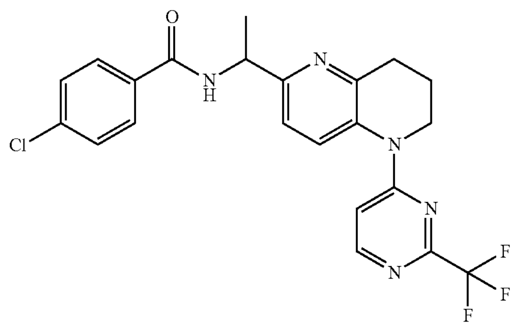 [SMILES: CC(NC(=O)c1ccc(Cl)cc1)c1ccc2c(n1)CCCN2c1ccnc(C(F)(F)F)n1] | 4-chloro-N-(1-(5-(2-(trifluoromethyl)pyrimidin-4-yl)-5,6,7,8-tetrahydro-1,5-naphthyridin-2-yl)ethyl)benzamide | Calc'd 461.8 found 462.1 | 1.72 |
| 346 | 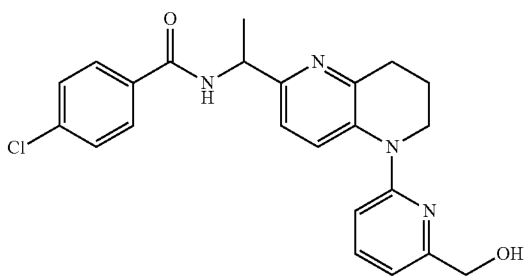 [SMILES: CC(NC(=O)c1ccc(Cl)cc1)c1ccc2c(n1)CCCN2c1cccc(CO)n1] | 4-chloro-N-(1-(5-(6-(hydroxymethyl)pyridin-2-yl)-5,6,7,8-tetrahydro-1,5-naphthyridin-2-yl)ethyl)benzamide | Calc'd 422.1 found 423.1 | 8.22 |
| 347 | 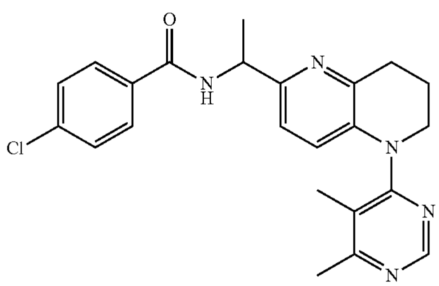 [SMILES: Cc1ncnc(N2CCCc3nc(C(C)NC(=O)c4ccc(Cl)cc4)ccc32)c1C] | 4-chloro-N-(1-(5-(5,6-dimethylpyrimidin-4-yl)-5,6,7,8-tetrahydro-1,5-naphthyridin-2-yl)ethyl)benzamide | Calc'd 421.1 found 422.1 | 156 |
| 348 | 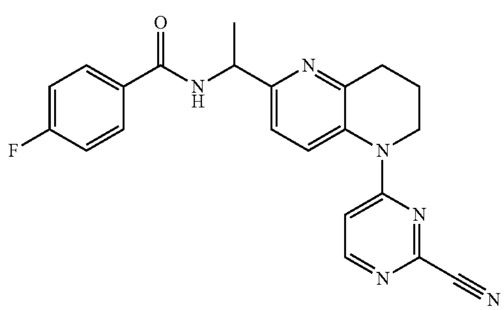 [SMILES: CC(NC(=O)c1ccc(F)cc1)c1ccc2c(n1)CCCN2c1ccnc(C#N)n1] | N-(1-(5-(2-cyanopyrimidin-4-yl)-5,6,7,8-tetrahydro-1,5-naphthyridin-2-yl)ethyl)-4-fluorobenzamide | Calc'd 421.1 found 422.1 | 13.4 |
| 349 | 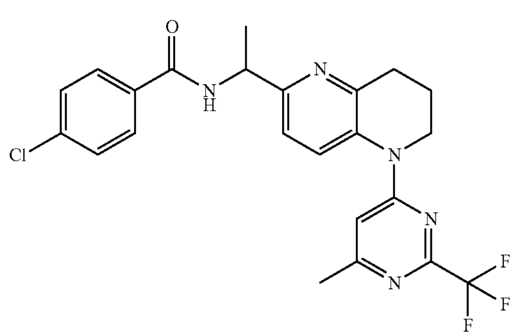 [SMILES: Cc1cc(N2CCCc3nc(C(C)NC(=O)c4ccc(Cl)cc4)ccc32)nc(C(F)(F)F)n1] | 4-chloro-N-(1-(5-(6-methyl-2-(trifluoromethyl)pyrimidin-4-yl)-5,6,7,8-tetrahydro-1,5-naphthyridin-2-yl)ethyl)benzamide | Calc'd 475 found 476.1 | 9.71 |

-continued

| Ex. # | Structure | Chemical Name | Mass [M + H⁺] | Hela IC$_{50}$, nM |
|---|---|---|---|---|
| 351 | 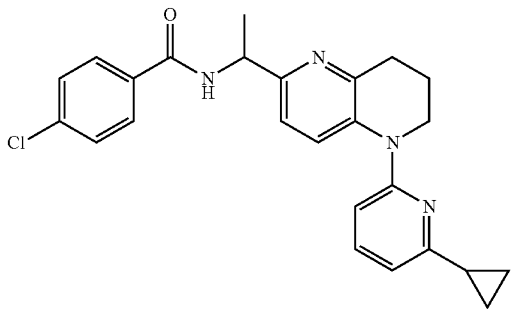 [SMILES: CC(NC(=O)c1ccc(Cl)cc1)c1ccc2c(n1)CCCN2c1cccc(C2CC2)n1] | 4-chloro-N-(1-(5-(6-cyclopropylpyridin-2-yl)-5,6,7,8-tetrahydro-1,5-naphthyridin-2-yl)ethyl)benzamide | Calc'd 433 found 434.1 | 3.38 |
| 352 | 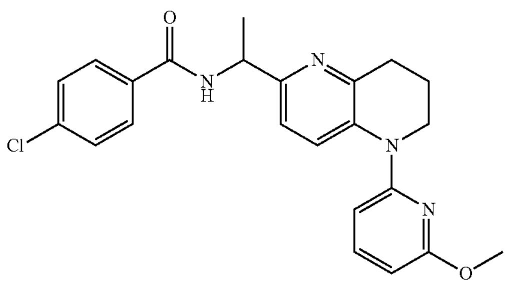 [SMILES: COc1cccc(N2CCCc3nc(C(C)NC(=O)c4ccc(Cl)cc4)ccc32)n1] | 4-chloro-N-(1-(5-(6-methoxypyridin-2-yl)-5,6,7,8-tetrahydro-1,5-naphthyridin-2-yl)ethyl)benzamide | Calc'd 422 found 423 | 4.01 |
| 353 | 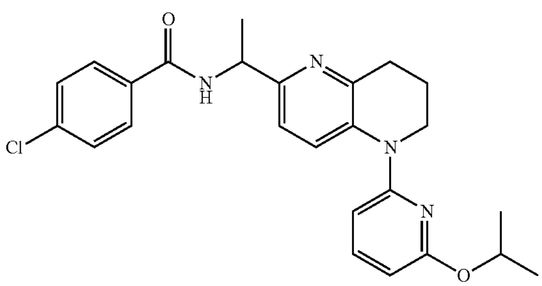 [SMILES: CC(C)Oc1cccc(N2CCCc3nc(C(C)NC(=O)c4ccc(Cl)cc4)ccc32)n1] | 4-chloro-N-(1-(5-(6-isopropoxypyridin-2-yl)-5,6,7,8-tetrahydro-1,5-naphthyridin-2-yl)ethyl)benzamide | Calc'd 450 found 451.1 | 77.2 |
| 354 | 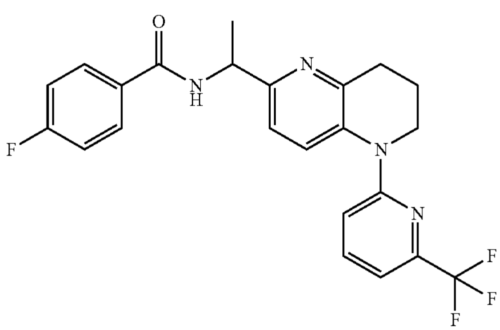 [SMILES: CC(NC(=O)c1ccc(F)cc1)c1ccc2c(n1)CCCN2c1cccc(C(F)(F)F)n1] | 4-fluoro-N-(1-(5-(6-(trifluoromethyl)pyridin-2-yl)-5,6,7,8-tetrahydro-1,5-naphthyridin-2-yl)ethyl)benzamide | Calc'd 444 found 445.1 | 10.53 |
| 356 | 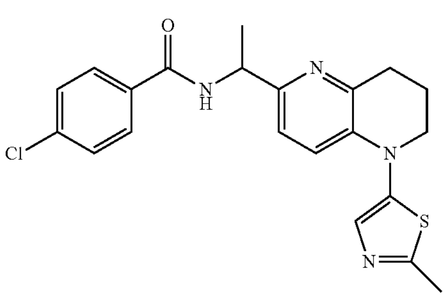 [SMILES: Cc1ncc(N2CCCc3nc(C(C)NC(=O)c4ccc(Cl)cc4)ccc32)s1] | 4-chloro-N-(1-(5-(2-methylthiazol-5-yl)-5,6,7,8-tetrahydro-1,5-naphthyridin-2-yl)ethyl)benzamide | Calc'd 412 found 413 | 13 |

-continued

| Ex. # | Structure | Chemical Name | Mass [M + H+] | Hela IC$_{50}$, nM |
|---|---|---|---|---|
| 357 | 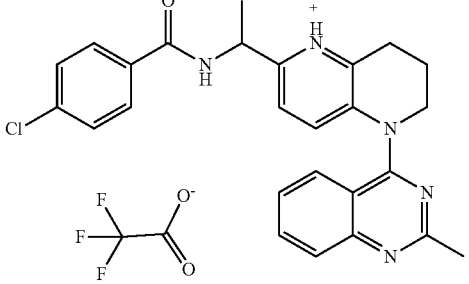 | 2-(1-(4-chlorobenzamido)ethyl)-5-(2-methylquinazolin-4-yl)-5,6,7,8-tetrahydro-1,5-naphthyridin-1-ium 2,2,2-trifluoroacetate | Calc'd 458 found 459 | 27.86 |
| 358 | 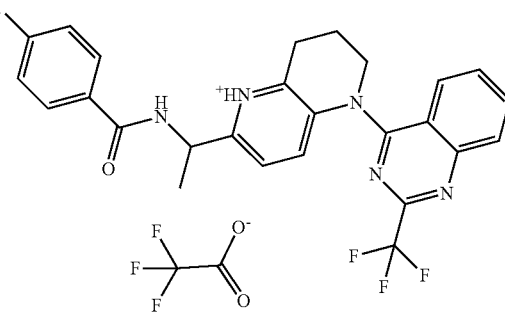 | 2-(1-(4-chlorobenzamido)ethyl)-5-(2-(trifluoromethyl)quinazolin-4-yl)-5,6,7,8-tetrahydro-1,5-naphthyridin-1-ium 2,2,2-trifluoroacetate | Calc'd 511 found 512.1 | 4.24 |
| 359 | 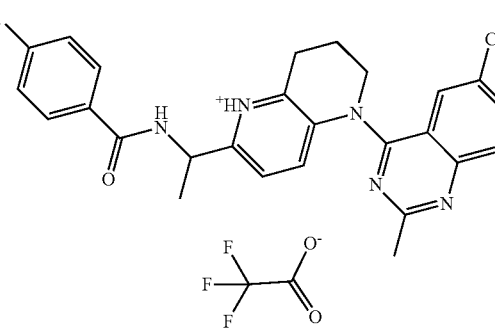 | 5-(6-chloro-2-methylquinazolin-4-yl)-2-(1-(4-chlorobenzamido)ethyl)-5,6,7,8-tetrahydro-1,5-naphthyridin-1-ium 2,2,2-trifluoroacetate | Calc'd 491 found 491.1 | 25.03 |
| 360 | 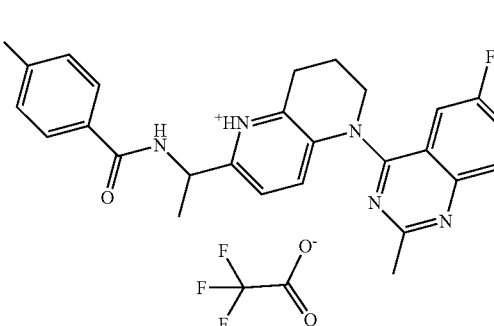 | 2-(1-(4-chlorobenzamido)ethyl)-5-(6-fluoro-2-methylquinazolin-4-yl)-5,6,7,8-tetrahydro-1,5-naphthyridin-1-ium 2,2,2-trifluoroacetate | Calc'd 475 found 476 | 25.62 |

| Ex. # | Structure | Chemical Name | Mass [M + H⁺] | Hela IC$_{50}$, nM |
|---|---|---|---|---|
| 361 | 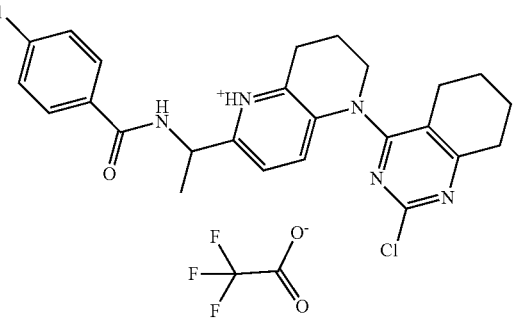 | 5-(2-chloro-5,6,7,8-tetrahydroquinazolin-4-yl)-2-(1-(4-chlorobenzamido)ethyl)-5,6,7,8-tetrahydro-1,5-naphthyridin-1-ium 2,2,2-trifluoroacetate | Calc'd 482.1 found 483 | 8.35 |
| 362 | 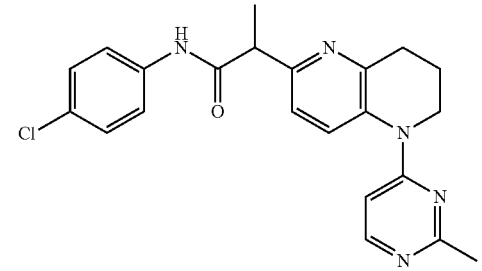  Isomer 1 | N-(4-chlorophenyl)-2-(5-(2-methylpyrimidin-4-yl)-5,6,7,8-tetrahydro-1,5-naphthyridin-2-yl)propanamide | Calc'd 407 found 408 | 0.69 |
| 363 | 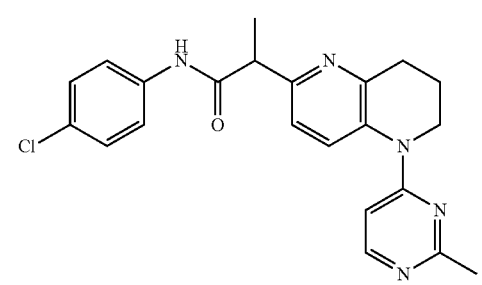  Isomer 2 | N-(4-chlorophenyl)-2-(5-(2-methylpyrimidin-4-yl)-5,6,7,8-tetrahydro-1,5-naphthyridin-2-yl)propanamide | Calc'd 407 found 407.9 | 0.93 |
| 364 | 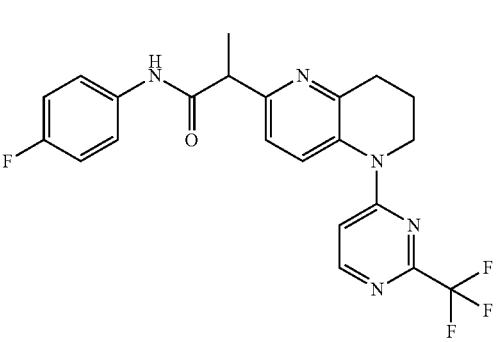 [SMILES: CC(C(=O)Nc1ccc(F)cc1)c1ccc2c(n1)CCCN2c1ccnc(C(F)(F)F)n1] | N-(4-fluorophenyl)-2-(5-(2-(trifluoromethyl)pyrimidin-4-yl)-5,6,7,8-tetrahydro-1,5-naphthyridin-2-yl)propanamide | Calc'd 445.2 found 445.9 | 4.99 |
| 365 | 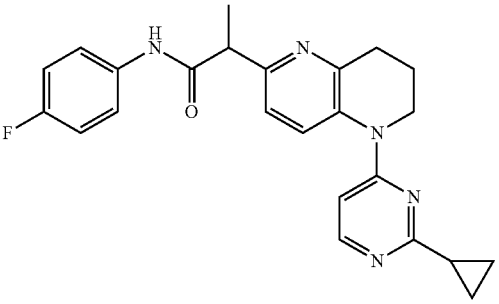 [SMILES: CC(C(=O)Nc1ccc(F)cc1)c1ccc2c(n1)CCCN2c1ccnc(C2CC2)n1] | 2-(5-(2-cyclopropylpyrimidin-4-yl)-5,6,7,8-tetrahydro-1,5-naphthyridin-2-yl)-N-(4-fluorophenyl)propanamide | Calc'd 417 found 418.2 | 3.62 |

| Ex. # | Structure | Chemical Name | Mass [M + H⁺] | Hela IC₅₀, nM |
|---|---|---|---|---|
| 366 | Isomer 1 | 2-(5-(2-cyclopropylpyrimidin-4-yl)-5,6,7,8-tetrahydro-1,5-naphthyridin-2-yl)-N-(4-fluorophenyl)propanamide | Calc'd 417 found 418.2 | 3.82 |
| 367 | Isomer 2 | 2-(5-(2-cyclopropylpyrimidin-4-yl)-5,6,7,8-tetrahydro-1,5-naphthyridin-2-yl)-N-(4-fluorophenyl)propanamide | Calc'd 417 found 418.2 | 1.81 |
| 368 | 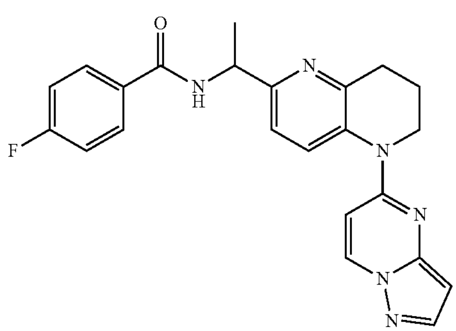 [SMILES: CC(NC(=O)c1ccc(F)cc1)c1ccc2c(n1)CCCN2c1ccn2nccc2n1] | 4-fluoro-N-(1-(5-(pyrazolo[1,5-a]pyrimidin-5-yl)-5,6,7,8-tetrahydro-1,5-naphthyridin-2-yl)ethyl)benzamide | Calc'd 416 found 417 | 17.96 |
| 369 | 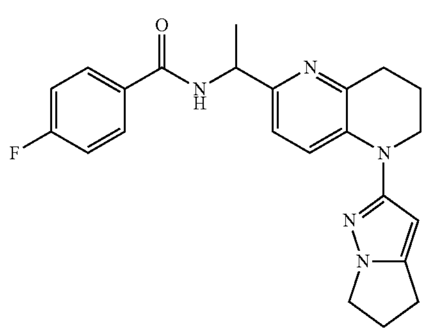 [SMILES: CC(NC(=O)c1ccc(F)cc1)c1ccc2c(n1)CCCN2c1cc2n(n1)CCC2] | N-(1-(5-(5,6-dihydro-4H-pyrrolo[1,2-b]pyrazol-2-yl)-5,6,7,8-tetrahydro-1,5-naphthyridin-2-yl)ethyl)-4-fluorobenzamide | Calc'd 405 found 406 | 697 |

| Ex. # | Structure | Chemical Name | Mass [M + H+] | Hela IC50, nM |
|---|---|---|---|---|
| 370 | 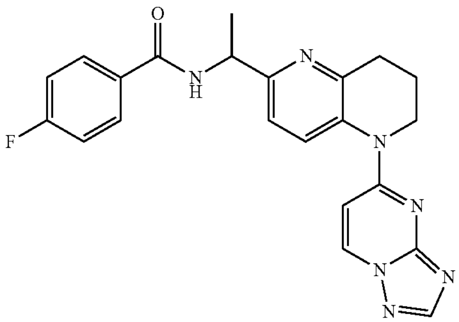 [SMILES: CC(NC(=O)c1ccc(F)cc1)c1ccc2c(n1)CCCN2c1ccn2ncnc2n1] | N-(1-(5-([1,2,4]triazolo[1,5-a]pyrimidin-5-yl)-5,6,7,8-tetrahydro-1,5-naphthyridin-2-yl)ethyl)-4-fluorobenzamide | Calc'd 417.2 found 418 | 1800 |
| 371 | Racemic | N-(4-fluorophenyl)-2-(5-(2-methylpyrimidin-4-yl)-5,6,7,8-tetrahydro-1,5-naphthyridin-2-yl)propanamide | Calc'd 391 found 392 | 2.72 |
| 372 | Isomer 1 | N-(4-fluorophenyl)-2-(5-(2-methylpyrimidin-4-yl)-5,6,7,8-tetrahydro-1,5-naphthyridin-2-yl)propanamide | Calc'd 391 found 392 | 5.34 |
| 373 | Isomer 2 | N-(4-fluorophenyl)-2-(5-(2-methylpyrimidin-4-yl)-5,6,7,8-tetrahydro-1,5-naphthyridin-2-yl)propanamide | Calc'd 391 found 392 | 6.38 |

-continued

| Ex. # | Structure | Chemical Name | Mass [M + H⁺] | Hela IC$_{50}$, nM |
|---|---|---|---|---|
| 374 | 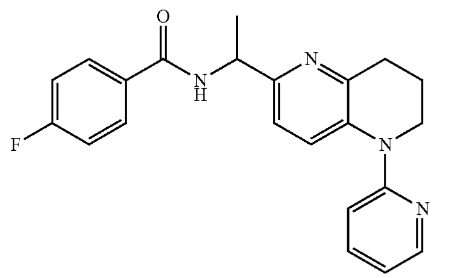 [SMILES: CC(NC(=O)c1ccc(F)cc1)c1ccc2c(n1)CCCN2c1ccccn1] | 4-fluoro-N-(1-(5-(pyridin-2-yl)-5,6,7,8-tetrahydro-1,5-naphthyridin-2-yl)ethyl)benzamide | Calc'd 376 found 377.1 | 1700 |
| 375 | 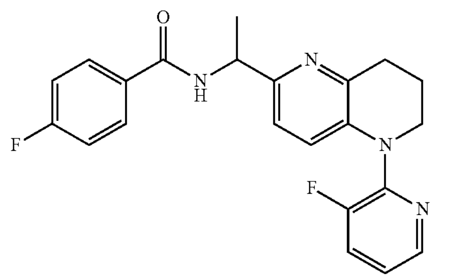 [SMILES: CC(NC(=O)c1ccc(F)cc1)c1ccc2c(n1)CCCN2c1ncccc1F] | 4-fluoro-N-(1-(5-(3-fluoropyridin-2-yl)-5,6,7,8-tetrahydro-1,5-naphthyridin-2-yl)ethyl)benzamide | Calc'd 394.2 found 395.1 | 1530 |
| 376 | 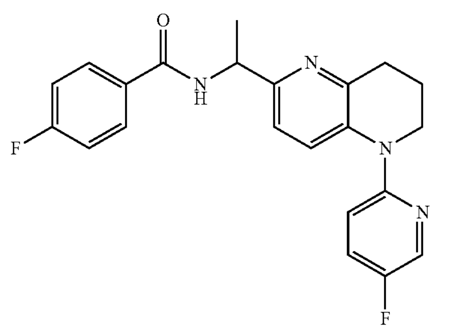 [SMILES: CC(NC(=O)c1ccc(F)cc1)c1ccc2c(n1)CCCN2c1ccc(F)cn1] | 4-fluoro-N-(1-(5-(5-fluoropyridin-2-yl)-5,6,7,8-tetrahydro-1,5-naphthyridin-2-yl)ethyl)benzamide | Calc'd 394.2 found 395.1 | 99.56 |
| 377 | 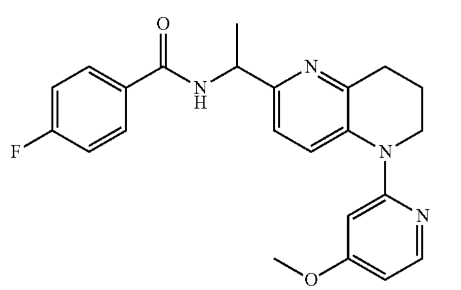 [SMILES: COc1ccnc(N2CCCc3nc(C(C)NC(=O)c4ccc(F)cc4)ccc32)c1] | 4-fluoro-N-(1-(5-(4-methoxypyridin-2-yl)-5,6,7,8-tetrahydro-1,5-naphthyridin-2-yl)ethyl)benzamide | Calc'd 406.2 found 407.1 | 314.9 |
| 378 | 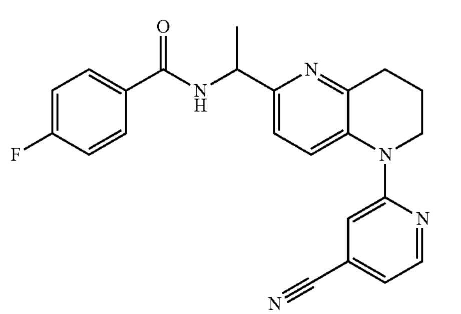 [SMILES: CC(NC(=O)c1ccc(F)cc1)c1ccc2c(n1)CCCN2c1cc(C#N)ccn1] | N-(1-(5-(4-cyanopyridin-2-yl)-5,6,7,8-tetrahydro-1,5-naphthyridin-2-yl)ethyl)-4-fluorobenzamide | Calc'd 410 found 402.1 | 352 |

-continued

| Ex. # | Structure | Chemical Name | Mass [M + H⁺] | Hela IC$_{50}$, nM |
|---|---|---|---|---|
| 379 | 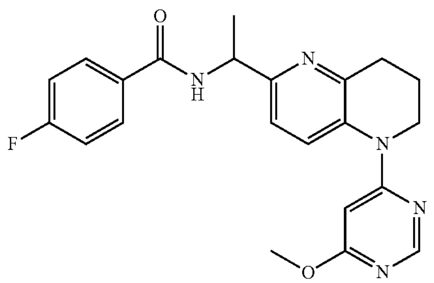 [SMILES: COc1cc(N2CCCc3nc(C(C)NC(=O)c4ccc(F)cc4)ccc32)ncn1] | 4-fluoro-N-(1-(5-(6-methoxypyrimidin-4-yl)-5,6,7,8-tetrahydro-1,5-naphthyridin-2-yl)ethyl)benzamide | Calc'd 407.2 found 408.1 | 12.96 |
| 380 | 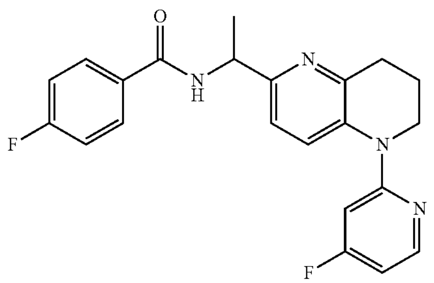 [SMILES: CC(NC(=O)c1ccc(F)cc1)c1ccc2c(n1)CCCN2c1cc(F)ccn1] | 4-fluoro-N-(1-(5-(4-fluoropyridin-2-yl)-5,6,7,8-tetrahydro-1,5-naphthyridin-2-yl)ethyl)benzamide | Calc'd 394.2 found 395 | 74.5 |
| 384 | 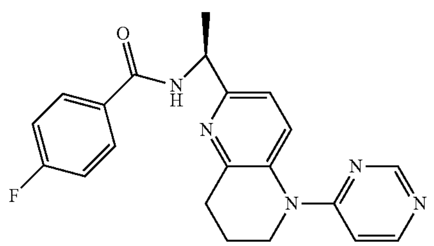 [SMILES: C[C@H](NC(=O)c1ccc(F)cc1)c1ccc2c(n1)CCCN2c1ccncn1] | (S)-4-fluoro-N-(1-(5-(pyrimidin-4-yl)-5,6,7,8-tetrahydro-1,5-naphthyridin-2-yl)ethyl)benzamide | Calc'd 377 found 378.1 | 10.32 |
| 385 | 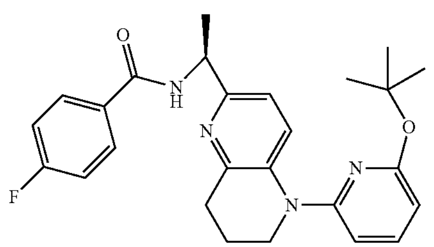 [SMILES: C[C@H](NC(=O)c1ccc(F)cc1)c1ccc2c(n1)CCCN2c1cccc(OC(C)(C)C)n1] | (S)-N-(1-(5-(6-(tert-butoxy)pyridin-2-yl)-5,6,7,8-tetrahydro-1,5-naphthyridin-2-yl)ethyl)-4-fluorobenzamide | Calc'd 448.2 found 449.0 | 968 |
| 386 | 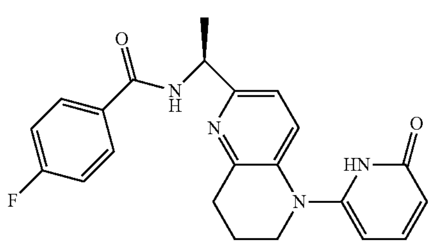 [SMILES: C[C@H](NC(=O)c1ccc(F)cc1)c1ccc2c(n1)CCCN2c1cccc(=O)[nH]1] | (S)-2-(1-(4-fluorobenzamido)ethyl)-5-(6-oxo-1,6-dihydropyridin-2-yl)-5,6,7,8-tetrahydro-1,5-naphthyridin-1-ium 2,2,2-trifluoroacetate | Calc'd 392 found 393.1 | 41.4 |
| 387 | 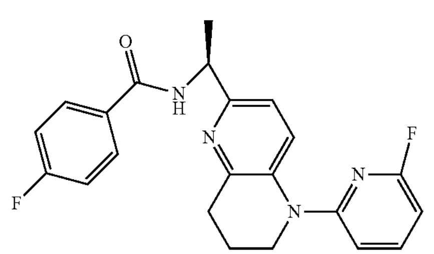 [SMILES: C[C@H](NC(=O)c1ccc(F)cc1)c1ccc2c(n1)CCCN2c1cccc(F)n1] | (S)-4-fluoro-N-(1-(5-(6-fluoropyridin-2-yl)-5,6,7,8-tetrahydro-1,5-naphthyridin-2-yl)ethyl)benzamide | Calc'd 394 found 395 | 25.74 |

Compounds in the following table were synthesized using the common intermediate N-(4-fluorophenyl)-2-methyl-2-(5,6,7,8-tetrahydro-1,5-naphthyridin-2-yl)propanamide from Step 4 of Example 184. The final step was done using the corresponding halo heterocycle following the procedure described in Step 1 of Example #244 using Method A or Method B.

The compounds in the following table were synthesized using common intermediate 3-(5-(tert-butoxycarbonyl)-5,6,7,8-tetrahydro-1,5-naphthyridin-2-yl)oxetane-3-carboxylic acid, obtained from Step 6 of Example 266, with corresponding acid. The final step was done using the procedure described in Step 2 of Example #244 using either Method A or Method B.

| Ex. # | Structure | Chemical Name | Mass, [M + H+] | Hela IC$_{50}$, nM |
|---|---|---|---|---|
| 389 | 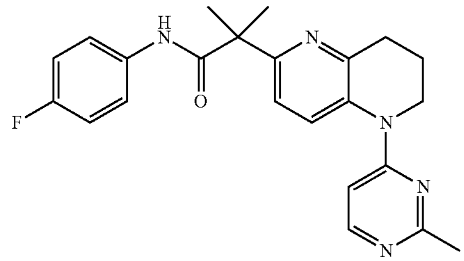 [SMILES: Cc1nccc(N2CCCc3nc(C(C)(C)C(=O)Nc4ccc(F)cc4)ccc32)n1] | N-(4-fluorophenyl)-2-methyl-2-(5-(2-methylpyrimidin-4-yl)-5,6,7,8-tetrahydro-1,5-naphthyridin-2-yl)propanamide | Calc'd 405 found 406 | 2.92 |
| 390 | Racemic | N-(4-chlorophenyl)-2-methyl-2-(5-(2-methylpyrimidin-4-yl)-5,6,7,8-tetrahydro-1,5-naphthyridin-2-yl)propanamide | Calc'd 421 found 422 | 2.42 |
| 391 | Isomer 1 | N-(4-chloro-3-fluorophenyl)-2-methyl-2-(5-(2-methylpyrimidin-4-yl)-5,6,7,8-tetrahydro-1,5-naphthyridin-2-yl)propanamide | Calc'd 439 found 440 | 5.7 |
| 392 | Isomer 2 | 4-chloro-N-(2-(5-(2-methylpyrimidin-4-yl)-5,6,7,8-tetrahydro-1,5-naphthyridin-2-yl)propan-2-yl)benzamide | Calc'd 421.2 found 422 | 4.28 |

| Ex. # | Structure | Chemical Name | Mass [M + H⁺] | Hela IC$_{50}$, nM |
|---|---|---|---|---|
| 393 | 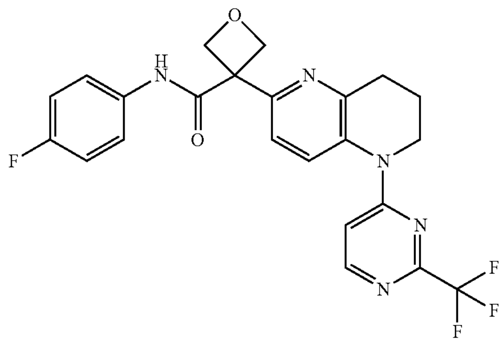 [SMILES: O=C(Nc1ccc(F)cc1)C1(c2ccc3c(n2)CCCN3c2ccnc(C(F)(F)F)n2)COC1] | N-(4-fluorophenyl)-3-(5-(2-(trifluoromethyl)pyrimidin-4-yl)-5,6,7,8-tetrahydro-1,5-naphthyridin-2-yl)oxetane-3-carboxamide | Calc'd 473 found 474.1 | 1.6 |
| 394 | 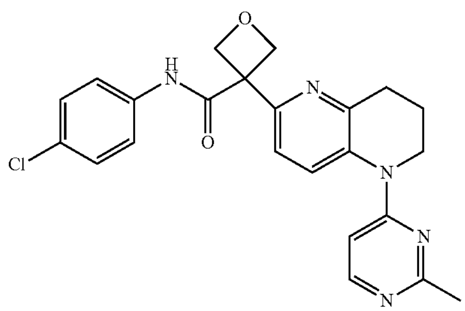 [SMILES: Cc1nccc(N2CCCc3nc(C4(C(=O)Nc5ccc(Cl)cc5)COC4)ccc32)n1] | N-(4-chlorophenyl)-3-(5-(2-methylpyrimidin-4-yl)-5,6,7,8-tetrahydro-1,5-naphthyridin-2-yl)oxetane-3-carboxamide | Calc'd 435 found 436.1 | 1.93 |
| 395 | 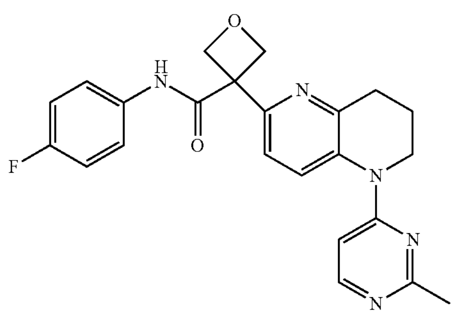 [SMILES: Cc1nccc(N2CCCc3nc(C4(C(=O)Nc5ccc(F)cc5)COC4)ccc32)n1] | N-(4-fluorophenyl)-3-(5-(2-methylpyrimidin-4-yl)-5,6,7,8-tetrahydro-1,5-naphthyridin-2-yl)oxetane-3-carboxamide | Calc'd 419.2 found 420 | 1.23 |
| 396 | 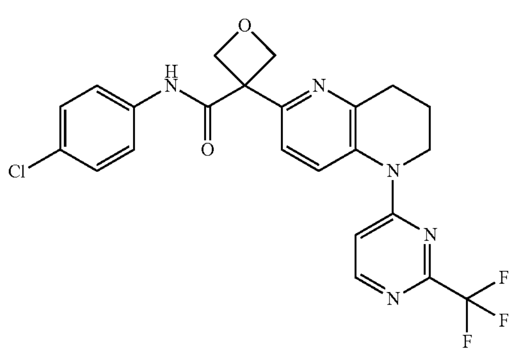 [SMILES: O=C(Nc1ccc(Cl)cc1)C1(c2ccc3c(n2)CCCN3c2ccnc(C(F)(F)F)n2)COC1] | N-(4-chlorophenyl)-3-(5-(2-(trifluoromethyl)pyrimidin-4-yl)-5,6,7,8-tetrahydro-1,5-naphthyridin-2-yl)oxetane-3-carboxamide | Calc'd 489.1 found 490 | 1.82 |

Example 398 in the following table was synthesized using the procedures as described in Step 7 and Step 9 of Example #266.

| Ex. # | Structure | Chemical Name | Mass [M + H⁺] | Hela IC₅₀, nM |
|---|---|---|---|---|
| 398 | 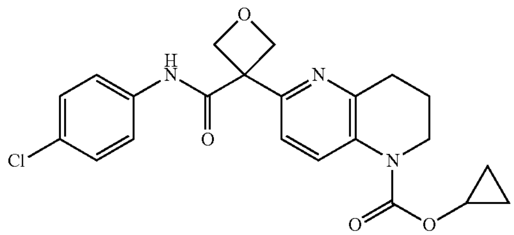 [SMILES: O=C(OC1CC1)N1CCCc2nc(C3(C(=O)Nc4ccc(Cl)cc4)COC3)ccc21] | cyclopropyl 6-(3-((4-chlorophenyl)carbamoyl)oxetan-3-yl)-3,4-dihydro-1,5-naphthyridine-1(2H)-carboxylate | Calc'd 427.1 found 428 | 1.48 |

Examples in the following table were prepared following a procedure used for the synthesis of Example #267 using the corresponding acid.

| Ex. # | Structure | Chemical Name | Mass [M + H⁺] | Hela IC₅₀, nM |
|---|---|---|---|---|
| 399 | 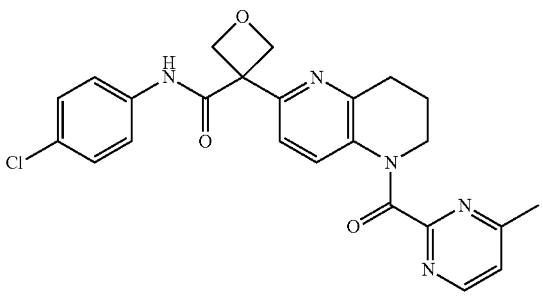 [SMILES: Cc1ccnc(C(=O)N2CCCc3nc(C4(C(=O)Nc5ccc(Cl)cc5)COC4)ccc32)n1] | N-(4-chlorophenyl)-3-(5-(4-methylpyrimidine-2-carbonyl)-5,6,7,8-tetrahydro-1,5-naphthyridin-2-yl)oxetane-3-carboxamide | Calc'd 463.1 found 464 | 1.72 |
| 400 | 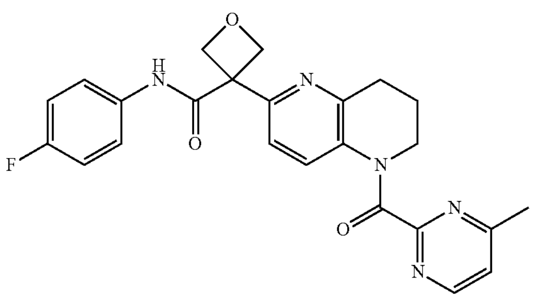 [SMILES: Cc1ccnc(C(=O)N2CCCc3nc(C4(C(=O)Nc5ccc(F)cc5)COC4)ccc32)n1] | N-(4-fluorophenyl)-3-(5-(4-methylpyrimidine-2-carbonyl)-5,6,7,8-tetrahydro-1,5-naphthyridin-2-yl)oxetane-3-carboxamide | Calc'd 447.2 found 448 | 1.91 |

The compounds in the following table were made following a similar procedure as described for Example #244 with the corresponding halo heterocycles using the procedure described in Method B.

| Ex. # | Structure | Chemical Name | Mass [M + H⁺] | Hela IC₅₀, nM |
|---|---|---|---|---|
| 401 | 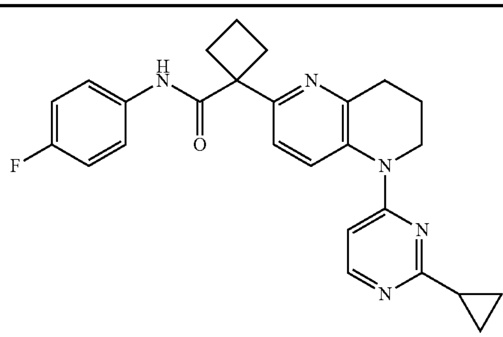 | 1-(5-(2-cyclopropylpyrimidin-4-yl)-5,6,7,8-tetrahydro-1,5-naphthyridin-2-yl)-N-(4-fluorophenyl)cyclobutane-1-carboxamide | Calc'd 443.2 found 444 | 1.87 |

-continued

| Ex. # | Structure | Chemical Name | Mass [M + H+] | Hela IC50, nM |
|---|---|---|---|---|
| 402 | Isomer 1 | 4-fluoro-N-(1-(5-(2-methylpyrimidin-4-yl)-5,6,7,8-tetrahydro-1,5-naphthyridin-2-yl)cyclobutyl)benzamide | Calc'd 417.2 found 418 | 1.68 |
| 403 | Isomer 2 | N-(4-fluorophenyl)-1-(5-(2-methylpyrimidin-4-yl)-5,6,7,8-tetrahydro-1,5-naphthyridin-2-yl)cyclobutane-1-carboxamide | Calc'd 417.2 found 418 | 2.15 |
| 404 | Racemic | N-(4-chlorophenyl)-1-(5-(6-methylpyridin-2-yl)-5,6,7,8-tetrahydro-1,5-naphthyridin-2-yl)cyclobutane-1-carboxamide | Calc'd 432.2 found 433 | 3.30 |
| 405 | Isomer 1 | 4-chloro-N-(1-(5-(6-methylpyridin-2-yl)-5,6,7,8-tetrahydro-1,5-naphthyridin-2-yl)cyclobutyl)benzamide | Calc'd 432.2 found 433 | 1.91 |

-continued

| Ex. # | Structure | Chemical Name | Mass [M + H⁺] | Hela IC₅₀, nM |
|---|---|---|---|---|
| 406 | Isomer 2 | 4-chloro-N-(1-(5-(5-methylpyridin-3-yl)-5,6,7,8-tetrahydro-1,5-naphthyridin-2-yl)cyclobutyl)benzamide | Calc'd 432.2 found 433 | 3.18 |
| 407 | 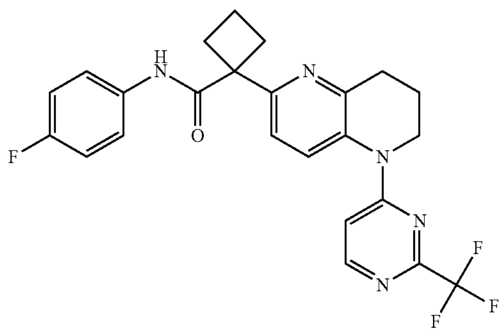 [SMILES: O=C(Nc1ccc(F)cc1)C1(c2ccc3c(n2)CCCN3c2ccnc(C(F)(F)F)n2)CCC1] | N-(4-fluorophenyl)-1-(5-(2-(trifluoromethyl)pyrimidin-4-yl)-5,6,7,8-tetrahydro-1,5-naphthyridin-2-yl)cyclobutane-1-carboxamide | Calc'd 471.2 found 472 | 1.49 |
| 408 | 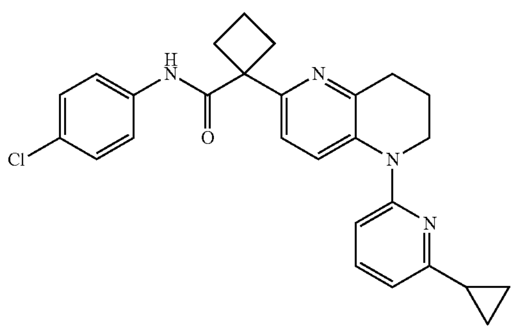 [SMILES: O=C(Nc1ccc(Cl)cc1)C1(c2ccc3c(n2)CCCN3c2cccc(C3CC3)n2)CCC1] | N-(4-chlorophenyl)-1-(5-(6-cyclopropylpyridin-2-yl)-5,6,7,8-tetrahydro-1,5-naphthyridin-2-yl)cyclobutane-1-carboxamide | Calc'd 458.2 found 459 | 11.49 |
| 409 | 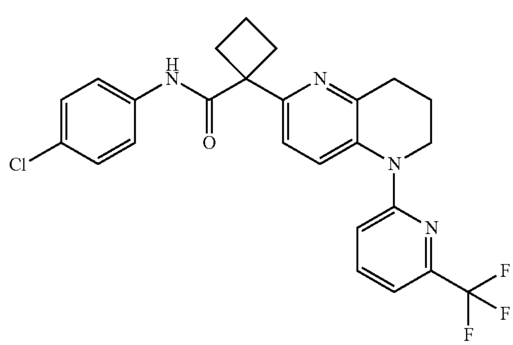 [SMILES: O=C(Nc1ccc(Cl)cc1)C1(c2ccc3c(n2)CCCN3c2cccc(C(F)(F)F)n2)CCC1] | N-(4-chlorophenyl)-1-(5-(6-(trifluoromethyl)pyridin-2-yl)-5,6,7,8-tetrahydro-1,5-naphthyridin-2-yl)cyclobutane-1-carboxamide | Calc'd 486.2 found 487.1 | 1.74 |

The examples in the following table were synthesized following the same procedure as that reported for Example #205.

| Ex. # | Structure | Chemical Name | Mass [M + H⁺] | Hela IC₅₀, nM |
|---|---|---|---|---|
| 410 | 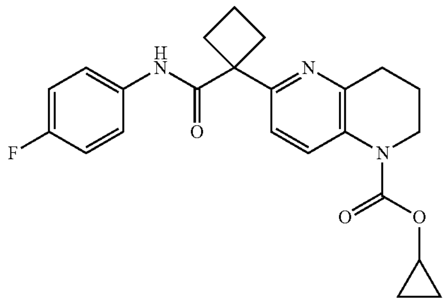 [SMILES: O=C(OC1CC1)N1CCCc2nc(C3(C(=O)Nc4ccc(F)cc4)CCC3)ccc21] | cyclopropyl 6-(1-((4-fluorophenyl)carbamoyl)cyclobutyl)-3,4-dihydro-1,5-naphthyridine-1(2H)-carboxylate | Calc'd 486.2 found 487.1 | 0.79 |
| 411 | Isomer 1 | cyclopropyl 6-(1-((4-chlorophenyl)carbamoyl)cyclobutyl)-3,4-dihydro-1,5-naphthyridine-1(2H)-carboxylate | Calc'd 425.2 found 426 | 0.73 |
| 412 | Isomer 2 | cyclopropyl 6-(1-((6-chloropyridin-3-yl)carbamoyl)cyclobutyl)-3,4-dihydro-1,5-naphthyridine-1(2H)-carboxylate | Calc'd 426.1 found 427 | 0.92 |
| 413 | Isomer 1 | 2-methoxyethyl 6-(1-(4-chlorobenzamido)cyclobutyl)-3,4-dihydro-1,5-naphthyridine-1(2H)-carboxylate | Calc'd 443.2 found 444 | 3.79 |
| 414 | Isomer 2 | 2-methoxyethyl 6-(1-((4-chlorophenyl)carbamoyl)cyclobutyl)-3,4-dihydro-1,5-naphthyridine-1(2H)-carboxylate | Calc'd 443.2 found 444 | 2.37 |

Example 415: N-(4-fluorophenyl)-5-(5-(2-(trifluoromethyl)pyrimidin-4-yl)-5,6,7,8-tetrahydro-1,5-naphthyridin-2-yl)spiro[2.3]hexane-5-carboxamide

Example 416: Synthesis of N-(4-fluorophenyl)-5-(5-(2-(trifluoromethyl)pyrimidin-4-yl)-5,6,7,8-tetrahydro-1,5-naphthyridin-2-yl)spiro[2.3]hexane-5-carboxamide

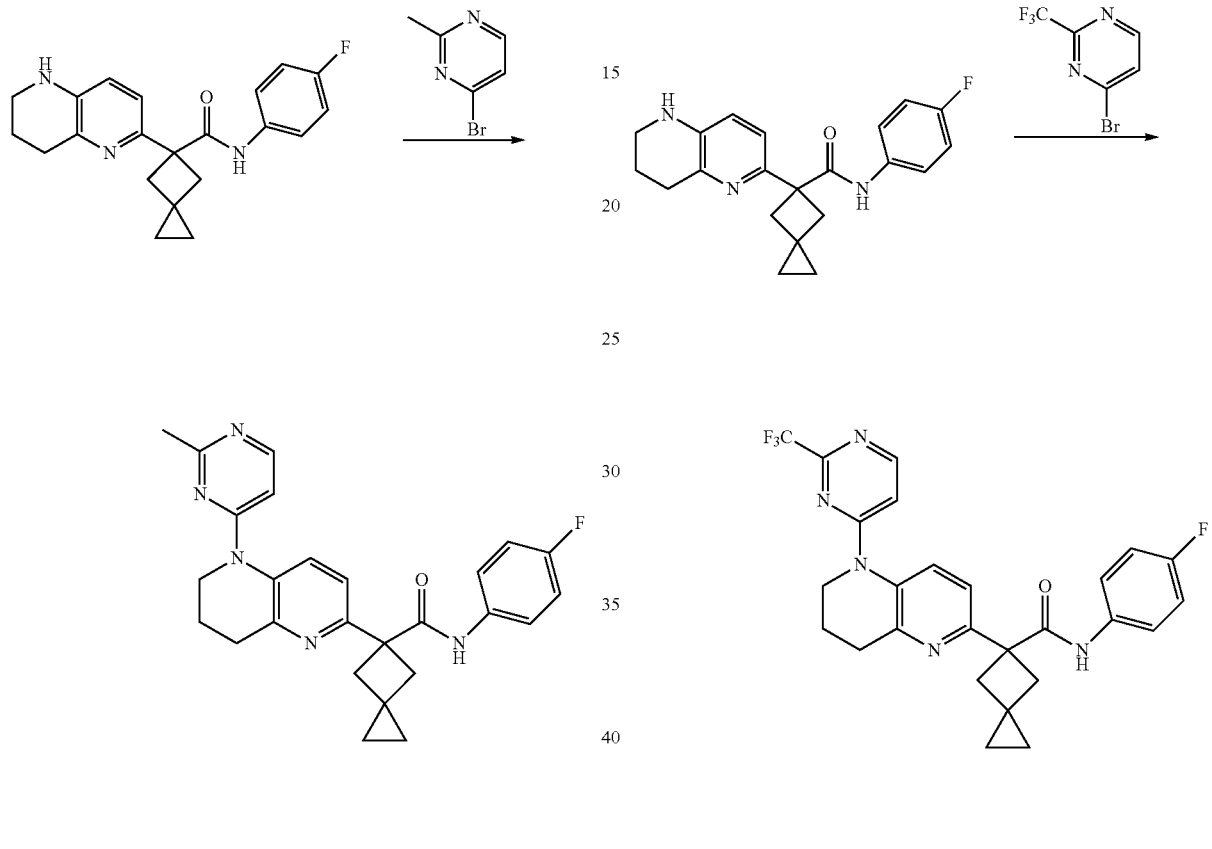

N-(4-fluorophenyl)-5-(5,6,7,8-tetrahydro-1,5-naphthyridin-2-yl)spiro[2.3]hexane-5-carboxamide (100 mg, 0.29 mmol), BINAP G3 (17 mg, 0.017 mmol), 4-bromo-2-methylpyrimidine (59 mg, 0.34 mmol), and sodium tert-butoxide (68 mg, 0.71 mmol) were added to a dried vial equipped with a stir bar. To this was added toluene (1 ml). It was then heated to 105° C. for 15 h while stirring. When done, it was evaporated in vacuo and filtered.

Then the crude material was purified via chromatography (Isco CombiFlash system, using hexanes and ethyl acetate as eluent) to afford the title compound. MS (ESI) m/z calc'd for $C_{26}H_{27}FN_5O$ [M+H]$^+$, 444, found, 444.

$^1$H NMR (500 MHz, DMSO-d$_6$) δ 9.63 (s, 1H), 8.40-8.33 (m, 1H), 8.02-7.95 (m, 1H), 7.66-7.60 (m, 2H), 7.38 (d, J=8.4 Hz, 1H), 7.20-7.15 (m, 1H), 7.12-7.05 (m, 2H), 4.05-3.97 (m, 2H), 2.96-2.90 (m, 2H), 2.88 (d, J=11.9 Hz, 2H), 2.76 (d, J=11.9 Hz, 2H), 2.51 (s, 3H), 2.07-1.97 (m, 2H), 0.48-0.36 (m, 4H).

N-(4-fluorophenyl)-5-(5,6,7,8-tetrahydro-1,5-naphthyridin-2-yl)spiro[2.3]hexane-5-carboxamide (30 mg, 0.085 mmol), methanesulfonato (2-bis(3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium (II) (15 mg, 0.013 mmol), 4-bromo-2-trifluoromethylpyrimidine (23 mg, 0.10 mmol), and sodium tert-butoxide (13 mg, 0.12 mmol) were added to a dried vial equipped with a stir bar. To this was added CPME (0.75 ml). It was then heated to 95° C. for 15 h while stirring. When done, it was evaporated in vacuo and filtered. Then the crude material was purified via chromatography (Isco CombiFlash system, using hexanes and ethyl acetate as eluent) to afford the title compound. MS (ESI) m/z calc'd for $C_{26}H_{24}F_4N_5O$ [M+H]$^+$, 498, found, 498.

$^1$H NMR (600 MHz, DMSO-d$_6$) δ 9.62 (s, 1H), 8.45 (d, J=5.8 Hz, 1H), 7.97 (d, J=8.4 Hz, 1H), 7.67-7.59 (m, 2H), 7.32 (d, J=8.4 Hz, 1H), 7.24 (d, J=5.8 Hz, 1H), 7.11-7.03 (m, 2H), 3.92-3.83 (m, 2H), 2.93-2.81 (m, 4H), 2.79-2.70 (m, 2H), 2.04-1.95 (m, 2H), 0.47-0.33 (m, 4H).

| Ex. # | Structure | Chemical Name | Mass [M + H⁺] | Hela IC₅₀, nM |
|---|---|---|---|---|
| 415 | 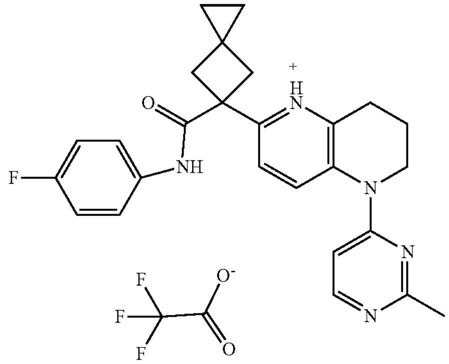 | 2-(5-((4-fluorophenyl)carbamoyl)spiro[2.3]hexan-5-yl)-5-(2-methylpyrimidin-4-yl)-5,6,7,8-tetrahydro-1,5-naphthyridin-1-ium 2,2,2-trifluoroacetate | Calc'd 443.2 found 444.3 | 3.19 |
| 416 | 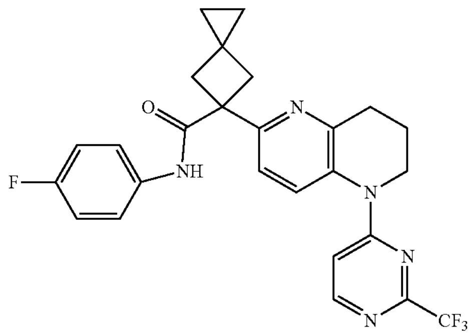 [SMILES: O=C(Nc1ccc(F)cc1)C1(c2ccc3c(n2)CCCN3c2ccnc(C(F)(F)F)n2)CC2(CC2)C1] | N-(4-fluorophenyl)-5-(5-(2-(trifluoromethyl)pyrimidin-4-yl)-5,6,7,8-tetrahydro-1,5-naphthyridin-2-yl)spiro[2.3]hexane-5-carboxamide | Calc'd 497.2 found 497.2 | 0.79 |

Example 417: cyclopropyl 6-(5-(((4-fluorophenyl)carbamoyl)spiro[2.3]hexan-5-yl)-3,4-dihydro-1,5-naphthyridine-1(2H)-carboxylate

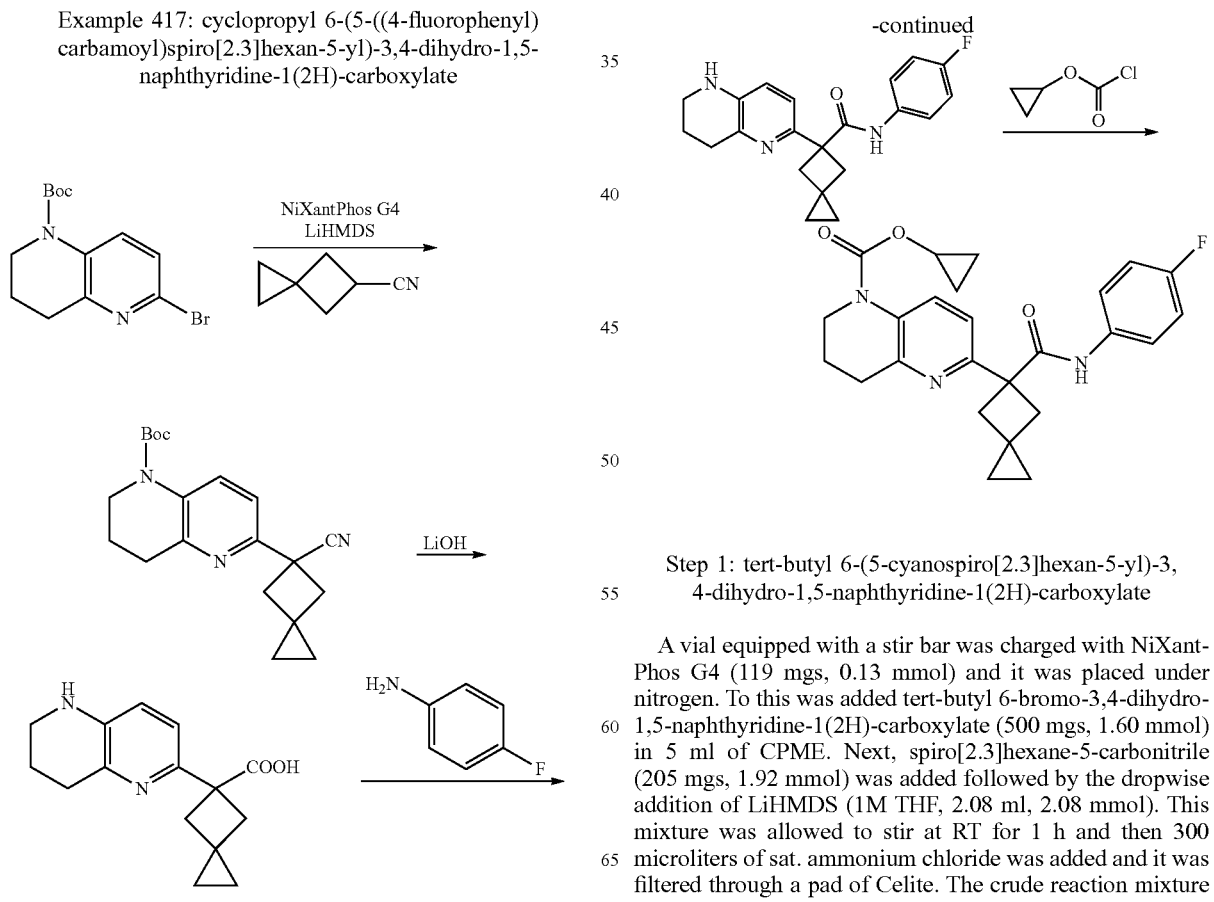

Step 1: tert-butyl 6-(5-cyanospiro[2.3]hexan-5-yl)-3,4-dihydro-1,5-naphthyridine-1(2H)-carboxylate A vial equipped with a stir bar was charged with NiXantPhos G4 (119 mgs, 0.13 mmol) and it was placed under nitrogen. To this was added tert-butyl 6-bromo-3,4-dihydro-1,5-naphthyridine-1(2H)-carboxylate (500 mgs, 1.60 mmol) in 5 ml of CPME. Next, spiro[2.3]hexane-5-carbonitrile (205 mgs, 1.92 mmol) was added followed by the dropwise addition of LiHMDS (1M THF, 2.08 ml, 2.08 mmol). This mixture was allowed to stir at RT for 1 h and then 300 microliters of sat. ammonium chloride was added and it was filtered through a pad of Celite. The crude reaction mixture was then concentrated in vacuo, and purified by chromatography (Isco CombiFlash system, using hexanes and ethyl acetate as eluent) to give the title compound. MS (ESI) m/z calc'd for $C_2H_{26}N_3O_2$ [M+H]$^+$, 340, found, 340.

Step 2: 5-(5,6,7,8-tetrahydro-1,5-naphthyridin-2-yl)spiro[2.3]hexane-5-carboxylic acid A vial equipped with a stir bar was charged with tert-butyl 6-(5-cyanospiro[2.3]hexan-5-yl)-3,4-dihydro-1,5-naphthyridine-1(2H)-carboxylate (515 mg, 1.52 mmol) and to this was added 2.5 ml of ethanol and 2.5 ml of water. Then lithium hydroxide (254 mg, 10.62 mmol) was added. The vial was then purged with argon, sealed, and then heated to 65° C. for 96 h. The reaction was then cooled to RT and made acidic with 1M HCl to pH ~2. This was then extracted 3× with ethyl acetate (5 ml) and the combined organics were saved for later. The aqueous layer was frozen and then put on the lyophylizer and dried to afford the title compound. MS (ESI) m/z calc'd for $C_{15}H_{19}N_2O_2$ [M+H]$^+$, 259, found, 259.

Step 3: N-(4-fluorophenyl)-5-(5,6,7,8-tetrahydro-1,5-naphthyridin-2-yl)spiro[2.3]hexane-5-carboxamide 5-(5,6,7,8-Tetrahydro-1,5-naphthyridin-2-yl)spiro[2.3]hexane-5-carboxylic acid (60 mg, 0.23 mmol), 4-fluoroaniline (103 mg, 0.93 mmol), and HATU (97 mg, (0.26 mmol) were added to a vial and placed under nitrogen. To this was added 1.5 ml of DMF followed by DIPEA (0.122 ml, 0.70 mmol). The reaction mixture was then allowed to stir for 15 h at RT. After this time, the solvent was evaporated in vacuo and the crude material was purified via chromatography (Isco CombiFlash system, using hexanes and ethyl acetate as eluent) to afford the title compound. MS (ESI) m/z calc'd for $C_{21}H_{23}FN_3O$ [M+H]$^+$, 352.1, found, 352.

Step 4: cyclopropyl 6-(5-((4-fluorophenyl)carbamoyl)spiro[2.3]hexan-5-yl)-3,4-dihydro-1,5-naphthyridine-1(2H)-carboxylate N-(4-fluorophenyl)-5-(5,6,7,8-tetrahydro-1,5-naphthyridin-2-yl)spiro[2.3]hexane-5-carboxamide (30 mg, 0.085 mmol) and potassium carbonate (35 mg, 0.26 mmol) were added to a vial with 2 ml DCM. To this was added cyclopropyl carbonochloridate (21 mg, 0.17 mmol). It was allowed to stir for 12 h at RT. When done, it was evaporated in vacuo. The crude material was purified by mass-directed reverse phase chromatography (ACN/water gradient with 0.1% TFA modifier) to afford the title compound. MS (ESI) m/z calc'd for $C_{25}H_{27}FN_3O_3$ [M+H]$^+$, 436.2, found, 436.

$^1$H NMR (600 MHz, DMSO-d$_6$) δ 9.54 (s, 1H), 8.03-7.93 (m, 1H), 7.65-7.57 (m, 2H), 7.27 (d, J=8.6 Hz, 1H), 7.10-7.02 (m, 2H), 4.09-4.02 (m, 1H), 3.66-3.58 (m, 2H), 2.88-2.79 (m, 4H), 2.73-2.66 (m, 2H), 1.92-1.84 (m, 2H), 0.69-0.62 (m, 4H), 0.43-0.33 (m, 4H).

Example 418: Synthesis of cyclopropyl 6-(5-((6-chloropyridin-3-yl)carbamoyl)spiro[2.3]hexan-5-yl)-3,4-dihydro-1,5-naphthyridine-1(2H)-carboxylate The title compound was prepared in an analogous manner to compound 417 above except that 6-chloropyridin-3-amine was used in the amide coupling step to afford the title compound. MS (ESI) m/z calc'd for $C_{24}H_{26}ClN_4O_3$ [M+H]$^+$, 453, found, 453.

$^1$H NMR (600 MHz, DMSO-d$_6$) δ 9.92 (s, 1H), 8.66 (s, 1H), 8.16-8.03 (m, 2H), 7.47-7.31 (m, 2H), 4.14-4.05 (m, 1H), 3.70-3.61 (m, 2H), 2.94-2.81 (m, 4H), 2.78-2.66 (m, 2H), 1.94-1.84 (m, 2H), 0.75-0.62 (m, 4H), 0.50-0.36 (m, 4H).

| Ex. # | Structure | Chemical Name | Mass [M + H$^+$] | Hela IC$_{50}$, nM |
|---|---|---|---|---|
| 417 | 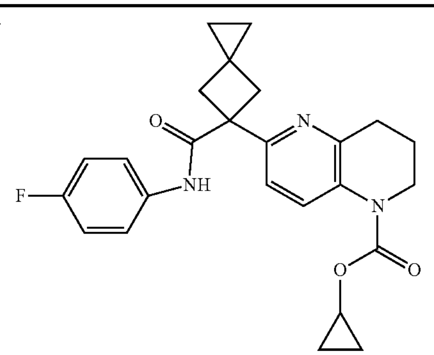 | cyclopropyl 6-(5-((4-fluorophenyl)carbamoyl)spiro[2.3]hexan-5-yl)-3,4-dihydro-1,5-naphthyridine-1(2H)-carboxylate | Calc'd 435.2 found 436.2 | 0.73 |
| 418 | 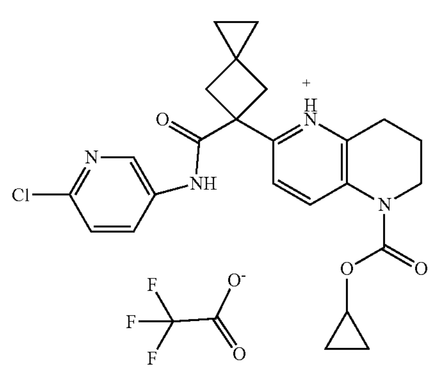 | 2-(5-((6-chloropyridin-3-yl)carbamoyl)spiro[2.3]hexan-5-yl)-5-(cyclopropoxycarbonyl)-5,6,7,8-tetrahydro-1,5-naphthyridin-1-ium 2,2,2-trifluoroacetate | Calc'd 452.16 found 453.3 | 1.35 |

285

Example 419-422: 3-(benzyloxy)-N-(4-fluorophenyl)-1-(5-(2-methylpyrimidin-4-yl)-5,6,7,8-tetrahydro-1,5-naphthyridin-2-yl)cyclobutane-1-carboxamide

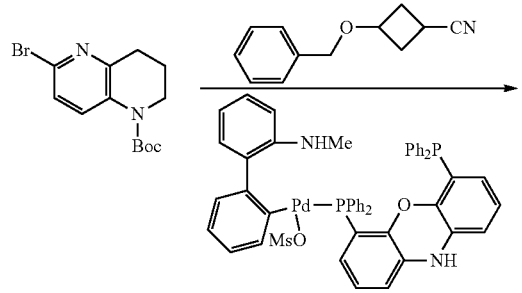

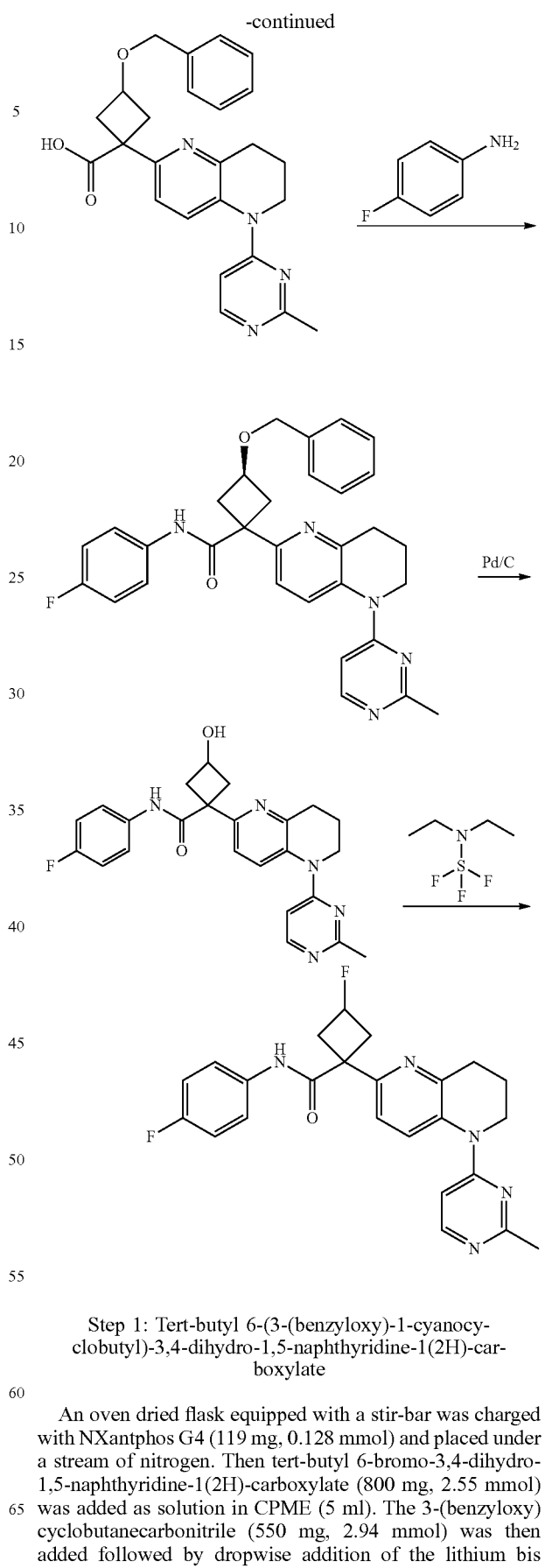

Step 1: Tert-butyl 6-(3-(benzyloxy)-1-cyanocyclobutyl)-3,4-dihydro-1,5-naphthyridine-1(2H)-carboxylate An oven dried flask equipped with a stir-bar was charged with NXantphos G4 (119 mg, 0.128 mmol) and placed under a stream of nitrogen. Then tert-butyl 6-bromo-3,4-dihydro-1,5-naphthyridine-1(2H)-carboxylate (800 mg, 2.55 mmol) was added as solution in CPME (5 ml). The 3-(benzyloxy)cyclobutanecarbonitrile (550 mg, 2.94 mmol) was then added followed by dropwise addition of the lithium bis (trimethylsilyl)amide (3.32 ml, 3.32 mmol). The reaction was stirred at RT for 16 h. The reaction was quenched with sat. NH₄Cl (40 mL), and extracted with ethyl acetate (50 mL×2). The organic layers were collected, washed with brine (30 mL), and dried over anhydrous Na₂SO₄. The solid was removed by filtration and the filtrate was concentrated in vacuo. The residue was purified by column chromatography on silica gel (SiO₂) (eluting with 0-50% hexanes and 3:1 mixture of ethyl acetate and ethanol) to give the title compound as an oil. MS (ESI) calc'd. for C₂₅H3N₃O₃ [M+H]⁺ 420.2, found 420.1.

Step 2: 3-(benzyloxy)-1-(5-(2-methylpyrimidin-4-yl)-5,6,7,8-tetrahydro-1,5-naphthyridin-2-yl)cyclobutanecarbonitrile To a stirred solution of tert-butyl 6-(3-(benzyloxy)-1-cyanocyclobutyl)-3,4-dihydro-1,5-naphthyridine-1(2H)-carboxylate (930 mg, 2.217 mmol) in dichloromethane (5 mL) was added HCl solution (4M HCl in Dioxane, 2.771 mL, 11.08 mmol) and the reaction was stirred at RT for 16 h. After the completion of the reaction, the solvents were removed under reduced pressure to give the title compound. The crude product was used in the next step without further purification. MS (ESI) calc'd. for C₂H₂₂N₃O [M+H]⁺ 320.1, found 320.1

Step 3: 3-(benzyloxy)-1-(5-(2-methylpyrimidin-4-yl)-5,6,7,8-tetrahydro-1,5-naphthyridin-2-yl)cyclobutanecarbonitrile To a stirring solution of 3-(benzyloxy)-1-(5,6,7,8-tetrahydro-1,5-naphthyridin-2-yl)cyclobutanecarbonitrile (930 mg, 2.91 mmol) in dioxane (10 ml) inside a microwave vial, were added 4-chloro-2-methylpyrimidine (374 mg, 2.91 mmol) and p-toluenesulfonic acid monohydrate (554 mg, 2.91 mmol) and heated at 160° C. for 15 min in a microwave reactor. The reaction was monitored by LCMS. When complete, the reaction was cooled to RT and neutralized using NH₄OH in MeOH and concentrated down. The crude obtained was purified by column chromatography 0-10% DCM/MeOH containing 2% NH₄OH to give the title compound. MS (ESI) calc'd. For C₂₅H₂₆N₅O [M+H]⁺ 412.2 found 412.1

Step 4: 3-(benzyloxy)-1-(5-(2-methylpyrimidin-4-yl)-5,6,7,8-tetrahydro-1,5-naphthyridin-2-yl)cyclobutane-1-carboxylic acid To a stirred solution of 3-(benzyloxy)-1-(5-(2-methylpyrimidin-4-yl)-5,6,7,8-tetrahydro-1,5-naphthyridin-2-yl)cyclobutanecarbonitrile (625 mg, 1.519 mmol) in ethanol (5 ml) and water (5.00 ml) was added KOH (256 mg, 4.56 mmol) at 25° C. After addition, the reaction was stirred at 80° C. for 15 h and then cooled to RT. The reaction was concentrated to remove ethanol, then adjusted to pH ~7 with 6 N HCl (aqueous), and extracted by ethyl acetate (30 mL×2). The organic layers were collected, washed with brine (30 mL), dried over Na₂SO₄ and filtered. After filtration, the filtrate was concentrated in vacuo to give the title compound as an oil which was used directly for the next step without any further purification. MS (ESI) calc'd. for C₂₅H₂₇N₄O₃ [M+H]⁺ 431.2, found 431.

Example #423: 3-(Benzyloxy)-N-(4-fluorophenyl)-1-(5-(2-methylpyrimidin-4-yl)-5,6,7,8-tetrahydro-1,5-naphthyridin-2-yl)cyclobutane-1-carboxamide

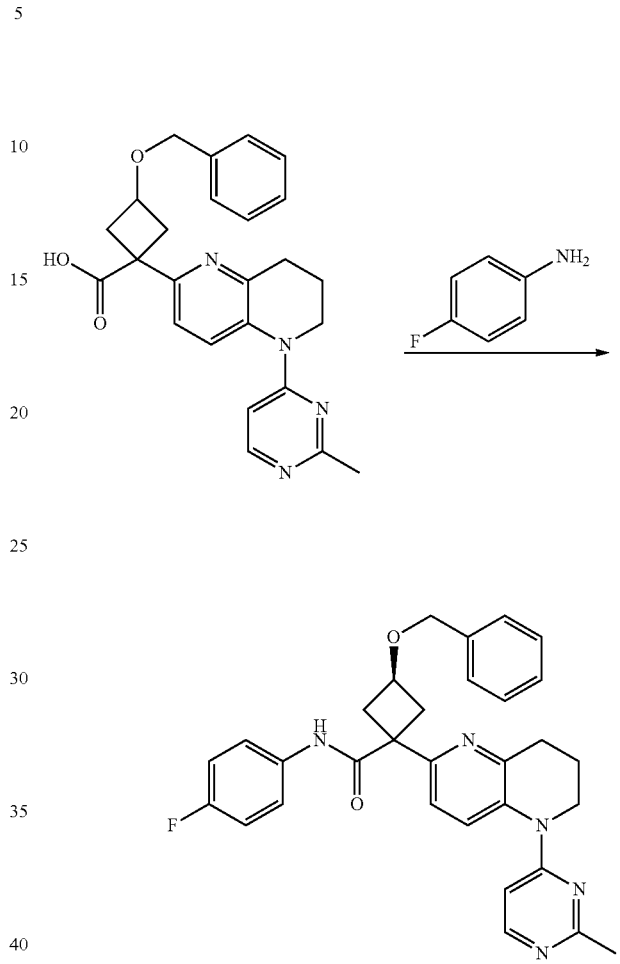

To a stirred solution of 3-(benzyloxy)-1-(5-(2-methylpyrimidin-4-yl)-5,6,7,8-tetrahydro-1,5-naphthyridin-2-yl)cyclobutanecarboxylic acid (650 mg, 1.510 mmol) in DMF (2 mL) were added N-ethyl-N-isopropylpropan-2-amine (2.64 mL, 15.10 mmol), HATU (861 mg, 2.265 mmol) and 4-fluoroaniline (0.218 ml, 2.265 mmol). The reaction was stirred at RT for 16 h. After stirring for 16h, the reaction was finished. The reaction was washed with NaHCO₃ (30 mL), extracted with ethyl acetate (50 mL×2), washed with brine (30 ml), dried over MgSO₄, filtered, and concentrated in vacuo. The crude was purified by column chromatography using 0-60% hexanes and 3:1 mixture of ethyl acetate and ethanol to give the title compound as a solid. MS (ESI) calc'd. for C₃₁H₃₁FN₅O₂ [M+H]⁺ 524.6, found 524.1

¹H NMR (499 MHz, DMSO-d₆) δ 9.63 (s, 1H), 8.40 (d, J=6.8 Hz, 1H), 8.03 (d, J=8.7 Hz, 1H), 7.66 (dd, J=9.1, 5.1 Hz, 2H), 7.45-7.35 (m, 1H), 7.35-7.18 (m, 4H), 7.13 (t, J=8.9 Hz, 2H), 4.41 (s, 2H), 4.11-4.00 (m, 4H), 2.98 (q, J=6.8 Hz, 3H), 2.72-2.63 (m, 2H), 2.56 (s, 3H), 2.17-1.91 (m, 2H). Hela IC₅₀=6.8 nm.

Example 425: N-(4-fluorophenyl)-3-hydroxy-1-(5-(pyrimidin-4-yl)-5,6,7,8-tetrahydro-1,5-naphthyridin-2-yl)cyclobutane-1-carboxamide compound with methane (1:1)

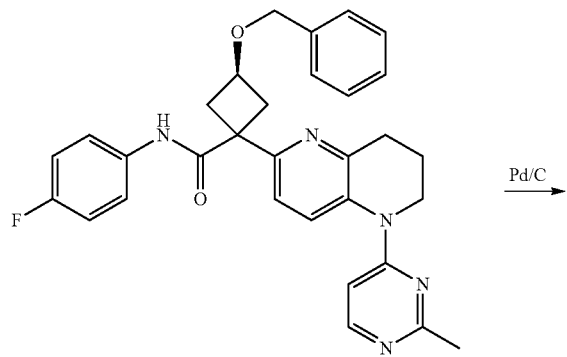

A stirring solution of 3-(benzyloxy)-N-(4-fluorophenyl)-1-(5-(2-methylpyrimidin-4-yl)-5,6,7,8-tetrahydro-1,5-naphthyridin-2-yl)cyclobutanecarboxamide (535 mg, 1.022 mmol), Example 423 in ethanol (10 mL) was placed under an argon atmosphere by performing 6 vacuum/argon cycle, and Pd/C (130 mg, 1.226 mmol) was added. The reaction flask was degassed again and filled with H$_2$ gas from balloon by performing 6 vacuum/hydrogen cycle. The reaction was stirred at 70° C. for 12 h. The reaction was monitored by LCMS. Once complete, the reaction was filtered through a pad of Celite, and the filtrate was concentrated. The mixture was filtered and purified by mass triggered reverse phase HPLC (ACN/water with 0.1% TFA modifier to afford the title compound as the TFA salt. N-(4-fluorophenyl)-3-hydroxy-1-(5-(2-methylpyrimidin-4-yl)-5,6,7,8-tetrahydro-1,5-naphthyridin-2-yl)cyclobutanecarboxamide was obtained as ae solid. MS (ESI) calc'd. for C$_{24}$H$_{25}$FN$_5$O$_2$ [M+H]$^+$ 434, found 434.

$^1$H NMR (499 MHz, DMSO-d$_6$) δ 9.63 (s, 1H), 8.40 (d, J=6.8 Hz, 1H), 8.03 (d, J=8.7 Hz, 1H), 7.66 (dd, J=9.1, 5.1 Hz, 2H), 7.25-7.18 (m, 4H), 4.20-4.00 (m, 3H), 3.20 (q, J=6.8 Hz, 2H), 3.00-2.98 (m, 2H), 2.56 (s, 3H), 2.48 (m, 2H), 2.17-1.91 (m, 2H) Hela IC$_{50}$=71 nm.

Example 419: 3-fluoro-N-(4-fluorophenyl)-1-(5-(2-methylpyrimidin-4-yl)-5,6,7,8-tetrahydro-1,5-naphthyridin-2-cyclobutane-1-carboxamide

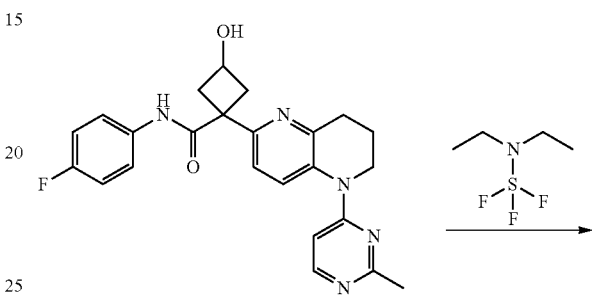

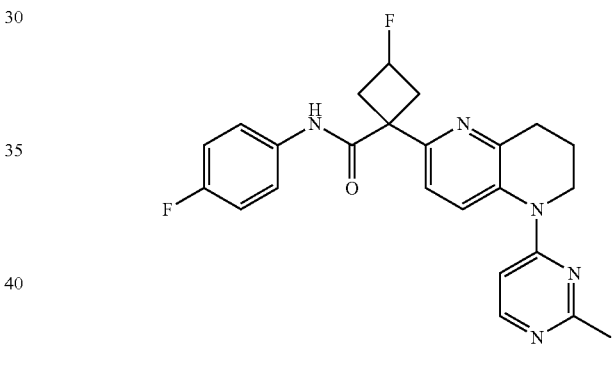

A solution of N-(4-fluorophenyl)-3-hydroxy-1-(5-(2-methylpyrimidin-4-yl)-5,6,7,8-tetrahydro-1,5-naphthyridin-2-yl)cyclobutanecarboxamide (100 mg, 0.231 mmol) in DCM (5 mL) was treated with a solution of diethylaminosulfur trifluoride (74.4 mg, 0.461 mmol) in DCM (1 mL) at −78° C. After addition, the reaction was warmed up to RT and then to 40° C. and stirred for 3 h. The reaction was quenched with sat. NaHCO$_3$ (10 mL) and diluted with DCM (10 mL×2). The organic layers were dried over Na$_2$SO$_4$, filtered and concentrated under reduced pressure. The mixture was filtered and purified by mass triggered reverse phase HPLC (ACN/water with 0.1% TFA modifier to afford the title compound as the TFA salt. MS (ESI) calc'd. for C$_{24}$H$_{24}$F$_2$N$_5$O [M+H]$^+$ 436, found 436.

$^1$H NMR (499 MHz, DMSO-d$_6$) δ 9.78 (s, 1H), 8.40 (d, J=7.1 Hz, 1H), 8.03 (d, J=8.0 Hz, 1H), 7.72-7.60 (m, 2H), 7.27 (d, J=8.5 Hz, 1H), 7.23-7.06 (m, 3H), 5.30-5.05 (m, 1H), 4.08-3.99 (m, 2H), 3.33-3.22 (m, 2H), 3.00 (t, J=6.6 Hz, 2H), 2.84 (d, J=22.9, 9.8, 8.3, 4.8 Hz, 2H), 2.55 (s, 3H), 2.08 (p, J=6.5 Hz, 2H).

Hela IC50=1 nm.

| Ex. # | Structure | Chemical Name | Mass [M + H⁺] | Hela IC$_{50}$, nM |
|---|---|---|---|---|
| 419 | 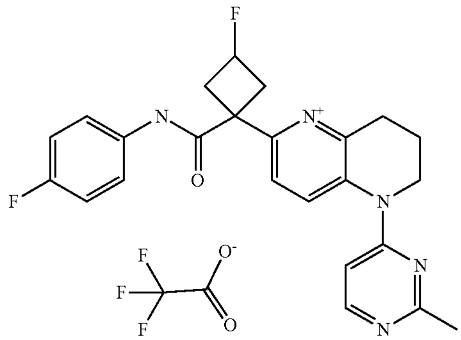 [SMILES: Cc1nccc(N2CCCc3[nH+]c(C4(C(=O)Nc5ccc(F)cc5)CC(F)C4)ccc32)n1 ; O=C([O-])C(F)(F)F] | 2-(3-fluoro-1-((4-fluorophenyl)carbamoyl)cyclobutyl)-5-(2-methylpyrimidin-4-yl)-5,6,7,8-tetrahydro-1,5-naphthyridin-1-ium 2,2,2-trifluoroacetate | Calc'd 435 found 436 | 1.09 |
| 420 | 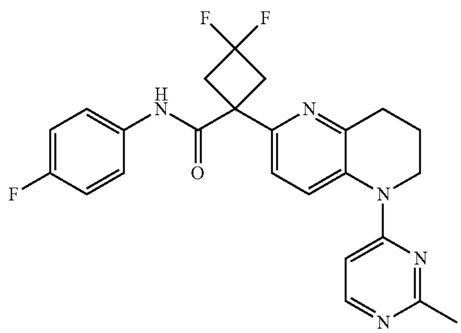 [SMILES: Cc1nccc(N2CCCc3nc(C4(C(=O)Nc5ccc(F)cc5)CC(F)(F)C4)ccc32)n1] | 3,3-difluoro-N-(4-fluorophenyl)-1-(5-(2-methylpyrimidin-4-yl)-5,6,7,8-tetrahydro-1,5-naphthyridin-2-yl)cyclobutane-1-carboxamide | Calc'd 453 found 454 | 1.09 |
| 421 | 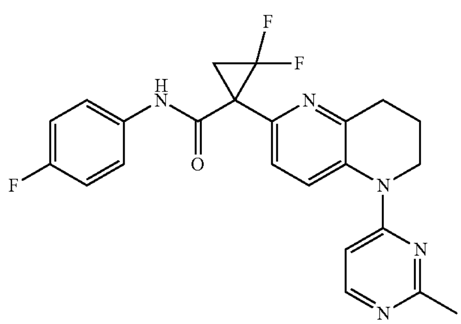 [SMILES: Cc1nccc(N2CCCc3nc(C4(C(=O)Nc5ccc(F)cc5)CC4(F)F)ccc32)n1] | 2,2-difluoro-N-(4-fluorophenyl)-1-(5-(2-methylpyrimidin-4-yl)-5,6,7,8-tetrahydro-1,5-naphthyridin-2-yl)cyclopropane-1-carboxamide | Calc'd 439.16 found 440.1 | 2.64 |
| 422 | 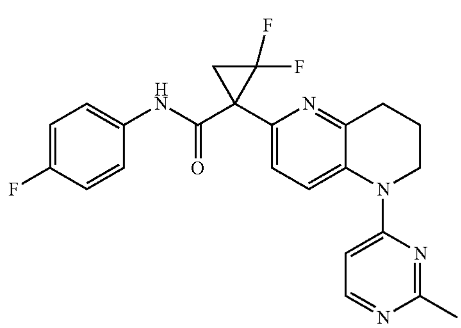 [SMILES: Cc1nccc(N2CCCc3nc(C4(C(=O)Nc5ccc(F)cc5)CC4(F)F)ccc32)n1] | 2,2-difluoro-N-(4-fluorophenyl)-1-(5-(2-methylpyrimidin-4-yl)-5,6,7,8-tetrahydro-1,5-naphthyridin-2-yl)cyclopropane-1-carboxamide | Calc'd 439.16 found 440.1 | 1.70 |

-continued

| Ex. # | Structure | | Chemical Name | Mass [M + H+] | Hela IC50, nM |
|---|---|---|---|---|---|
| 423 | 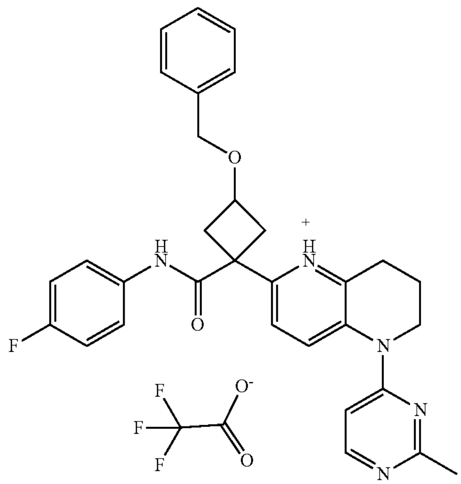 | | 2-(3-(benzyloxy)-1-((4-fluorophenyl)carbamoyl)cyclo-butyl)-5-(2-methylpyrimidin-4-yl)-5,6,7,8-tetrahydro-1,5-naphthyridin-1-ium 2,2,2-trifluoroacetate | Calc'd 523 found 524 | 6.84 |
| 424 | 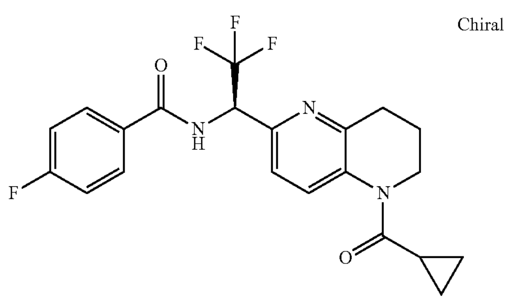 [SMILES: O=C(N[C@H](c1ccc2c(n1)CCCN2C(=O)C1CC1)C(F)(F)F)c1ccc(F)cc1] | Chiral | (R)-N-(1-(5-(cyclopropanecarbonyl)-5,6,7,8-tetrahydro-1,5-naphthyridin-2-yl)-2,2,2-trifluoroethyl)-4-fluorobenzamide | Calc'd 421.1 found 422.2 | 44.75 |
| 425 | 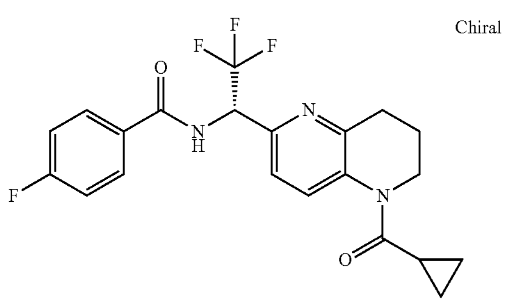 [SMILES: O=C(N[C@@H](c1ccc2c(n1)CCCN2C(=O)C1CC1)C(F)(F)F)c1ccc(F)cc1] | Chiral | (S)-N-(1-(5-(cyclopropanecarbonyl)-5,6,7,8-tetrahydro-1,5-naphthyridin-2-yl)-2,2,2-trifluoroethyl)-4-fluorobenzamide | Calc'd 421.1 found 422.0 | 235 |
| 426 | 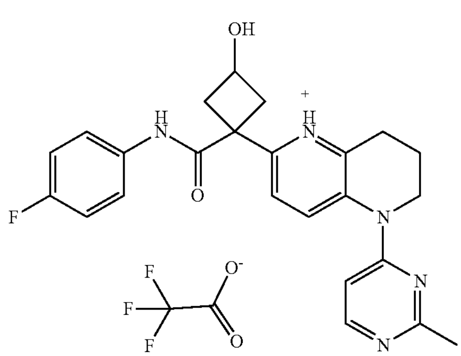 | | 2-(1-((4-fluorophenyl)carbamoyl)-3-hydroxycyclobutyl)-5-(2-methylpyrimidin-4-yl)-5,6,7,8-tetrahydro-1,5-naphthyridin-1-ium 2,2,2-trifluoroacetate | Calc'd 421.1 found 422.2 | 71 |

Example 420: 3,3-difluoro-N-(4-fluorophenyl)-1-(5-(2-methylpyrimidin-4-yl)-5,6,7,8-tetrahydro-1,5-naphthyridin-2-yl)cyclobutanecarboxamide

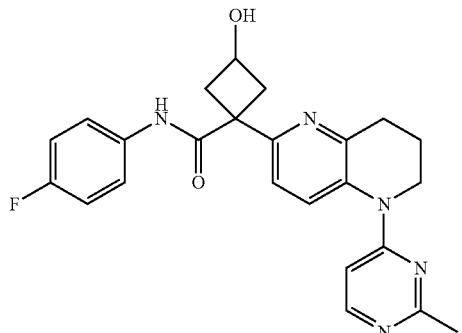

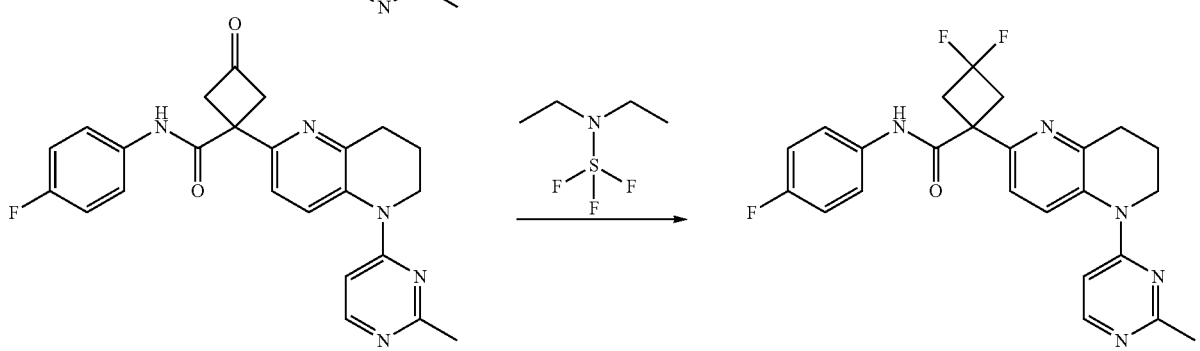

Step 1. N-(4-fluorophenyl)-1-(5-(2-methylpyrimidin-4-yl)-5,6,7,8-tetrahydro-1,5-naphthyridin-2-yl)-3-oxacyclobutane-1-carboxamide Dess-Martin-periodinane (117 mg, 0.277 mmol) was added to a solution of N-(4-fluorophenyl)-3-hydroxy-1-(5-(2-methylpyrimidin-4-yl)-5,6,7,8-tetrahydro-1,5-naphthyridin-2-yl)cyclobutanecarboxamide (100 mg, 0.231 mmol) in DCM (1 mL) at 0° C. The reaction was stirred at RT for 16 h. The reaction was quenched with sat. sodium thiosulfate (5 mL) and sat. sodium bicarbonate (5 mL) and stirred for 1 h at RT. The mixture was extracted with DCM (10 mL×2) and the organic layers were separated using a hydrophobic frit, and the filtrate was concentrated under reduced pressure. The residue was purified by column chromatography 0-60% hexanes and 3:1 mixture of ethyl acetate and ethanol to give the title compound. MS (ESI) calc'd. for $C_{24}H_{23}FN_5O_2$ [M+H]$^+$ 432.1, found 432.

Step 2. 3,3-Difluoro-N-(4-fluorophenyl)-1-(5-(2-methylpyrimidin-4-yl)-5,6,7,8-tetrahydro-1,5-naphthyridin-2-yl)cyclobutane-1-carboxamide A solution of N-(4-fluorophenyl)-1-(5-(2-methylpyrimidin-4-yl)-5,6,7,8-tetrahydro-1,5-naphthyridin-2-yl)-3-oxo cyclobutanecarboxamide (50 mg, 0.116 mmol) was treated with solution of diethylaminosulfur trifluoride (187 mg, 1.159 mmol) at 0° C. The reaction was warmed up to 40° C. and stirred for 3 h. The reaction was quenched with sat. NaHCO$_3$ (10 mL) and diluted with DCM (10 mL×2). The organic layers were dried over Na$_2$SO$_4$, filtered and concentrated under reduced pressure. The mixture was filtered and purified by mass triggered reverse phase HPLC (ACN/water with 0.1% TFA modifier to afford the title compound as a TFA salt.

$^1$H NMR (499 MHz, DMSO-d$_6$) δ 9.96 (s, 1H), 8.25 (d, J=6.0 Hz, 1H), 7.98 (d, J=8.5 Hz, 1H), 7.67 (dd, J=8.8, 5.0 Hz, 2H), 7.30 (dd, J=17.7, 8.2 Hz, 1H), 7.15 (t, J=8.8 Hz, 2H), 6.87 (d, J=6.1 Hz, 1H), 3.88 (t, J=5.9 Hz, 2H), 3.48-3.39 (m, 2H), ), 3.33-3.23 (m, 2H), 2.93 (dq, J=15.6, 8.3, 6.0 Hz, 2H), 2.43 (s, 3H), 2.00 (q, J=5.9 Hz, 2H).

MS (ESI) calc'd. for $C_{24}H_{23}F_3N_5O$ M+H]$^+$ 454.4, found 454.1

Hela IC50=1 nm.

Examples 421-422: 2,2-difluoro-N-(4-fluorophenyl)-1-(5-(2-methylpyrimidin-4-yl)-5,6,7,8-tetrahydro-1,5-naphthyridin-2-yl)cyclopropanecarboxamide (Peak 1) and 2,2-difluoro-N-(4-fluorophenyl)-1-(5-(2-methylpyrimidin-4-yl)-5,6,7,8-tetrahydro-1,5-naphthyridin-2-yl)cyclopropanecarboxamide (Peak 2)

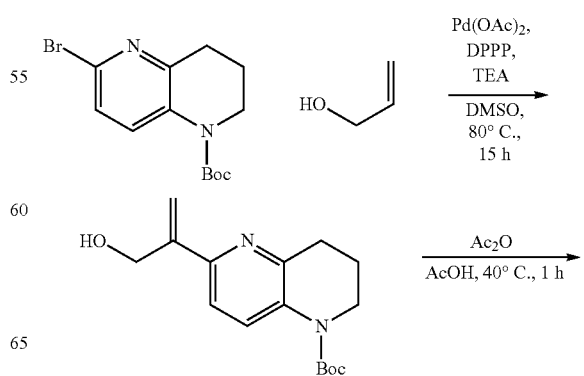

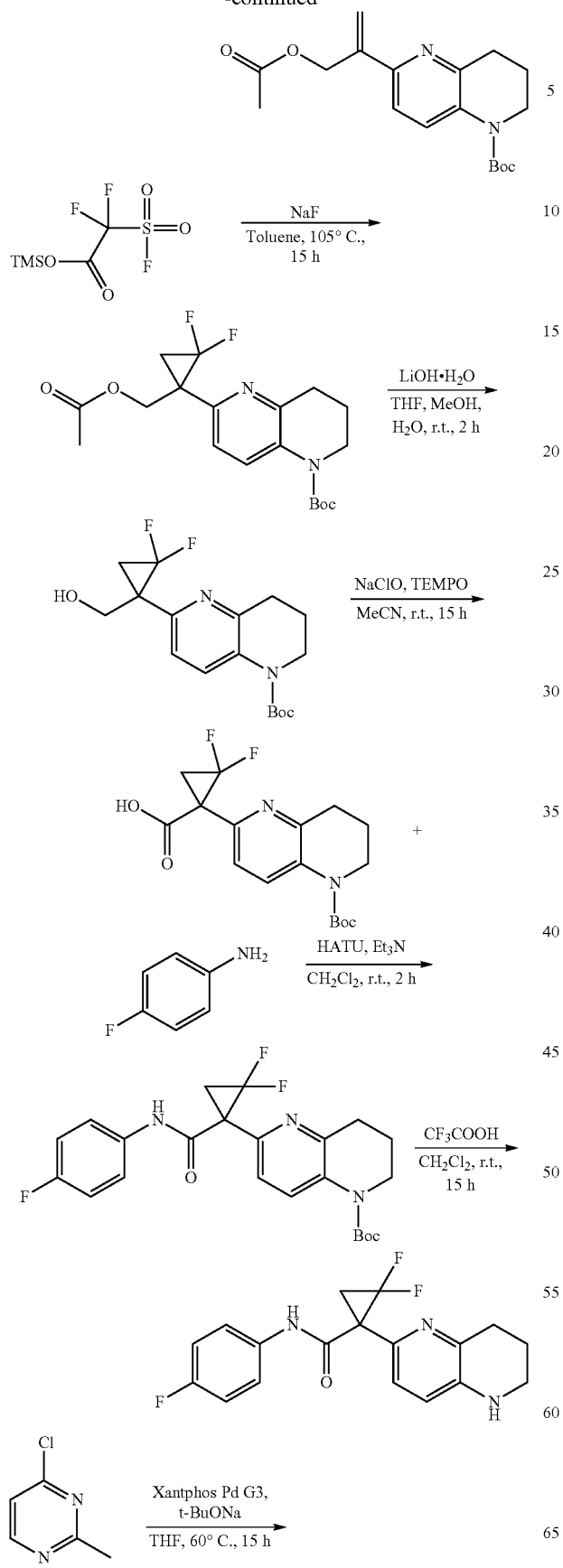

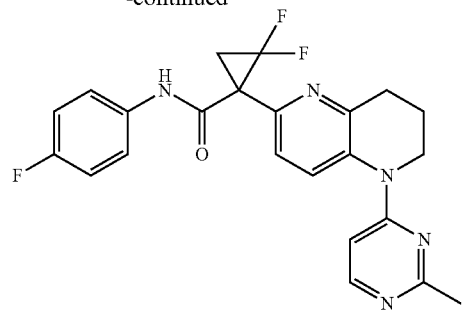

Step 1. tert-butyl 6-(3-hydroxyprop-1-en-2-yl)-3,4-dihydro-1,5-naphthyridine-1(2H)-carboxylate To a stirred solution of tert-butyl 6-bromo-3,4-dihydro-1,5-naphthyridine-1(2H)-carboxylate (5 g, 15.96 mmol) in DMSO (20 mL) were added 1,3-bis(diphenylphosphino)propane (1.317 g, 3.19 mmol), prop-2-en-1-ol (4.64 g, 80 mmol), diacetoxypalladium (0.358 g, 1.596 mmol) and TEA (3.34 mL, 23.95 mmol) at RT. After the addition was finished, the reaction was stirred at 80° C. The reaction was monitored by LC-MS, after stirring at 80° C. for 15 h and then cooled to RT. The reaction was quenched with water (50 mL), and extracted with ethyl acetate (50 mL×2). The organic layers were collected, washed with brine (20 mL), and dried over $Na_2SO_4$. After filtration, the filtrate was concentrated in vacuo. The residue was purified by silica gel chromatography ($SiO_2$, petroleum ether/ethyl acetate 20:1-10:1) to give the title compound as an oil. MS (ESI) calc'd. for $C_{16}H_{23}N_2O_3$ $[M+H]^+$ 291.0, found 291.0

$^1$H NMR (400 MHz, $CDCl_3$) δ 8.1 (br d, J=8.8 Hz, 1H), 7.4 (d, J=8.8 Hz, 1H), 5.7 (s, 1H), 5.4 (s, 1H), 4.9 (br s, 1H), 4.5 (s, 2H), 3.7-3.8 (m, 2H), 2.9 (t, J=6.6 Hz, 2H), 2.0-2.0 (m, 2H), 1.5 (s, 9H).

Step 2. tert-butyl 6-(3-acetoxyprop-1-en-2-yl)-3,4-dihydro-1,5-naphthyridine-1(2H)-carboxylate To a stirred solution of tert-butyl 6-(3-hydroxyprop-1-en-2-yl)-3,4-dihydro-1,5-naphthyridine-1(2H)-carboxylate (1.513 g, 5.21 mmol) in acetic acid (10 mL) was added acetic anhydride (1 ml, 5.21 mmol) at RT, after addition the reaction was stirred at 40° C. for 1 h. The reaction was monitored by TLC (petroleum ether/ethyl acetate 10:1). The reaction mixture was cooled to RT and quenched with water (20 mL) and concentrated to remove the acetic acid. Then water (30 mL) was added to the mixture and extracted by ethyl acetate (30 mL×3), the organic layers were collected, washed with brine (20 mL), dried over $Na_2SO_4$, filtered and the filtrate was concentrated in vacuo. The residue was purified by silica gel chromatography (petroleum ether/ethyl acetate 20:1) to give the title compound as an oil.

$^1$H NMR (400 MHz, $CDCl_3$) δ 8.1 (br d, J=8.6 Hz, 1H), 7.3 (d, J=8.8 Hz, 1H), 5.9 (s, 1H), 5.5 (d, J=1.0 Hz, 1H), 5.1 (s, 2H), 3.7 (d, J=5.9 Hz, 1H), 3.7-3.7 (m, 1H), 3.8 (s, 1H), 2.9 (t, J=6.6 Hz, 2H), 2.1 (s, 3H), 2.0 (quin, J=6.3 Hz, 2H), 1.5 (s, 8H), 1.5-1.5 (m, 1H).

Step 3. tert-butyl 6-(3-acetoxyprop-1-en-2-yl)-3,4-dihydro-1,5-naphthyridine-1(2H)-carboxylate To a stirred solution of tert-butyl 6-(3-acetoxyprop-1-en-2-yl)-3,4-dihydro-1,5-naphthyridine-1(2H)-carboxylate (1.5 g, 4.51 mmol) in toluene (10 mL) was added sodium fluoride (0.019 g, 0.451 mmol) at RT, and the reaction was stirred at 105° C. for 1 h. Then, trimethylsilyl 2,2-difluoro-2-(fluorosulfonyl)acetate (38 mg, 0.152 mmol) in toluene (1 mL) was added slowly using a syringe with a Teflon needle at the rate of 0.30 mL/h. The reaction was monitored by LC-MS and TLC (Petroleum ether/EtOAc=5:1) and stirred at 105° C. for 15 h. Solvent was removed and purified by flash silica gel chromatography (ISCO®; Agela® Flash Column Silica-CS (12 g), Eluent of 15 18% Ethyl acetate/Petroleum ether gradient @ 15 mL/min) to give the title compound as an oil. MS (ESI) calc'd. For $C_{19}H_{25}F_2N_2O_4$ [M+H]$^+$ 383, found 383.1. H NMR (400 MHz, CDCl$_3$) δ 8.1 (br d, J=8.3 Hz, 1H), 7.2 (d, J=8.3 Hz, 1H), 4.4-4.6 (m, 2H), 3.7 (t, J=5.9 Hz, 2H), 2.9 (t, J=6.8 Hz, 2H), 2.2-2.2 (m, 1H), 2.0 (s, 3H), 2.0 (br d, J=5.7 Hz, 2H), 1.7 (ddd, J=12.7, 7.9, 5.3 Hz, 1H), 1.5 (s, 9H).

Step 4. tert-butyl 6-(2,2-difluoro-1-(hydroxymethyl) cyclopropyl)-3,4-dihydro-1,5-naphthyridine-1(2H)-carboxylate To a stirred solution of tert-butyl 6-(1-(acetoxymethyl)-2,2-difluorocyclopropyl)-3,4-dihydro-1,5-naphthyridine-1 (2H)-carboxylate (877 mg, 2.293 mmol) in THF (5 mL), ethanol (5 mL) and water (2.5 mL) was added lithium hydroxide hydrate (192 mg, 4.59 mmol) at RT. After the addition was finished, the reaction was stirred at RT. The reaction was monitored by LC-MS, after stirring at RT for 2 h, the reaction was finished. The solvent was concentrated, diluted with water (20 mL), and extracted by ethyl acetate (30 mL×2). The organic layers were collected, washed with brine (20 mL), and dried over Na$_2$SO$_4$. After filtration, the filtrate was concentrated in vacuo to give the title compound as an oil, which was used directly in the next step without any further purification. MS (ESI) calc'd. For $C_{17}H_{23}F_2N_2O_3$ [M+H]$^+$ 340.1, found 340.9

Step 5. 1-(5-(tert-butoxycarbonyl)-5,6,7,8-tetrahydro-1,5-naphthyridin-2-yl)-2,2-difluorocyclopropanecarboxylic acid To a stirred solution of tert-butyl 6-(2,2-difluoro-1-(hydroxymethyl)cyclopropyl)-3,4-dihydro-1,5-naphthyridine-1 (2H)-carboxylate (150 mg, 0.441 mmol) in CH$_3$CN (20 mL) were added TEMPO (7 mg, 0.045 mmol) and chlorosylsodium (6561 mg, 8.81 mmol) (10%, in water) at RT. The reaction was stirred at RT for 15 h. Excess solvent was concentrated, then the mixture was adjusted to pH~6, and extracted with ethyl acetate (20 mL×2). The organic layers were collected, washed with brine (20 mL), dried over Na$_2$SO$_4$, filtered, and the filtrate was concentrated in vacuo to give the title compound as a solid, which was used directly in the next step without any further purification. MS (ESI) calc'd. For $C_7H_{21}F_2N_2O_4$ [M+H]$^+$ 355.0, found 355.0

Step 6. tert-butyl 6-(2,2-difluoro-1-((4-fluorophenyl)carbamoyl)cyclopropyl)-3,4-dihydro-1,5-naphthyridine-1(2H)-carboxylate To a stirred solution of 1-(5-(tert-butoxycarbonyl)-5,6,7, 8-tetrahydro-1,5-naphthyridin-2-yl)-2,2-difluorocyclopropanecarboxylic acid (156 mg, 0.440 mmol) in CH$_2$Cl$_2$ (5 mL) were added TEA (0.2 mL, 1.435 mmol), HATU (251 mg, 0.660 mmol) and 4-fluoroaniline (60 mg, 0.540 mmol) at RT. The reaction was stirred for 2 h and the mixture was quenched with water (20 mL) and extracted by CH$_2$Cl$_2$ (30 mL×2). The organic layers were collected, washed with brine, dried over Na$_2$SO$_4$, filtered and the filtrate was concentrated in vacuo to give the title compound as an oil. MS (ESI) calc'd. for $C_{23}H_{25}F_3N_3O_3$ [M+H]$^+$ 448.1, found 448.0

$^1$H NMR (400 MHz, CDCl$_3$) δ 10.8 (s, 1H), 8.2 (br d, J=8.3 Hz, 1H), 7.5-7.6 (m, 2H), 7.1 (d, J=8.8 Hz, 1H), 6.9 (t, J=8.8 Hz, 1H), 6.6-6.7 (m, 1H), 3.8-3.8 (m, 2H), 3.1-3.2 (m, 1H), 3.0-3.1 (m, 1H), 2.9 (dt, J=11.7, 7.5 Hz, 1H), 2.1-2.2 (m, 3H), 1.5 (s, 9H).

Step 7. 2,2-difluoro-N-(4-fluorophenyl)-1-(5,6,7,8-tetrahydro-1,5-naphthyridin-2-yl)cyclopropanecarboxamide To a stirred solution of tert-butyl 6-(2,2-difluoro-1-((4-fluorophenyl)carbamoyl)cyclopropyl)-3,4-dihydro-1,5-naphthyridine-1(2H)-carboxylate (140 mg, 0.313 mmol) in CH$_2$Cl$_2$ (5 mL) was added 2,2,2-trifluoroacetic acid (1 mL, 0.313 mmol) at RT and the reaction mixture was stirred for 15 h. The solvent was concentrated in vacuo. The residue was purified by silica gel chromatography (SiO$_2$, petroleum ether/ethyl acetate 5:1-2:1) to give the title compound as an oil. MS (ESI) calc'd. For $C_{18}H_{17}F_3N_3O$ [M+H]$^+$ 347.1, found 347.9

Step 8. 2,2-difluoro-N-(4-fluorophenyl)-1-(5-(2-methylpyrimidin-4-yl)-5,6,7,8-tetrahydro-1,5-naphthyridin-2-yl)cyclopropanecarboxamide To a stirred solution of 2,2-difluoro-N-(4-fluorophenyl)-1-(5,6,7,8-tetrahydro-1,5-naphthyridin-2-yl)cyclopropanecarboxamide (100 mg, 0.288 mmol) in dioxane (5 mL) were added 4-chloro-2-methylpyrimidine (55.5 mg, 0.432 mmol) and sodium 2-methylpropan-2-olate (83 mg, 0.864 mmol) and the reaction was stirred at 60° C. for 15 h. After cooling to RT, the reaction was quenched with water (20 mL) and concentrated for removing dioxane and extracted with ethyl acetate (30 mL×2), the organic layers were collected, washed with brine (20 mL), dried over Na$_2$SO$_4$, filtered, and the filtrate was concentrated in vacuo. The residue was purified by reverse phase HPLC on a GILSON 281 instrument fitted with a Waters Xbridge Prep OBD C18 100×19 mm×5 um using water (0.225% FA)-ACN, Mobile phase B acetonitrile, Detective wavelength: 220 nm to give the title compound as a solid. MS (ESI) calc'd. For $C_{23}H_{21}F_3N_5O$ [M+H]$^+$ 440.1, found 440.1

After SFC separation, two chiral isomers were obtained.
Column: DAICEL CHIRALPAK AS-H (250 mm×30 mm, 5 um);
Mobile phase: A: CO$_2$ B: 0.1% NH$_3$H$_2$O EtOH; Begin B 30% End B 30%;
Flow Rate (ml/min) 60; Injections: 120
Example #421: Isomer 1, retention time: 2.015 min
$^1$H NMR (400 MHz, CDCl$_3$) δ 10.7 (s, 1H), 8.3 (d, J=6.1 Hz, 1H), 7.9 (d, J=8.3 Hz, 1H), 7.5 (dd, J=8.8, 4.8 Hz, 2H), 7.1 (d, J=8.8 Hz, 1H), 7.0 (t, J=8.8 Hz, 2H), 6.8 (d, J=5.7 Hz, 1H), 3.9-4.1 (m, 2H), 3.2-3.3 (m, 1H), 3.0-3.1 (m, 1H), 2.9 (dt, J=11.8, 7.9 Hz, 1H), 2.6 (s, 3H), 2.1-2.2 (m, 3H). MS (ESI) calc'd. For $C_{23}H_{21}F_3N_5O$ [M+H]$^+$ 440.1, found 440.1
Example #422: Isomer 2, retention time: 2.722 min
$^1$H NMR (400 MHz, CDCl$_3$) δ 10.7 (s, 1H), 8.3 (d, J=5.7 Hz, 1H), 7.9 (d, J=8.3 Hz, 1H), 7.5-7.6 (m, 2H), 7.1 (d, J=8.3 Hz, 1H), 7.0 (t, J=8.8 Hz, 2H), 6.8 (d, J=6.1 Hz, 1H), 3.9-4.1 (m, 2H), 3.2-3.3 (m, 1H), 3.0-3.1 (m, 1H), 2.9 (dt, J=11.8, 7.7 Hz, 1H), 2.6 (s, 3H), 2.1-2.2 (m, 3H). MS (ESI) calc'd. For $C_{23}H_{21}F_3N_5O$ [M+H]$^+$ 440.1, found 440.1

Example #424. (R)—N-(1-(5-(cyclopropanecarbonyl)-5,6,7,8-tetrahydro-1,5-naphthyridin-2-yl)-2,2,2-trifluoroethyl)-4-fluorobenzamide

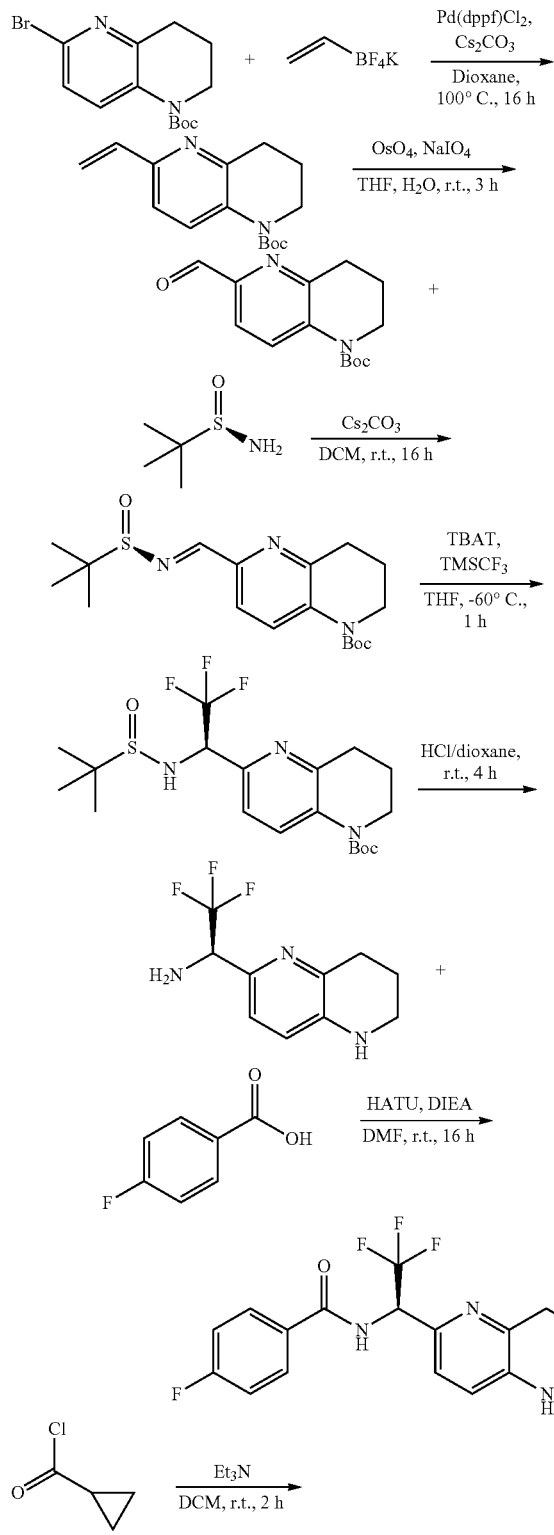

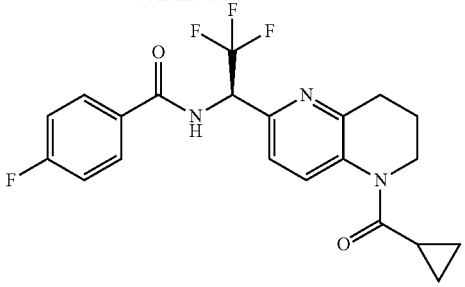

Step 1. tert-butyl 6-vinyl-3,4-dihydro-1,5-naphthyridine-1(2H)-carboxylate

To a stirred solution of tert-butyl 6-bromo-3,4-dihydro-1,5-naphthyridine-1(2H)-carboxylate in 1,4-dioxane (20 mL) were successively added Pd(dppf)$_2$Cl$_2$ (262 mg, 0.319 mmol), Potassium Vinyltrifluoroborate (976 mg, 6.39 mmol) and Cs$_2$CO$_3$ (3.12 g, 9.58 mmol) at RT, and stirred at 100° C. for 16 h. It was cooled to RT, filtered and concentrated, and diluted with water (50 mL), extracted by ethyl acetate (50 mL×2). The organic layers were collected, washed with brine (30 mL), dried over Na$_2$SO$_4$, filtered and the filtrate was concentrated in vacuo. The residue was purified by flash silica gel chromatography (ISCO®; Agela® Flash Column Silica-CS (20 g), Eluent of 020% Ethyl acetate/Petroleum ether gradient @ 30 mL/min) to give the title compound as an oil.

$^1$H NMR (400 MHz, CDCl$_3$) δ 8.02 (br d, J=8.3 Hz, 1H), 7.19 (d, J=8.3 Hz, 1H), 6.75 (dd, J=17.6, 11.0 Hz, 1H), 6.04 (dd, J=17.6, 1.3 Hz, 1H), 5.38 (dd, J=10.8, 1.1 Hz, 1H), 3.69-3.75 (m, 2H), 2.95 (t, J=6.8 Hz, 2H), 1.96-2.05 (m, 2H), 1.53 (s, 9H).

Step 2. tert-butyl 6-formyl-3,4-dihydro-1,5-naphthyridine-1(2H)-carboxylate

To a solution of tert-butyl 6-vinyl-3,4-dihydro-1,5-naphthyridine-1(2H)-carboxylate (0.7 g, 2.69 mmol) in THF (10 mL) and water (2 mL) were added NaIO4 (2.3 g, 10.76 mmol, 4.0 eq) and osmium tetroxide (0.068 g, 0.269 mmol, 0.1 eq) at RT. The reaction was monitored by LC-MS, and allowed to stir at RT for 16 h. The mixture was diluted with ethyl acetate (20 mL), cooled to 0° C. and sat. Na$_2$S$_2$O$_3$ (~20 mL) was added and stirred for 30 min, and extracted by ethyl acetate (30 mL×2). The organic layers were collected, washed with brine (20 mL), dried over Na$_2$SO$_4$ and after filtration, the filtrate was concentrated in vacuo. The residue was purified by flash silica gel chromatography (ISCO®; Agela® Flash Column Silica-CS (12 g), Eluent of 0-50% Ethyl acetate/Petroleum ether gradient @ 20 mL/min) to give the title compound as an oil. MS (ESI) m/z calc'd for $C_{14}H9N_2O_3$ [M+H]$^+$ 263.0, found 263.0

$^1$H NMR (400 MHz, CDCl$_3$) δ 9.88 (d, J=0.7 Hz, 1H), 8.26 (d, J=8.6 Hz, 1H), 7.71 (d, J=8.6 Hz, 1H), 3.68-3.76 (m, 2H), 2.98 (t, J=6.5 Hz, 2H), 1.99 (dt, J=12.4, 6.3 Hz, 2H), 1.48 (s, 9H).

Step 3. (R,E)-tert-butyl 6-(((tert-butylsulfinyl)imino)methyl)-3,4-dihydro-1,5-naphthyridine-1(2H)-carboxylate To a solution of tert-butyl 6-formyl-3,4-dihydro-1,5-naphthyridine-1(2H)-carboxylate (0.4 g, 1.52 mmol) and (R)-2-methylpropane-2-sulfinamide (185 mg, 1.52 mmol, 1 eq) in anhydrous DCM (10 mL) was added Cs$_2$CO$_3$ (596 mg, 1.83 mmol, 1.2 eq) at RT. The resulting solution was stirred at RT for 16 h. The reaction was monitored by LCMS. The reaction was quenched with water (20 mL), and extracted with DCM (20 mL×3). The combined organic layer was washed with brine (20 mL), dried over Na$_2$SO$_4$ and concentrated. The residue was purified by flash silica gel chromatography (ISCO®; Agela® Flash Column Silica-CS (12 g), Eluent of 0-15% Ethyl acetate/Petroleum ether gradient @ 30 mL/min) to give the title compound as an oil. MS (ESI) m/z calc'd for C$_{18}$H$_{28}$N$_3$O$_3$S [M+H]$^+$ 366, found 366.0

Step 4. (R)-tert-butyl 6-(1-((tert-butylthio)amino)-2,2,2-trifluoroethyl)-3,4-dihydro-1,5-naphthyridine-1(2H)-carboxylate To a stirred solution of (R,E)-tert-butyl 6-(((tert-butylsulfinyl)imino)methyl)-3,4-dihydro-1,5-naphthyridine-1(2H)-carboxylate (300 mg, 0.821 mmol) in THF (10 mL) was added tetrabutylammonium difluorotriphenylsilicate (532 mg, 0.985 mmol) at RT, and the reaction was stirred for 0.5 h. Then the mixture was cooled to −60° C., trimethyl (trifluoromethyl)silane (584 mg, 4.10 mmol) was added to the mixture. The reaction was monitored by LC-MS, and stirred for 1 h. The mixture was quenched with aq. NH$_4$Cl (~20 mL), and extracted by EtOAc (20 mL×2). The organic layers were collected, washed with brine (20 mL), dried over Na$_2$SO$_4$, after filtration, the filtrate was concentrated in vacuo. The residue was purified by prep-TLC (Petroleum ether/EtOAc=5:1) to give the title compound as a solid. MS (ESI) m/z calc'd for C$_{19}$H$_{29}$F$_3$N$_3$O$_2$S [M+H]$^+$ 420, found 420.0

$^1$H NMR (400 MHz, CD$_3$D) δ 8.14 (d, J=8.6 Hz, 1H), 7.31 (d, J=8.6 Hz, 1H), 4.41 (q, J=7.8 Hz, 1H), 3.76 (dd, J=6.4, 5.5 Hz, 2H), 2.96 (t, J=6.6 Hz, 2H), 1.98-2.05 (m, 2H), 1.53 (s, 9H), 1.18 (s, 9H).

Step 5. (R)-2,2,2-trifluoro-1-(5,6,7,8-tetrahydro-1,5-naphthyridin-2-yl)ethanamine To a stirred solution of (R)-tert-butyl 6-(1-((tert-butylthio)amino)-2,2,2-trifluoroethyl)-3,4-dihydro-1,5-naphthyridine-1(2H)-carboxylate (220 mg, 0.524 mmol) in DCM (5 mL) was added 4 M HCl (15 mL, 60.0 mmol, in dioxane) at RT and stirred for 16 h. The solvent was evaporated to give the title compound as an oil, which was used in next step without purification. MS (ESI) m/z calc'd for C$_{10}$H$_{13}$F$_3$N$_3$ [M+H]$^+$ 232, found 232.0

Step 6. (R)-4-fluoro-N-(2,2,2-trifluoro-1-(5,6,7,8-tetrahydro-1,5-naphthyridin-2-yl)ethyl)benzamide (Intermediate B)

To a stirred solution of (R)-2,2,2-trifluoro-1-(5,6,7,8-tetrahydro-1,5-naphthyridin-2-yl)ethanamine dihydrochloride (150 mg, 0.493 mmol) in DMF (5 mL) were successively added Et$_3$N (250 mg, 2.466 mmol), HATU (281 mg, 0.740 mmol) and 4-fluorobenzoic acid (104 mg, 0.740 mmol) at RT for 16 h. This was diluted with 40 mL of water, and extracted with EtOAc (15 mL×2). The organic layers were collected, washed with brine (10 mL), dried over Na$_2$SO$_4$, after filtration, the filtrate was concentrated in vacuo. The residue was purified by prep-TLC (Petroleum ether/EtOAc=2:1) to give the title compound, Intermediate B, as an oil. MS (ESI) m/z calc'd for C$_{17}$H$_{16}$F$_4$N$_3$O [M+H]$^+$ 354, found 354.0

Step 7. (R)—N-(1-(5-(cyclopropanecarbonyl)-5,6,7,8-tetrahydro-1,5-naphthyridin-2-yl)-2,2,2-trifluoroethyl)-4-fluorobenzamide To a solution of (R)-4-fluoro-N-(2,2,2-trifluoro-1-(5,6,7,8-tetrahydro-1,5-naphthyridin-2-yl)ethyl)benzamide (102 mg, 0.289 mmol), Intermediate B, from previous Step 6, in DCM (5 mL) were added Et$_3$N (59 mg, 0.583 mmol) and cyclopropanecarbonyl chloride (60 mg, 0.574 mmol) at RT and allowed to stir for 1 h. The reaction was concentrated, the residue was purified by reverse phase HPLC on a GILSON 281 instrument fitted with a Agela ASB 150×25 mm×5 um, Condition water (0.1% TFA)-MeCN Begin B 38, End B 58 Gradient Time (min) 10, 100% B Hold Time (min) 1, FlowRate (ml/min) 25 Injections 6) to give the title compound as an oil. MS (ESI) m/z calc'd for C$_{21}$H$_2$F$_4$N$_3$O$_2$ [M+H]$^+$ 422.4, found 422.1

$^1$H NMR (400 MHz, CD$_3$OD) δ 8.04-8.08 (m, 1H), 7.92-7.99 (m, 2H), 7.51 (d, J=8.4 Hz, 1H), 7.20-7.26 (m, 2H), 6.04 (q, J=8.0 Hz, 1H), 3.93 (tq, J=13.1, 6.3 Hz, 2H), 3.03 (t, J=6.6 Hz, 2H), 2.04-2.12 (m, 2H), 1.96-2.03 (m, 1H), 1.00-1.07 (m, 2H), 0.89-0.94 (m, 2H).

Example #425. (S)—N-(1-(5-(cyclopropanecarbonyl)-5,6,7,8-tetrahydro-1,5-naphthyridin-2-yl)-2,2,2-trifluoroethyl)-4-fluorobenzamide

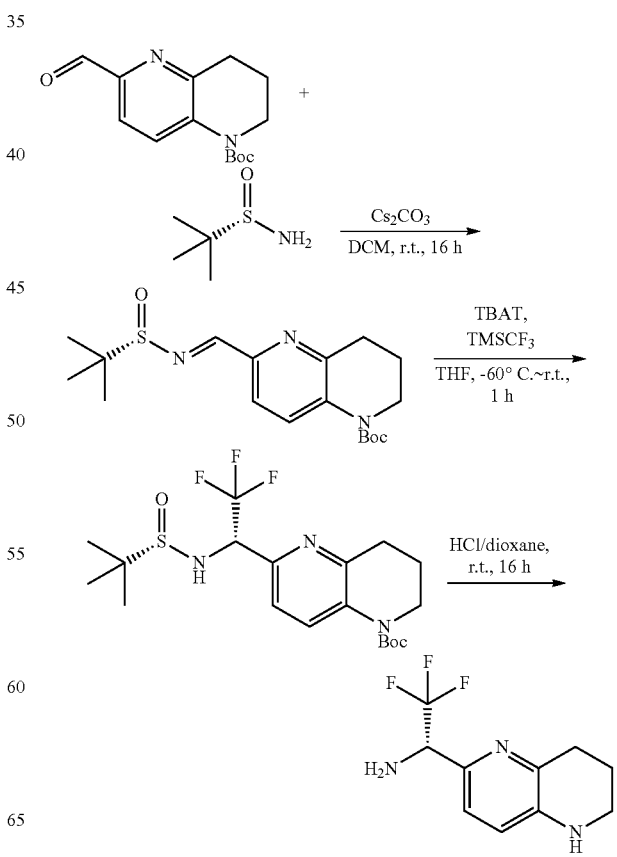

-continued

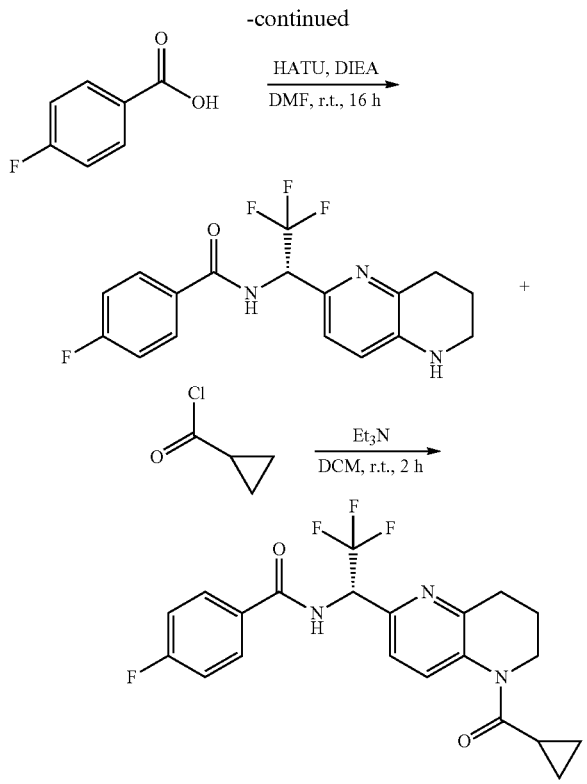

Step 1. (S,E)-tert-butyl 6-(((tert-butylsulfinyl)imino)methyl)-3,4-dihydro-1,5-naphthyridine-1(2H)-carboxylate To a stirred solution of tert-butyl 6-formyl-3,4-dihydro-1,5-naphthyridine-1(2H)-carboxylate (1.5 g, 5.72 mmol) in DCM (15 mL) were added $Cs_2CO_3$ (1.324 g, 6.86 mmol) and (S)-2-methylpropane-2-sulfinamide (0.693 g, 5.72 mmol) at RT for 16 h. The reaction was monitored by LC-MS. The mixture was diluted with water (20 mL), sat. $Na_2S_2O_3$ (~20 mL) was added and stirred for 30 min. Then extracted by $CH_2Cl_2$ (30 mL×3), the organic layers were collected, washed with brine (20 mL), and dried over $Na_2SO_4$. After filtration, the filtrate was concentrated in vacuo. The residue was purified by flash silica gel chromatography (ISCO®; Agela® Flash Column Silica-CS (20 g), Eluent of 0-60% Ethyl acetate/Petroleum ether gradient @ 30 mL/min) to give the title compound as an oil. MS (ESI) m/z calc'd for $C_{18}H_{28}N_3O_3S$ [M+H]⁺ 366.1, found 366.2 ¹H NMR (400 MHz, CDCl₃) δ 8.60 (s, 1H), 8.24 (d, J=8.6 Hz, 1H), 7.83 (d, J=8.6 Hz, 1H), 3.78 (dd, J=6.4, 5.5 Hz, 2H), 3.02 (t, J=6.5 Hz, 2H), 2.00-2.09 (m, 2H), 1.55 (s, 9H), 1.27 (s, 9H).

Step 2. tert-butyl 6-((S)-1-((S)-1,1-dimethylethylsulfinamido)-2,2,2-trifluoroethyl)-3,4-dihydro-1,5-naphthyridine-1(2H)-carboxylate To a stirred solution of (S,E)-tert-butyl 6-(((tert-butylsulfinyl)imino)methyl)-3,4-dihydro-1,5-naphthyridine-1(2H)-carboxylate (500 mg, 1.368 mmol) in THF (5 mL) was added TBAT (886 mg, 1.642 mmol) at RT, and after the addition was stirred at RT for 0.5 h. Then the mixture was cooled to −60° C., TMSCF₃ (973 mg, 6.84 mmol) was added to the mixture and the reaction mixture and stirred for 1 h. The mixture was quenched with aq. $NH_4Cl$ (15 mL), extracted by EtOAc (15 mL×2), the organic layers were collected, washed with brine (15 mL), and dried over $Na_2SO_4$. After filtration, the filtrate was concentrated in vacuo. The residue was purified by flash silica gel chromatography (ISCO®; Agela® Flash Column Silica-CS (20 g), Eluent of 080% Ethyl acetate/Petroleum ether gradient @ 40 mL/min) to give the title compound as a solid. MS (ESI) m/z calc'd for $C_9H_{29}F_3N_3O_3S$ [M+H]⁺ 436.1, found 4366.2

Step 3. (S)-2,2,2-trifluoro-1-(5,6,7,8-tetrahydro-1,5-naphthyridin-2-yl)ethanamine dihydrochloride To a stirred solution of tert-butyl 6-(((1S)-1-(1,1-dimethylethylsulfinamido)-2,2,2-trifluoroethyl)-3,4-dihydro-1,5-naphthyridine-1(2H)-carboxylate (310 mg, 0.712 mmol) in dioxane was added 4 M HCl (26.0 mg, 0.712 mmol, in dioxane) at RT and stirred for 16 h. The reaction was monitored by LC-MS. The solvent was concentrated under reduced pressure to give the title compound as a solid, which was used directly in next step without further purification. MS (ESI) m/z calc'd for $C_{10}H_{13}F_3N_3$ [M+H]⁺ 232.0, found 232.0

Step 4. (S)-4-fluoro-N-(2,2,2-trifluoro-1-(5,6,7,8-tetrahydro-1,5-naphthyridin-2-yl)ethyl)benzamide To a stirred solution of (S)-2,2,2-trifluoro-1-(5,6,7,8-tetrahydro-1,5-naphthyridin-2-yl)ethanamine dihydrochloride (100 mg, 0.329 mmol) in DCM (5 mL) were successively added Et₃N (0.14 mL, 0.986 mmol), HATU (138 mg, 0.362 mmol) and 4-fluorobenzoic acid (55 mg, 0.395 mmol) at RT and allowed to stir for 16 h. Water (15 mL) was added and extracted by $CH_2Cl_2$ (10 mL×3), the organic layers were collected, washed with brine (10 mL), and dried over $Na_2SO_4$. After filtration, the filtrate was concentrated in vacuo. The residue was purified by flash silica gel chromatography (ISCO®; Agela® Flash Column Silica-CS (12 g), Eluent of 030% Ethyl acetate/Petroleum ether gradient @ 30 mL/min) to give the title compound as a solid. MS (ESI) m/z calc'd for $C_{10}H_{13}F_3N_3$ [M+H]⁺ 354.1, found 354.1 ¹H NMR (400 MHz, CDCl₃) δ 8.01-8.08 (m, 1H), 7.91-7.98 (m, 2H), 7.11-7.21 (m, 2H), 7.01 (d, J=7.9 Hz, 1H), 6.75 (d, J=8.3 Hz, 1H), 5.73 (quin, J=7.6 Hz, 1H), 3.34 (t, J=5.5 Hz, 2H), 2.87-3.04 (m, 2H), 1.96-2.12 (m, 2H)

Step 5. (S)—N-(1-(5-(cyclopropanecarbonyl)-5,6,7,8-tetrahydro-1,5-naphthyridin-2-yl)-2,2,2-trifluoroethyl)-4-fluorobenzamide To a solution of (S)-4-fluoro-N-(2,2,2-trifluoro-1-(5,6,7,8-tetrahydro-1,5-naphthyridin-2-yl)ethyl)benzamide (50 mg, 0.142 mmol) in DCM (5 mL) was added Et₃N (0.04 mL, 0.287 mmol) and cyclopropanecarbonyl chloride (23 mg, 0.220 mmol) at RT and allowed to stir for 1 h. The reaction was monitored by LC-MS. The solvent was concentrated, the residue was purified by reverse phase HPLC on a GILSON 281 instrument fitted with a Waters XSELECT C18 (150*30 mm*5 um) using water (0.1% TFA)—CAN (Mobile phase A water (0.1% TFA), Mobile phase B ACN, Detective wavelength: 220 nm) to give the title compound as an oil. MS (ESI) m/z calc'd for $C_{21}H_{19}F_4N_3O_2$ [M+H]⁺ 422.0 found 422.1 ¹H NMR (400 MHz, CD₃OD) δ 8.09 (br d, J=8.3 Hz, 1H), 7.93-8.00 (m, 2H), 7.52 (d, J=8.3 Hz, 1H), 7.24 (t, J=8.8 Hz, 2H), 6.06 (q, J=8.0 Hz, 1H), 3.93 (tq, J=13.0, 6.4 Hz, 2H), 3.04 (t, J=6.6 Hz, 2H), 2.09 (quin, J=6.6 Hz, 2H), 1.98-2.05 (m, 1H), 1.02-1.08 (m, 2H), 0.90-0.96 (m, 2H).

Example #431: cyclopropyl 6-(1-(4-fluorobenzamido)ethyl)-2-methyl-3,4-dihydro-1,5-naphthridine-1(2H)-carboxylate

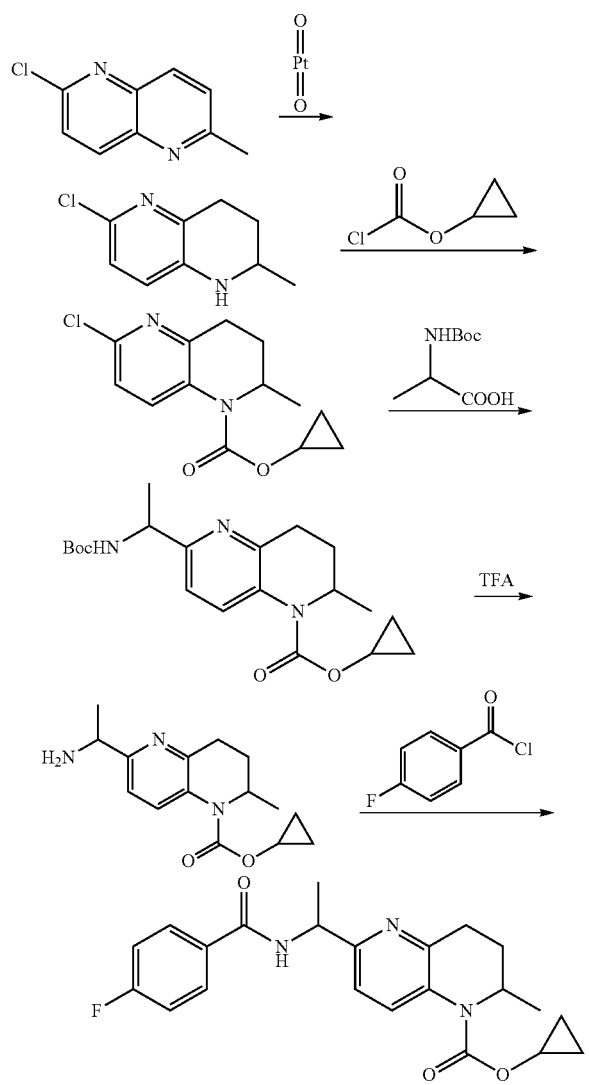

Step 1. 6-chloro-2-methyl-1,2,3,4-tetrahydro-1,5-naphthyridine

2-Chloro-6-methyl-1,5-naphthyridine (2.5 g, 14.00 mmol) was dissolved in ethanol (70.0 ml), degassed and charged with platinum(IV) oxide (0.636 g, 2.80 mmol) and allowed to react under a hydrogen atmosphere for 2.5 h. The reaction was filtered through a pad of Celite, and concentrated under reduced pressure. The material was purified by column chromatography (0-30% MeOH/CH$_2$Cl$_2$) to afford the title compound.

MS ESI calc'd. for C$_9$H$_{12}$CN$_2$ [M+H]$^+$ 183, found 183.1

Step 2. cyclopropyl 6-chloro-2-methyl-3,4-dihydro-1,5-naphthyridine-1(2H)-carboxylate To a solution of 6-chloro-2-methyl-1,2,3,4-tetrahydro-1,5-naphthyridine (0.28 g, 1.533 mmol), cyclopropyl carbonochloridate (0.169 ml, 1.840 mmol), and cyclopropyl carbonochloridate (0.169 ml, 1.840 mmol) in DCM (3.07 ml) was added DIEA (0.803 ml, 4.60 mmol) and the reaction was allowed to stir for 18 h at RT. The reaction was diluted with water and extracted with 25% IPA/CHCl$_3$ (3×). The extract was dried with sodium sulfate. Purification was done by column chromatography (0-30% EtOAc/Hex) to afford the title compound. MS ESI calc'd. for C$_{13}$H$_6$ClN$_2$O$_2$ [M+H]$^+$ 267, found 267.0

Step 3. cyclopropyl 6-(1-((tert-butoxycarbonyl)amino)ethyl)-2-methyl-3,4-dihydro-1,5-naphthyridine-1(2H)-carboxylate A mixture of DTBBPY (0.026 g, 0.096 mmol) and Nickel(II) chloride ethylene glycol dimethyl ether complex (0.021 g, 0.096 mmol) in DMSO (1.275 ml) was bubbled with nitrogen for 10 min and the resulting solution was added to 20 ml reaction vial containing a mixture of 2-((tert-butoxycarbonyl)amino)propanoic acid (0.181 g, 0.956 mmol), cesium carbonate (0.415 g, 1.275 mmol), cyclopropyl 6-chloro-2-methyl-3,4-dihydro-1,5-naphthyridine-1(2H)-carboxylate (0.17 g, 0.637 mmol), and [Ir{dF(CF$_3$)ppy}$_2$(dtbpy)]PF$_6$ (0.063 g, 0.064 mmol). The resulting mixture was bubbled with nitrogen for 10 min. The reaction mixture was sealed and iridiated in Photo reactor for 10 h. The reaction mixture was diluted with ethyl acetate and then washed with water 3 times. The organic layer was dried over Na$_2$SO$_4$ and the organic solvent was removed under reduced pressure. The material was purified by column chromatography (0-40% MeOH/DCM) to afford the title compound.

MS ESI calc'd. for C$_{20}$H$_{30}$N$_3$O$_4$ [M+H]$^+$ 376, found 376.2

Step 4. cyclopropyl 6-(1-aminoethyl)-2-methyl-3,4-dihydro-1,5-naphthyridine-1(2H)-carboxylate To a flask containing cyclopropyl 6-(1-((tert-butoxycarbonyl)amino)ethyl)-2-methyl-3,4-dihydro-1,5-naphthyridine-1(2H)-carboxylate (0.020 g, 0.053 mmol) and CH$_2$Cl$_2$ (2.131 ml) was added trifluoroacetic acid (0.245 ml, 3.20 mmol). The mixture was stirred at RT for 2 h. The solvent was removed under reduced pressure and the resulting material was pushed forward without further purification. MS ESI calc'd. for C$_{15}$H$_{22}$N$_3$O$_2$ [M+H]$^+$ 276, found 276.2

Step 5. cyclopropyl 6-(1-(4-fluorobenzamido)ethyl)-2-methyl-3,4-dihydro-1,5-naphthyridine-1(2H)-carboxylate To a solution of cyclopropyl 6-(1-aminoethyl)-2-methyl-3,4-dihydro-1,5-naphthyridine-1(2H)-carboxylate (0.015 g, 0.054 mmol) and 4-fluorobenzoyl chloride (0.013 ml, 0.109 mmol) in THF (0.545 ml) at RT was added DIEA (0.076 ml, 0.436 mmol). The mixture was stirred at RT for 1 h at RT. The reaction mixture was diluted with sat. NaHCO$_3$ and extracted with EtOAc. The organic layer was separated, washed with brine, dried over sodium sulfate, and concentrated. The material was purified by mass triggered reverse phase HPLC (ACN/water with 0.1% TFA for the modifier) to afford the title compound. MS ESI calc'd. for C$_{22}$H$_{25}$FN$_3$O$_3$ TFA [M+H]$^+$ 398, found 398.1 $^1$H NMR (499

MHz, DMSO-d$_6$) δ 8.92 (brs, 1H), 8.10-7.94 (m, 3H), 7.40-7.26 (m, 3H), 5.19-5.12 (m, 1H), 4.54-4.49 (m, 1H), 4.15-4.09 (m, 1H), 2.91-2.80 (m, 2H), 2.16-2.08 (m, 1H), 1.75-1.67 (m, 1H), 1.52-1.46 (m, 3H), 1.12-1.05 (m, 3H), 0.74-0.65 (m, 4H).

Example #432. 4-fluoro-N-(1-(5-(2-methylpyrimidin-4-yl)-6,7,8,9-tetrahydro-5H-pyrido[3,2-b]azepin-2-yl)cyclopropyl)benzamide

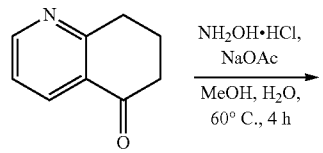

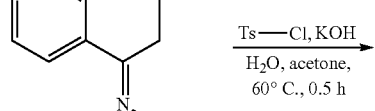

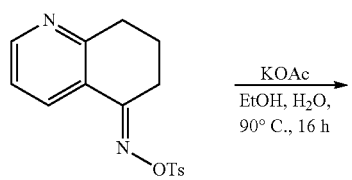

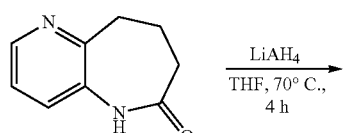

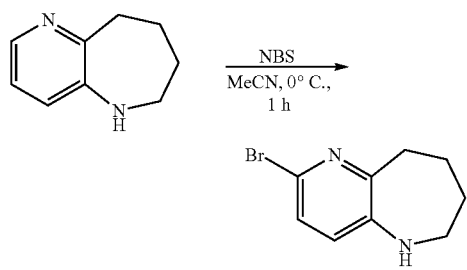

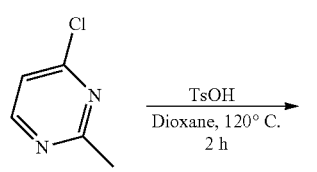

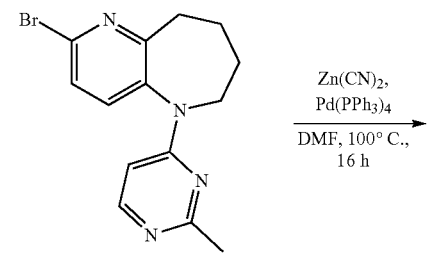

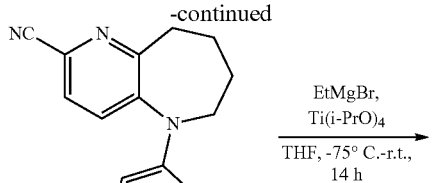

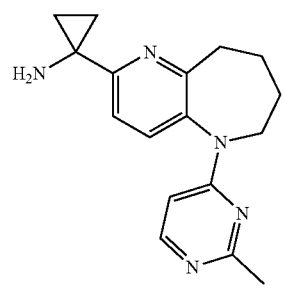

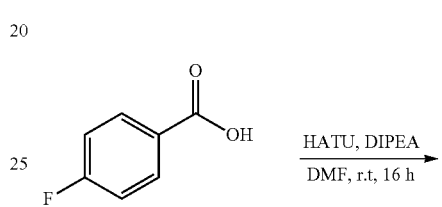

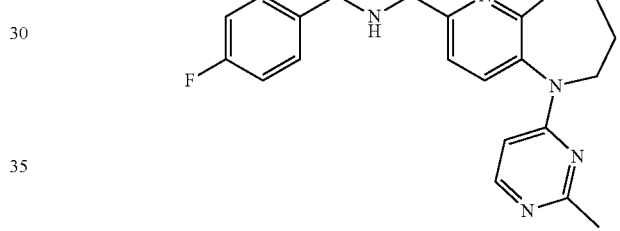

Step 1. (E)-7,8-dihydroquinolin-5(6H)-one oxime

To a stirred solution of 7,8-dihydroquinolin-5(6H)-one (2 g, 13.59 mmol) in MeOH (10 mL) and water (3 mL) were added sodium acetate (3.34 g, 40.8 mmol) and hydroxylamine hydrochloride (2.83 g, 40.8 mmol) at RT and then the reaction was stirred at 60° C. for 4 h. The mixture was concentrated in vacuo. To the residue water (30 mL) and MeOH (50 mL) were added and filtered, the filter cake was collected and dried to give the title compound which was used directly in the next step without further purification. MS ESI calc'd. for C$_9$H$_{11}$N$_2$O [M+H]$^+$ 163.8, found 163

Step 2. (E)-7,8-dihydroquinolin-5(6H)-one O-tosyl oxime

To a stirred solution of (E)-7,8-dihydroquinolin-5(6H)-one oxime (1.8 g, 11.10 mmol) in acetone (40 mL) and water (12 mL) were added 4-methylbenzene-1-sulfonyl chloride (3.17 g, 16.65 mmol) and KOH (0.623 g, 11.10 mmol) at RT. After the addition was finished, the reaction was stirred at 60° C. The reaction was monitored by LC-MS, after stirring at 60° C. for 0.5 h, the reaction was finished. The mixture was concentrated in vacuo, and the residue was washed with water (50 mL). Then further triturated with petroleum ether to give the title compound as a solid. MS ESI calc'd. for C$_{16}$H$_{17}$N$_2$O$_3$S [M+H]$^+$ 317.3, found 317.1

Step 3. 5,7,8,9-tetrahydro-6H-pyrido[3,2-b]azepin-6-one

To a stirred solution of (E)-7,8-dihydroquinolin-5(6H)-one O-tosyl oxime (3 g, 9.48 mmol) in EtOH (30 mL) and water (60 mL) was added potassium acetate (2.140 g, 21.81 mmol) at RT. After the addition was finished, the reaction was stirred at 90° C. The reaction was monitored by LC-MS, after stirring at 90° C. for 16 h, the reaction was finished. After cooling to RT, the mixture was concentrated in vacuo. The residue was extracted with DCM (50 mL×2), the organic layers were collected, washed with brine (20 mL), and dried over $Na_2SO_4$. After filtration, the filtrate was concentrated in vacuo to give the title compound as a solid, which was used for the next step without any further purification.

MS ESI calc'd. for $C_9H_{11}N_2O$ [M+H]$^+$ 163.1, found 163.1

Step 4. 6,7,8,9-tetrahydro-5H-pyrido[3,2-b]azepine

To a stirred solution of 8,9-dihydro-5H-pyrido[3,2-b]azepin-6(7H)-one (1.2 g, 7.40 mmol) in THF (30 mL) was added LiAlH$_4$ (2.53 g, 66.6 mmol) at RT. After the addition was finished, the reaction was stirred at 70° C. for 4 h. After cooling to RT, MeOH (60 mL) was added, then filtered, and the filtrate was concentrated in vacuo. The residue was diluted with water (50 mL), and extracted with EtOAc (40 mL×3). The organic layers were collected, washed with brine (20 mL), dried over $Na_2SO_4$, filtered, and the filtrate was concentrated in vacuo to give the title compound as a solid, which was used to the next step without any further purification.

Step 5. 2-bromo-6,7,8,9-tetrahydro-5H-pyrido[3,2-b]azepine

To a stirred solution of 6,7,8,9-tetrahydro-5H-pyrido[3,2-b]azepine (600 mg, 4.05 mmol) in ACN (3 mL) was added NBS (685 mg, 3.85 mmol) in ACN (2 mL) dropwise at 0° C. and stirred for 1 h. After warming to RT, the mixture was concentrated in vacuo, then diluted with water (20 mL), and extracted with EtOAc (20 mL×3). The organic layers were collected, washed with brine (10 mL), dried over $Na_2SO_4$, filtered, and the filtrate was concentrated in vacuo. The residue was purified by flash silica gel chromatography (ISCO®; Agela® Flash Column Silica-CS (4 g) Eluent of 030% Ethyl acetate/Petroleum ether gradient @ 30 mL/min) to give the title compound as an oil. MS ESI calc'd. for $C_9H_{12}BrN_2$ [M+H]$^+$ 226/228, found 226.8/228.8

Step 6. 2-bromo-5-(2-methylpyrimidin-4-yl)-6,7,8,9-tetrahydro-5H-pyrido[3,2-b]azepine To a stirred solution of 2-bromo-6,7,8,9-tetrahydro-5H-pyrido[3,2-b]azepine (690 mg, 3.04 mmol) in dioxane (5 mL) were added 4-chloro-2-methylpyrimidine (781 mg, 6.08 mmol) and 4-methylbenzenesulfonic acid (523 mg, 3.04 mmol) at RT and the reaction was heated at 120° C. for 2 h. The mixture was cooled, sat. NaHCO$_3$ solution was added to adjust pH>7, and extracted with EtOAc (20 mL×3). The organic layers were collected, washed with brine (10 mL), dried over $Na_2SO_4$, filtered and the filtrate was concentrated in vacuo. The residue was purified by flash silica gel chromatography (ISCO®; Agela® Flash Column Silica-CS (4 g) Eluent of 080% Ethyl acetate/Petroleum ether gradient @ 30 mL/min) to give the title compound as an oil. MS ESI calc'd. for $C_{14}H_{16}BrN_4$ [M+H]$^+$ 318/320, found 320.8

Step 7. 5-(2-methylpyrimidin-4-yl)-6,7,8,9-tetrahydro-5H-pyrido[3,2-b]azepine-2-carbonitrile To a stirred solution of 2-bromo-5-(2-methylpyrimidin-4-yl)-6,7,8,9-tetrahydro-5H-pyrido[3,2-b]azepine (720 mg, 2.256 mmol) in DMF (8 mL) were added Zn(CN)$_2$ (795 mg, 6.77 mmol) and Pd(PPh$_3$)$_4$ (261 mg, 0.226 mmol) and the mixture was stirred at 100° C. under nitrogen atmosphere for 16 h. After cooling to RT, water (100 mL) was added to the mixture, which was extracted with EtOAc (30 mL×3). The organic layers were collected, washed with brine (20 mL), dried over $Na_2SO_4$, filtered and the filtrate was concentrated in vacuo. The residue was purified by flash silica gel chromatography (ISCO®; Agela® Flash Column Silica-CS (4 g) Eluent of 070% Ethyl acetate/Petroleum ether gradient @ 30 mL/min) to give the title compound as an oil. MS ESI calc'd. $C_{15}H_{16}N5$ [M+H]$^+$ 266.1, found 266.2

Step 8. 1-(5-(2-methylpyrimidin-4-yl)-6,7,8,9-tetrahydro-5H-pyrido[3,2-b]azepin-2-yl)cyclopropan-1-amine To a stirred solution of 5-(2-methylpyrimidin-4-yl)-6,7,8,9-tetrahydro-5H-pyrido[3,2-b]azepine-2-carbonitrile (300 mg, 1.131 mmol) in THF (5 mL) was added Ti(i-PrO)$_4$ (0.84 mL, 2.270 mmol) dropwise at −75° C. for 5 min. Ethylmagnesium bromide (1.32 mL, 3.96 mmol) (3.0 M) was added dropwise at −75° C. After the addition, the reaction was warmed to RT slowly and stirred for 14 h. The mixture was quenched with water (30 mL), extracted with EtOAc (30 mL×2), and filtered. The filtrate was collected, washed with brine (10 mL), dried over $Na_2SO_4$, filtered and the filtrate was concentrated in vacuo. The residue was purified by flash silica gel chromatography (ISCO®; Agela® Flash Column Silica-CS (4 g) Eluent of 0-10% DCM/MeOH gradient @ 30 mL/min) to give the title compound as a solid.

MS ESI calc'd. $C_{17}H_{22}N_5$ [M+H]$^+$ 296, found 296.9

Step 9. 4-fluoro-N-(1-(5-(2-methylpyrimidin-4-yl)-6,7,8,9-tetrahydro-5H-pyrido[3,2-b]azepin-2-yl)cyclopropyl)benzamide To a stirred solution of 1-(5-(2-methylpyrimidin-4-yl)-6,7,8,9-tetrahydro-5H-pyrido[3,2-b]azepin-2-yl)cyclopropanamine (100 mg, 0.339 mmol) in DMF (3 mL) were added N-ethyl-N-isopropylpropan-2-amine (0.17 mL, 1.029 mmol), HATU (129 mg, 0.339 mmol) and 4-fluorobenzoic acid (48 mg, 0.343 mmol) at RT and stirred for 16 h. The mixture was diluted with water (20 mL), and extracted with EtOAc (10 mL×2). The organic layers were collected, washed with brine (10 mL), dried over $Na_2SO_4$, filtered, and the filtrate was concentrated in vacuo. The residue was purified by reverse phase HPLC on a GILSON 281 instrument fitted with a Column Phenomenex Synergi C18 (150× 30 mm×5 μm) using water (0.225% FA and acetonitrile as eluents (Mobile phase A water (0.225% FA), Mobile phase B acetonitrile, Detective wavelength: 220 nm) followed by lyophilization to give the title compound as a solid. MS ESI calc'd. $C_{24}H_{25}FN_5O$ [M+H]$^+$ 418.2, found 418.0

$^1$H NMR (400 MHz, CD$_3$OD) δ=8.00-7.94 (m, 2H), 7.92 (br s, 1H), 7.47 (d, J=8.3 Hz, 1H), 7.31 (d, J=8.3 Hz, 1H), 7.22 (t, J=8.8 Hz, 2H), 6.01 (br s, 1H), 3.47 (s, 1H), 2.83 (br d, J=19.6 Hz, 3H), 2.46 (br s, 3H), 2.05-1.80 (m, 3H), 1.76-1.68 (m, 2H), 1.53 (br s, 1H), 1.38-1.31 (m, 2H).
Hela Cell IC$_{50}$: 3.3 nM.

Examples 433-436: 4-fluoro-N-2-methyl-1-(5-(2-methylpyrimidin-4-yl)-5,6,7,8-tetrahydro-1,5-naphthyridin-2-yl)cyclopropyl)benzamide Step 1: tert-butyl 6-cyano-3,4-dihydro-1,5-naphthyridine-1(2H)-carboxylate To a 250 ml of round bottle flask were added tert-butyl 6-bromo-3,4-dihydro-1,5-naphthyridine-1(2H)-carboxylate (10 g, 31.9 mmol), Zinc cyanide (7.50 g, 63.9 mmol) and DMF (106 ml). The mixture was vacuumed and back-filled with nitrogen for 3 times, then tetrakis(triphenylphosphine)palladium(0) (1.845 g, 1.596 mmol) was added, and the mixture was vacuum dried and back-filled with nitrogen 3 times. Then the mixture was heated at 100° C. for 14 h under nitrogen atmosphere. LCMS showed complete conversion. The mixture was cooled down, filtered through a pad of Celite, and rinsed with EtOAc. The filtrate was diluted with water, and extracted with EtOAc. The organic layer was separated, washed with water twice and then brine, dried over anhydrous MgSO$_4$, and concentrated. The residue was purified by flash chromatography (0-100% EtOAc/hexanes) to give the title compound as a solid.
MS (ESI) m/z: 260.1 [M+H$^+$].

Step 2. tert-butyl 6-(1-amino-2-methylcyclopropyl)-3,4-dihydro-1,5-naphthyridine-1(2H)-carboxylate To a solution of tert-butyl 6-cyano-3,4-dihydro-1,5-naphthyridine-1(2H)-carboxylate from 0053 (1.0 g, 3.86 mmol) in Me-THF (12.85 ml) at RT was added Titanium(IV) isopropoxide (1.370 ml, 4.63 mmol), followed by the addition of N-propylmagnesium chloride (9.26 ml, 9.26 mmol). The reaction was slightly exothermic during the addition. Water bath was used to maintain internal temp below 30° C. After the addition, the reaction mixture was kept stirring at RT for 30 min. Then Boron trifluoride diethyl etherate (1.142 ml, 9.26 mmol) was added while maintaining internal temperature under 35° C. during the addition by cooling with water bath. The mixture was kept stirring for 30 min. The mixture was quenched by pouring slowly into a beaker containing 5 ml 1N NaOH and 5 ml of water and extracted with 1:1 EtOAc/Me-THF 100 ml×3. The combined organics were dried over Na$_2$SO$_4$, and concentrated. The title compound was carried over to next step. MS (ESI) m/z: 304.2 [M+H$^+$].

Step 3. tert-butyl 6-(1-(4-fluorobenzamido)-2-methylcyclopropyl)-3,4-dihydro-1,5-naphthyridine-1(2H)-carboxylate To a solution of tert-butyl 6-(1-amino-2-methylcyclopropyl)-3,4-dihydro-1,5-naphthyridine-1(2H)-carboxylate (1.17 g, 3.86 mmol) in DCM (12.85 ml) at RT was added Et3N (2.150 ml, 15.43 mmol), followed by the addition of 4-fluorobenzoyl chloride (0.183 ml, 1.543 mmol). The mixture was stirred at RT for 20 min. LCMS showed complete conversion. The reaction mixture was diluted with aq. NaHCO$_3$, and extracted with DCM. The organic layer was separated, washed with brine, dried over MgSO$_4$, and concentrated. The residue was purified by flash chromatography (0-100% EtOAc/hexanes) to give two peaks. Peak 1 was the cis isomer and Peak 2 was the trans isomer.
Peak 1—MS (ESI) m/z: 426.1 [M+H$^+$].
Peak 2—MS (ESI) m/z: 426.1 [M+H$^+$].

Step 4. 4-fluoro-N-((1R,2R)-2-methyl-1-(5,6,7,8-tetrahydro-1,5-naphthyridin-2-yl)cyclopropyl)benzamide To a flask containing tert-butyl 6-((1R,2R)-1-(4-fluorobenzamido)-2-methylcyclopropyl)-3,4-dihydro-1,5-naphthyridine-1(2H)-carboxylate from Step 3 Peak 2—trans (275 mg, 0.646 mmol) was added HCl, 4 M in dioxane (1061 µl, 12.93 mmol). The mixture was stirred at RT for 14 h, neutralized with sat. NaHCO$_3$, and extracted with DCM. The combined organics were dried over MgSO$_4$, and concentrated. MS (ESI) m/z: 326.2[M+H$^+$].

Step 5. 4-fluoro-N-((1S,2S)-2-methyl-1-(5-(2-methylpyrimidin-4-yl)-5,6,7,8-tetrahydro-1,5-naphthyridin-2-yl)cyclopropyl)benzamide, Peak 1—trans A mixture of 4-fluoro-N-(2-methyl-1-(5,6,7,8-tetrahydro-1,5-naphthyridin-2-yl)cyclopropyl)benzamide from previous Step 4, Peak 2 (210 mg, 0.645 mmol), 4-chloro-2-methylpyrimidine (166 mg, 1.291 mmol), 4-chloro-2-methylpyrimidine (166 mg, 1.291 mmol) and 4-methylbenzenesulfonic acid (122 mg, 0.710 mmol) in dioxane (3227 µl) was heated at 100° C. for 14 h. The mixture was cooled down and neutralized with sat. NaHCO$_3$, and extracted with DCM. The combined organics were dried over MgSO$_4$, and concentrated. The residue was purified by flash chromatography (0-80% (1:3 EtOH/EtOAc)/hexanes) to give the title compound. The relative stereochemistry was determined to be trans (NH vs Me). The material was chirally separated to give two enantiomers.
Column & dimensions (mm): OJ-H, 21×250 (220 nm
Outlet Pressure (bar): 100; UV wavelength (nm): 220; Flow rate (ml/min): 70
Modifier: MeOH w/0.25% DMEA; % modifier in CO2: 15; Diluent: MeOH
Retention time (min): 2.4, 3.5
Example #433: Peak 1: at 2.4 min, MS (ESI) m/z: 418.1 [M+H$^+$].
Example #434: Peak 2 at 3.5 min, MS (ESI) m/z: 418.1 [M+H$^+$].
Tert-butyl 6-(1-(4-fluorobenzamido)-2-methylcyclopropyl)-3,4-dihydro-1,5-naphthyridine-1(2H)-carboxylate, from Step 3 in the above example was processed similarly following Steps 4 through 5 and then resolved chirally to give the two cis enantiomers. Retention time (min): 4.1, 6.1
Example #435: Peak 1 MS (ESI) m/z: 418.1 [M+H$^+$]
Example #436: Peak 2 MS (ESI) m/z: 418.1 [M+H$^+$]

Example #437: 4-chloro-N-(1-(3-fluoro-1-(2-methylpyrimidin-4-yl)-1,2,3,4-tetrahydroquinolin-6-yl)cyclopropyl)benzamide, 2,2,2-trifluoroacetate salt Step 1. Synthesis of 6-bromo-1,2,3,4-tetrahydroquinolin-3-ol To a solution of 1,2,3,4-tetrahydroquinolin-3-ol (1.50 g, 10.05 mmol) in DMF (6.00 ml) at 0° C. was added a solution of NBS (2.147 g, 12.07 mmol) in DMF (4 ml). The mixture was stirred at 0° C. for 1 h, then at RT for 4 h. LCMS showed both the mono an di-bromo products. The mixture was diluted with sat. NaHCO$_3$, and extracted with EtOAc. The organic layer was separated, washed with brine, dried over MgSO$_4$, filtered, and concentrated. The residue was purified by flash chromatography (0-50% EtOAc/hexanes) to give the title compound as a solid. MS (ESI) m/z calc'd for C9H11BrNO [M+H]+, 228, found 228/230

Step 2. 6-bromo-3-((tert-butyldimethylsilyl)oxy)-1,2,3,4-tetrahydroquinoline To a solution of 6-bromo-1,2,3,4-tetrahydroquinolin-3-ol (870.40 mg, 3.82 mmol) in DCM (12.00 ml) at 0° C. was added a solution of TBDMS-Cl (863 mg, 5.72 mmol) in DMF (3 ml). The mixture was stirred at 0° C. for 2 h. The mixture was diluted with sat. $NaHCO_3$, and extracted with EtOAc. The organic layer was separated, washed with brine, dried over anhydrous $MgSO_4$, filtered, and concentrated. The residue was purified by flash chromatography (0-50% EtOAc/hexanes) to give the title compound as a solid. MS (ESI) m/z calc'd for C15H25BrNOSi[M+H]+, 342/344, found 342/344

Step 3. 6-bromo-1-(2-methylpyrimidin-4-yl)-1,2,3,4-tetrahydroquinolin-3-ol

To a vial containing 6-bromo-3-((tert-butyldimethylsilyl)oxy)-1,2,3,4-tetrahydroquinoline (664.00 mg, 1.940 mmol), 4-chloro-2-methylpyrimidine (499 mg, 3.88 mmol), and 4-methylbenzenesulfonic acid (367 mg, 2.134 mmol) was added dioxane (9698 μl). The mixture was subjected to microwave irradiation at 160° C. for 60 min. The mixture was cooled down, neutralized with sat. $NaHCO_3$, and extracted with DCM. The combined organics were dried over $MgSO_4$, and concentrated. The residue was purified on a silica gel column using 20-80% (Hex—1:3 EtOH/EtOAc-mixture) to give the title compound.
MS (ESI) m/z calc'd for $C_{14}H_{15}BrN_3O$ [M+H]+, 322/324, found, 324.1

Step 4. 6-bromo-3-fluoro-1-(2-methylpyrimidin-4-yl)-1,2,3,4-tetra hydroquinoline To a solution of 6-bromo-1-(2-methylpyrimidin-4-yl)-1,2,3,4-tetrahydroquinolin-3-ol (324.0 mg, 1.012 mmol) in DCM (3.00 ml) at 0° C. was added DAST (0.668 ml, 5.06 mmol) and allowed to stir for 2 h. Additional 2.00 eq. of DAST was added and this was allowed to stir for 1 h. The reaction mixture was quenched with aq. $NaHCO_3$ solution, and diluted with excess DCM. The organic layer was separated, washed with brine, dried over anhydrous $MgSO_4$, filtered, and excess solvent was removed under reduced pressure to give an oil. LC showed a mixture of the title compound and some alkene. This mixture was purified on a silica gel column using 0-40% (Hex-Ethyl Acetate/Ethanol (3:1 Mixture). Appropriate fractions were pooled together, excess solvent was removed under reduced pressure and the oil obtained was vacuum dried to give the title compound. MS (ESI) m/z calc'd for C14H14BrFN3 [M+H]+, 322/324, found, 324.1

Step 5. 3-fluoro-1-(2-methylpyrimidin-4-yl)-1,2,3,4-tetrahydroquinoline-6-carbonitrile To a solution of 6-bromo-3-fluoro-1-(2-methylpyrimidin-4-yl)-1,2,3,4-tetrahydroquinoline (100.0 mg, 0.310 mmol) in DMF (1.00 ml) and zinc cyanide (72.9 mg, 0.621 mmol) was added tetrakis(triphenylphosphine)palladium (0) (25.1 mg, 0.022 mmol) and this mixture was thoroughly flushed with nitrogen and then subjected to microwave irradiation at 140° C., 40 min. The reaction was filtered and the filtrate was diluted with EtOAc, washed with aq. $NaHCO_3$ solution, water and brine, dried over $MgSO_4$, filtered, and excess solvent was removed under reduced pressure. This was purified on a silica gel column using Hex-Ethyl Acetate/Ethanol mix. Appropriate fractions were pooled together, excess solvent was removed under reduced pressure and this was vacuum dried to give the title compound as a solid. MS (ESI) m/z calc'd for C15H14FN4 [M+H]+, 269.2, found, 269.1

Step 6. 1-(3-fluoro-1-(2-methylpyrimidin-4-yl)-1,2,3,4-tetrahydroquinolin-6-yl)cyclopropanamine To a solution of 3-fluoro-1-(2-methylpyrimidin-4-yl)-1,2,3,4-tetrahydroquinoline-6-carbonitrile) (72.00 mg, 0.268 mmol) in THF (1.00 ml) was added titanium (IV) isopropoxide (0.119 ml, 0.403 mmol) at RT. To this stirred solution, ethylmagnesium bromide 3.4 M in Me-THF (0.273 ml, 0.819 mmol) was added at RT and this was allowed to stir at RT for 40 min. The reaction mixture was allowed to stir for 5 h. There was some unreacted starting material. Initially the reaction was very dark almost black in color. Over time, after formation of the amine it was light yellow. This was quenched with water. This was partitioned into ethyl acetate. The aq. layer was extracted thrice, the organic layers were combined, dried over $MgSO_4$, filtered, and excess solvent was removed under reduced pressure. The title compound oil obtained was used directly for the next step. MS (ESI) m/z calc'd for C17H20FN4 [M+H]+, 299.3, found, 299.1

Step 7. 4-chloro-N-(1-(3-fluoro-1-(2-methylpyrimidin-4-yl)-1,2,3,4-tetrahydroquinolin-6-yl)cyclopropyl)benzamide, 2,2,2-trifluoroacetate salt To a solution of 1-(3-fluoro-1-(2-methylpyrimidin-4-yl)-1,2,3,4-tetrahydroquinolin-6-yl)cyclopropanamine (76.00 mg, 0.255 mmol) in DCM (1.00 ml) at 0° C., DIEA (0.133 ml, 0.764 mmol) and 4-chlorobenzoyl chloride (0.036 ml, 0.280 mmol) were added. This was stirred at 0° C. for an hour. The reaction mixture was red in color. The mixture was diluted with sat. $NaHCO_3$, and extracted with EtOAc. The organic layer was separated, washed with brine, dried over anhydrous $MgSO_4$, filtered and concentrated. The residue was purified on HPLC using gradient elution with ACN/Water and TFA as a modifier. The fractions were lyophilized to give the title compound as a racemic mixture. MS (ESI) m/z calc'd for C24H22ClFN4O·C2F3O2- [M+H]+ 437.9, found, 437.1.

$^1$H NMR (499 MHz, DMSO-$d_6$) δ 9.31 (s, 1H), 8.36-8.23 (m, 1H), 7.92 (d, J=8.6 Hz, 2H), 7.56 (d, J=8.6 Hz, 2H), 7.45 (d, J=9.1 Hz, 1H), 7.17 (d, J=6.2 Hz, 3H), 5.44 (dd, J=49.7, 6.7 Hz, 1H), 4.80-4.59 (m, 1H), 3.96 (dd, J=34.7, 14.2 Hz, 2H), 3.18-3.07 (m, 2H), 2.59 (s, 3H), 1.56-1.10 (m, 4H).

| Ex. # | Structure | Chemical Name | Mass [M + H+] | Hela IC50, nM |
|---|---|---|---|---|
| 433 | Isomer 1 | 4-fluoro-N-((1S,2S)-2-methyl-1-(5-(2-methyl-pyrimidin-4-yl)-5,6,7,8-tetrahydro-1,5-naphthyridin-2-yl)cyclopropyl)benzamide, peak 1 | Calc'd 417.4 found 418.1 | 1.11 |
| 434 | Isomer 2 | 4-fluoro-N-((1R,2R)-2-methyl-1-(5-(2-methyl-pyrimidin-4-yl)-5,6,7,8-tetrahydro-1,5-naphthyridin-2-yl)cyclopropyl)benzamide peak 2 | Calc'd 417.4 found 418.1 | 5.24 |
| 435 | Isomer 1 | 4-fluoro-N-((1R,2S)-2-methyl-1-(5-(2-methyl-pyrimidin-4-yl)-5,6,7,8-tetrahydro-1,5-naphthyridin-2-yl)cyclopropyl)benzamide, peak1 | Calc'd 417.4 found 418.1 | 1.23 |
| 436 | Isomer 2 | 4-fluoro-N-((1S,2R)-2-methyl-1-(5-(2-methyl-pyrimidin-4-yl)-5,6,7,8-tetrahydro-1,5-naphthyridin-2-yl)cyclopropyl)benzamide, peak 2 | Calc'd 417.4 found 418.1 | 1.29 |
| 437 | Racemic | 4-chloro-N-(1-(3-fluoro-1-(2-methylpyrimidin-4-yl)-1,2,3,4-tetrahydro-quinolin-6-yl)cyclopropyl)benzamide, 2,2,2-trifluoroacetate salt | Calc'd 436 found 437.1 | 1.82 |

Reversed phase preparatory HPCL Chromatography and Mass Spectrometry:
TFA (Acidic) Conditions:

Isolation of compound from the reaction mixture was carried out under reverse-phase purification using an Agilent 1200 HPLC-MSD system consisting of a 6130B single quadrupole mass-selective detector (MSD), G1315B diode array detector (DAD), G2258A autosampler, two G1361A preparative pumps, one G1379A quaternary pump with degasser, one G1312A binary pump, and three G1364B fraction collectors from Agilent Technologies (Agilent Technologies, Palo Alto, CA.). System control and data analysis were performed using Agilent's ChemStation software, revision B.04.03. A Waters SunFire C18 OBD Prep Column, 100A, 5 µm, 19 mm×150 mm column was used as the stationary phase (Waters Corporation, Milford, MA., USA). Gradient elution was carried out using water (solvent A) and acetonitrile (solvent B) as a mobile phase. A 10% trifluoroacetic acid solution was teed into the mobile phase as a modifier using a static mixer prior to the column, pumped at 1% of the total mobile phase flowrate. Electrospray (ESI) Mass-triggered fraction collected was employed using positive ion polarity scanning to monitor for the target mass.
HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

NH₄OH (Basic) Conditions:
Chromatography and Mass Spectrometry:

Isolation of compound name from the reaction mixture was carried out under reverse-phase purification using an Agilent 1200 HPLC-MSD system consisting of a 6130B single quadrupole mass-selective detector (MSD), G1315B diode array detector (DAD), G2258A autosampler, two G1361A preparative pumps, one G1379A quaternary pump with degasser, one G1312A binary pump, and three G1364B fraction collectors from Agilent Technologies (Agilent Technologies, Palo Alto, CA.). System control and data analysis were performed using Agilent's ChemStation software, revision B.04.03. A Waters XBridge C18 OBD Prep Column, 100A, 5 µm, 19 mm×150 mm column was used as the stationary phase (Waters Corporation, Milford, MA., USA). Gradient elution was carried out using water (solvent A) and acetonitrile (solvent B) as a mobile phase. A 10% Ammonium Hydroxide solution was teed into the mobile phase as a modifier using a static mixer prior to the column, pumped at 1% of the total mobile phase flowrate. Electrospray (ESI) Mass-triggered fraction collected was employed using positive ion polarity scanning to monitor for the target mass.
HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Biological Assays
IDO1 Cellular Assay in HeLa Cells Stimulated with IFNγ

HeLa cells were cultured in complete HeLa culture medium (90% EMEM, 10% heat-inactivated fetal bovine serum) and expanded to about $1\times10^9$ cells. The cells were then collected and frozen down at $1\times10^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of $2\times10^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% $CO_2$ incubator. Afterwards, 12 µL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific $IC_{50}$ activity data for the exemplified compounds disclosed herein is provided in the tables.
IDO1 Human Whole Blood Assay Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2 isotope labeled standard of kynurenine and tryptophan was made in water at 10x concentration and 30 μL was added to the blood at 3 M final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volume of Acetonitrile. The plates were centrifuged at 4000×G for 60 min. 20 μL of supernatant was carefully transferred to a 384 well plate contain 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 m particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Example # | Human whole blood assay, $IC_{50}$ (nM) |
|---|---|
| 1 | 1154 |
| 14 | 1630 |
| 28 | 33 |
| 38 | 36 |
| 48 | 321 |
| 50 | 43 |
| 51 | 96 |
| 52 | 372 |
| 53 | 45 |
| 55 | 19 |
| 57 | 51 |
| 65 | 2606 |
| 67 | 150 |
| 81 | 99 |
| 87 | 22 |
| 89 | 38 |
| 92 | 378 |
| 93 | 450 |
| 96 | 223 |
| 97 | 11 |
| 98 | 361 |
| 100 | 90 |
| 101 | 502 |
| 104 | 115 |
| 105 | 61 |
| 106 | 12 |
| 115 | 480 |
| 120 | 214 |
| 125 | 289 |
| 127 | 109 |
| 128 | 13 |
| 137 | 29 |
| 138 | 67 |
| 141 | 26 |
| 145 | 125 |
| 149 | 33 |
| 150 | 1144 |
| 151 | 26 |
| 154 | 613 |
| 162 | 29 |
| 165 | 34 |
| 175 | 19 |
| 187 | 2043 |
| 189 | 780 |
| 191 | 130 |
| 205 | 70 |
| 207 | 17 |
| 208 | 41 |
| 212 | 35 |
| 213 | 393 |
| 224 | 545 |
| 225 | 149 |
| 229 | 245 |
| 232 | 557 |
| 236 | 44 |
| 239 | 1704 |
| 241 | 10 |
| 242 | 7.0 |
| 244 | 64 |
| 245 | 2577 |
| 248 | 163 |
| 249 | 63 |
| 250 | 32 |
| 251 | 41 |
| 254 | 263 |
| 256 | 50 |
| 257 | 35 |
| 259 | 41 |
| 266 | 4 |
| 268 | 325 |
| 270 | 41 |
| 272 | 336 |
| 273 | 90 |
| 275 | 93 |
| 277 | 71 |
| 278 | 50 |
| 279 | 135 |
| 286 | 89 |
| 287 | 6 |
| 289 | 17 |
| 296 | 163 |
| 300 | 63 |
| 301 | 21 |
| 303 | 106 |
| 304 | 81 |
| 307 | 63 |

-continued

| Example # | Human whole blood assay, IC$_{50}$ (nM) |
|---|---|
| 309 | 78 |
| 310 | 46 |
| 312 | 47 |
| 315 | 18 |
| 316 | 245 |
| 320 | 1689 |
| 322 | 58 |
| 324 | 239 |
| 330 | 4947 |
| 331 | 8 |
| 334 | 46 |
| 341 | 49 |
| 345 | 32 |
| 346 | 100 |
| 347 | 340 |
| 351 | 18 |
| 356 | 167 |
| 357 | 436 |
| 358 | 1000 |
| 362 | 984 |
| 363 | 178 |
| 364 | 198 |
| 365 | 254 |
| 366 | 140 |
| 368 | 16 |
| 384 | 228 |
| 389 | 44 |
| 390 | 73 |
| 391 | 101 |
| 393 | 131 |
| 394 | 7 |
| 395 | 26 |
| 396 | 27 |
| 398 | 10,000 |
| 399 | 13 |
| 401 | 4 |
| 402 | 3 |
| 404 | 20 |
| 405 | 42 |
| 406 | 2984 |
| 408 | 2984 |
| 410 | 70 |
| 413 | 17 |
| 414 | 26 |
| 415 | 18 |
| 417 | 12 |
| 418 | 239 |
| 419 | 69 |
| 420 | 12 |
| 421 | 65 |
| 422 | 12 |
| 423 | 26 |
| 424 | 143 |
| 425 | 29 |
| 426 | 1000 |
| 432 | 4.0 |
| 433 | 8 |
| 434 | 264 |
| 435 | 8 |
| 436 | 167 |
| 437 | 16 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (Ia), formula (If), or formula (Ig), or a pharmaceutically acceptable salt thereof:

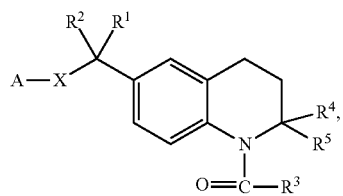

(Ia)

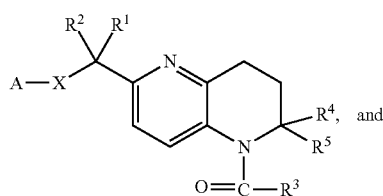

(If)

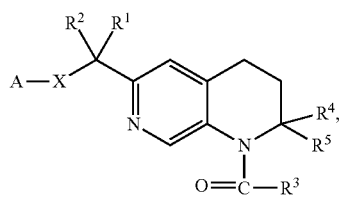

(Ig)

wherein:
A is phenyl, optionally substituted with 1-3 halogens;
X is selected from (1)-NHC(O)— and (2)—C(O)NH—;
each of $R^1$ and $R^2$ is independently selected from:
   (1) H, and
   (2) $C_{1-4}$ alkyl, optionally substituted with 1-3 halogens;
or alternatively, $R^1$ and $R^2$ together with the carbon to which they are attached form a 3-5 membered ring selected from:
   (1) cyclopropyl, optionally substituted with 1-3 halogens,
   (2) cyclobutyl, optionally substituted with 1-3 halogens,
   (3) oxiranyl, and
   (4) oxetanyl;
$R^3$ is selected from:
   (1) phenyl, optionally substituted with 1-3 halogens, and
   (2) a 4-6 membered monocyclic aromatic heterocyclyl selected from oxadiazolyl, oxazolyl, pyrazolyl, pyrazinyl, pyridinyl, pyrimidinyl, thiazolyl, and triazolyl, each of which is optionally substituted with 1-3 substituents independently selected from:
      (a) halogen,
      (b)—CH$_3$, optionally substituted with 1-3 halogens,
      (c)—O—CH$_3$, and
      (d) cyclopropyl; and
each of $R^4$ and $R^5$ is H.

2. The compound of claim 1, or a pharmaceutically acceptable salt thereof, wherein:
A is phenyl, optionally substituted with 1-3 halogens;
each of $R^1$ and $R^2$ is independently selected from:
   (1) H, and
   (2) $C_{1-4}$ alkyl, optionally substituted with 1-3 halogens;
or alternatively, $R^1$ and $R^2$ together with the carbon to which they are attached form a 3-5 membered ring selected from:

(1) cyclopropyl, optionally substituted with 1-3 halogens, and
(2) cyclobutyl, optionally substituted with 1-3 halogens; and R³ is selected from:
(1) phenyl, optionally substituted with 1-3 halogens, and
(2) a 4-6 membered monocyclic aromatic heterocyclyl selected from pyridinyl and pyrimidinyl, each of which is optionally substituted with 1-3 substituents independently selected from:
(a) halogen,
(b)—CH₃, optionally substituted with 1-3 halogens, and
(c) cyclopropyl.

3. The compound of claim 1, or a pharmaceutically acceptable salt thereof, selected from:
4-chloro-N-((1-(3-chlorobenzoyl)-1,2,3,4-tetrahydroquinolin-6-yl)methyl)benzamide;
3-chloro-N-((1-(3-chlorobenzoyl)-1,2,3,4-tetrahydroquinolin-6-yl)methyl)benzamide;
4-chloro-N-{1-[1-(3-chlorobenzene-1-carbonyl)-1,2,3,4-tetrahydroquinolin-6-yl]ethyl}benzamide;
2-{1-[4-(difluoromethyl)pyridine-2-carbonyl]-1,2,3,4-tetrahydroquinolin-6-yl}-N-(4-fluorophenyl)propanamide;
N-(4-fluorophenyl)-2-[1-(5-methyl-1,3-thiazole-2-carbonyl)-1,2,3,4-tetrahydroquinolin-6-yl]propanamide;
N-(4-fluorophenyl)-2-[1-(3-methyl-1H-1,2,4-triazole-5-carbonyl)-1,2,3,4-tetrahydroquinolin-6-yl] propanamide;
N-(4-fluorophenyl)-2-[1-(3-methyl-1,2,4-oxadiazole-5-carbonyl)-1,2,3,4-tetrahydroquinolin-6-yl]propanamide;
N-(4-fluorophenyl)-2-[1-(5-methyl-1,3,4-oxadiazole-2-carbonyl)-1,2,3,4-tetrahydroquinolin-6-yl]propanamide;
N-(4-fluorophenyl)-2-[1-(2-methyl-1,3-oxazole-4-carbonyl)-1,2,3,4-tetrahydroquinolin-6-yl]propanamide;
N-(4-fluorophenyl)-2-[1-(5-methyl-1,2-oxazole-3-carbonyl)-1,2,3,4-tetrahydroquinolin-6-yl]propanamide;
N-(4-fluorophenyl)-2-[1-(5-methyl-1,2,4-oxadiazole-3-carbonyl)-1,2,3,4-tetrahydroquinolin-6-yl]propanamide;
N-(4-fluorophenyl)-2-[1-(1-methyl-1H-pyrazole-4-carbonyl)-1,2,3,4-tetrahydroquinolin-6-yl]propanamide;
N-(4-fluorophenyl)-2-[1-(1,3-oxazole-5-carbonyl)-1,2,3,4-tetrahydroquinolin-6-yl] propanamide;
2-[1-(3-chlorobenzene-1-carbonyl)-1,2,3,4-tetrahydroquinolin-6-yl]-N-(4-fluorophenyl)propanamide;
2-[1-(3-chlorobenzene-1-carbonyl)-1,2,3,4-tetrahydroquinolin-6-yl]-N-(4-chlorophenyl)propanamide;
(2S)-2-[1-(3-chlorobenzene-1-carbonyl)-1,2,3,4-tetrahydroquinolin-6-yl]-N-(4-fluorophenyl)propanamide;
(2R)-2-[1-(3-chlorobenzene-1-carbonyl)-1,2,3,4-tetrahydroquinolin-6-yl]-N-(4-fluorophenyl)propanamide;
(2S)-2-[1-(3-chlorobenzene-1-carbonyl)-1,2,3,4-tetrahydroquinolin-6-yl]-N-(4-chlorophenyl)propanamide;
(2R)-2-[1-(3-chlorobenzene-1-carbonyl)-1,2,3,4-tetrahydroquinolin-6-yl]-N-(4-chlorophenyl)propanamide;
N-(4-fluorophenyl)-1-[1-(5-methyl-1,2,4-oxadiazole-3-carbonyl)-1,2,3,4-tetrahydroquinolin-6-yl]cyclobutane-1-carboxamide;
N-(5-fluoropyridin-2-yl)-1-[1-(5-methyl-1,2,4-oxadiazole-3-carbonyl)-1,2,3,4-tetrahydroquinolin-6-yl]cyclobutane-1-carboxamide;
N-(4-fluorophenyl)-1-[1-(3-methyl-1H-1,2,4-triazole-5-carbonyl)-1,2,3,4-tetrahydroquinolin-6-yl]cyclobutane-1-carboxamide;
N-(4-fluorophenyl)-1-{1-[5-(trifluoromethyl)-4H-1,2,4-triazole-3-carbonyl]-1,2,3,4-tetrahydroquinolin-6-yl}cyclobutane-1-carboxamide;
1-[1-(1,5-dimethyl-1H-pyrazole-4-carbonyl)-1,2,3,4-tetrahydroquinolin-6-yl]-N-(4-fluorophenyl)cyclobutane-1-carboxamide;
1-[1-(1-ethyl-1H-pyrazole-4-carbonyl)-1,2,3,4-tetrahydroquinolin-6-yl]-N-(4-fluorophenyl)cyclobutane-1-carboxamide;
N-(4-fluorophenyl)-1-{1-[3-(trifluoromethyl)-1H-pyrazole-5-carbonyl]-1,2,3,4-tetrahydroquinolin-6-yl}cyclobutane-1-carboxamide;
1-[1-(3-cyclopropyl-1H-pyrazole-5-carbonyl)-1,2,3,4-tetrahydroquinolin-6-yl]-N-(4-fluorophenyl)cyclobutane-1-carboxamide;
4-chloro-N-{1-[5-(3-chlorobenzene-1-carbonyl)-5,6,7,8-tetrahydro-1,5-naphthyridin-2-yl] ethyl}benzamide;
4-fluoro-N-{1-[5-(1-methyl-1H-pyrazole-3-carbonyl)-5,6,7,8-tetrahydro-1,5-naphthyridin-2-yl] ethyl}benzamide;
N-{1-[5-(2-chlorobenzene-1-carbonyl)-5,6,7,8-tetrahydro-1,5-naphthyridin-2-yl] ethyl}-4-fluorobenzamide;
N-{(1R)-1-[5-(1-cyclopropyl-1H-pyrazole-3-carbonyl)-5,6,7,8-tetrahydro-1,5-naphthyridin-2-yl] ethyl}-4-fluorobenzamide;
N-{1-[5-(2,3-dichlorobenzene-1-carbonyl)-5,6,7,8-tetrahydro-1,5-naphthyridin-2-yl] ethyl}-4-fluorobenzamide;
N-{1-[5-(3,5-dichlorobenzene-1-carbonyl)-5,6,7,8-tetrahydro-1,5-naphthyridin-2-yl] ethyl}-4-fluorobenzamide;
N-{1-[5-(2,6-dichlorobenzene-1-carbonyl)-5,6,7,8-tetrahydro-1,5-naphthyridin-2-yl] ethyl}-4-fluorobenzamide;
2-[5-(3-chlorobenzene-1-carbonyl)-5,6,7,8-tetrahydro-1,5-naphthyridin-2-yl]-N-(4-fluorophenyl)propanamide;
4-chloro-N-(1-(1-(3-chlorobenzoyl)-1,2,3,4-tetrahydro-1,7-naphthyridin-6-yl) ethyl)benzamide;
N-{1-[5-(3-chlorobenzene-1-carbonyl)-5,6,7,8-tetrahydro-1,5-naphthyridin-2-yl]cyclopropyl}-4-fluorobenzamide;
4-fluoro-N-{1-[5-(1-methyl-1H-pyrazole-4-carbonyl)-5,6,7,8-tetrahydro-1,5-naphthyridin-2-yl]cyclopropyl}benzamide;
2-[1-(3-chlorobenzene-1-carbonyl)-1,2,3,4-tetrahydroquinolin-6-yl]-N-(4-chlorophenyl)-2-methylpropanamide;
2-[5-(3-chlorobenzene-1-carbonyl)-5,6,7,8-tetrahydro-1,5-naphthyridin-2-yl]-N-(4-fluorophenyl)-2-methylpropanamide; and
3-(5-(3-chlorobenzoyl)-5,6,7,8-tetrahydro-1,5-naphthyridin-2-yl)-N-(4-fluorophenyl) oxetane-3-carboxamide.

4. The compound of claim 1, which is:
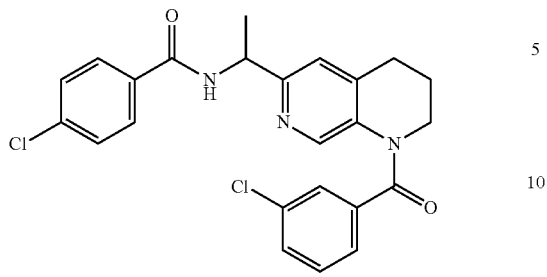
or a pharmaceutically acceptable salt thereof.
5. A composition which comprises an inert carrier and the compound of claim 1 or a pharmaceutically acceptable salt thereof.
* * * * *